US006806351B2

(12) United States Patent
Ruben et al.

(10) Patent No.: US 6,806,351 B2
(45) Date of Patent: Oct. 19, 2004

(54) SECRETED PROTEIN HBJFE12

(75) Inventors: Steven M. Ruben, Olney, MD (US); Daniel R. Soppet, Centreville, VA (US); Reinhard Ebner, Gaithersburg, MD (US); Henrik S. Olsen, Gaithersburg, MD (US); Paul E. Young, Gaithersburg, MD (US); John M. Greene, Gaithersburg, MD (US); Ann M. Ferrie, Tewksbury, MA (US); Guo-Liang Yu, Berkeley, CA (US); Jian Ni, Rockville, MD (US); Craig A. Rosen, Laytonsville, MD (US); Laurie A. Brewer, St. Paul, MN (US); Fouad Janat, Westerly, RI (US)

(73) Assignee: Human Genome Sciences, Inc., Rockville, MD (US)

( * ) Notice: Subject to any disclaimer, the term of this patent is extended or adjusted under 35 U.S.C. 154(b) by 242 days.

(21) Appl. No.: 09/774,639

(22) Filed: Feb. 1, 2001

(65) Prior Publication Data
US 2003/0003555 A1 Jan. 2, 2003

Related U.S. Application Data

(63) Continuation of application No. 09/244,112, filed on Feb. 4, 1999, now abandoned, which is a continuation-in-part of application No. PCT/US98/16235, filed on Aug. 4, 1998.
(60) Provisional application No. 60/055,386, filed on Aug. 5, 1997, provisional application No. 60/054,807, filed on Aug. 5, 1997, provisional application No. 60/055,312, filed on Aug. 5, 1997, provisional application No. 60/055,309, filed on Aug. 5, 1997, provisional application No. 60/054,798, filed on Aug. 5, 1997, provisional application No. 60/055,310, filed on Aug. 5, 1997, provisional application No. 60/054,806, filed on Aug. 5, 1997, provisional application No. 60/054,809, filed on Aug. 5, 1997, provisional application No. 60/054,804, filed on Aug. 5, 1997, provisional application No. 60/054,803, filed on Aug. 5, 1997, provisional application No. 60/054,808, filed on Aug. 5, 1997, provisional application No. 60/055,311, filed on Aug. 5, 1997, provisional application No. 60/055,986, filed on Aug. 18, 1997, provisional application No. 60/055,970, filed on Aug. 18, 1997, provisional application No. 60/056,563, filed on Aug. 19, 1997, provisional application No. 60/056,557, filed on Aug. 19, 1997, provisional application No. 60/056,731, filed on Aug. 19, 1997, provisional application No. 60/056,365, filed on Aug. 19, 1997, provisional application No. 60/056,367, filed on Aug. 19, 1997, provisional application No. 60/056,370, filed on Aug. 19, 1997, provisional application No. 60/056,364, filed on Aug. 19, 1997, provisional application No. 60/056,366, filed on Aug. 19, 1997, provisional application No. 60/056,732, filed on Aug. 19, 1997, and provisional application No. 60/056,371, filed on Aug. 19, 1997.

(51) Int. Cl.[7] .................... C07K 14/435; C07K 5/00; C07H 21/04; C12P 21/00
(52) U.S. Cl. .................... 530/350; 530/323; 530/324; 435/69.1; 435/69.8; 435/71.1; 536/23.5
(58) Field of Search .................... 530/350; 435/69.1, 435/71.1, 69.8; 536/23.5, 23.31

(56) References Cited

U.S. PATENT DOCUMENTS 5,882,879 A * 3/1999 Veenstra et al.

OTHER PUBLICATIONS

Charnock–Jones et al., "Extension of incomplete cDNAs (ESTs) by biotin/streptavidin–mediated walking using the polymerase chain reaction," *J. Biotech.*, 35:205–215 (1994).
Venter et al., "Genome sequence analysis: scientific objectives and practical strategies," *Trends in Biotechnology*, 10:8–11 (Jan./Feb. 1992).
GenBank Accession No. N39230, Hillier et al., "yy50c03s1 Homo sapiens cDNA clone 276964 3'," Jan. 19, 1996.
GenBank Accession No. D87433, Nagase et al., "Human mRNA for KIAA0246 gene, partial cds.," Jul. 10, 1997.
GenBank Accession No. AA034571, Marra et al., "mi49b11.r1 Soares mouse embryo NbME 13.5 14.5 Mus musculus cDNA clone 466845 5', mRNA sequence," Aug. 23, 1996.
GenBank Accession No. R49134, Hillier et al., "yg69g01.s1 Homo sapiens cDNA clone 38705 3'," May 22, 1995.
GenBank Accession No. W96505, Hillier et al., "ze11f01.r1 Soares fetal heart NbHH19W Homo sapiens cDNA clone 358681 5', mRNA sequence," Jul. 16, 1996.
GenBank Accession No. AA364889, Adams et al., "EST75775 Pineal gland II Homo sapiens cDNA 5' end, mRNA sequence," Apr. 21, 1997.
GenBank Accession No. R66361, Hillier et al., "yi34h09.r1 Homo sapiens cDNA clone 141185 5'," May 30, 1995.
GenBank Accession No. AA028292, Marra et al., "mi20d08.r1 Soares mouse p3NMF 19.5 Mus musculus cDNA clone 464079 5', mRNA sequence," Sep. 11, 1996.
GenBank Accession No. T91259, Hillier et al., "yd60d09.s1 Homo sapiens cDNA clone 112625 3'," Mar. 22, 1995.
GenBank Accession No. H75934, Hillier et al., "yr96b08.s1 Homo sapiens cDNA clone 213111 3', " Nov. 1, 1995.

* cited by examiner

Primary Examiner—Carla J. Myers
(74) Attorney, Agent, or Firm—Human Genome Sciences, Inc.

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

26 Claims, No Drawings

SECRETED PROTEIN HBJFE12

This application is a Continuation of U.S. application Ser. No. 09/244,112 filed Feb. 4, 1999 now abandoned, which is hereby incorporated by reference, which is a continuation-in-part of, and claims benefit under 35 U.S.C. §120 of United States patent application Serial No. PCT/US98/16235, filed Aug. 4, 1998, which is hereby incorporated by reference, which claims benefit under 35 U.S.C. §119(e) based on U.S. Provisional Applications:

|     | Filing Date   | application Ser. No. |
| --- | ------------- | -------------------- |
| 1.  | Aug. 5, 1997  | 60/055,386           |
| 2.  | Aug. 5, 1997  | 60/054,807           |
| 3.  | Aug. 5, 1997  | 60/055,312           |
| 4.  | Aug. 5, 1997  | 60/055,309           |
| 5.  | Aug. 5, 1997  | 60/054,798           |
| 6.  | Aug. 5, 1997  | 60/055,310           |
| 7.  | Aug. 5, 1997  | 60/054,806           |
| 8.  | Aug. 5, 1997  | 60/054,809           |
| 9.  | Aug. 5, 1997  | 60/054,804           |
| 10. | Aug. 5, 1997  | 60/054,803           |
| 11. | Aug. 5, 1997  | 60/054,808           |
| 12. | Aug. 5, 1997  | 60/055,311           |
| 13. | Aug. 18, 1997 | 60/055,986           |
| 14. | Aug. 18, 1997 | 60/055,970           |
| 15. | Aug. 19, 1997 | 60/056,563           |
| 16. | Aug. 19, 1997 | 60/056,557           |
| 17. | Aug. 19, 1997 | 60/056,731           |
| 18. | Aug. 19, 1997 | 60/056,365           |
| 19. | Aug. 19, 1997 | 60/056,367           |
| 20. | Aug. 19, 1997 | 60/056,370           |
| 21. | Aug. 19, 1997 | 60/056,364           |
| 22. | Aug. 19, 1997 | 60/056,366           |
| 23. | Aug. 19, 1997 | 60/056,732           |
| 24. | Aug. 19, 1997 | 60/056,371           |

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of the coding sequence, but do not comprise all or a portion of any intron. In another embodiment, the nucleic acid comprising the coding sequence does not contain coding sequences of a genomic flanking gene (i.e., 5' or 3' to the gene in the genome).

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The polynucleotide of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention

Features of Protein Encoded by Gene No: 1

In specific embodiments, polypeptides of the invention comprise the following amino acid sequence: TFKSLWKH-WTLAGPGNIGKNWIGR (SEQ ID NO:203). Polynucleotides encoding these polypeptides are also encompassed by the invention.

This gene is expressed primarily in bone marrow tissue, and to a lesser extent in eosinophils and fetal liver tissue.

Therefore, polynucleotides and polypeptides of the invention are useful as reagents for differential identification of the tissue(s) or cell type(s) present in a biological sample and for diagnosis of diseases and conditions which include, but are not limited to, hematopoietic or immune disorders and diseases, particularly recovery of the hematopoietic system after anticancer therapy. Similarly, polypeptides and antibodies directed to these polypeptides are useful in providing immunological probes for differential identification of the tissue(s) or cell type(s). For a number of disorders of the above tissues or cells, particularly of the immune, expression of this gene at significantly higher or lower levels may be routinely detected in certain tissues or cell types (e.g., immune, bone marrow and hemopoietic cells and tissue, eosinophils and other blood cells, hepatic tissue, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in bone marrow and fetal liver tissues indicates that polynucleotides and polypeptides corresponding to this gene are useful for the regulation and/or reconstitution of hematopoietic cells after cancer therapy. This gene product is primarily expressed in hematopoietic cells and tissues, suggesting that it plays a role in the survival, proliferation, and/or differentiation of hematopoieitic lineages. This is particularly supported by the expression of this gene product in fetal liver and bone marrow, the two primary sites of definitive hematopoiesis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 961 of SEQ ID NO:11, b is an integer of 15 to 975, where both a and b correspond to the positions of nucleotide residues shown in SEQ ID NO:11, and where b is greater than or equal to a+14.

Features of Protein Encoded by Gene No: 2

When tested against K562 cell lines, supernatants removed from cells containing this gene activated the ISRE (interferon-sensitive responsive element) pathway. Thus, it is likely that this gene activates kidney cells, and to a lesser extent other cells or cells types, through the JAK-STAT signal transduction pathway. ISRE (interferon-sensitive responsive element)—also a promoter element found upstream in many genes which are involved in the JAK-STAT pathway. The JAK-STAT pathway is a large, signal transduction pathway involved in the differentiation and proliferation of cells. Therefore, activation of the JAK-STATs pathway, reflected by the binding of the ISRE element, can be used to indicate proteins involved in the proliferation and differentiation of cells.

In specific embodiments, polypeptides of the invention comprise the following amino acid sequence: HEGTWRWEAPTPLQSLGPTTPSLPSVADLCQDGHG-GCSEHANCSQVGT (SEQ ID NO:204). Polynucleotides encoding these polypeptides are also encompassed by the invention. The gene encoding the disclosed cDNA is thought to reside on chromosome 3. Accordingly, polynucleotides related to this invention are useful as a marker in linkage analysis for chromosome 3.

The protein product of this clone is a homolog of a secreted protein member of the hyaladherin family. It's closest match is TSG-6. The expression of TSG-6 is TNF- and IL-1-inducible, and is found in elevated amounts in synovial fluid from rheumatoid versus normal joints. There is a strong link between the TSG-6 protein and inflammation. The gene was isolated from TNF-induced fibroblasts. It is transcriptionally induced by TNF, LPS, and IL-1. Tissues that express TSG-6 include fibroblasts, monocytes, and synovial cells. It binds hyaluronic acid, as does another member of the CD44 family, which functions as the lymphocyte homing receptor. TSG-6 also complexes with the serpin, inter-alpha-inhibitor (IaI). IaI inhibits proteases such as cathepsin G and leukocyte elastase, which are involved in tissue damage during inflammation. A higher level of TSG-6 protein is found in the synovial fluid of rheumatoid versus normal joints. The most compelling evidence for TSGF-6 as an anti-inflammatory is that it can inhibit IL-1-induced acute inflammation, as well as dexamethasone in the mouse air pouch inflammation model.

This gene is expressed primarily in myoloid progenitor cell line, spleen and bone marrow and to a lesser extent in synovial tissue and adipose tissue.

Therefore, polynucleotides and polypeptides of the invention are useful as reagents for differential identification of the tissue(s) or cell type(s) present in a biological sample and for diagnosis of diseases and conditions which include, but are not limited to, inflammation caused by acute injury or chronic disease, and other immune system disorders. Similarly, polypeptides and antibodies directed to these polypeptides are useful in providing immunological probes for differential identification of the tissue(s) or cell type(s). For a number of disorders of the above tissues or cells, particularly of the immune, expression of this gene at significantly higher or lower levels may be routinely detected in certain tissues or cell types (e.g., inflammed, immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:108 as residues: Pro-8 to Trp-15, Cys-17 to Asn-36, Leu-42 to Cys-49, Glu-63 to Val-68.

The tissue distribution in immune tissues, in conjunction with the biological activity data, suggests that the protein product of this clone is useful for the treatment and diagnosis of hematopoetic related disorders such as anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

In addition, the expression of this gene product in synovium, as well as the homology to TSG-6, suggests a role in the detection and treatment of disorders and conditions affecting the skeletal system, in particular osteoporosis as well as disorders afflicting connective tissues (e.g., arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial arthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2739 of SEQ ID NO:12, b is an integer of 15 to 2753, where both a and b correspond to the positions of nucleotide residues shown in SEQ ID NO:12, and where b is greater than or equal to a+14.

Features of Protein Encoded by Gene No: 3

When tested against PC12 cell lines, supernatants removed from cells containing this gene activated the EGR1 pathway. Thus, it is likely that this gene activates sensory neuron cells, and to a lesser extent other neuronal cells, through the EGR1 signal transduction pathway. EGR1 is a separate signal transduction pathway from JAK-STAT, genes containing the EGR1 promoter are induced in various tissues and cell types upon activation, leading the cells to undergo differentiation and proliferation.

This gene is expressed primarily in chondrosarcoma tissue, and to a lesser extent in glioblastoma and bone marrow.

Therefore, polynucleotides and polypeptides of the invention are useful as reagents for differential identification of the tissue(s) or cell type(s) present in a biological sample and for diagnosis of diseases and conditions which include, but are not limited to, cancers of the bone and CNS. Similarly, polypeptides and antibodies directed to these polypeptides are useful in providing immunological probes for differential identification of the tissue(s) or cell type(s). For a number of disorders of the above tissues or cells, particularly of the skeletal, expression of this gene at significantly higher or lower levels may be routinely detected in certain tissues or cell types (e.g., skeletal, hematopoietic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:109 as residues: Ala-15 to Gly-22, Asp-44 to Ile-53.

The tissue distribution in chondrosarcoma tissue, in conjunction with the detected biological activity in sensory neurons, indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system.

Alternatively, the expression of this gene product in synovium would suggest a role in the detection and treatment of disorders and conditions affecting the skeletal system, in particular osteoporosis as well as disorders aflicting connective tissues (e.g., arthritis, trauma, tendonitis, chrondomalacia and inflammation) in the diagnosis or treatment of various autoimmune disorders such as rheumatoid arthritis, lupus, scleroderma, and dermatomyositis as well as dwarfism, spinal deformation, and specific joint abnormalities as well as chondrodysplasias ie. spondyloepiphyseal dysplasia congenita, familial osteoarthritis, Atelosteogenesis type II, metaphyseal chondrodysplasia type Schmid. Furthermore, the tissue distribution in chondrosarcoma tissue indicates that the translation product of this gene is useful for the detection and/or treatment of cancers of catrilage, connective tissues, and synovium, for example, as well as cancers of other tissues where expression has been observed. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1011 of SEQ ID NO:13, b is an integer of 15 to 1025, where both a and b correspond to the positions of nucleotide residues shown in SEQ ID NO:13, and where b is greater than or equal to a+14.

Features of Protein Encoded by Gene No: 4

In specific embodiments, polypeptides of the invention comprise the following amino acid sequence: LKVPT-CYSANT (SEQ ID NO:205). Polynucleotides encoding these polypeptides are also encompassed by the invention.

This gene is expressed primarily in cerebellum and infant brain tissues.

Therefore, polynucleotides and polypeptides of the invention are useful as reagents for differential identification of the tissue(s) or cell type(s) present in a biological sample and for diagnosis of diseases and conditions which include, but are not limited to, neural or developmental disorders, particularly neurodegenerative conditions in the central nervous system, and congenital defects. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., brain and other tissue of the nervous system, developmental, and cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 110 as residues: Gly-40 to Lys-45.

The tissue distribution in brain and cerebellum tissues indicates that polynucleotides and polypeptides corresponding to this gene are useful for treating cell loss in the central nervous system due to trauma, ischaemia, or disease. Furthermore, the tissue distribution indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders.

Moreover, the expression within infant tissue suggests this protein may play a role in the regulation of cellular division, and may show utility in the diagnosis and treatment of cancer and other proliferative disorders. Similarly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may also be involved in apoptosis or tissue differentiation and could again be useful in cancer therapy. Protein, as well as, antibodies directed against the protein may show utility as a tumor marker and/or immunotherapy targets for the above listed tissues. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 767 of SEQ ID NO:14, b is an integer of 15 to 781, where both a and b correspond to the positions of nucleotide residues shown in SEQ ID NO:14, and where b is greater than or equal to a+14.

Features of Protein Encoded by Gene No: 5

In specific embodiments, polypeptides of the invention comprise the following amino acid sequence:

(SEQ ID NO:206)
WQVPAPVIPGXDPRVRGARKRTLLGVAGGWRRFERLWAGSLS, (SEQ ID NO:207)
SRSLALAAAPSSNGSPWRLLGALCLQRPPVVSKPLTPLQEE.

Polynucleotides encoding these polypeptides are also encompassed by the invention. The gene encoding the disclosed cDNA is thought to reside on chromosome 15. Accordingly, polynucleotides related to this invention are useful as a marker in linkage analysis for chromosome 15.

This gene is expressed primarily in colon cancer cell line and glioblastoma tissue, and to a lesser extent in synovial fluid, placenta, and fetal liver tissues.

Therefore, polynucleotides and polypeptides of the invention are useful as reagents for differential identification of the tissue(s) or cell type(s) present in a biological sample and for diagnosis of diseases and conditions which include, but are not limited to, cancers of the colon and glial cells. Similarly, polypeptides and antibodies directed to these polypeptides are useful in providing immunological probes for differential identification of the tissue(s) or cell type(s). For a number of disorders of the above tissues or cells, particularly of the digestive tract, expression of this gene at significantly higher or lower levels may be routinely detected in certain tissues or cell types (e.g., gastrointestinal tissue, synovial tissue, hepatic tissue, nervous tissue, vascular, developmental, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:111 as residues: Arg-12 to Asp-17, Leu-23 to Ala-34, His-37 to Gln-43, Thr-69 to Arg-86, Pro-140 to Lys-147, Lys-188 to Tyr-199.

The tissue distribution in cancerous colon tissues and glioblastoma indicates that polynucleotides and polypeptides corresponding to this gene are useful for diagnosing and/or treating cancers of the colon and glia, as well as cancers of other tissues where expression has been observed. The protein product of this clone is useful for the treatment and diagnosis of hematopoietic related disorders such as anemia, pancytopenia, leukopenia, thrombocytopenia or leukemia since stromal cells are important in the production of cells of hematopoietic lineages.

The uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

The protein is useful for the modulation of the immune response to various tissues and cell types, thought particularly to developmental and gastrointestinal cell and tissues. The protein is useful for modulating apoptosis and may show utility in combating cancer and degenerative disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1026 of SEQ ID NO:15, b is an integer of 15 to 1040, where both a and b correspond to the positions of nucleotide residues shown in SEQ ID NO:15, and where b is greater than or equal to a+14.

Features of Protein Encoded by Gene No: 6

When tested against K562 leukemia cell lines, supernatants removed from cells containing this gene activated the ISRE assay. Thus, it is likely that this gene activates leukemia cells, and to a lesser extent immune cells, in addition to other cells or cell-types, through the JAK-STAT signal transduction pathway. The interferon-sensitive response element is a promoter element found upstream of many genes which are involved in the JAK-STAT pathway. The JAK-STAT pathway is a large, signal transduction pathway involved in the differentiation and proliferation of cells. Therefore, activation of the JAK-STAT pathway, reflected by the binding of the ISRE element, can be used to indicate proteins involved in the proliferation and differentiation of cells.

This gene is expressed primarily in embryonic tissue.

Therefore, polynucleotides and polypeptides of the invention are useful as reagents for differential identification of the tissue(s) or cell type(s) present in a biological sample and for diagnosis of diseases and conditions which include, but are not limited to, diseases affecting embryonal development and developmental abnormalities, in addition to cancer and degenerative conditions. Similarly, polypeptides and antibodies directed to these polypeptides are useful in providing immunological probes for differential identification of the tissue(s) or cell type(s). For a number of disorders of the above tissues or cells, particularly of the developing fetus or embryo, expression of this gene at significantly higher or lower levels may be routinely detected in certain tissues or cell types (e.g., developing and differentiating tissue, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:112 as residues: Arg-12 to Gly-18, Pro-51 to Lys-57, Glu-64 to Lys-78, Lys-102 to Lys-109.

The tissue distribution in embryonic tissues indicates that polynucleotides and polypeptides corresponding to this gene are useful for the diagnosis of developmental defects or as a growth or differentiation factor that may affect specific populations of cells. Furthermore, expression within embryonic tissue, in conjunction with the biological activity data, as well as other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus, this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 698 of SEQ ID NO:16, b is an integer of 15 to 712, where both a and b correspond to the positions of nucleotide residues shown in SEQ ID NO:16, and where b is greater than or equal to a+14.

Features of Protein Encoded by Gene No: 7

In specific embodiments, polypeptides of the invention comprise the following amino acid sequence:

(SEQ ID NO:208)
MEEEAYSKGFQEGLKKTKELQDLKEEEEEQKSESPEEPEEV, and/or (SEQ ID NO:209)
EETEEEEKGPRSSKLEELVHFLQVMYPKLCQHWQVIW.

Polynucleotides encoding these polypeptides are also encompassed by the invention.

This gene is expressed primarily in brain tissue from patients with dementia.

Therefore, polynucleotides and polypeptides of the invention are useful as reagents for differential identification of the tissue(s) or cell type(s) present in a biological sample and for diagnosis of diseases and conditions which include, but are not limited to, neurological diseases and disorders, including dementia. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., brain, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:113 as residues: Gln-53 to Thr-60.

The tissue distribution in brain tissue indicates that polynucleotides and polypeptides corresponding to this gene are useful as a factor that may enhance survival of neuronal cells. Furthermore, the tissue distribution indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1309 of SEQ ID NO:17, b is an integer of 15 to 1323, where both a and b correspond to the positions of nucleotide residues shown in SEQ ID NO:17, and where b is greater than or equal to a+14.

Features of Protein Encoded by Gene No: 8

In specific embodiments, polypeptides of the invention comprise the following amino acid sequence:

ILYLVWAFIPESWLNSLGLTYWPQKYWAVALPVYLLIAIVI, (SEQ ID NO:210)

YGFVLFLSSQFGFILYLVWA, (SEQ ID NO:211)

TSPLDSIHTITD, (SEQ ID NO:212)

PLPERAIYGFVLFLSSQFGF, and/or (SEQ ID NO:213)

PTRGGSLCACPGWGLPSRLGLSLRFSSSPLRLPSRRLRENSALRLSKA PGK. (SEQ ID NO:214)

Polynucleotides encoding these polypeptides are also encompassed by the invention.

This gene is expressed primarily in activated T cells, synovial cells, osteoblasts and microvascular endothelium, and to a lesser extent in fetal brain and hodgkins lymphoma tissues.

Therefore, polynucleotides and polypeptides of the invention are useful as reagents for differential identification of the tissue(s) or cell type(s) present in a biological sample and for diagnosis of diseases and conditions which include, but are not limited to, proliferative disorders of the hematopoeitic system, including lymphomas. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., T-cells and other cells and tissue of the immune system, bone, synovial tissue, endothelial cells, vascular cells and tissues, brain and other tissue of the nervous system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:114 as residues: Glu-3 to Pro-10, Thr-91 to Glu-105.

The tissue distribution in immune tissues indicates that polynucleotides and polypeptides corresponding to this gene are useful for treating disorders of the immune system involving abnormal growth of specific types of cells, as well as of other cell types where expression has been observed. Furthermore, elevated levels of expression of this gene product in T cell lineages indicates that it may play an active role in normal T cell function and in the regulation of the immune response. For example, this gene product may be involved in T cell activation, in the activation or control of differentiation of other hematopoietic cell lineages, in antigen recognition, or in T cell proliferation. Protein is useful in the detection, treatment, and/or prevention of skeletal and/or vascular disorders and conditions, which include, but are not limited to arthritis, stroke, embolism, microvascular disease, aneurysm, and atherosclerosis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 772 of SEQ ID NO:18, b is an integer of 15 to 786, where both a and b correspond to the positions of nucleotide residues shown in SEQ ID NO:18, and where b is greater than or equal to a+14.

Features of Protein Encoded by Gene No: 9

In specific embodiments, polypeptides of the invention comprise the following amino acid sequence: PPGCRNSARE (SEQ ID NO:215). Polynucleotides encoding these polypeptides are also encompassed by the invention.

This gene is expressed primarily in frontal cortex tissue of the brain, and in fetal liver/spleen tissue.

Therefore, polynucleotides and polypeptides of the invention are useful as reagents for differential identification of the tissue(s) or cell type(s) present in a biological sample and for diagnosis of diseases and conditions which include, but are not limited to, seizures and/or disorders associated with the central nervous system and hematopoeitic systems. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., brain and other tissue of the nervous system, hepatic tissue, hematopoietic, and cells and tissue of the immune system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:115 as residues: Thr-56 to Arg-62.

The tissue distribution in frontal cortex tissue of the brain indicates that polynucleotides and polypeptides corresponding to this gene are useful for treating seizure induced damage in the cortical regions of the central nervous system. Furthermore, elevated expression of this gene product within the frontal cortex of the brain indicates that it may be involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. The protein product of this clone is useful for the treatment and diagnosis of hematopoietic related disorders such as anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia.

The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. The protein is useful in modulating the immune response to neural cells and tissues, and particularly in regulating apoptosis, proliferative and/or degenerative conditions. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 496 of SEQ ID NO:19, b is an integer of 15 to 510, where both a and b correspond to the positions of nucleotide residues shown in SEQ ID NO:19, and where b is greater than or equal to a+14.

Features of Protein Encoded by Gene No: 10

In specific embodiments, polypeptides of the invention comprise the following amino acid sequence: PPGCRN-SARE (SEQ ID NO:216). Polynucleotides encoding these polypeptides are also encompassed by the invention.

This gene is expressed primarily in frontal cortex tissue of the brain.

Therefore, polynucleotides and polypeptides of the invention are useful as reagents for differential identification of the tissue(s) or cell type(s) present in a biological sample and for diagnosis of diseases and conditions which include, but are not limited to, neural disorders and diseases, particularly ischeamic damage to the cortex. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., brain and other tissues of the nervous system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:116 as residues: Glu-29 to Gly-36.

The tissue distribution in frontal cortex tissue of the brain indicates that polynucleotides and polypeptides corresponding to this gene are useful for reducing the damage resulting from ischaemic injury in the central nervous system. Furthermore, elevated expression of this gene product within the frontal cortex of the brain indicates that it may be involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 736 of SEQ ID NO:20, b is an integer of 15 to 750, where both a and b correspond to the positions of nucleotide residues shown in SEQ ID NO:20, and where b is greater than or equal to a+14.

Features of Protein Encoded by Gene No: 11

When tested against K562 leukemia cell lines, supernatants removed from cells containing this gene activated the ISRE assay. Thus, it is likely that this gene activates leukemia cells, and to a lesser extent immune cells and tissues, in addition to other cells and cell-types, through the JAK-STAT signal transduction pathway. The interferon-sensitive response element is a promoter element found upstream of many genes which are involved in the JAK-STAT pathway. The JAK-STAT pathway is a large, signal transduction pathway involved in the differentiation and proliferation of cells. Therefore, activation of the JAK-STAT pathway, reflected by the binding of the ISRE element, can be used to indicate proteins involved in the proliferation and differentiation of cells.

This gene is expressed primarily in liver tissue.

Therefore, polynucleotides and polypeptides of the invention are useful as reagents for differential identification of the tissue(s) or cell type(s) present in a biological sample and for diagnosis of diseases and conditions which include, but are not limited to, hepatic and metabolic disorders and conditions, particularly hepatitis, cirrosis and hepatomas. Similarly, polypeptides and antibodies directed to these polypeptides are useful in providing immunological probes for differential identification of the tissue(s) or cell type(s). For a number of disorders of the above tissues or cells, particularly of the hepatic system, expression of this gene at significantly higher or lower levels may be routinely detected in certain tissues or cell types (e.g., hepatic tissue, and cancerous and wounded tissues) or bodily fluids (e.g., lymph, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in liver tissue indicates that polynucleotides and polypeptides corresponding to this gene are useful for the treatment and/or diagnosis for diseases of the liver, including cirrosis and hepatitis, and may act as a factor for the regeneration of cells of epithelial cell origin. Furthermore, additional disorders and/or diseases that the translation product of this gene is useful for in the detection and/or treatment of include hepatoblastoma, jaundice, hepatitis, and liver metabolic diseases and conditions that are attributable to the differentiation of hepatocyte progenitor cells. Protein, as well as, antibodies directed against the protein may show utility as a tumor marker and immunotherapy targets for the above listed tumors and tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 824 of SEQ ID NO:21, b is an integer of 15 to 838, where both a and b correspond to the positions of nucleotide residues shown in SEQ ID NO:21, and where b is greater than or equal to a+14.

Features of Protein Encoded by Gene No: 12

When tested against K562 cell lines, supernatants removed from cells containing this gene activated the ISRE (interferon-sensitive responsive element) pathway. Thus, it is likely that this gene activates kidney cells, and to a lesser extent other uro-genital cells, through the JAK-STAT signal transduction pathway. ISRE is a promoter element found upstream in many genes which are involved in the JAK-STAT pathway. The JAK-STAT pathway is a large, signal transduction pathway involved in the differentiation and proliferation of cells. Therefore, activation of the JAK-STAT pathway, reflected by the binding of the ISRE element, can be used to indicate proteins involved in the proliferation and differentiation of cells. In specific embodiments, polypeptides of the invention comprise the following amino acid sequence:

(SEQ ID NO:217)
GASSRPRLELGRLMGPKGVAVDRNXHIIVVDNKSCCVFTFQPNG, (SEQ ID NO:218)
KLVGRFGGRGATDRHFAGPHFVAVNNKNEIVVTDFHNHSVKVYS, (SEQ ID NO:219)
ADGEFLFKFGSHGEGNGQFNAPTGVAVDSNGNIIVADWGNSR, (SEQ ID NO:220)
IXGIRXLWLLPVLYQHICRTTVWSTGPGTDLGWPCGGG.

Polynucleotides encoding these polypeptides are also encompassed by the invention.

This gene is expressed primarily in 7 week old embryonic tissue, and to a lesser extent in Jurkat T-cells.

Therefore, polynucleotides and polypeptides of the invention are useful as reagents for differential identification of the tissue(s) or cell type(s) present in a biological sample and for diagnosis of diseases and conditions which include, but are not limited to, developmental, urogenital, and immune disorders. Similarly, polypeptides and antibodies directed to these polypeptides are useful in providing immunological probes for differential identification of the tissue(s) or cell type(s). For a number of disorders of the above tissues or cells, particularly of the immune and urogenital systems, expression of this gene at significantly higher or lower levels may be routinely detected in certain tissues or cell types (e.g., immune, developmental, urogenital, cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:118 as residues: Trp-29 to Gly-42, Gly-46 to His-51.

The tissue distribution in Jurkat cells indicates that polynucleotides and polypeptides corresponding to this gene are useful for the diagnosis and/or treatment of a variety of immune system disorders. Expression of this gene product in T-cells indicates the protein may play a role in regulating the proliferation; survival; differentiation; and/or activation of potentially all hematopoietic cell lineages, including blood stem cells. Elevated levels of expression of this gene product in T cell lineages indicates that it may play an active role in normal T cell function and in the regulation of the immune response. For example, this gene product may be involved in T cell activation, in the activation or control of differentiation of other hematopoietic cell lineages, in antigen recognition, or in T cell proliferation.

This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis.

In addition, this gene product may have commercial utility in the expansion of stem cells and committed progenitors of various blood lineages, and in the differentiation and/or proliferation of various cell types. Alternatively, the tissue distribution indicates that polynucleotides and polypeptides corresponding to this gene are useful for the diagnosis and/or treatment of disorders of the placenta. Specific expression within the placenta indicates that this gene product may play a role in the proper establishment and maintenance of placental function. Alternately, this gene product may be produced by the placenta and then transported to the embryo, where it may play a crucial role in the development and/or survival of the developing embryo or fetus.

Expression of this gene product in a vascular-rich tissue such as the placenta also indicates that this gene product may be produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1047 of SEQ ID NO:22, b is an integer of 15 to 1061, where both a and b correspond to the positions of nucleotide residues shown in SEQ ID NO:22, and where b is greater than or equal to a+14.

Features of Protein Encoded by Gene No: 13

In specific embodiments, polypeptides of the invention comprise the following amino acid sequence: MEWEG-GAIRHPSTELG (SEQ ID NO:221), RPTRPPDGCH PSC-CRMEAAMEWEGGAIRHPSTELGI (SEQ ID NO:222). Polynucleotides encoding these polypeptides are also encompassed by the invention. The gene encoding the disclosed cDNA is thought to reside on chromosome 15. Accordingly, polynucleotides related to this invention are useful as a marker in linkage analysis for chromosome 15.

This gene is expressed primarily in endometrial stromal cells, and to a lesser extent in neutrophils.

Therefore, polynucleotides and polypeptides of the invention are useful as reagents for differential identification of the tissue(s) or cell type(s) present in a biological sample and for diagnosis of diseases and conditions which include, but are not limited to, reproductive disorders and diseases, particularly diseases of the female reproductive system including endometriosis, and diseases of the immune system. Similarly, polypeptides and antibodies directed to these polypeptides are useful in providing immunological probes for differential identification of the tissue(s) or cell type(s). For a number of disorders of the above tissues or cells, particularly of the female reproductive system, expression of this gene at significantly higher or lower levels may be routinely detected in certain tissues or cell types (e.g., reproductive tissues, immune system tissues, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:119 as residues: Pro-30 to Ala-35.

The tissue distribution in endometrium indicates that polynucleotides and polypeptides corresponding to this gene are useful for the treatment and/or diagnosis of endometriosis. Furthermore, this gene could be transfected in gene-replacement treatments into the cells of the endometrium, and the protein products could be produced. These treatments could be performed during artificial insemination for the purpose of increasing the likelyhood of implantation and development of a healthy embryo. In this case the gene or its gene product could be administered at later stages of pregnancy to promote heathy development of the endometrium. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 870 of SEQ ID NO:23, b is an integer of 15 to 884, where both a and b correspond to the positions of nucleotide residues shown in SEQ ID NO:23, and where b is greater than or equal to a+14.

Features of Protein Encoded by Gene No: 14

When tested against Jurkat T-cell cell lines, supernatants removed from cells containing this gene activated the GAS assay. Thus, it is likely that this gene activates T-cells, and to a lesser extent other immune cells, through the JAK-STAT signal transduction pathway. The gamma activating sequence (GAS) is a promoter element found upstream of many genes which are involved in the JAK-STAT pathway. The JAK-STAT pathway is a large, signal transduction pathway involved in the differentiation and proliferation of cells. Therefore, activation of the JAK-STAT pathway, reflected by the binding of the GAS element, can be used to indicate proteins involved in the proliferation and differentiation of cells.

This gene is expressed primarily in stomach cancer tissue.

Therefore, polynucleotides and polypeptides of the invention are useful as reagents for differential identification of the tissue(s) or cell type(s) present in a biological sample and for diagnosis of diseases and conditions which include, but are not limited to, gastrointestinal disorders and cancers, particularly of endothelial tissues. Similarly, polypeptides and antibodies directed to these polypeptides are useful in providing immunological probes for differential identification of the tissue(s) or cell type(s). For a number of disorders of the above tissues or cells, particularly of the metabolic and gastrointestinal systems, expression of this gene at significantly higher or lower levels may be routinely detected in certain tissues or cell types (e.g., endothelial, gastrointestinal, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:120 as residues: Met-1 to Ser-11.

The tissue distribution in stomach cancer tissue, combined with the observed GAS biological activity, indicates that polynucleotides and polypeptides corresponding to this gene are useful for the diagnosis and/or treatment of stomach cancer and other proliferative disorders, as well as cancers of other tissues where expression has been observed. Expression within cellular sources marked by proliferating cells indicates that this protein may play a role in the regulation of cellular division. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 697 of SEQ ID NO:24, b is an integer of 15 to 711, where both a and b correspond to the positions of nucleotide residues shown in SEQ ID NO:24, and where b is greater than or equal to a+14.

Features of Protein Encoded by Gene No: 15

The translation product of this gene was shown to have homology to the human reverse transcriptase, which may suggest that the translation product of this gene is useful as part of a viral vaccination strategy, particularly for retroviruses which require the participation of their encoded reverse transcriptase for provirus rescue and propagation (See Genebank Accession No.gi|439877). One embodiment of this gene comprises polypeptides of the following amino acid sequence:

ECQEYEILEHCWWECKLVQPFWKSSCRIPAARGIH, (SEQ ID NO:223)

HCWWECKLVQPFWKS, and/or (SEQ ID NO:224)

FTFPPT. (SEQ ID NO:225)

An additional embodiment is the polynucleotides encoding these polypeptides. The gene encoding the disclosed cDNA is believed to reside on chromosome 10. Accordingly, polynucleotides related to this invention are useful as a marker in linkage analysis for chromosome 10.

This gene is expressed primarily in human chronic synovitis tissue.

Therefore, polynucleotides and polypeptides of the invention are useful as reagents for differential identification of the tissue(s) or cell type(s) present in a biological sample and for diagnosis of diseases and conditions which include, but are not limited to, joint and skeletal disorders. Similarly, polypeptides and antibodies directed to these polypeptides are useful in providing immunological probes for differential identification of the tissue(s) or cell type(s). For a number of disorders of the above tissues or cells, particularly of the synovium, expression of this gene at significantly higher or lower levels may be routinely detected in certain tissues or cell types (e.g., musculoskeletal, immune, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:121 as residues: Glu-28 to Ser-33.

The tissue distribution in chronic synovitis tissue indicates that polynucleotides and polypeptides corresponding to this gene are useful for the diagnosis and/or treatment of joint and musculoskeletal conditions. In addition, the expression of this gene product in synovium would suggest a role in the detection and treatment of disorders and conditions affecting the skeletal system, in particular osteoporosis as well as disorders afflicting connective tissues (e.g., arthritis, trauma, tendonitis, chrondomalacia and inflammation) in the diagnosis or treatment of various autoimmune disorders such as rheumatoid arthritis, lupus, scleroderma, and dermatomyositis as well as dwarfism, spinal deformation, and specific joint abnormalities as well as chondrodysplasias ie. spondyloepiphyseal dysplasia congenita, familial osteoarthritis, Atelosteogenesis type II, metaphyseal chondrodysplasia type Schmid. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 493 of SEQ ID NO:25, b is an integer of 15 to 507, where both a and b correspond to the positions of nucleotide residues shown in SEQ ID NO:25, and where b is greater than or equal to a+14.

Features of Protein Encoded by Gene No: 16

The translation product of this gene shares sequence homology with mouse testin, which is thought to be important in normal cell function, particularly in testes (See Genebank Accession No.gi|475210). In specific embodiments, polypeptides of the invention comprise the following amino acid sequence:

HHHLRVGSPWSHPETGTAVHGAHPQGEAASDRHRGCFYRRRQLMHQLPI (SEQ ID NO:226)

YDQDPSRCRGLLENELKLMEEFVKQYKSEALGVGEVALPGXGWLAKEEG

KQQEKPEGAETXAXTTNGXXSDPSKEEAC,

TYEWAPP, (SEQ ID NO:227)

PKEKQPV, (SEQ ID NO:228)

and/or

PRPANLAIQPPLSPLRALAPLPEKPGAVPPPQKR. (SEQ ID NO:229)

Polynucleotides encoding these polypeptides are also encompassed by the invention.

This gene is expressed primarily in placental tissue and osteoblasts, and to a lesser extent, in prostate, smooth muscle tissue, heart tissue, fibroblasts, and adipose tissues.

Therefore, polynucleotides and polypeptides of the invention are useful as reagents for differential identification of the tissue(s) or cell type(s) present in a biological sample and for diagnosis of diseases and conditions which include, but are not limited to, vascular, cardiovascular, reproductive, skeletal, metabolic, and growth disorders. Similarly, polypeptides and antibodies directed to these polypeptides are useful in providing immunological probes for differential identification of the tissue(s) or cell type(s). For a number of disorders of the above tissues or cells, particularly of the vascular and cardiovascular, reproductive and skeletal systems, expression of this gene at significantly higher or lower levels may be routinely detected in certain tissues or cell types (e.g., vascular, cardiovascular, developmental, reproductive, skeletal, or cancerous and wounded tissues) or bodily fluids (e.g., lymph, amniotic fluid, serum, plasma, seminal fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:122 as residues: Pro-40 to Lys-48, Cys-50 to Leu-59, Asp-62 to Ile-69, Pro-138 to Pro-143.

The tissue distribution in placental tissue, osteoblasts, prostate tissue, and adipose tissue, combined with the homology to the murine testin protein, indicates that polynucleotides and polypeptides corresponding to this gene are useful for the study, diagnosis and/or treatment of disorders affecting normal cell functioning, including reproductive, developmental and metabolic disorders. The tissue distribution indicates that polynucleotides and polypeptides corresponding to this gene are useful for the diagnosis and/or treatment of disorders of the placenta. Specific expression within the placenta indicates that this gene product may play a role in the proper establishment and maintenance of placental function.

Alternately, this gene product may be produced by the placenta and then transported to the embryo, where it may play a crucial role in the development and/or survival of the developing embryo or fetus. Expression of this gene product in a vascular-rich tissue such as the placenta also indicates that this gene product may be produced more generally in endothelial cells or within the circulation. In such instances, it may play more generalized roles in vascular function, such as in angiogenesis or may play a role as a therapeutic in ameliorating or preventing stroke, aneurysm, atherosclerosis, and emboli. It may also be produced in the vasculature and have effects on other cells within the circulation, such as hematopoietic cells. It may serve to promote the proliferation, survival, activation, and/or differentiation of hematopoietic cells, as well as other cells throughout the body.

The tissue distribution in smooth muscle and heart tissues indicates that polynucleotides and polypeptides corresponding to this gene are useful for the diagnosis and treatment of conditions and pathologies of the cardiovascular system, such as heart disease, restenosis, atherosclerosis, stoke, angina, thrombosis, and wound healing. Protein, as well as, antibodies directed against the protein may show utility as a tumor marker and/or immunotherapy targets for the above listed tissues.

The secreted protein can also be used to determine biological activity, to raise antibodies, as tissue markers, to isolate cognate igands or receptors, to identify agents that modulate their interactions and as nutritional supplements. It may also have a very wide range of biological activities although no evidence for any is provided in the specification. Typical of these are cytokine, cell proliferation/ differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Protein, as well as, antibodies directed against the protein may show utility as a tumor marker and/or immunotherapy targets for the above listed tissues Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2218 of SEQ ID NO:26, b is an integer of 15 to 2232, where both a and b correspond to the positions of nucleotide residues shown in SEQ ID NO:26, and where b is greater than or equal to a+14.

Features of Protein Encoded by Gene No: 17

The translation product of this gene was shown to have homology to the LW opsin-long-wave visual pigment gene, which is known to play an integral role in establishing long wave spectrum absorption in higher primates (See Genebank Accession No.bbs|162162). The gene encoding the disclosed cDNA is believed to reside on chromosome 9. Accordingly, polynucleotides related to this invention are useful as a marker in linkage analysis for chromosome 9.

This gene is expressed primarily in melanocytes, human cornea, and to a lesser extent, in spleen and pineal gland tissues.

Therefore, polynucleotides and polypeptides of the invention are useful as reagents for differential identification of the tissue(s) or cell type(s) present in a biological sample and for diagnosis of diseases and conditions which include, but are not limited to, disorders involving the epithelial, hemopoietic, visual, and endocrine systems. Similarly, polypeptides and antibodies directed to these polypeptides are useful in providing immunological probes for differential identification of the tissue(s) or cell type(s). For a number of disorders of the above tissues or cells, particularly of the epithelial, endocrine and hemopoietic systems, expression of this gene at significantly higher or lower levels may be routinely detected in certain tissues or cell types (e.g., epithelial, endocrine, hemopoietic, visual, and cancerous and wounded tissues) or bodily fluids (e.g., lymph, serum, plasma, urine, aqueous humor, vitreous humor, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in human cornea, combined with its homology to a conserved opsin gene, indicates that polynucleotides and polypeptides corresponding to this gene are useful for the detection, diagnosis, and/or prevention of a variety of visual disorders and afflictions, and may potential play a role in amelorating, treating, or preventing biological clock disorders, DNA repair aberrations, and cancer. Alternatively, the tissue distribution in melanocytes indicates that polynucleotides and polypeptides corresponding to this gene are useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm). Protein, as well as, antibodies directed against the protein may show utility as a tumor marker and/or immunotherapy targets for the above listed tumors Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 626 of SEQ ID NO:27, b is an integer of 15 to 640, where both a and b correspond to the positions of nucleotide residues shown in SEQ ID NO:27, and where b is greater than or equal to a+14.

Features of Protein Encoded by Gene No: 18

The translation product of this gene shares sequence homology with adaptor protein 150, which is thought to be important in post-synthesis protein sorting to vacuoles.

This gene is expressed primarily in testes.

Therefore, polynucleotides and polypeptides of the invention are useful as reagents for differential identification of the tissue(s) or cell type(s) present in a biological sample and for diagnosis of diseases and conditions which include, but are not limited to, reproductive and endocrine disorders. Similarly, polypeptides and antibodies directed to these polypeptides are useful in providing immunological probes for differential identification of the tissue(s) or cell type(s). For a number of disorders of the above tissues or cells, particularly of the reproductive and endocrine systems, expression of this gene at significantly higher or lower levels may be routinely detected in certain tissues or cell types (e.g., reproductive, endocrine, or cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:124 as residues: Arg-24 to Arg-41, Pro-56 to Trp-64.

The tissue distribution in testes tissue, and the homology to adaptor protein 150, indicates that polynucleotides and polypeptides corresponding to this gene are useful for the diagnosis, prevention, and/or treatment of various metabolic disorders such as Tay-Sachs disease, phenylkenonuria, galactosemia, porphyrias, and Hurler's syndrome. Alternatively, expression in human testes would suggest a role for this gene in the the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopitultarism), thyroid (e.g., hyper-, hypothyroidism), parathyroid (e.g., hyper-, hypoparathyroidism), hypothallamus, and testes.

Furthermore, the tissue distribution indicates that polynucleotides and polypeptides corresponding to this gene are useful for the treatment and diagnosis of conditions concerning proper testicular function (e.g. endocrine function, sperm maturation), as well as cancer. Therefore, this grene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 399 of SEQ ID NO:28, b is an integer of 15 to 413, where both a and b correspond to the positions of nucleotide residues shown in SEQ ID NO:28, and where b is greater than or equal to a+14.

Features of Protein Encoded by Gene No: 19

The translation product of this gene shares sequence homology with the human acetyl coenzyme A: cholesterol acyltransferase II protein, which is thought to be important in metabolism of oxidized LDL (See Genebank Accession No.W43406). As such, the translation product of this gene may be useful in the diagnosis, treatment, and/or prevention of lipid disorders, and their accompanying secondary conditions such as atherosclerosis or hyperlipidaemia. In specific embodiments, polypeptides of the invention comprise the following amino acid sequence:

(SEQ ID NO:230)
AHAVWRPGVLPGLVELRVCHLLLAELEHPCAQVVHQVGGVCVCVMWNMA

VNLNRFPCPLLCRHFYKPMLRRGSSKWMARTGVFLASAFFHEYLVSVPL

RMFRLWAFTGMMAQIPLAWFVGRFFQGNYGNAAVWLSLIIGQPIAVLMY

VHDYYVLNYEAPAAEA, (SEQ ID NO:231)
YFLFAPTL, (SEQ ID NO:232)
NLNRFPCPLLCRHFYK, (SEQ ID NO:233)
QGNYGNAAVWLSLIIG, (SEQ ID NO:234)
LYYFLFAPTLCYELNFP,

-continued

```
                                              (SEQ ID NO:235)
EMLFFTQLQVGLIQQWMVPTIQNSMK, (SEQ ID NO:236)
VTYFWQNWNIPVHKWCIR, (SEQ ID NO:237)
PFKDMDYSRIIERLLKLAVPNHLIWLIFFYWLFHSCLNAVAELMQFGD

REFYRDWWNSES, (SEQ ID NO:238)
RHFYKPMLRRGSSKWMARTGVFLASAFFHEYLVSVPLRMFRLWAFTGM, and/or (SEQ ID NO:239)
MAQIPLAWFVGRFFQGNYGNAAVWLSLIIGQPIAVLMYVHDYYVLNY.
```

Polynucleotides encoding these polypeptides are also encompassed by the invention.

This gene is expressed primarily in pancreatic tumors and breast cancer, and to a lesser extent, in early stage human brain and fetal liver.

Therefore, polynucleotides and polypeptides of the invention are useful as reagents for differential identification of the tissue(s) or cell type(s) present in a biological sample and for diagnosis of diseases and conditions which include, but are not limited to, developmental and central nervous system disorders, including cancers thereof. Similarly, polypeptides and antibodies directed to these polypeptides are useful in providing immunological probes for differential identification of the tissue(s) or cell type(s). For a number of disorders of the above tissues or cells, particularly of the developmental, metabolic, and the central nervous system, expression of this gene at significantly higher or lower levels may be routinely detected in certain tissues or cell types (e.g., endocrine, neural, metabolic, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:125 as residues: Gly-43 to Ser-56.

The tissue distribution in cancerous and neural tissues, combined with the homology to acetyl coenzyme A, indicates that polynucleotides and polypeptides corresponding to this gene are useful for the study, diagnosis and/or treatment of disorders of the central nervous system, and metabolic and developmental disorders, including Tay-Sachs disease, phenylkenonuria, galactosemia, porphyrias, and Hurler's syndrome. Alternatively, the tissue distribution in various cancers indicates that polynucleotides and polypeptides corresponding to this gene are useful for the diagnosis and/or treatment of cancer and other proliferative disorders, as well as cancers of other tissues where expression has been observed. Expression within embryonic tissue and other cellular sources marked by proliferating cells indicates that this protein may play a role in the regulation of cellular division. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1108 of SEQ ID NO:29, b is an integer of 15 to 1122, where both a and b correspond to the positions of nucleotide residues shown in SEQ ID NO:29, and where b is greater than or equal to a+14.

Features of Protein Encoded by Gene No: 20

The translation product of this gene has been found to have homology to the vacuolar protein sorting homolog r-vps33b of *Rattus norvegicus*, which has been implicated in Golgi-to-lysosome trafficking (See Genebank Accession No.gi|1477470). In specific embodiments, polypeptides of the invention comprise the following amino acid sequence:

```
                                              (SEQ ID NO:240)
SGXWQGLDEVVRLLNXSDFAFTD and/or (SEQ ID NO:241)
GSLAKRSNFRAISKKLNLIPRVDGEYDLKVPRDMAYVFXGAYVPLSCRI

IEQVLERRXAGP.
```

Polynucleotides encoding these polypeptides are also encompassed by the invention. The gene encoding the disclosed cDNA is thought to reside on chromosome 15. Accordingly, polynucleotides related to this invention are useful as a marker in linkage analysis for chromosome 15.

This gene is expressed primarily in thymus and amygdala tissues, and to a lesser extent in infant brain tissues.

Therefore, polynucleotides and polypeptides of the invention are useful as reagents for differential identification of the tissue(s) or cell type(s) present in a biological sample and for diagnosis of diseases and conditions which include, but are not limited to, metabolic, immune, or central nervous system disorders. Similarly, polypeptides and antibodies directed to these polypeptides are useful in providing immunological probes for differential identification of the tissue(s) or cell type(s). For a number of disorders of the above tissues or cells, particularly of the metabolic and central nervous system, expression of this gene at significantly higher or lower levels may be routinely detected in certain tissues or cell types (e.g., immune, neural, or cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:126 as residues: Met-1 to Glu-10, Gly-35 to Tyr-40.

The tissue distribution in fetal brain and amygdala tissues indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system.

Alternatively, expression in thymus tissue, combined with the homology to a vacuolar protein, indicates that polynucleotides and polypeptides corresponding to this gene are useful for the diagnosis and/or treatment of a variety of immune system disorders. Expression of this gene product in thymus indicates the protein may play a role in regulating the proliferation; survival; differentiation; and/or activation of potentially all hematopoietic cell lineages, including blood stem cells.

This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. Protein is useful in the treatment, detection, and/or prevention of neural disorders involving aberrant neurotransmitter secretion. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 764 of SEQ ID NO:30, b is an integer of 15 to 778, where both a and b correspond to the positions of nucleotide residues shown in SEQ ID NO:30, and where b is greater than or equal to a+14.

Features of Protein Encoded by Gene No: 21

The translation product of this gene was shown to have homology to the CIT987SK-A-589H1__1 protein (See Genebank Accession No. gi|2342743). In specific embodiments, polypeptides of the invention comprise the following amino acid sequence:

(SEQ ID NO:242)
EVINTLADHRHRGTDFGGSPWLLIITVFLRSYKFAISLCTSYLCVSFLK

TIFPSQNGHDGSTDVQQRARRSNXRRQEGIKIVLEDIFTLWRQVETKVR

AKIRKMKVTTKVNRHDKINGKRKTAKEHLRKLSMKEREHGEKERQVSEA

EENGKLDMKEIHTYMEMFQRAQVCGGGQRTTTDAKSPLLQESLFATG, (SEQ ID NO:243)
ICVKTFPPLALQVRMAAXEHRHSSGLPXWPYLTAETLKNRMGHQPPPPT

-continued
QQHSIXDNSLSLKTPAECLLYPLPPSADDNLKTPXECLLTPLPPSAPPS

ADDNLKTPPECVC SLPFHPQLHPQRMIISRHLPSVSAHSPSTLSG, (SEQ ID NO:244)
RARRSNXRRQEGIKIVLEDI, and/or (SEQ ID NO:245)
LSLKTPAECLLYPLPP.

Polynucleotides encoding these polypeptides are also encompassed by the invention.

This gene is expressed primarily in cerebellum and other brain tissues such as amygdala and frontal cortex, testes tumor, and to a lesser extent, in synovium and adipocytes.

Therefore, polynucleotides and polypeptides of the invention are useful as reagents for differential identification of the tissue(s) or cell type(s) present in a biological sample and for diagnosis of diseases and conditions which include, but are not limited to, reproductive, neural, or skeletal disorders. Similarly, polypeptides and antibodies directed to these polypeptides are useful in providing immunological probes for differential identification of the tissue(s) or cell type(s). For a number of disorders of the above tissues or cells, particularly of the central nervous system and reproductive system, expression of this gene at significantly higher or lower levels may be routinely detected in certain tissues or cell types (e.g., reproductive, skeletal, neural, and cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:127 as residues: Ala-23 to Cys-34.

The tissue distribution in brain tissues such as cerebellum, frontal cortex, and amygdala indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception.

Elevated expression of this gene product within the frontal cortex of the brain indicates that it may be involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. In addition, the gene or gene product may also play a role in the treatment and/or detection of developmental disorders associated with the developing embryo, sexually-linked disorders, or disorders of the cardiovascular system. Alternatively, the expression of this gene product in synovium would suggest a role in the detection and treatment of disorders and conditions affecting the skeletal system, in particular osteoporosis as well as disorders afflicting connective tissues (e.g., arthritis, trauma, tendonitis, chrondomalacia and inflammation) in the diagnosis or treatment of various autoimmune disorders such as rheumatoid arthritis, lupus, scleroderma, and dermatomyositis as well as dwarfism, spinal deformation, and specific joint abnormalities as well as chondrodysplasias ie. spondyloepiphyseal dysplasia congenita, familial osteoarthritis, Atelosteogenesis type II, metaphyseal chondrodysplasia type Schmid. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2462 of SEQ ID NO:31, b is an integer of 15 to 2476, where both a and b correspond to the positions of nucleotide residues shown in SEQ ID NO:31, and where b is greater than or equal to a+14.

Features of Protein Encoded by Gene No: 22

In specific embodiments, polypeptides of the invention comprise the following amino acid sequence: FLLIESYQKLRNKTNLSLHVFLFHTEV (SEQ ID NO:246). Polynucleotides encoding these polypeptides are also encompassed by the invention.

This gene is expressed primarily in human testicular tumors.

Therefore, polynucleotides and polypeptides of the invention are useful as reagents for differential identification of the tissue(s) or cell type(s) present in a biological sample and for diagnosis of diseases and conditions which include, but are not limited to, reproductive or endocrine disorders, particularly cancers. Similarly, polypeptides and antibodies directed to these polypeptides are useful in providing immunological probes for differential identification of the tissue(s) or cell type(s). For a number of disorders of the above tissues or cells, particularly of the endocrine and reproductive systems, expression of this gene at significantly higher or lower levels may be routinely detected in certain tissues or cell types (e.g., reproductive, endocrine, or cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in tesiticular cancer tissue indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Alternatively, the tissue distribution indicates that polynucleotides and polypeptides corresponding to this gene are useful for the diagnosis and treatment of cancer and other proliferative disorders, as well as cancers of other tissues where expression has been observed. Expression within tumor tissues and other cellular sources marked by proliferating cells indicates that this protein may play a role in the regulation of cellular division. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 677 of SEQ ID NO:32, b is an integer of 15 to 691, where both a and b correspond to the positions of nucleotide residues shown in SEQ ID NO:32, and where b is greater than or equal to a+14.

Features of Protein Encoded by Gene No: 23

This gene is expressed primarily in resting T cells and CD34(+) cells.

Therefore, polynucleotides and polypeptides of the invention are useful as reagents for differential identification of the tissue(s) or cell type(s) present in a biological sample and for diagnosis of diseases and conditions which include, but are not limited to, immune and hematopoietic disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in CD34(+) cells and T-cells indicates that polynucleotides and polypeptides corresponding to this gene are useful for the diagnosis and/or treatment of a variety of immune system disorders. Elevated levels of expression of this gene product in T cell lineages indicates that it may play an active role in normal T cell function and in the regulation of the immune response. For example, this gene product may be involved in T cell activation, in the activation or control of differentiation of other hematopoietic cell lineages, in antigen recognition, or in T cell proliferation. Expression of this gene product in T cells also strongly indicates a role for this protein in immune function and immune surveillance.

Expression of this gene product in T-cells further indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types.

The secreted protein can also be used to determine biological activity, to raise antibodies, as tissue markers, to isolate cognate igands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 686 of SEQ ID NO:33, b is an integer of 15 to 700, where both a and b correspond to the positions of nucleotide residues shown in SEQ ID NO:33, and where b is greater than or equal to a+14.

Features of Protein Encoded by Gene No: 24

The translation product of this gene was shown to have homology to the yeast WD-40 domain-containing YCW2 protein (See Genebank Accession No.R85881), which is thought to modulate protein—protein interactions via its WD-40 domain between proteins involved in intracellular signalling. An example of such an interaction is between protein kinase C and receptors of activated protein kinase. In specific embodiments, polypeptides of the invention comprise the following amino acid sequence:

(SEQ ID NO:247)
YALRTGAFEPAEASVNPQDLQGSLQELKERALSRYNLVRGQGPERLVSG

SDDFTLFLWSPAEXKKPLTRMTGHQALINQVLFSPDSRIVASASFDKSI
KLWDGRTGKYLASLRGHVAAVYQIAWSADSRLLVSGSSXQHTEGVGCEG

-continued

PEAGHGPARPRG, and/or (SEQ ID NO:248)
LKERALSRYNLVRGQGPERLV.

Polynucleotides encoding these polypeptides are also encompassed by the invention.

This gene is expressed primarily in infant brain and breast tissues, and to a lesser extent, in various other endocrine and neuronal tissues.

Therefore, polynucleotides and polypeptides of the invention are useful as reagents for differential identification of the tissue(s) or cell type(s) present in a biological sample and for diagnosis of diseases and conditions which include, but are not limited to, immune, developmental, and neurodegenerative diseases. Similarly, polypeptides and antibodies directed to these polypeptides are useful in providing immunological probes for differential identification of the tissue(s) or cell type(s). For a number of disorders of the above tissues or cells, particularly of the immune and central nervous systems; expression of this gene at significantly higher or lower levels may be routinely detected in certain tissues or cell types (e.g., immune, neural, reproductive, or cancerous and wounded tissues) or bodily fluids (e.g., lymph, breast milk, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:130 as residues: Pro-13 to Ser-20.

The tissue distribution in infant brain and neural tissues indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system.

Expression within embryonic tissue and other cellular sources marked by proliferating cells indicates that this protein may play a role in the regulation of cellular division. Similarly, embryonic development also involves decisions involving cell differentiation and/or apoptosis in pattern formation. Thus, this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1708 of SEQ ID NO:34, b is an integer of 15 to 1722, where both a and b correspond to the positions of nucleotide residues shown in SEQ ID NO:34, and where b is greater than or equal to a+14.

Features of Protein Encoded by Gene No: 25

The translation product of this gene shares sequence homology with preprotein translocase, which is thought to be important in mitochondrial protein import (See Genebank Accession No.P39515). In specific embodiments, polypeptides of the invention comprise the following amino acid sequence:

```
                                        (SEQ ID NO:249)
MPTPSMRANRMPPIIAEPTMASGPLRAASTAPVNAPLVIEFQGSSLPRS

RTRPQSMVENRPPHTAKLPPIWGARILTALALPLNRCRIPTGALRKPLM

AWKTPPPMTPIVKAPPQSSTIRHGQGSRAYSGRVGGRVG, (SEQ ID NO:250)
GARILTALALPLNRCRIPTGALRKP, (SEQ ID NO:251)
PTRPPTRPEYAREPCPWRIVDDCGGNFTMGVIGGGVFQ, (SEQ ID NO:252)
AIKGFRNAPVGIRHRLRGSANAVRIRAPQIGGSFAVWGG, (SEQ ID NO:253)
LFSTIDCGLVRLRGKEDPWNSITSGALTGAVLAARSGPLA.
```

Polynucleotides encoding these polypeptides are also encompassed by the invention.

This gene is expressed primarily in activated T-cells, and to a lesser extent, in other tissues and transformed cell lines.

Therefore, polynucleotides and polypeptides of the invention are useful as reagents for differential identification of the tissue(s) or cell type(s) present in a biological sample and for diagnosis of diseases and conditions which include, but are not limited to, inflammatory, metabolic, and immune conditions or diseases, particularly immunodeficiencies such as AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:131 as residues: Tyr-25 to Ala-33, Asp-39 to Thr-49, Ala-51 to His-61.

The tissue distribution in T-cells indicates that polynucleotides and polypeptides corresponding to this gene are useful for the diagnosis and/or treatment of a variety of immune system disorders. Expression of this gene product in T-cells indicates the protein may play a role in regulating the proliferation; survival; differentiation; and/or activation of potentially all hematopoietic cell lineages, including blood stem cells. Expression of this gene product in T cells also strongly indicates a role for this protein in immune function and immune surveillance. Furthermore, elevated levels of expression of this gene product in T cell lineages indicates that it may play an active role in normal T cell function and in the regulation of the immune response. For example, this gene product may be involved in T cell activation, in the activation or control of differentiation of other hematopoietic cell lineages, in antigen recognition, or in T cell proliferation.

This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Alternatively, homology to a known mitochondrial protein indicates that polynucleotides and polypeptides corresponding to this gene are useful for the diagnosis, prevention, and/or treatment of various metabolic disorders such as Tay-Sachs disease, phenylkenonuria, galactosemia, porphyrias, and Hurler's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 864 of SEQ ID NO:35, b is an integer of 15 to 878, where both a and b correspond to the positions of nucleotide residues shown in SEQ ID NO:35, and where b is greater than or equal to a+14.

Features of Protein Encoded by Gene No: 26

In specific embodiments, polypeptides of the invention comprise the following amino acid sequence:

```
                                        (SEQ ID NO:254)
IRHERKSARACCPLTGAQRRGQALPTPRAGPGHSPAPV, (SEQ ID NO:255)
APSAPQEDGGSPPAPQGQPDPGPGAGQPAQLGPLLAFL), (SEQ ID NO:256)
PLLHQDCKESPHLGSSGSPVQALDLSSIQTRTAVSCVDGVRLWA.
```

Polynucleotides encoding these polypeptides are also encompassed by the invention. The gene encoding the disclosed cDNA is thought to reside on chromosome 6. Accordingly, polynucleotides related to this invention are useful as a marker in linkage analysis for chromosome 6.

This gene is expressed primarily in bone marrow and brain tissues, and to a lesser extent in placental tissue and other sources.

Therefore, polynucleotides and polypeptides of the invention are useful as reagents for differential identification of the tissue(s) or cell type(s) present in a biological sample and for diagnosis of diseases and conditions which include, but are not limited to, immune, neurological, and reproductive disorders or diseases. Similarly, polypeptides and antibodies directed to these polypeptides are useful in providing immunological probes for differential identification of the tissue(s) or cell type(s). For a number of disorders of the above tissues or cells, particularly of the immune and nervous systems, expression of this gene at significantly higher or lower levels may be routinely detected in certain tissues or cell types (e.g., reproductive, neural, or cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:132 as residues: Ser-42 to Arg-47, Thr-115 to Ser-127, Ser-130 to Trp-136.

The tissue distribution in bone marrow indicates that polynucleotides and polypeptides corresponding to this gene are useful for the treatment and/or diagnosis of hematopoietic related disorders such as anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

Alternatively, the tissue distribution in brain indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. The secreted protein can also be used to determine biological activity, to raise antibodies, as tissue markers, to isolate cognate igands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 940 of SEQ ID NO:36, b is an integer of 15 to 954, where both a and b correspond to the positions of nucleotide residues shown in SEQ ID NO:36, and where b is greater than or equal to a+14.

Features of Protein Encoded by Gene No: 27

This gene is expressed primarily in activated T-cells.

Therefore, polynucleotides and polypeptides of the invention are useful as reagents for differential identification of the tissue(s) or cell type(s) present in a biological sample and for diagnosis of diseases and conditions which include, but are not limited to, hematopoietic and immune disorders or diseases, particularly inflammatatory conditions and immunodeficiencies such as AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells indicates that polynucleotides and polypeptides corresponding to this gene are useful for the diagnosis and/or treatment of a variety of immune system disorders. Elevated levels of expression of this gene product in T cell lineages indicates that it may play an active role in normal T cell function and in the regulation of the immune response. For example, this gene product may be involved in T cell activation, in the activation or control of differentiation of other hematopoietic cell lineages, in antigen recognition, or in T cell proliferation. Furthermore, expression of this gene product in T cells also strongly indicates a role for this protein in immune function and immune surveillance. Expression of this gene product in T-cells indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types.

The secreted protein can also be used to determine biological activity, to raise antibodies, as tissue markers, to isolate cognate igands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 779 of SEQ ID NO:37, b is an integer of 15 to 793, where both a and b correspond to the positions of nucleotide residues shown in SEQ ID NO:37, and where b is greater than or equal to a+14.

Features of Protein Encoded by Gene No: 28

This gene is expressed primarily in placental tissue, and to a lesser extent, in various infant and adult tissues.

Therefore, polynucleotides and polypeptides of the invention are useful as reagents for differential identification of the tissue(s) or cell type(s) present in a biological sample and for diagnosis of diseases and conditions which include, but are not limited to, developmental, placental, reproductive, and metabolic disorders. Similarly, polypeptides and antibodies directed to these polypeptides are useful in providing immunological probes for differential identification of the tissue(s) or cell type(s). For a number of disorders of the above tissues or cells, particularly of the reproductive system and placenta, expression of this gene at significantly higher or lower levels may be routinely detected in certain tissues or cell types (e.g., developing, reproductive, placental, and cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in placental tissue indicates that polynucleotides and polypeptides corresponding to this gene are useful for the study, diagnosis, treatment, and/or prevention of various growth and reproductive disorders. Specific expression within the placenta indicates that this gene product may play a role in the proper establishment and maintenance of placental function. Alternately, this gene product may be produced by the placenta and then transported to the embryo, where it may play a crucial role in the development and/or survival of the developing embryo or fetus. Expression of this gene product in a vascular-rich tissue such as the placenta also indicates that this gene product may be produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body.

Alternatively, expression within embryonic tissue and other cellular sources marked by proliferating cells indicates that this protein may play a role in the regulation of cellular division. Similarly, embryonic development also involves decisions involving cell differentiation and/or apoptosis in pattern formation. Thus this protein may also be involved in apoptosis or tissue differentiation and could again be useful in cancer therapy. The secreted protein can also be used to determine biological activity, to raise antibodies, as tissue markers, to isolate cognate igands or receptors, to identify agents that modulate their interactions and as nutritional supplements. It may also have a very wide range of biological activities although no evidence for any is provided in the specification.

Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 545 of SEQ ID NO:38, b is an integer of 15 to 559, where both a and b correspond to the positions of nucleotide residues shown in SEQ ID NO:38, and where b is greater than or equal to a+14.

Features of Protein Encoded by Gene No: 29

The translation product of this gene shares sequence homology with the C2H2 type zinc finger protein, which is important in gene regulation. Furthermore, since the C2H2 zinc finger protein has significant homology to the human BRCA1-associated protein (hBRAP), this gene may be implicated as playing a central role in the modulation of cell cycle control. (See Genebank Accession Nos. gi|328223 and W52187, respectively). In specific embodiments, polypeptides of the invention comprise the following amino acid sequence: HRLQVFSFPILGSHN (SEQ ID NO:257). Polynucleotides encoding these polypeptides are also encompassed by the invention.

This gene is expressed primarily in several transformed cell lines, and to a lesser extent, in some normal tissues.

Therefore, polynucleotides and polypeptides of the invention are useful as reagents for differential identification of the tissue(s) or cell type(s) present in a biological sample and for diagnosis of diseases and conditions which include, but are not limited to, immune and growth disorders. Similarly, polypeptides and antibodies directed to these polypeptides are useful in providing immunological probes for differential identification of the tissue(s) or cell type(s). For a number of disorders of the above tissues or cells, expression of this gene at significantly higher or lower levels may be routinely detected in certain tissues or cell types (e.g., immune, hematopoietic, developmental, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:135 as residues: Gly-25 to Asn-31, Leu-42 to Lys-50.

The tissue distribution in transformed cell lines, combined with the homology to both a zinc-finger protein as well as a transforming protein associated with human breast cancer, indicates that polynucleotides and polypeptides corresponding to this gene are useful for the diagnosis and/or treatment of cancer and other proliferative disorders. Expression within cellular sources marked by proliferating cells indicates that this protein may play a role in the regulation of cellular division. Protein is useful in modulating apoptosis which would be useful in the detection, treatment, and/or prevention of degenerative and/or proliferative conditions. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1249 of SEQ ID NO:39, b is an integer of 15 to 1263, where both a and b correspond to the positions of nucleotide residues shown in SEQ ID NO:39, and where b is greater than or equal to a+14.

Features of Protein Encoded by Gene No: 30

This gene is expressed primarily in adult bladder tissue.

Therefore, polynucleotides and polypeptides of the invention are useful as reagents for differential identification of the tissue(s) or cell type(s) present in a biological sample and for diagnosis of diseases and conditions which include, but are not limited to, gastrointestinal and urogenital diseases. Similarly, polypeptides and antibodies directed to these polypeptides are useful in providing immunological probes for differential identification of the tissue(s) or cell type(s). For a number of disorders of the above tissues or cells, particularly of the excretory system, expression of this gene at significantly higher or lower levels may be routinely detected in certain tissues or cell types (e.g., urogenital, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in adult bladder tissue indicates that polynucleotides and polypeptides corresponding to this gene are useful for the study, diagnosis, treatment, and/or prevention of various gastrointestinal and urogenital disorders and afflications. The secreted protein can also be used to determine biological activity, to raise antibodies, as tissue markers, to isolate cognate igands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 441 of SEQ ID NO:40, b is an integer of 15 to 455, where both a and b correspond to the positions of nucleotide residues shown in SEQ ID NO:40, and where b is greater than or equal to a+14.

Features of Protein Encoded by Gene No: 31

The gene encoding the disclosed cDNA is believed to reside on chromosome 5. Accordingly, polynucleotides related to this invention are useful as a marker in linkage analysis for chromosome 5.

This gene is expressed primarily in infant brain and placental tissues, and to a lesser extent, in various normal and neoplastic cell types.

Therefore, polynucleotides and polypeptides of the invention are useful as reagents for differential identification of the tissue(s) or cell type(s) present in a biological sample and for diagnosis of diseases and conditions which include, but are not limited to, neurological and reproductive disorders. Similarly, polypeptides and antibodies directed to these polypeptides are useful in providing immunological probes for differential identification of the tissue(s) or cell type(s). For a number of disorders of the above tissues or cells, particularly of the nervous and reproductive systems, expression of this gene at significantly higher or lower levels may be routinely detected in certain tissues or cell types (e.g., neural, reproductive, and cancerous and wounded tissues) or bodily fluids (e.g., amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:137 as residues: Gly-35 to Ser-41, Glu-45 to Tyr-57.

The tissue distribution in infant brain tissue and placental tissue indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception.

In addition, the gene or gene product may also play a role in the treatment and/or detection of developmental disorders associated with the developing embryo, sexually-linked disorders, or disorders of the cardiovascular system. Moreover, the expression within infant tissue and other cellular sources marked by proliferating cells suggests this protein may play a role in the regulation of cellular division, and may show utility in the diagnosis and treatment of cancer and other proliferative disorders. Similarly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1114 of SEQ ID NO:41, b is an integer of 15 to 1128, where both a and b correspond to the positions of nucleotide residues shown in SEQ ID NO:41, and where b is greater than or equal to a+14.

Features of Protein Encoded by Gene No: 32

In specific embodiments, polypeptides of the invention comprise the following amino acid sequence: GKVEIEVFIFPYEYPVVPTPLIKNTILYPLSLFCTFIKN-QFSIYLWIKFFIF (SEQ ID NO:258). Polynucleotides encoding these polypeptides are also encompassed by the invention.

This gene is expressed primarily in B-cell lymphoma.

Therefore, polynucleotides and polypeptides of the invention are useful as reagents for differential identification of the tissue(s) or cell type(s) present in a biological sample and for diagnosis of diseases and conditions which include, but are not limited to, immune and haemopoietic disorders, including cancer. Similarly, polypeptides and antibodies directed to these polypeptides are useful in providing immunological probes for differential identification of the tissue(s) or cell type(s). For a number of disorders of the above tissues or cells, particularly of the immune and haemopoietic system, expression of this gene at significantly higher or lower levels may be routinely detected in certain tissues or cell types (e.g., immune, haemopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:138 as residues: Trp-27 to Ile-39.

The tissue distribution in B-cell lymphoma indicates that polynucleotides and polypeptides corresponding to this gene are useful for the diagnosis and treatment of a variety of immune system disorders. Expression of this gene product in B-cells indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 634 of SEQ ID NO:42, b is an integer of 15 to 648, where both a and b correspond to the positions of nucleotide residues shown in SEQ ID NO:42, and where b is greater than or equal to a+14.

Features of Protein Encoded by Gene No: 33

In specific embodiments, polypeptides of the invention comprise the following amino acid sequence: RATTHVSREFFGHT (SEQ ID NO:259). Polynucleotides encoding these polypeptides are also encompassed by the invention.

This gene is expressed primarily in B-cell lymphoma.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic system disorders, including cancers. Similarly, polypeptides and antibodies directed to these polypeptides are useful in providing immunological probes for differential identification of the tissue(s) or cell type(s). For a number of disorders of the above tissues or cells, particularly of the immune and hematopoietic system, expression of this gene at significantly higher or lower levels may be routinely detected in certain tissues or cell types (e.g., immune, hematopoietic, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in B-cell lymphoma indicates that polynucleotides and polypeptides corresponding to this gene are useful for the diagnosis and treatment of a variety of immune system disorders. Expression of this gene product in B-cells indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. The secreted protein can also be used to determine biological activity, to raise antibodies, as tissue markers, to isolate cognate igands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:43 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 722 of SEQ ID NO:43, b is an integer of 15 to 736, where both a and b correspond to the positions of nucleotide residues shown in SEQ ID NO:43, and where b is greater than or equal to a+14.

Features of Protein Encoded by Gene No: 34

This gene is expressed primarily in prostate tissue.

Therefore, polynucleotides and polypeptides of the invention are useful as reagents for differential identification of the tissue(s) or cell type(s) present in a biological sample and for diagnosis of diseases and conditions which include, but are not limited to, diseases or disorders of the prostate and reproductive organs. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, prostatic, and cancerous and wounded tissues) or bodily fluids (e.g., seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:140 as residues: Arg-18 to Ser-29.

The tissue distribution in prostate tissue indicates that polynucleotides and polypeptides corresponding to this gene are useful for the treatment and/or diagnosis of disorders of the reproductive system and prostate. The secreted protein can also be used to determine biological activity, to raise antibodies, as tissue markers, to isolate cognate igands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Protein is useful as a contraceptive, either directly or indirectly. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:44 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 586 of SEQ ID NO:44, b is an integer of 15 to 600, where both a and b correspond to the positions of nucleotide residues shown in SEQ ID NO:44, and where b is greater than or equal to a+14.

Features of Protein Encoded by Gene No: 35

In specific embodiments, polypeptides of the invention comprise the following amino acid sequence:

(SEQ ID NO:263)
TLFSMFSGPLGRQTQLDFRADIGEENMALSVLSPDKCYLYT and/or (SEQ ID NO:264)
HPNLKRKCISLGFKHCNRYKAKIKTCCKVQKKKKKKKKKKKKKGR.

Polynucleotides encoding these polypeptides are also encompassed by the invention.

This gene is expressed primarily in endometrium, osteoclastoma, and bladder tissues, and to a lesser extent in T-cells, infant brain and other tissues.

Therefore, polynucleotides and polypeptides of the invention are useful as reagents for differential identification of the tissue(s) or cell type(s) present in a biological sample and for diagnosis of diseases and conditions which include, but are not limited to, disorders or diseases of the skeletal, developmental, reproductive, and urogenital system. Similarly, polypeptides and antibodies directed to these polypeptides are useful in providing immunological probes for differential identification of the tissue(s) or cell type(s). For a number of disorders of the above tissues or cells, particularly of the urogenital, skeletal and haemopoietic systems, expression of this gene at significantly higher or lower levels may be routinely detected in certain tissues or cell types (e.g., endothelial, skeletal, reproductive, urogenital, developmental, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:141 as residues: Gly-8 to His-18.

The tissue distribution in endometrium, T-cells, osteoclasts, and bladder tissues indicates that polynucleotides and polypeptides corresponding to this gene are useful for the treatment and/or diagnosis of disorders of the urogenital, skeletal, and haemopoietic systems. Elevated levels of expression of this gene product in osteoclastoma indicates that it may play a role in the survival, proliferation, and/or growth of osteoclasts. Therefore, it may be useful in influencing bone mass in such conditions as osteoporosis. Alternatively, this gene could be transfected in gene-replacement treatments into the cells of the endometrium, and the protein products could be produced. These treatments could be performed during artificial insemination for the purpose of increasing the likelyhood of implantation and development of a healthy embryo. In this case, the gene or its gene product could be administered at later stages of pregnancy to promote heathy development of the endometrium.

The secreted protein can also be used to determine biological activity, to raise antibodies, as tissue markers, to isolate cognate igands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:45 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 673 of SEQ ID NO:45, b is an integer of 15 to 687, where both a and b correspond to the positions of nucleotide residues shown in SEQ ID NO:45, and where b is greater than or equal to a+14.

Features of Protein Encoded by Gene No: 36

This gene is expressed primarily in induced T-cells.

Therefore, polynucleotides and polypeptides of the invention are useful as reagents for differential identification of the tissue(s) or cell type(s) present in a biological sample and for diagnosis of diseases and conditions which include, but are not limited to, disorders or diseases of the immune or haemopoietic system. Similarly, polypeptides and antibodies directed to these polypeptides are useful in providing immunological probes for differential identification of the tissue(s) or cell type(s). For a number of disorders of the above tissues or cells, particularly of the immune and haemopoietic system, expression of this gene at significantly higher or lower levels may be routinely detected in certain tissues or cell types (e.g., immune, haemopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:142 as residues: Arg-6 to Lys-13, Tyr-19 to Val-27, Ser-40 to Tyr-46.

The tissue distribution in T-cells indicates that polynucleotides and polypeptides corresponding to this gene are useful for the diagnosis and/or treatment of a variety of immune system disorders. Elevated levels of expression of this gene product indicates that it may play an active role in normal T cell function and in the regulation of the immune response. For example, this gene product may be involved in T cell activation, in the activation or control of differentiation of other hematopoietic cell lineages, in antigen recognition, or in T cell proliferation. Expression of this gene product in T cells also strongly indicates a role for this protein in immune function and immune surveillance.

Further, expression of this gene product in T-cells indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 683 of SEQ ID NO:46, b is an integer of 15 to 697, where both a and b correspond to the positions of nucleotide residues shown in SEQ ID NO:46, and where b is greater than or equal to a+14.

Features of Protein Encoded by Gene No: 37

In specific embodiments, polypeptides of the invention comprise the following amino acid sequence: HSGVQ-TIAFGLEC (SEQ ID NO:262). Polynucleotides encoding these polypeptides are also encompassed by the invention.

This gene is expressed primarily in induced T-cells.

Therefore, polynucleotides and polypeptides of the invention are useful as reagents for differential identification of the tissue(s) or cell type(s) present in a biological sample and for diagnosis of diseases and conditions which include, but are not limited to, disorders or diseases of the immune and haemopoietic systems. Similarly, polypeptides and antibodies directed to these polypeptides are useful in providing immunological probes for differential identification of the tissue(s) or cell type(s). For a number of disorders of the above tissues or cells, particularly of the immune and haemopoietic system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells indicates that polynucleotides and polypeptides corresponding to this gene are useful for the diagnosis and treatment of a variety of immune system disorders. Elevated levels of expression of this gene product in T cell lineages indicates that it may play an active role in normal T cell function and in the regulation of the immune response. For example, this gene product may be involved in T cell activation, in the activation or control of differentiation of other hematopoietic cell lineages, in antigen recognition, or in T cell proliferation. Expression of this gene product in T cells also strongly indicates a role for this protein in immune function and immune surveillance.

Further, expression of this gene product in T-cells indicates the protein may play a role in regulating the proliferation; survival, differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:47 and may have-been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 272 of SEQ ID NO:47, b is an integer of 15 to 286, where both a and b correspond to the positions of nucleotide residues shown in SEQ ID NO:47, and where b is greater than or equal to a+14.

Features of Protein Encoded by Gene No: 38

In specific embodiments, polypeptides of the invention comprise the following amino acid sequence: KVQDRDGKERRKQEEVKLGRWCQWH (SEQ ID NO:263). Polynucleotides encoding these polypeptides are also encompassed by the invention. The gene encoding the disclosed cDNA is believed to reside on chromosome 3. Accordingly, polynucleotides related to this invention are useful as a marker in linkage analysis for chromosome 3.

This gene is expressed primarily in induced T-cells, and to a lesser extent in neutrophils and bone marrow.

Therefore, polynucleotides and polypeptides of the invention are useful as reagents for differential identification of the tissue(s) or cell type(s) present in a biological sample and for diagnosis of diseases and conditions which include, but are not limited to, diseases or disorders of the haemopoietic and immune system. Similarly, polypeptides and antibodies directed to these polypeptides are useful in providing immunological probes for differential identification of the tissue(s) or cell type(s). For a number of disorders of the above tissues or cells, particularly of the immune and haemopoietic system, expression of this gene at significantly higher or lower levels may be routinely detected in certain tissues or cell types (e.g., haemopoietic, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:144 as residues: Ser-17 to Trp-22, Lys-34 to Arg-39.

The tissue distribution in immune cells and tissues, such as T-cells, bone marrow, and neutrophils, indicates that polynucleotides and polypeptides corresponding to this gene are useful for the diagnosis and/or treatment of a variety of immune system disorders. Expression of this gene product in T cells and neutrophils strongly indicates a role for this protein in immune function and immune surveillance. Elevated levels of expression of this gene product in T cell lineages indicates-that it may play an active role in normal T cell function and in the regulation of the immune response. For example, this gene product may be involved in T cell activation, in the activation or control of differentiation of other hematopoietic cell lineages, in antigen recognition, or in T cell proliferation.

The polypeptides or polynucleotides are also useful to enhance or protect proliferation, differentiation, and functional activation of hematopoietic progenitor cells (e.g., bone marrow cells), useful in treating cancer patients undergoing chemotherapy or patients undergoing bone marrow transplantation. Furthermore, expression of this gene product in tonsils indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types.

The secreted protein can also be used to determine biological activity, to raise antibodies, as tissue markers, to isolate cognate igands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:48 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 844 of SEQ ID NO:48, b is an integer of 15 to 858, where both a and b correspond to the positions of nucleotide residues shown in SEQ ID NO:48, and where b is greater than or equal to a+14.

Features of Protein Encoded by Gene No: 39

In specific embodiments, polypeptides of the invention comprise the following amino acid sequence: ACGAPEE-AGG (SEQ ID NO:264). Polynucleotides encoding these polypeptides are also encompassed by the invention. The translation product of this gene shares sequence homology with a *C. elegans* protein F21D5.6 (See Genbank Accession No. gi|3876107) which is thought to be important in development.

This gene is expressed primarily in T-cells and haemopoietic tissues, and to a lesser extent in several other tissues and organs.

Therefore, polynucleotides and polypeptides of the invention are useful as reagents for differential identification of the tissue(s) or cell type(s) present in a biological sample and for diagnosis of diseases and conditions which include, but are not limited to, hematopoietic, immune, and/or developmental disorders. Similarly, polypeptides and antibodies directed to these polypeptides are useful in providing immunological probes for differential identification of the tissue(s) or cell type(s). For a number of disorders of the above tissues or cells, particularly of the immune and hematopoietic system, expression of this gene at significantly higher or lower levels may be routinely detected in certain tissues or cell types (e.g., hematopoietic, developmental, immune, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:145 as residues: Leu-24 to Asn-33, Ala-104 to Lys-109, Thr-142 to Thr-163, Leu-167 to Asn-172, Asp-198 to Asp-207, Glu-223 to Lys-230, Leu-232 to Ser-238, Pro-242 to Ser-252, Glu-254 to Lys-278.

The tissue distribution in T-cells and immune cells and tissues indicates that polynucleotides and polypeptides corresponding to this gene are useful for the diagnosis and/or treatment of a variety of immune system disorders. Elevated levels of expression of this gene product in T cell lineages indicates that it may play an active role in normal T cell function and in the regulation of the immune response. For example, this gene product may be involved in T cell activation, in the activation or control of differentiation of other hematopoietic cell lineages, in antigen recognition, or in T cell proliferation. Expression of this gene product in T cells also strongly indicates a role for this protein in immune function and immune surveillance. Furthermore, expression of this gene product in T-cells indicates a role in the regulation of the proliferation; survival; differentiation; and/or activation of potentially all hematopoietic cell lineages, including blood stem cells. Therefore, the protein may show utility in the treatment of various hematopoietic disorders such as anemia, pancytopenia, leukopenia, thrombocytopenia or leukemia since stromal cells are important in the production of cells of hematopoietic lineages.

The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Protein is useful in the treatment, detection, and/or prevention of developmental disorders and conditions, particularly congenital defects and metabolic conditions. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:49 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1293 of SEQ ID NO:49, b is an integer of 15 to 1307, where both a and b correspond to the positions of nucleotide residues shown in SEQ ID NO:49, and where b is greater than or equal to a+14.

Features of Protein Encoded by Gene No: 40

In specific embodiments, polypeptides of the invention comprise the following amino acid sequence:

(SEQ ID NO:265)
LFSSFLGDTTVHKVLSRATLHLHPAPYLTGVDSYS and/or (SEQ ID NO:266)
DFSSYSHPSLGTQLSIRCYPEPHCICTQHHTSQESTPTL.

Polynucleotides encoding these polypeptides are also encompassed by the invention. The gene encoding the disclosed cDNA is believed to reside on chromosome 1. Accordingly, polynucleotides related to this invention are useful as a marker in linkage analysis for chromosome 1.

This gene is expressed primarily in stimulated T-cells, and to a lesser extent in smooth muscle tissue.

Therefore, polynucleotides and polypeptides of the invention are useful as reagents for differential identification of the tissue(s) or cell type(s) present in a biological sample and for diagnosis of diseases and conditions which include, but are not limited to, immune, hematopoietic, vascular and cardiovascular disorders or diseases. Similarly, polypeptides and antibodies directed to these polypeptides are useful in providing immunological probes for differential identification of the tissue(s) or cell type(s). For a number of disorders of the above tissues or cells, particularly of the haemopoietic and vascular systems, expression of this gene at significantly higher or lower levels may be routinely detected in certain tissues or cell types (e.g., vascular, haemopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:146 as residues: Met-1 to Thr-10.

The tissue distribution in T-cells indicates that polynucleotides and polypeptides corresponding to this gene are useful for the diagnosis and/or treatment of a variety of immune system disorders. Expression of this gene product in T cells also strongly indicates a role for this protein in immune function and immune surveillance. Elevated levels of expression of this gene product in T cell lineages indicates that it may play an active role in normal T cell function and in the regulation of the immune response. For example, this gene product may be involved in T cell activation, in the activation or control of differentiation of other hematopoietic cell lineages, in antigen recognition, or in T cell proliferation.

Furthermore, expression of this gene product in T-cells indicates the protein may play a role in regulating the proliferation; survival; differentiation; and/or activation of potentially all hematopoietic cell lineages, including blood stem cells. Therefore, this indicates that the protein is useful for treating various hematopoietic disorders such as anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

This gene product may be involved in the regulation of cytokine production, antigen presentation, or other processes that may also suggest a usefulness in the treatment of cancer (e.g., by boosting immune responses). Since the gene is-expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Alternatively, the tissue distribution in smooth muscle tissue indicates that polynucleotides and polypeptides corresponding to this gene are useful for the diagnosis and treatment of conditions and pathologies of the cardiovascular system, such as heart disease, restenosis, atherosclerosis, stoke, angina, thrombosis, and wound healing. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:50 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 592 of SEQ ID NO:50, b is an integer of 15 to 606, where both a and b correspond to the positions of nucleotide residues shown in SEQ ID NO:50, and where b is greater than or equal to a+14.

Features of Protein Encoded by Gene No: 41

In specific embodiments, polypeptides of the invention comprise the following amino acid sequence:

(SEQ ID NO:267)
APQKFPXGFFFFFLFSRRKKQCSKVVQNTGAGAIQTQV, (SEQ ID NO:268)
QLLTSPTFSTVLSNYTCQAPSQWTDWQALLPTGIQTEH, (SEQ ID NO:269)
HQGWDKQKQCKRKCEHEHAPLHHNLWKQSGKTRLGD.

Polynucleotides encoding these polypeptides are also encompassed by the invention.

This gene is expressed primarily in CD34 depleted blood cells, and to a lesser extent in prostate cancer tissue.

Therefore, polynucleotides and polypeptides of the invention are useful as reagents for differential identification of the tissue(s) or cell type(s) present in a biological sample and for diagnosis of diseases and conditions which include, but are not limited to, immune, hematopoietic, or reproductive diseases and disorders, particularly cancers. Similarly, polypeptides and antibodies directed to these polypeptides are useful in providing immunological probes for differential identification of the tissue(s) or cell type(s). For a number of disorders of the above tissues or cells, particularly of the haemopoietic system, expression of this gene at significantly higher or lower levels may be routinely detected in certain tissues or cell types (e.g., immune, hematopoietic, reproductive, and cancerous and wounded tissues) or bodily fluids (e.g., lymph, serum, plasma, seminal fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:147 as residues: Glu-9 to Thr-17, Thr-19 to His-34, Thr-36 to Thr-42, Gln-44 to Lys-53.

The tissue distribution in CD34 depleted blood cells indicates that polynucleotides and polypeptides corresponding to this gene are useful for the treatment and/or diagnosis of hematopoietic related disorders such as anemia, pancytopenia, leukopenia, thrombocytopenia or leukemia since stromal cells are important in the production of cells of hematopoietic lineages. Expression of this gene product in CD34 depleted blood cells indicates a role in the regulation of the proliferation; survival; differentiation; and/or activation of potentially all hematopoietic cell lineages, including blood stem cells.

This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

The secreted protein can also be used to determine biological activity, to raise antibodies, as tissue markers, to isolate cognate igands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Thr protein is useful as a contraceptive, in addition to its applicability as a diagnostic for prostate cancer or other reproductive disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:51 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 533 of SEQ ID NO:51, b is an integer of 15 to 547, where both a and b correspond to the positions of nucleotide residues shown in SEQ ID NO:51, and where b is greater than or equal to a+14.

Features of Protein Encoded by Gene No: 42

In specific embodiments, polypeptides of the invention comprise the following amino acid sequence: KHVIFFM-FISNLFLILCFLFRPTKTTV (SEQ ID NO:270). Polynucleotides encoding these polypeptides are also encompassed by the invention.

This gene is expressed primarily in immune system cells, such as T-cells, tonsils, and primary dendritic cells.

Therefore, polynucleotides and polypeptides of the invention are useful as reagents for differential identification of the tissue(s) or cell type(s) present in a biological sample and for diagnosis of diseases and conditions which include, but are not limited to, tonsillitis and other infectious conditions; immune dysfunction, particularly immunodeficiencies; hematopoietic disorders; lymphomas and leukemias. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ED NO:148 as residues: Lys-74 to Tyr-79.

The tissue distribution in immune system cells indicates that polynucleotides and polypeptides corresponding to this gene are useful for the diagnosis and/or treatment of infectious diseases such as tonsillitis, in a non-surgical way or without the use of antibiotics. It could be used to trigger the body's own defense mechanisms to fight infections. Likewise, expression of this gene product in a variety of immune or blood cells indicates a general role in hematopoietic function, and it may control the proliferation, survival, or differentiation of a variety of blood cell lineages. Expression of this gene product in tonsils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types.

Alternatively, it may be involved in immune functions, such as immune surveillance or immune modulation, or may be involved in the recruitment of blood cells to sites of injury or inflammation. The secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of hematopoiesis (e.g., for treating anaemia or as adjunct to chemotherapy); stimulation or growth of bone, cartilage, tendons, ligaments and/or nerves (e.g., for treating wounds, stimulation of follicle stimulating hormone (for control of fertility); chemotactic and chemokinetic activities (e.g., for treating infections, tumors); hemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:52 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 851 of SEQ ID NO:52, b is an integer of 15 to 865, where both a and b correspond to the positions of nucleotide residues shown in SEQ DID NO:52, and where b is greater than or equal to a+14.

Features of Protein Encoded by Gene No: 43

The translation product of this gene shares sequence homology with the P195 protein of *Plasmodium falciparum* which is thought to be important in the incidence of malarial infection.

This gene is expressed primarily in activated helper T-cells.

Therefore, polynucleotides and polypeptides of the invention are useful as reagents for differential identification of the tissue(s) or cell type(s) present in a biological sample and for diagnosis of diseases and conditions which include, but are not limited to, Malaria and other insect borne blood diseases; defects in immune modulation; immune dysfunction; susceptibility to general infections. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution and homology to the P195 protein of plasmodium falciparum indicates that polynucleotides and polypeptides corresponding to this gene are useful for the treatment or diagnosis of malaria and other blood diseases where the peptide of the P195 protein could be used as a vaccine for malaria immunity. Likewise, expression of this protein by helper T cells indicates that it may play a more general role in immune system function, and may be involved in immune surveillance, immune modulation, or in host defenses.

Alternatively, the tissue distribution indicates that polynucleotides and polypeptides corresponding to this gene are useful for the treatment and diagnosis of hematopoetic related disorders such as anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:53 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 675 of SEQ ID NO:53, b is an integer of 15 to 689, where both a and b correspond to the positions of nucleotide residues shown in SEQ ID NO:53, and where b is greater than or equal to a+14.

Features of Protein Encoded by Gene No: 44

The translation product of this gene was shown to have homology to the conserved opioid binding protein/cell adhesion molecule, which is thought to be important in the dual role of binding intracellular opioids, in addition to the facilitation of cell—cell contact (See Genebank Accession No. P11834). When tested against PC12 (Sensory neuron) cell lines, supernatants removed from cells containing this gene activated the EGR1 (early growth response gene 1) pathway. Thus, it is likely that this gene activates sensory neuron cells, or more generally, neuronal cells, in addition to other cells or cell-types, through the EGR1 signal transduction pathway.

EGR1 is a separate signal transduction pathway from JAK-STAT, genes containing the EGR1 promoter are induced in various tissues and cell types upon activation, leading the cells to undergo differentiation and proliferation. In specific embodiments, polypeptides of the invention comprise the following amino acid sequence: KWKGDL-HCILGLLA (SEQ ID NO:272). Polynucleotides encoding these polypeptides are also encompassed by the invention. The gene encoding the disclosed cDNA is thought to reside on chromosome 11. Accordingly, polynucleotides related to this invention are useful as a marker in linkage analysis for chromosome 11.

This gene is expressed primarily in hypothalamus, and other brain tissues such as infant and adult whole brain, frontal lobe tissue, and amygdala tissue.

Therefore, polynucleotides and polypeptides of the invention are useful as reagents for differential identification of the tissue(s) or cell type(s) present in a biological sample and for diagnosis of diseases and conditions which include, but are not limited to, anorexia/bulimia, high blood pressure, migrane headaches, insomnia, or other neural disorders associated with anomalous neural chemistry or neurotransmitter activation. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may be routinely detected in certain tissues or cell types (e.g., neural, endocrine, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in the hypothalamus and other neural tissues, in conjunction with the biological activity data and the homology to an opioid binding protein, indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, perception, in addition to disorders associated with neurotransmitter homeostasis or regulation. In addition, the gene or gene product may also play a role in the treatment and/or detection of developmental disorders associated with the developing embryo, sexually-linked disorders, or disorders of the cardiovascular system. Alternatively, expression within the hypothalamus may suggest that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes. Protein is useful in the amelioration and prevention of pain. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:54 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 501 of SEQ ID NO:54, b is an integer of 15 to 515, where both a and b correspond to the positions of nucleotide residues shown in SEQ ID NO:54, and where b is greater than or equal to a+14.

Features of Protein Encoded by Gene No: 45

In specific embodiments, polypeptides of the invention comprise the following amino acid sequence:

LAPSSVGSAS, (SEQ ID NO:273)

REATKNPTHHRSTPHAAGSQLNVPPQPCFPLHHQIKTSP, (SEQ ID NO:275)

SQTIFKQSRHRCDSRQESTWLCSHEKDATKMMHLNDNS, (SEQ ID NO:276)

and/or

VTGSPILQLALLQLPAWPLRGRLRGKRHCTGLNLAISGNGGEWGGRGE. (SEQ ID NO:277)

Polynucleotides encoding these polypeptides are also encompassed by the invention.

This gene is expressed primarily in hypothalmus tissue which was derived from patients with schizophrenia.

Therefore, polynucleotides and polypeptides of the invention are useful as reagents for differential identification of the tissue(s) or cell type(s) present in a biological sample and for diagnosis of diseases and conditions which include, but are not limited to, schizophrenia and other neurodegenerative disorders. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may be routinely detected in certain tissues or cell types (e.g., neural, endocrine, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in hypothalamus tissue indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception.

In addition, the gene or gene product may also play a role in the treatment and/or detection of developmental disorders associated with the developing embryo, sexually-linked disorders, or disorders of the cardiovascular system. Alternatively, the expression within the hypothalamus may suggest that the polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:55 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 733 of SEQ ID NO:55, b is an integer of 15 to 747, where both a and b correspond to the positions of nucleotide residues shown in SEQ ID NO:55, and where b is greater than or equal to a+14.

Features of Protein Encoded by Gene No: 46

In specific embodiments, polypeptides of the invention comprise the following amino acid sequence: IRHEDEVKLLEWS (SEQ ID NO:277). Polynucleotides encoding these polypeptides are also encompassed by the invention.

This gene is expressed primarily in hypothalamus, derived from patients with schizophrenia.

Therefore, polynucleotides and polypeptides of the invention are useful as reagents for differential identification of the tissue(s) or cell type(s) present in a biological sample and for diagnosis of diseases and conditions which include, but are not limited to, neurodegenerative disorders, particularly schizophrenia. Similarly, polypeptides and antibodies directed to these polypeptides are useful in providing immunological probes for differential identification of the tissue(s) or cell type(s). For a number of disorders of the above tissues or cells, particularly of the nervous or endocrine systems, expression of this gene at significantly higher or lower levels may be routinely detected in certain tissues or cell types (e.g., neural, endocrine, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in hypothalamus indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Alternatively, expression within the hypothalamus indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:56 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 662 of SEQ ID NO:56, b is an integer of 15 to 676, where both a and b correspond to the positions of nucleotide residues shown in SEQ ID NO:56, and where b is greater than or equal to a+14.

Features of Protein Encoded by Gene No: 47

Contact of cells with supernatant expressing the product of this gene has been shown to increase the permeability of the plasma membrane of THP-1 cells to calcium. Thus it is likely that the product of this gene is involved in a signal transduction pathway that is initiated when the product binds a receptor on the surface of the plasma membrane of monocytes, or more generally, immune or hemapoietic cells, in addition to other cell-lines or tissue cell types. Thus, polynucleotides and polypeptides have uses which include, but are not limited to, activating monocytes. The translation product of this gene shares sequence homology with NADH dehydrogenase ubiquinone which is known to be important for the establishment of an electron transport chain in mitochondrial metabolism (See Genebank Accession No.gi|1935056). In specific embodiments, polypeptides of the invention comprise the following amino acid sequence:

SLHSSAVAATYKYVNMQDPEMDMKSVTDRAARTLL, (SEQ ID NO:278)

WTELFRGLGMTLSYLFREPATINYPFEKGPLSPRFRGEHALRRYPSGEE (SEQ ID NO:279)

RCIACKLCEAI,

CPAQAIIEAEPRADGSRRTTRYDIDMTKCIYCGFCQEACPVDA (SEQ ID NO:280)

IVEGPNFEFSTETH, and/or

GDKWEAEIAANIQADYLYR. (SEQ ID NO:281)

Polynucleotides encoding these polypeptides are also encompassed by the invention.

This gene is expressed primarily in pituitary, and to a lesser extent, in kidney and liver.

Therefore, polynucleotides and polypeptides of the invention are useful as reagents for differential identification of the tissue(s) or cell type(s) present in a biological sample and for diagnosis of diseases and conditions which include, but are not limited to, developmental and/or metabolic disorder and diseases, particularly mitochondrial disorders; kidney dysfunction; abnormal growth; liver disease. Similarly, polypeptides and antibodies directed to these polypeptides are useful in providing immunological probes for differential identification of the tissue(s) or cell type(s). For a number of disorders of the above tissues or cells, particularly of the endocrine, hepatic, renal, and haemolymphoid systems, expression of this gene at significantly higher or lower levels may be routinely detected in certain tissues or cell types (e.g., endocrine, metabolic, developmental, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:153 as residues: Gly-20 to Leu-27, Pro-85 to Leu-91, Arg-102 to Glu-108.

The tissue distribution in liver, combined with the homology to the conserved NADH dehydrogenase ubiquinone and the detected calcium flux activity suggest that polynucleotides and polypeptides corresponding to this gene are useful for the detection or treatment of the problems associated with energy metabolism, since it is the first component of the electron transport chain. This may result specifically in renal dysfunction, abnormal growth, and/or liver disorders such as Tay-Sachs disease, phenylkenonuria, galactosemia, porphyrias, and Hurler's syndrome. Alternatively, expression within the pituitary indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:57 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 818 of SEQ ID NO:57, b is an integer of 15 to 832, where both a and b correspond to the positions of nucleotide residues shown in SEQ ID NO:57, and where b is greater than or equal to a+14.

Features of Protein Encoded by Gene No: 48

The translation product of this gene shares sequence homology with an insulin-like growth factor-binding complex and acid-labile subunit (ALS) which is thought to be important in protein—protein interactions involved in intracellular signalling. In specific embodiments, polypeptides of the invention comprise the following amino acid sequence:

SAADPATQPGDSRALPEPRGVPAVHPAGSGSEWERPPPAAPSPEHRDK, (SEQ ID NO:282)

and/or

DSRALPEPRGVPAVHPAGSGSEWE. (SEQ ID NO:283)

Polynucleotides encoding these polypeptides are also encompassed by the invention.

This gene is expressed primarily in merkel cells.

Therefore, polynucleotides and polypeptides of the invention are useful as reagents for differential identification of the tissue(s) or cell type(s) present in a biological sample and for diagnosis of diseases and conditions which include, but are not limited to, endocrine disorders, particularly diabetes. Similarly, polypeptides and antibodies directed to these polypeptides are useful in providing immunological probes for differential identification of the tissue(s) or cell type(s). For a number of disorders of the above tissues or cells, particularly of the lymphoid or endocrine system, expression of this gene at significantly higher or lower levels may be routinely detected in certain tissues or cell types (e.g., endocrine, proliferating, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:154 as residues: Ala-68 to His-74.

The tissue distribution in merkel cells indicates that polynucleotides and polypeptides corresponding to this gene are useful for the detection, treatment, and/or prevention of various endocrine disorders and cancers, particularly diabetes, Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper, hypoparathyroidism), hypothallamus, and testes.

Alternatively, the homology to an insulin-like growth factor indicates that polynucleotides and polypeptides corresponding to this gene are useful for the diagnosis and treatment of cancer and other proliferative disorders, and may potentially play a role in the regulation of cellular division. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:58 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 989 of SEQ ID NO:58, b is an integer of 15 to 1003, where both a and b correspond to the positions of nucleotide residues shown in SEQ ID NO:58, and where b is greater than or equal to a+14.

Features of Protein Encoded by Gene No: 49

In specific embodiments, polypeptides of the invention comprise the following amino acid sequence: EFGTSWV (SEQ ID NO:284). Polynucleotides encoding these polypeptides are also encompassed by the invention.

This gene is expressed primarily in kidney cortex.

Therefore, polynucleotides and polypeptides of the invention are useful as reagents for differential identification of the tissue(s) or cell type(s) present in a biological sample and for diagnosis of diseases and conditions which include, but are not limited to, renal, urogenital, or metabolic disorders, and diseases, particularly kidney rejection, kidney stones, or kidney failure. Similarly, polypeptides and antibodies directed to these polypeptides are useful in providing immunological probes for differential identification of the tissue(s) or cell type(s). For a number of disorders of the above tissues or cells, particularly of the renal, endocrine, or haemolymphoid system, expression of this gene at significantly higher or lower levels may be routinely detected in certain tissues or cell types (e.g., kidney, metabolic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:155 as residues: Phe-7 to Asn-12, Thr-18 to Asp-27, Glu-33 to Ile-42, Ser-62 to Asp-80, Gln-84 to Asn-89, Gln-108 to Leu-132, Lys-137 to Ser-156, Ser-163 to Leu-179, Glu-190 to Gln-195, Lys-204 to Lys-212, Ile-219 to Arg-227.

The tissue distribution in kidney indicates that this gene or gene product could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilms Tumor Disease, and congenital kidney abnormalities such as horseshoe kidney, polycystic kidney, and Falconi's syndrome. Alternatively, expression within the kidney cortex indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:59 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 688 of SEQ ID NO:59, b is an integer of 15 to 702, where both a and b correspond to the positions of nucleotide residues shown in SEQ ID NO:59, and where b is greater than or equal to a+14.

Features of Protein Encoded by Gene No: 50

The translation product of this gene was shown to have homology to the human complexin I and II (See Genebank Accession No. gi|2465459) which are part of a family of proteins that compete with alpha-SNAP, but not synaptotagmin, for SNAP receptor binding which are important in vesicular transport within the cell. In specific embodiments, polypeptides of the invention comprise the following amino acid sequence:

(SEQ ID NO:285)
TLHPPQEPQRPEAPDAGDPAPLPSTSSVGSSSGGACGVPCAHWRVCGLI

HLVALRGGIRAPVSPPFMFNLHHNLLNLR, (SEQ ID NO:286)
EPQRPEAPDAGDPAPLPSTSS, and/or (SEQ ID NO:287)
RVCGLIHLVALRGGI.

Polynucleotides encoding these polypeptides are also encompassed by the invention. The gene encoding the disclosed cDNA is believed to reside on chromosome 4. Accordingly, polynucleotides related to this invention are useful as a marker in linkage analysis for chromosome 4.

This gene is expressed primarily in adult brain, and to a lesser extent, in kidney cortex.

Therefore, polynucleotides and polypeptides of the invention are useful as reagents for differential identification of the tissue(s) or cell type(s) present in a biological sample and for diagnosis of diseases and conditions which include, but are not limited to, neural or renal disorders, particularly depression, Alzheimers, schizophrenia; acute renal failure; or renal dysfunction. Similarly, polypeptides and antibodies directed to these polypeptides are useful in providing immunological probes for differential identification of the tissue(s) or cell type(s). For a number of disorders of the above tissues or cells, particularly of the nervous, renal, or endocrine systems, expression of this gene at significantly higher or lower levels may be routinely detected in certain tissues or cell types (e.g., neural, urogenital, renal, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:156 as residues: Cys-32 to Ser-62, Tyr-86 to Gly-94, Ser-106 to Ala-114.

The tissue distribution in brain combined with its homology to a conserved vesicular transport protein (significant for proper neurotransmitter synthesis and release) indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system.

Alternatively, the tissue distribution in kidney indicates that this gene or gene product could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilms Tumor Disease, and congenital kidney abnormalities such as horseshoe kidney, polycystic kidney, and Falconi's syndrome. Protein, as well as, antibodies directed against the protein may show utility as a tumor marker and/or immunotherapy targets for the above listed tissues. It is also expressed in kidney, suggesting a role in kidney functions such as proximal tubule regeneration or glomerular filtration. Thus it may be useful in the treatment of acute renal failure and or kidney disorders, such as Wilm's tumor.

Many polynucleotide sequences, such as EST sequences, are publicly available and accessible through sequence databases. Some of these sequences are related to SEQ ID NO:60 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1081 of SEQ ID NO:60, b is an integer of 15 to 1095, where both a and b correspond to the positions of nucleotide residues shown in SEQ ID NO:60, and where b is greater than or equal to a+14.

Features of Protein Encoded by Gene No: 51

The translation product of this gene shares sequence homology with Apo E4L1 protease which is thought to be important in catalyzing the formation of abnormal beta/A4 variants of beta-amyloid protein. The gene encoding the disclosed cDNA is believed to reside on chromosome 2. Accordingly, polynucleotides related to this invention are useful as a marker in linkage analysis for chromosome 2.

This gene is expressed primarily in kidney medulla.

Therefore, polynucleotides and polypeptides of the invention are useful as reagents for differential identification of the tissue(s) or cell type(s) present in a biological sample and for diagnosis of diseases and conditions which include, but are not limited to, renal, urogenital, or metabolic disorders and diseases. Similarly, polypeptides and antibodies directed to these polypeptides are useful in providing immunological probes for differential identification of the tissue(s) or cell type(s). For a number of disorders of the above tissues or cells, particularly of the renal system, expression of this gene at significantly higher or lower levels may be routinely detected in certain tissues or cell types (e.g., immune, renal, urogenital, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:157 as residues: Trp-17 to Ala-25, Ser-33 to Ser-42.

The tissue distribution in kindey tissue, combined with the homology to the Apo E4L1 indicates the protein product of this gene could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Alternatively, polynucleotides and polypeptides corresponding to this gene are useful for the diagnosis, prevention, and/or treatment of various metabolic disorders which include, but are not limited to, Tay-Sachs disease, phenylkenonuria, galactosemia, hyperlipidemias, porphyrias, and Hurler's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:61 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 853 of SEQ ID NO:61, b is an integer of 15 to 867, where both a and b correspond to the positions of nucleotide residues shown in SEQ ID NO:61, and where b is greater than or equal to a+14.
Features of Protein Encoded by Gene No: 52

The translation product of this gene was shown to have homology to the human T-lymphocyte maturation associated protein which is thought to be involved in T-cell specific vesicular trafficing (See Genebank Accession No.P21145).

This gene is expressed primarily in synovial hypoxia, and to a lesser extent in breast lymph node.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particularly breast cancer; hematopoietic disorders; immune dysfunction; arthritis, or joint replacement. Similarly, polypeptides and antibodies directed to these polypeptides are useful in providing immunological probes for differential identification of the tissue(s) or cell type(s). For a number of disorders of the above tissues or cells, particularly of the skeletal and immune system, expression of this gene at significantly higher or lower levels may be routinely detected in certain tissues or cell types (e.g., skeletal, developmental, immune, and cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in lymph nodes, combined with the homology to the conserved T-lymphocyte maturation protein indicates that polynucleotides and polypeptides corresponding to this gene are useful for the treatment or diagnosis of immune disorders and related diseases. Likewise, the expression of this gene in breast lymph node indicates a role in hematopoietic cells or immmune function, and the gene product may be involved in immune surveillance, immune modulation, or in the activation or priming of leukocytes. Alternatively, the expression of this gene product in synovium would suggest a role in the detection and treatment of disorders and conditions affecting the skeletal system, in particular osteoporosis as well as disorders afflicting connective tissues (e.g., arthritis, trauma, tendonitis, chrondomalacia and inflammation) in the diagnosis or treatment of various autoimmune disorders such as rheumatoid arthritis, lupus, scleroderma, and dermatomyositis as well as dwarfism, spinal deformation, and specific joint abnormalities as well as chondrodysplasias ie. spondyloepiphyseal dysplasia congenita, familial osteoarthritis, Atelosteogenesis type II, metaphyseal chondrodysplasia type Schmid. Protein is useful in the modulation of the immune response to autoimmune, proliferative, or degenerative cells or tissues, particularly of the skeletal system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:62 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1120 of SEQ ID NO:62, b is an integer of 15 to 1134, where both a and b correspond to the positions of nucleotide residues shown in SEQ ID NO:62, and where b is greater than or equal to a+14.
Features of Protein Encoded by Gene No: 53

The translation product of this gene was shown to have homology to the human E2F-6 protein which is thought to serve as a transcriptional repressor in the establishment of proper cell-cycle regulation (See Genebank Accession No.gi|3080767). One embodiment of this gene comprises polypeptides of the following amino acid sequence:

(SEQ ID NO:288)
QGYSTKPRLMVPLKMDSITVHIRSTNGPIDVYLCEVEQGQTSNKRSEGV

GTSSSESTHPEGPEEEENPQQSEELLEVSN, (SEQ ID NO:289)
DSITVHIRSTNGPIDVYLCEVEQGQTSNKR, (SEQ ID NO:290)
LMVPLKMDSITVHIRSTNGPIDVYL, and/or (SEQ ID NO:291)
QGQTSNKRSEGVGTSSSESTHPEGPE.

An additional embodiment is the polynucleotides encoding these polypeptides.

This gene is expressed primarily in hematopoietic cells and tissues (e.g., T cells; B cell lymphoma; bone marrow), and to a lesser extent, in adrenal gland tumors.

Therefore, polynucleotides and polypeptides of the invention are useful as reagents for differential identification of the tissue(s) or cell type(s) present in a biological sample and for diagnosis of diseases and conditions which include, but are not limited to, hematopoietic disorders; B cell lymphoma; adrenal gland tumor; Addison's disease; Cushing's syndrome; defects in immune function. Similarly, polypeptides and antibodies directed to these polypeptides are useful in providing immunological probes for differential identification of the tissue(s) or cell type(s). For a number of disorders of the above tissues or cells, particularly of the immune and/or endocrine systems, expression of this gene at significantly higher or lower levels may be routinely detected in certain tissues or cell types (e.g., immune, hematopoietic, developmental, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in hematopoietic cells and tissues, combined with the homology to the human E2F-6 protein indicates that polynucleotides and polypeptides corresponding to this gene are useful for the treatment of hematopoietic disorders and/or disorders of the endocrine system. Elevated levels of expression of this gene in T cells indicates that it may be useful in the modulation of immune function or in immune surveillance, and may influence cytokine production. Likewise, expression in bone marrow indicates that it may play a role in the regulation of hematopoiesis, either through effects on the proliferation or the differentiation of blood cell lineages, or in the maintenance or expansion of stem cells.

Expression in the adrenal gland or adrenal gland tumor indicates that this gene may play a role in the proliferation of cells within the adrenal gland—and in the proliferation of cells in general. Additionally, expression in the adrenal gland indicates that this may be useful in the treatment and/or diagnosis of disorders of the adrenal gland, including Addison's disease, Cushing's syndrome, and masculinization and/or feminization. It may also exert effects on the secretion of adrenaline and noradrenaline. Moreover, the protein is useful in inhibiting the proliferation of tumor cells and tissues, either directly or indirectly. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:63 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1434 of SEQ ID NO:63, b is an integer of 15 to 1448, where both a and b correspond to the positions of nucleotide residues shown in SEQ ID NO:63, and where b is greater than or equal to a+14.

Features of Protein Encoded by Gene No: 54

In specific embodiments, polypeptides of the invention comprise the following amino acid sequence: RPTRPSILGLYVDLYVFCI (SEQ ID NO:292). Polynucleotides encoding these polypeptides are also encompassed by the invention. The gene encoding the disclosed cDNA is believed to reside on chromosome 14. Accordingly, polynucleotides related to this invention are useful as a marker in linkage analysis for chromosome 14.

This gene is expressed primarily in melanocytes, and to a lesser extent in placenta.

Therefore, polynucleotides and polypeptides of the invention are useful as reagents for differential identification of the tissue(s) or cell type(s) present in a biological sample and for diagnosis of diseases and conditions which include, but are not limited to, integumentary, developmental, and/or vascular disorders and diseases, particularly skin cancer; vascular leak syndrome; tumors of an endothelial cell origin; tumors of an epidermal cell origin. Similarly, polypeptides and antibodies directed to these polypeptides are useful in providing immunological probes for differential identification of the tissue(s) or cell type(s). For a number of disorders of the above tissues or cells, particularly of the skin and/or endothelium, expression of this gene at significantly higher or lower levels may be routinely detected in certain tissues or cell types (e.g., reproductive, developmental, integumentary, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:160 as residues: Lys-20 to Leu-28.

The tissue distribution in melanocytes indicates that polynucleotides and polypeptides corresponding to this gene are useful for the treatment, diagnosis, and/or prevention of various skin disorders including congenital disorders (i.e. nevi, moles, freckles, Mongolian spots, hemangiomas, portwine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm).

Alternatively, expression within placental tissue and other cellular sources marked by proliferating cells indicates that this protein may play a role in the regulation of cellular division. Moreover, the protein is useful in the detection, treatment, and/or prevention of various vascular conditions, which include, but are not limited to vascular leak syndrome, stroke, embolism, aneurysm, atherosclerosis, or microvascular disease. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:64 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 742 of SEQ ID NO:64, b is an integer of 15 to 756, where both a and b correspond to the positions of nucleotide residues shown in SEQ ID NO:64, and where b is greater than or equal to a+14.

Features of Protein Encoded by Gene No: 55

The translation product of this gene shares sequence homology with a IC. elegans protein which may be important in development (See Genebank Accession No.gi|289768). In specific embodiments, polypeptides of the invention comprise the following amino acid sequence: CGACTXLSLSDSRRCGCCKGSSLRHTAVA (SEQ ID NO:293). Polynucleotides encoding these polypeptides are also encompassed by the invention. The gene encoding the disclosed cDNA is believed to reside on chromosome 5. Accordingly, polynucleotides related to this invention are useful as a marker in linkage analysis for chromosome 5.

This gene is expressed primarily in cancers, and hematopoietic cells.

Therefore, polynucleotides and polypeptides of the invention are useful as reagents for differential identification of the tissue(s) or cell type(s) present in a biological sample and for diagnosis of diseases and conditions which include, but are not limited to, hematopoietic disorders; cancers; prostate cancer; Hodgkin's lymphoma; chronic lymphocytic leukemia; bone cancer; disorders of the vasculature. Similarly, polypeptides and antibodies directed to these polypeptides are useful in providing immunological probes for differential identification of the tissue(s) or cell type(s). For a number of disorders of the above tissues or cells, particularly of the immune and circulatory systems, expression of this gene at significantly higher or lower levels may be routinely detected in certain tissues or cell types (e.g., hematopoietic, developmental, immune, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:161 as residues: Lys-6 to Leu-12, Phe-36 to Pro-45.

The tissue distribution in hematopoietic cells indicates that polynucleotides and polypeptides corresponding to this gene are useful for the diagnosis and/or treatment of hematopoietic disorders and cancer. This gene product is expressed at elevated levels in a variety of cancers, suggesting that it may be involved in the control or regulation of aberrant cell proliferation and/or cell transformation. It is also expressed in endothelial cells, suggesting that it may be involved in angiogenesis that supports the development of cancer. Likewise, it is expressed at elevated levels in a variety of hematopoietic tissues, suggesting that it may be involved in the proliferation, survival, and/or differentiation of blood cell lineages. The uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:65 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 482 of SEQ ID NO:65, b is an integer of 15 to 496, where both a and b correspond to the positions of nucleotide residues shown in SEQ ID NO:65, and where b is greater than or equal to a+14.

Features of Protein Encoded by Gene No: 56

This gene is expressed primarily in spleen (from patients with chronic lymphocytic leukemia), and to a lesser extent in placenta.

Therefore, polynucleotides and polypeptides of the invention are useful as reagents for differential identification of the tissue(s) or cell type(s) present in a biological sample and for diagnosis of diseases and conditions which include, but are not limited to, hematopoietic disorders; chronic lymphocytic leukemia; placental insufficiency; disorders of the vasculature; tumors of an endothelial cell origin; aberrant angiogenesis. Similarly, polypeptides and antibodies directed to these polypeptides are useful in providing immunological probes for differential identification of the tissue(s) or cell type(s). For a number of disorders of the above tissues or cells, particularly of the immune, reproductive, and/or circulatory system, expression of this gene at significantly higher or lower levels may be routinely detected in certain tissues or cell types (e.g., reproductive, immune, vascular, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:162 as residues: Ser-18 to Gly-23.

The tissue distribution in spleen and placenta indicates that polynucleotides and polypeptides corresponding to this gene are useful for the diagnosis and/or treatment of hematopoietic disorders, such as CLL, as well as disorders of the circulatory system and/or female reproductive system. This gene product is expressed at elevated levels in the spleen—particularly of patients with chronic lymphocytic leukemia—and in the placenta, a highly vascularized tissue suggesting that this gene product may be expressed at higher levels by endothelial cells. These observations suggest that this gene may be involved in the survival, proliferation, and/or differentiation of blood cells, or may control their activation state or immune function. Likewise, it indicates that this gene product may be involved in endothelial cell function, such as angiogenesis, or may simply be produced by endothelial cells to be released into the circulation and have an effect on cells at scattered sites within the body.

Moreover, the protein is useful in the detection, treatment, and/or prevention of a variety of vascular disorders and condtions, which include, but are not limited to miscrovascular disease, vascular leak syndrome, aneurysm, stroke, embolism, thrombosis, and/or atherosclerosis. Protein, as well as, antibodies directed against the protein may show utility as a tumor marker and/or immunotherapy targets for the above listed tissues. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:66 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 543 of SEQ ID NO:66, b is an integer of 15 to 557, where both a and b correspond to the positions of nucleotide residues shown in SEQ ID NO:66, and where b is greater than or equal to a+14.

Features of Protein Encoded by Gene No: 57

In specific embodiments, polypeptides of the invention comprise the following amino acid sequence: GRPTRPI (SEQ ID NO:294). Polynucleotides encoding these polypeptides are also encompassed by the invention.

This gene is expressed primarily in T cells and spleen (from a patient with chronic lymphocytic leukemia), and to a lesser extent, in lung.

Therefore, polynucleotides and polypeptides of the invention are useful as reagents for differential identification of the tissue(s) or cell type(s) present in a biological sample and for diagnosis of diseases and conditions which include, but are not limited to, hematopoietic disorders; chronic lymphocytic leukemia; inflammation; immune dysfunction; autoimmune disorders; pulmonary disorders, particularly fibrosis; ARDS. Similarly, polypeptides and antibodies directed to these polypeptides are useful in providing immunological probes for differential identification of the tissue(s) or cell type(s). For a number of disorders of the above tissues or cells, particularly of the immune or respiratory system, expression of this gene at significantly higher or lower levels may be routinely detected in certain tissues or cell types (e.g., immune, hematopoietic, pulmonary, lung, and cancerous and wounded tissues) or bodily fluids (e.g., lymph, serum, plasma, urine, pulmonary surfactant or sputum, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells and lung indicates that polynucleotides and polypeptides corresponding to this gene are useful for the diagnosis and/or treatment of hematopoietic disorders or disorders of the lung. This gene product is expressed at elevated levels in T cells and the spleen of a patient with CLL, as well as in the lung. Thus, this gene product may play a role in the proliferation, survival and/or differentiation of blood cell lineages, or in the activation and modulation of hematopoietic cells and cell function. Alternately, this protein may be involved in lung function or disorders of the lung, including fibrosis, inflammation, or ARDS. The protein is useful in the modulation of the immune response to proliferative or aberrant cells or cell types, particularly in the lung. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:67 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 660 of SEQ ID NO:67, b is an integer of 15 to 674, where both a and b correspond to the positions of nucleotide residues shown in SEQ ID NO:67, and where b is greater than or equal to a+14.

Features of Protein Encoded by Gene No: 58

In specific embodiments, polypeptides of the invention comprise the following amino acid sequence:

(SEQ ID NO:295)
DPRVRDLQQKDIGVKPEFSFNIPRAKRELAQLNKCTSPQQKLVCLRKVV

QLITQSPSQRVNLET, (SEQ ID NO:296)
QQKDIGVKPEFSFNIPRAKRE, and/or (SEQ ID NO:297)
KCTSPQQKLVCLRKVVQLITQSPSQ.

Polynucleotides encoding these polypeptides are also encompassed by the invention.

This gene is expressed primarily in myeloid progenitor cells.

Therefore, polynucleotides and polypeptides of the invention are useful as reagents for differential identification of the tissue(s) or cell type(s) present in a biological sample and for diagnosis of diseases and conditions which include, but are not limited to, hematopoietic or immune disorders and diseases; leukemias; inflammation. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., hematopoietic, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in myeloid progenitor cells indicates that polynucleotides and polypeptides corresponding to this gene are useful for the diagnosis and/or treatment of hematopoietic disorders and immune dysfunction. This gene is expressed at elevated levels in a myeloid progenitor cell line, suggesting that it may be involved in the proliferation, survival, and/or differentiation of hematopoietic cell lineages. In addition, it may be produced by myeloid cells in order to recruit other blood cells to a particular site, such as a site of inflammation, or it may be responsible for activating hematopoietic cells, such as T cells. Similarly, the expression within myeloid progenitor cells indicates that polynucleotides and polypeptides corresponding to this gene are useful for the treatment and diagnosis of hematopoetic related disorders such as anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:68 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 780 of SEQ ID NO:68, b is an integer of 15 to 794, where both a and b correspond to the positions of nucleotide residues shown in SEQ ID NO:68, and where b is greater than or equal to a+14.

Features of Protein Encoded by Gene No: 59

In specific embodiments, polypeptides of the invention comprise the following amino acid sequence:

(SEQ ID NO:298)
EWKLFLRGRQNEKSGYQKLLELILLDQTVRVVTAGSAILQKCHFYEVLS

EIKRLGDHLAEKTSXLPNHSEPDHDTDAGLERTNPEYENEVEASMDMDL

LESSNISE, (SEQ ID NO:299)
GEIERLINLLEEVFHLMETAPHTMIQQPVKSFPTLRGRQNEK, (SEQ ID NO:300)
SGYQKLLELILLDQTVRVVILQKCHFYEVLSEIKRLGDHLAEKTS, (SEQ ID NO:301)
DAGLERTNPEYENEVEASMDMD and/or (SEQ ID NO:302)
NISEGEIERLINLLEEVFHLMETAPH.

Polynucleotides encoding these polypeptides are also encompassed by the invention. The gene encoding the disclosed cDNA is believed to reside on chromosome 8. Accordingly, polynucleotides related to this invention are useful as a marker in linkage analysis for chromosome 8.

This gene is expressed primarily in infant and fetal brain, and to a lesser extent, in hematopoietic tissues, such as T cells, B cell lymphoma, and bone marrow cell lines.

Therefore, polynucleotides and polypeptides of the invention are useful as reagents for differential identification of the tissue(s) or cell type(s) present in a biological sample and for diagnosis of diseases and conditions which include, but are not limited to, hematopoietic disorders; lymphoproliferative disorders; neurological disorders such as Alzheimers and schizophrenia, in addition to developmental disorders and diseases. Similarly, polypeptides and antibodies directed to these polypeptides are useful in providing immunological probes for differential identification of the tissue(s) or cell type(s). For a number of disorders of the above tissues or cells, particularly of the immune system and/or CNS, expression of this gene at significantly higher or lower levels may be routinely detected in certain tissues or cell types (e.g., neural, immune, developmental, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:165 as residues: Pro-7 to Tyr-14.

The tissue distribution in infant and fetal brain indicates that polynucleotides and polypeptides corresponding to this gene are useful for the diagnosis and/or treatment of neurodegenerative disorders and/or hematopoietic disorders. This gene displays elevated levels of expression in fetal/infant brain, as well as in a variety of hematopoietic tissues. Thus, this gene product may play a role in the development of the brain and/or nervous system, and may be involved in the survival or differentiation of neurons. It may therefore be useful in the treatment of neurological disorders such as Alzheimers, schizophrenia, or ALS, and may protect neurons or effect neuronal regeneration. Likewise, this gene product may play a role in hematopoietic development, and could be useful in their proliferation, survival, and/or differentiation of blood cell lineages.

The secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of hematopoiesis (e.g., for treating anaemia or as adjunct to chemotherapy); stimulation or growth of bone, cartilage, tendons, ligaments and/or nerves (e.g., for treating wounds, stimulation of follicle stimulating hormone (for control of fertility); chemotactic and chemokinetic activities (e.g., for treating infections, tumors); hemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures.

The protein may play a role in the regulation of cellular division, and may show utility in the diagnosis and treatment of cancer and other proliferative disorders. Similarly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:69 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1901 of SEQ ID NO:69, b is an integer of 15 to 1915, where both a and b correspond to the positions of nucleotide residues shown in SEQ ID NO:69, and where b is greater than or equal to a+14.

Features of Protein Encoded by Gene No: 60

In specific embodiments, polypeptides of the invention comprise the following amino acid sequence: RRTSGSPX-AAGIRHEGGFI (SEQ ID NO:303). Polynucleotides encoding these polypeptides are also encompassed by the invention.

This gene is expressed primarily in macrophages, and to a lesser extent, in bone marrow cells.

Therefore, polynucleotides and polypeptides of the invention are useful as reagents for differential identification of the tissue(s) or cell type(s) present in a biological sample and for diagnosis of diseases and conditions which include, but are not limited to, hematopoietic disorders; susceptibility to infection; leukemias; immune dysfunction. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., hematopoietic, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:166 as residues: Met-1 to Asn-7, Leu-18 to Gly-24.

The tissue distribution in macrophages and bone marrow cells indicates that polynucleotides and polypeptides corresponding to this gene are useful for the diagnosis and/or treatment of hematopoietic disorders. This gene is expressed at higher levels in hematopoietic cells such as macrophages, as well as in tissues that support hematopoietic development, such as bone marrow stromal cells. Thus, this gene product may effect hematopoietic cell proliferation, survival, and/or differentiation, as well as hematopoietic cell activation and immune function. Thus, this gene may be useful in boosting stem cell numbers, enhancing immune surveilance, or combatting leukemias or lymphoproliferative disorders.

The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:70 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 719 of SEQ ID NO:70, b is an integer of 15 to 733, where both a and b correspond to the positions of nucleotide residues shown in SEQ ID NO:70, and where b is greater than or equal to a+14.

Features of Protein Encoded by Gene No: 61

The translation product of this gene shares sequence homology with carboxyamido-triazole resistance proteins which are thought to be important in resistance to treatment of cancer with carboxyamido-triazole (CAI) (See Genebank Accession No.R77365). Moreover, the protein product of this gene shares homology with the human silencer of death domains protein (See Genbank Accession No.gi|4160014 (AF11116)). In specific embodiments, polypeptides of the invention comprise the following amino acid sequence:

(SEQ ID NO:304)
MNRHNFPCSVHQYESSGTVNNDDSDLLDSQVQYSAEPQLYGNATSDHPN

NQDQSSSLPEECVPSDESTPPSIKKIIHVLEKVQYLEQEVEEFVGKKTD

KAYWLLEEMLTKELLELDSVETGGQDSVRQARKEAVCKIQAILEKKKKK

NS, (SEQ ID NO:305)
GARATAPVTVRPTAATTGLGVEMCRYTHLHPYILFALNLPSLPFPGGCA

GAARRRPPGWEKAEEAMATIPREAPGQSLVEPEEATRV, (SEQ ID NO:306)
PVTVRPTAATTGLGVEMCRYTHLHP, (SEQ ID NO:307)
PYILFALNLPSLPFPGGCAGAARRR, (SEQ ID NO:308)
KAEEAMATIPREAPGQSLVE, (SEQ ID NO:309)
MNRHNFPCSVHQYESSGTVNNDDSDL, (SEQ ID NO:310)
DSQVQYSAEPQLYGNATSDHPNNQ, (SEQ ID NO:311)
HPNNQDQSSSLPEECVPSDESTPPS, (SEQ ID NO:312)
EVEEFVGKKTDKAYWLLEEMLTKE, and/or (SEQ ID NO:313)
LELDSVETGGQDSVRQARKEAVCK.

Polynucleotides encoding these polypeptides are also encompassed by the invention. The gene encoding the disclosed cDNA is believed to reside on chromosome 1. Accordingly, polynucleotides related to this invention are useful as a marker in linkage analysis for chromosome 8.

Numerous biological actions, for instance, response to certain stimuli and natural biological processes, are controlled by factors, such as cytokines. Many cytokines act through receptors by engaging the receptor and producing an intra-cellular response. For example, tumor necrosis factors (TNF) alpha and beta are cytokines, which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily.

So far, nine members of the TNF ligand superfamily have been identified and ten members of the TNF-receptor superfamily have been characterized. Among the ligands, there are included TNF-a, lymphotoxin-a (LT-a, also known as TNF-b), LT-b (found in complex heterotrimer LT-a2-b), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (Meager, A., Biologicals, 22:291–295 (1994)).

Many members of the TNF-ligand superfamily are expressed by activated T-cells, implying that they are necessary for T-cell interactions with other cell types which underlie cell ontogeny and functions. (Meager, A., supra). Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., Nature 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen, R. C. et al., Science 259:990 (1993)).

Targeted mutations of the low affinity nerve growth factor receptor cause a disorder characterized by faulty sensory innovation of peripheral structures (Lee, K. F. et al., Cell 69:737 (1992)). TNF and LT-a are capable of binding to two TNF receptors (the 55- and 75-kd TNF receptors). A large number of biological effects elicited by TNF and LT-a, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-a are involved in the pathogenesis of a wide range of diseases, including endotoxic shock, cerebral malaria, tumors, autoimmune disease, AIDS and graft-host rejection (Beutler, B. and Von Huffel, C., Science 264:667–668 (1994)).

Mutations in the p55 Receptor cause increased susceptibility to microbial infection. Moreover, an about 80 amino acid domain near the C-terminus of TNFR1 (p55) and Fas was reported as the "death domain," which is responsible for transducing signals for programmed cell death (Tartaglia et al., Cell 74:845 (1993)). Apoptosis, or programmed cell death, is a physiologic process essential for the normal development and homeostasis of multicellular organisms (H. Steller, Science 267:1445–1449 (1995)). Derangements of apoptosis contribute to the pathogenesis of several human diseases including cancer, neurodegenerative disorders, and acquired immune deficiency syndrome (C. B. Thompson, Science 267:1456–1462 (1995)).

Recently, much attention has focused on the signal transduction and biological function of two cell surface death receptors, Fas/APO-1 and TNFR-1 (J. L. Cleveland et al., Cell 81:479–482 (1995); A. Fraser, et al., Cell 85:781–784 (1996); S. Nagata et al., Science 267:1449–56 (1995)). Both are members of the TNF receptor family which also include TNFR-2, low affinity NGFR, CD40, and CD30, among others (C. A. Smith et al., Science 248:1019–23 (1990); M. Tewari et al., in Modular Texts in Molecular and Cell Biology M. Purton, Heldin, Carl, Ed. (Chapman and Hall, London, 1995).

While family members are defined by the presence of cysteine-rich repeats in their extracellular domains, Fas/APO-1 and TNFR-1 also share a region of intracellular homology, appropriately designated the "death domain", which is distantly related to the Drosophila suicide gene, reaper (P. Golstein, et al., Cell 81:185–186 (1995); K. White et al., Science 264:677–83 (1994)). This shared death domain indicates that both receptors interact with a related set of signal transducing molecules that, until recently, remained unidentified. Activation of Fas/APO-1 recruits the death domain-containing adapter molecule FADD/MORT1 (A. M. Chinnaiyan et al., Cell 81: 505–12 (1995); M. P. Boldin et al., J. Biol Chem 270:7795–8 (1995); F. C. Kischkel et al., EMBO 14:5579–5588 (1995)), which in turn binds and presumably activates FLICE/MACH1, a member of the ICE/CED-3 family of pro-apoptotic proteases (M. Muzio et al., Cell 85:817–827 (1996); M. P. Boldin et al., Cell 85:803–815 (1996)).

While the central role of Fas/APO-1 is to trigger cell death, TNFR-1 can signal an array of diverse biological activities-many of which stem from its ability to activate NF-kB (L. A. Tartaglia et al., Immunol Today 13:151–3 (1992)). Accordingly, TNFR-1 recruits the multivalent adapter molecule TRADD, which like FADD, also contains a death domain (H. Hsu et al., Cell 81:495–504 (1995); H. Hsu, et al., Cell 84:299–308 (1996)). Through its associations with a number of signaling molecules including FADD, TRAF2, and RIP, TRADD can signal both apoptosis and NF-kB activation (H. Hsu et al., Cell 84:299–308 (1996); H. Hsu, et al., Immunity 4:387–396 (1996)).

Recently, a new apoptosis-inducing TNF ligand has been discovered. S. R. Wiley et al. (Immunity 3:673–682 (1995)) named the molecule—ìTNF-related apoptosis-inducing ligandî or simply ìTRAIL.î The molecule was also called ìApo-2 ligandî or ìApo-2L.î R. M. Pitt et al., J. Biol. Chem. 271:12687–12690 (1996). This molecule was also disclosed in co-pending U.S. provisional application No. 60/013,405. For convenience, the molecule will be referred to herein as TRAIL. Unlike FAS ligand, whose transcripts appear to be largely restricted to stimulated T-cells, significant levels of TRAIL are detected in many human tissues (e.g., spleen, lung, prostate, thymus, ovary, small intestine, colon, peripheral blood lymphocytes, placenta, kidney), and is constitutively transcribed by some cell lines.

It has been shown that TRAIL acts independently from the Fas ligand (Wiley et al., supra). It has also been shown that TRAIL activates apoptosis rapidly, within a time frame that is similar to death signaling by Fas/Apo-1L, but much faster than TNF-induced apoptosis. S. A. Marsters et al., Current Biology 6:750–752 (1996). The inability of TRAIL to bind TNFR-1, Fas, or the recently identified DR3, indicates that TRAIL may interact with a unique receptor(s). Several unique receptors for TRAIL have already been identified. In co-pending U.S. provisional patent application No. 60/035,722, DR4, a novel death domain containing receptor for TRAIL, was disclosed. See, Pan et al., Science 276, 111–113 (April 1997). The TR5 receptor, the subject of co-pending U.S. provisional patent application No. 60/035, 496, has now been shown to bind TRAIL. Subsequently, it was predicted that the TR10 receptor would also bind TRAIL, owing to sequence homology with DR4.

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize additional novel receptors that bind to or antagonize TRAIL.

This gene is expressed primarily in fetal liver, and to a lesser extent in activated neutrophils.

Therefore, polynucleotides and polypeptides of the invention are useful as reagents for differential identification of the tissue(s) or cell type(s) present in a biological sample and for diagnosis of diseases and conditions which include, but are not limited to, cancer; hematopoietic, developmental, and hepatic disorders and disease. Similarly, polypeptides and antibodies directed to these polypeptides are useful in providing immunological probes for differential identification of the tissue(s) or cell type(s). For a number of disorders of the above tissues or cells, particularly for the immune system and for cancers such as melanomas and ovarian cancers, expression of this gene at significantly higher or lower levels may be routinely detected in certain tissues or cell types (e.g., hepatic, hematopoietic, developmental, and cancerous and wounded tissues) or bodily fluids (e.g., bile, lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:167 as residues: Arg-5 to Tyr-21, Arg-40 to Pro-46, Glu-65 to Gly-77, Pro-80 to Gly-109.

The tissue distribution in fetal liver and neutrophils, combined with the homology to the siliencer of death domain and CAI resistance proteins indicates that polynucleotides and polypeptides corresponding to this gene are useful for detection, treatment, and/or prevention of cancers, particularly those resistant to the anti-cancer compound, carboxyamido-triazole. Likewise, elevated expression in fetal liver and neutrophils indicates a potential role in the proliferation, survival, and/or differentiation of hematopoietic lineages.

Similarly, the tissue distribution indicates that polynucleotides and polypeptides corresponding to this gene are useful for the detection and treatment of liver disorders and cancers (e.g., hepatoblastoma, jaundice, hepatitis, liver metabolic diseases and conditions that are attributable to the differentiation of hepatocyte progenitor cells). In addition the expression in fetus would suggest a useful role for the protein product in developmental abnormalities, fetal deficiencies, pre-natal disorders and various would-healing models and/or tissue trauma.

Moreover, the expression within fetal tissue and other cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions.

Thus this protein may also be involved in the modulation of apoptosis or tissue differentiation and could again be useful in cancer therapy. The protein may be beneficial in protecting cells or tissues from initiating the pathway to apoptosis, which would provide tremendous therapeutic benefit to degenerative conditions, particularly in the developing embryo and diseased tissues and cells, and in autoimmune diseases, for example. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:71 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1252 of SEQ ID NO:71, b is an integer of 15 to 1266, where both a and b correspond to the positions of nucleotide residues shown in SEQ ID NO:71, and where b is greater than or equal to a+14.

Features of Protein Encoded by Gene No: 62

In specific embodiments, polypeptides of the invention comprise the following amino acid sequence: IRHEYPV-LIQFSVSYRKSFIFCLPE (SEQ ID NO:314). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, inflammatory and immune or hematopoietic diseases and disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for diagnosis and treatment of inflamatory diseases such as rheumatoid arthritis, psoriasis, inflamatory bowel disease, sepsis and autoimmune disorders. In addition, it may also represent a secreted factor that influences the differentiation or behavior of other blood cells, or that recruits hematopoietic cells to sites of injury. Similarly, the tissue distribution in neutrophils indicates that polynucleotides and polypeptides corresponding to this gene are useful for the treatment and diagnosis of hematopoetic related disorders such as anemia, pancytopenia, leukopenia, thrombocytopenia or leukemia since stromal cells are important in the production of cells of hematopoietic lineages.

The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:72 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 471 of SEQ ID NO:72, b is an integer of 15 to 485, where both a and b correspond to the positions of nucleotide residues shown in SEQ ID NO:72, and where b is greater than or equal to a+14.

Features of Protein Encoded by Gene No: 63

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders and diseases, particularly inflammatory conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:73 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 625 of SEQ ID NO:73, b is an integer of 15 to 639, where both a and b correspond to the positions of nucleotide residues shown in SEQ ID NO:73, and where b is greater than or equal to a+14.

Features of Protein Encoded by Gene No: 64

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders and diseases, particularly inflammatory conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:170 as residues: Ala-14 to Lys-19, Gln-67 to Trp-79, Pro-100 to Pro-110, Thr-126 to Arg-132.

The tissue distribution in neutrophils indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:74 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 518 of SEQ ID NO:74, b is an integer of 15 to 532, where both a and b correspond to the positions of nucleotide residues shown in SEQ ID NO:74, and where b is greater than or equal to a+14.

Features of Protein Encoded by Gene No: 65

The translation product of this gene was shown to have homology to the human diaphanous protein which is thought to regulate cytokinesis in meiosis and mitosis within various cell types and would likely be useful for regulating cellular division, particularly in treating cancer or other disorders involving proliferating cells or tissues (See Genebank Accession No. P48608). In specific embodiments, polypeptides of the invention comprise the following amino acid sequence: ADVELVDPXGCRNSARAPARKKEWHSWAWPRIRVIRARESLGS (SEQ ID NO:315). Polynucleotides encoding these polypeptides are also encompassed by the invention. The gene encoding the disclosed cDNA is believed to reside on chromosome 5. Accordingly, polynucleotides related to this invention are useful as a marker in linkage analysis for chromosome 5.

This gene is expressed primarily in dendritic cells, and to a lesser extent, in IL-4 induced endothelial cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders and diseases, particularly inflammatory conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, endothelial, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:171 as residues: Tyr-32 to Ala-39.

The tissue distribution in dendritic cells indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Alternatively, the homology to a cell-cycle regulatory protein indicates that polynucleotides and polypeptides corresponding to this gene are useful for the diagnosis and treatment of cancer and other proliferative disorders. Similarly, embryonic development involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:75 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 500 of SEQ ID NO:75, b is an integer of 15 to 514, where both a and b correspond to the positions of nucleotide residues shown in SEQ ID NO:75, and where b is greater than or equal to a+14.

Features of Protein Encoded by Gene No: 66

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders and diseases, particularly inflammatory disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:172 as residues: Ser-46 to Lys-55, Ser-67 to Pro-75.

The tissue distribution in neutrophils indicates that polynucleotides and polypeptides corresponding to this gene are useful for the diagnosis and treatment of a variety of immune system disorders. Expression of this gene product indicates a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:76 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 630 of SEQ ID NO:76, b is an integer of 15 to 644, where both a and b correspond to the positions of nucleotide residues shown in SEQ ID NO:76, and where b is greater than or equal to a+14.

Features of Protein Encoded by Gene No: 67

This gene is expressed primarily in thymus and neutrophils.

Therefore, polynucleotides and polypeptides of the invention are useful as reagents for differential identification of the tissue(s) or cell type(s) present in a biological sample and for diagnosis of diseases and conditions which include, but are not limited to, hematopoietic disorders; T cell lymphoma; inflammatory and immune disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, developmental, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:173 as residues: Cys-24 to Asn-31.

The tissue distribution in thymus and neutrophils indicates that polynucleotides and polypeptides corresponding to this gene are useful for the treatment, diagnosis, and/or prevention of inflammatory and immune disorders, particularly rheumatoid arthritis, sepsis, psoriasis, inflammatory bowel disorder, and autoimmune diseases such as lupus. Likewise, its expression in thymus and neutrophils indicates that it may play a more general role in immune function, immune surveillance, or in the activation or priming of immune cells, such as T cells. It may also be involved in the proliferation, survival, and/or differentiation of blood cell lineages—for example, in the microenvironment of the thymic stroma. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:77 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1185 of SEQ ID NO:77, b is an integer of 15 to 1199, where both a and b correspond to the positions of nucleotide residues shown in SEQ ID NO:77, and where b is greater than or equal to a+14.

Features of Protein Encoded by Gene No: 68

When tested against U937 cell lines, supernatants removed from cells containing this gene activated the GAS (gamma activating sequence) promoter element. Thus, it is likely that this gene activates myeloid cells, or more generally, immune or hematopoietic cells, in addition to other cells or cell-types through the JAK-STAT signal transduction pathway. GAS is a promoter element found upstream of many genes which are involved in the JAK-STAT pathway. The JAK-STAT pathway is a large, signal transduction pathway involved in the differentiation and proliferation of cells. Therefore, activation of the JAK-STAT pathway, reflected by the binding of the GAS element, can be used to indicate proteins involved in the proliferation and differentiation of cells. In specific embodiments, polypeptides of the invention comprise the following amino acid sequence: EFGTSRGPVPLSSTSPMPSRLVIRAH-SLLFA (SEQ ID NO:316). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or heamtopoietic diseases and disorders, particularly inflammatory conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:174 as residues: Glu-60 to Lys-66.

The tissue distribution in neutrophils, combined with the detected GAS biological activity, indicates that polynucleotides and polypeptides corresponding to this gene are useful for treatment and diagnosis of inflammatory and immune disorders, particularly rheumatoid arthritis, sepsis, psoriasis, inflammatory bowel disorder, and auto immune diseases such as lupus. Likewise, it may also be involved in influencing the activation of other blood cell lineages, or in the recruitment of hematopoietic cells to specific sites, such as sites of injury or inflammation.

The secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of hematopoiesis (e.g., for treating anaemia or as adjunct to chemotherapy); stimulation or growth of bone, cartilage, tendons, ligaments and/or nerves (e.g., for treating wounds, stimulation of follicle stimulating hormone (for control of fertility); chemotactic and chemokinetic activities (e.g., for treating infections, tumors); hemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:78 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 646 of SEQ ID NO:78, b is an integer of 15 to 660, where both a and b correspond to the positions of nucleotide residues shown in SEQ ID NO:78, and where b is greater than or equal to a+14.

Features of Protein Encoded by Gene No: 69

The translation product of this gene was shown to have homology to catalase (hydrogen-peroxide:hydrogen-peroxide oxidoreductase) which is known to be involved in the elimination of hydrogen peroxide produced during cellular metabolism. (See Genebank Accession No.gi|984737). In specific embodiments, polypeptides of the invention comprise the following amino acid sequence:

FRAWRNHGHSCFLCEIVIRSQFHTTYEPEA, (SEQ ID NO:317)

ADNNFTQETAMTMITPSSKLTLTKGNKSWSSTAVAAALELVDPPGCRNS (SEQ ID NO:318)

ARAVLLIWGHGSSGKMALCGVEVSPRVGGSVPVHRYLLAAHIHSEALLS

QLRM,

TAMTMITPSSKLTLTKGNKSWSST, (SEQ ID NO:319)

SSGKMALCGVEVSPRVGGSVPVHRYL, (SEQ ID NO:320)

and/or

VDPVKGG. (SEQ ID NO:321)

Polynucleotides encoding these polypeptides are also encompassed by the invention. The gene encoding the disclosed cDNA is believed to reside on chromosome 17. Accordingly, polynucleotides related to this invention are useful as a marker in linkage analysis for chromosome 17.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, inflammatory, immune, or metabolic disorders Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:175 as residues: Thr-36 to Pro-47, Pro-71 to Ser-77, Asn-117 to Lys-127.

The tissue distribution in neutrophils indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Alternatively, the homology to catalase indicates that polynucleotides and polypeptides corresponding to this gene are useful for the study, detection, treatment, and/or prevention of a variety of metabolic disorders. As elevated levels of peroxide in cells and tissues leads to oxidative damage, largely through the generation of oxide free-radicals, mutations within the catalase gene may lead to the accumulation of cellular mutations over time and could predispose an individual to cancer or other disorder and disease. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:79 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 510 of SEQ ID NO:79, b is an integer of 15 to 524, where both a and b correspond to the positions of nucleotide residues shown in SEQ ID NO:79, and where b is greater than or equal to a+14.

Features of Protein Encoded by Gene No: 70

In specific embodiments, polypeptides of the invention comprise the following amino acid sequence: IRHER-HELVPNSARDF (SEQ ID NO:322) Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders and diseases, particularly inflammatory conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:80 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 420 of SEQ ID NO:80, b is an integer of 15 to 434, where both a and b correspond to the positions of nucleotide residues shown in SEQ ID NO:80, and where b is greater than or equal to a+14.

Features of Protein Encoded by Gene No: 71

In specific embodiments, polypeptides of the invention comprise the following amino acid sequence: ATSHCG (SEQ ID NO:323). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders and diseases, particularly inflammatory conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells.

This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and contaminated progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:81 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 721 of SEQ ID NO:81, b is an integer of 15 to 735, where both a and b correspond to the positions of nucleotide residues shown in SEQ ID NO:81, and where b is greater than or equal to a+14.

Features of Protein Encoded by Gene No: 72

This gene has homology with galectin, and is a new member of the family of beta-galactoside binding protein, similar to the galaptin (S-lectin) family. Recently, it has been shown that galactin induced apoptosis of T cells and T cell leukaemia cell lines. It is believed that galactins function in growth regulation, immunomodulatory activity, cell—cell and cell-substrate interactions, and induce apoptosis of T cells. Likewise, it is proposed that the translation product of this gene is useful for the study, treatment, detection, and/or prevention of a variety of immune diseases, particularly autoimmune disease, cancer, and inflammatory disease. In specific embodiments, polypeptides of the invention comprise the following amino acid sequence: AHGQIEGKALTHDHTAEKWQRQDLNLEPLAPHTSNLNHSPYNTTYVVK (SEQ ID NO:324). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, hematopoietic or hematopoietic disorders; fibrosis; inflammation and immune response. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types.

The secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of hematopoiesis (e.g., for treating anaemia or as adjunct to chemotherapy); stimulation or growth of bone, cartilage, tendons, ligaments and/or nerves (e.g., for treating wounds, stimulation of follicle stimulating hormone (for control of fertility); chemotactic and chemokinetic activities (e.g., for treating infections, tumors); hemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:82 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 708 of SEQ ID NO:82, b is an integer of 15 to 722, where both a and b correspond to the positions of nucleotide residues shown in SEQ ID NO:82, and where b is greater than or equal to a+14.

Features of Protein Encoded by Gene No: 73

In specific embodiments, polypeptides of the invention comprise the following amino acid sequence: LNSSDCQLA (SEQ ID NO:325). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, hematopoietic or immune disorders and diseases. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., hematopoietic, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:179 as residues: Glu-21 to Thr-26.

The tissue distribution in neutrophils indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:83 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 771 of SEQ ID NO:83, b is an integer of 15 to 785, where both a and b correspond to the positions of nucleotide residues shown in SEQ ID NO:83, and where b is greater than or equal to a+14.

Features of Protein Encoded by Gene No: 74

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune and/or hemopoietic disorders and diseases, particularly cancers. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., hematopoietic, immune, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:180 as residues: Gly-11 to Gly-43.

The tissue distribution in neutrophils indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types. Protein is useful in modulating the immune response to proliferative cells and tissues. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:84 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 556 of SEQ ID NO:84, b is an integer of 15 to 570, where both a and b correspond to the positions of nucleotide residues shown in SEQ ID NO:84, and where b is greater than or equal to a+14.

Features of Protein Encoded by Gene No: 75

In specific embodiments, polypeptides of the invention comprise the following amino acid sequence: TPHNLSAR-RLSGTMYGFFALQLTVLLVHYFFLI (SEQ ID NO:326). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immunological or hematopoietic disorders, particularly inflammatory conditions, and cancer. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., hematopoietic, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. Protein, as well as, antibodies directed against the protein may show utility as, a tumor marker and/or immunotherapy targets for the above listed tumors and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:85 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 891 of SEQ ID NO:85, b is an integer of 15 to 905, where both a and b correspond to the positions of nucleotide residues shown in SEQ ID NO:85, and where b is greater than or equal to a+14.

Features of Protein Encoded by Gene No: 76

This gene was shown to have homology to the human IL-15 gene which is known to be play an integral role in immune modulation (See Genebank Accession No. gb|X91233|HSDNAIL15). In specific embodiments, polypeptides of the invention comprise the following amino acid sequence: NSARAKMRLSTNLCIILINILIQNVLN-FNRKIIFKFLPCA (SEQ ID NO:327). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immunological or hematopoietic disorders, particularly inflammatory conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:182 as residues: Gln-24 to Ser-31.

The tissue distribution in neutrophils combined with the homology to a conserved immune chemokine indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells.

This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:86 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 692 of SEQ ID NO:86, b is an integer of 15 to 706, where both a and b correspond to the positions of nucleotide residues shown in SEQ ID NO:86, and where b is greater than or equal to a+14.

Features of Protein Encoded by Gene No: 77

In specific embodiments, polypeptides of the invention comprise the following amino acid sequence: ISLCKRSG @. Polynucleotides encoding these polypeptides are also encompassed by the invention. The gene encoding the disclosed cDNA is believed to reside on chromosome 7. Accordingly, polynucleotides related to this invention are useful as a marker in linkage analysis for chromosome 7.

This gene is expressed primarily in melanocyte, activated monocyte, spleen and osteosarcoma.

Therefore, polynucleotides and polypeptides of the invention are useful as reagents for differential identification of the tissue(s) or cell type(s) present in a biological sample and for diagnosis of diseases and conditions which include, but are not limited to, immune, integumentary, and/or skeletal disorders. Similarly, polypeptides and antibodies directed to these polypeptides are useful in providing immunological probes for differential identification of the tissue(s) or cell type(s). For a number of disorders of the above tissues or cells, particularly of the immune and skeletal systems, expression of this gene at significantly higher or lower levels may be routinely detected in certain tissues or cell types (e.g., immune, skeletal, integumentary, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:183 as residues: Val-33 to Gly-42, Val-52 to Thr-57, Glu-65 to Leu-72.

The tissue distribution in activated monocyte and spleen tissues and cells indicates that polynucleotides and polypeptides corresponding to this gene are useful for the diagnosis and treatment of a variety of immune system disorders. The expression of this gene product indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types.

Alternatively, the expression in melanocyte tissues indicates that polynucleotides and polypeptides corresponding to this gene are useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm). Protein, as well as, antibodies directed against the protein may show-utility as a tumor marker and/or immunotherapy targets for the above listed tissues.

Many polynucleotide sequences, such as EST sequences, are publicly available and accessible through sequence databases. Some of these sequences are related to SEQ ID NO:87 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1530 of SEQ ID NO:87, b is an integer of 15 to 1544, where both a and b correspond to the positions of nucleotide residues shown in SEQ ID NO:87, and where b is greater than or equal to a+14.

Features of Protein Encoded by Gene No: 78

This gene is expressed primarily in lung, ovary, spinal cord, and hemangiopericytoma.

Therefore, polynucleotides and polypeptides of the invention are useful as reagents for differential identification of the tissue(s) or cell type(s) present in a biological sample and for diagnosis of diseases and conditions which include, but are not limited to, cardiovascular, reproductive, neural, or hematopoietic diseases or disorders, particularly ARDS, fibrosis, polycystic disease, spina bifida, and soft-tissue cancers, for example. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., pulmonary, reproductive, skeletal, hematopoietic, and cancerous and wounded tissues) or bodily fluids (e.g., pulmonary surfactant, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:184 as residues: Ser-6 to Ser-11, Lys-28 to Ser-39.

The tissue distribution in spinal cord tissue indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system.

Alternatively, expression in lung tissue may suggest that the translation product of this gene may be useful for the detection, treatment, and/or prevention of various disorders afflicting the cadiovascular system, particularly lung cancer, emphasema, tracheitis, croup, bronchitis, bronchiolitis, allergies, alveolitis, or cancer. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:88 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 826 of SEQ ID NO:88, b is an integer of 15 to 840, where both a and b correspond to the positions of nucleotide residues shown in SEQ ID NO:88, and where b is greater than or equal to a+14.

Features of Protein Encoded by Gene No: 79

In specific embodiments, polypeptides of the invention comprise the following amino acid sequence:

NXWIPRAAGIRHXAALGQAGT, (SEQ ID NO:328)

LLFHMKLRKEVERTGLVLWALLAGAPPPTAGLQLQGSEAISEKVGSGAE (SEQ ID NO:329)

GSRGQVPGQLLQQAQQAFHLCPQVIHGLLYHLLHDI,

RKEVERTGLVLWALLAGAPPPTAGL, (SEQ ID NO:330)

and/or

GSRGQVPGQLLQQAQQAFHLCPQ. (SEQ ID NO:331)

Polynucleotides encoding these polypeptides are also encompassed by the invention. The gene encoding the disclosed cDNA is believed to reside on chromosome 10. Accordingly, polynucleotides related to this invention are useful as a marker in linkage analysis for chromosome 10.

This gene is expressed primarily in chronic synovitis, epididymus, and fetal kidney.

Therefore, polynucleotides and polypeptides of the invention are useful as reagents for differential identification of the tissue(s) or cell type(s) present in a biological sample and for diagnosis of diseases and conditions which include, but are not limited to, skeletal, reproductive, renal, inflammatory, and developmental diseases and disorders. Similarly, polypeptides and antibodies directed to these polypeptides are useful in providing immunological probes for differential identification of the tissue(s) or cell type(s). For a number of disorders of the above tissues or cells, particularly of the immune system and developing tissues, expression of this gene at significantly higher or lower levels may be routinely detected in certain tissues or cell types (e.g., developmental, skeletal, renal, inflammatory, pulmonary, and cancerous and wounded tissues) or bodily fluids (e.g., lymph, serum, plasma, pulmonary surfactant or sputum, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:185 as residues: Pro-25 to Gln-35.

The tissue distribution in chronic synovitis suggest a role in the detection and treatment of disorders and conditions affecting the skeletal system, in particular osteoporosis as well as disorders aflicting connective tissues (e.g., arthritis, trauma, tendonitis, chrondomalacia and inflammation) in the diagnosis or treatment of various autoimmune disorders such as rheumatoid arthritis, lupus, scleroderma, and dermatomyositis as well as dwarfism, spinal deformation, and specific joint abnormalities as well as chondrodysplasias ie. spondyloepiphyseal dysplasia congenita, familial osteoarthritis, Atelosteogenesis type II, metaphyseal chondrodysplasia type Schmid.

Alternatively, expression in fetal kidney indicates that this gene or gene product could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilms Tumor Disease, and congenital kidney abnormalities such as horseshoe kidney, polycystic kidney, and Falconi's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:89 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 496 of SEQ ID NO:89, b is an integer of 15 to 510, where both a and b correspond to the positions of nucleotide residues shown in SEQ ID NO:89, and where b is greater than or equal to a+14.

Features of Protein Encoded by Gene No: 80

In specific embodiments, polypeptides of the invention comprise the following amino acid sequence: GSRRHVVGKPGTPCRYRAGIPXVDPRVRSITVIVKMWFLRVVATYGGVER (SEQ ID NO:332). Polynucleotides encoding these polypeptides are also encompassed by the invention. The gene encoding the disclosed cDNA is believed to reside on chromosome 1. Accordingly, polynucleotides related to this invention are useful as a marker in linkage analysis for chromosome 1.

This gene is expressed primarily in infant brain and ovary.

Therefore, polynucleotides and polypeptides of the invention are useful as reagents for differential identification of the tissue(s) or cell type(s) present in a biological sample and for diagnosis of diseases and conditions which include, but are not limited to, neural or reproductive disorders and diseases, particularly ovarian cancer. Similarly, polypeptides and antibodies directed to these polypeptides are useful in providing immunological probes for differential identification of the tissue(s) or cell type(s). For a number of disorders of the above tissues or cells, particularly of the Reproductive system, expression of this gene at significantly higher or lower levels may be routinely detected in certain tissues or cell types (e.g., neural, reproductive, or cancerous and wounded tissues) or bodily fluids (e.g., amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in infant brain indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. In addition the expression in fetus would suggest a useful role for the protein product in developmental abnormalities, fetal deficiencies, pre-natal disorders and various would-healing models and/or tissue trauma. Expression within embryonic tissue and other cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA).

Therefore, the polynucleotides and polypeptides of the present invention are useful in treating, detecting, and/or preventing said disorders and conditions, in addition to other types of degenerative conditions. Thus this protein may also be involved in apoptosis or tissue differentiation and could again be useful in cancer therapy. Protein is useful in the detection, treatment, and/or prevention of reproductive disorders, which include, but are not limited to polycystic disease, infertility, and related endocrine disorders and conditions. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:90 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 724 of SEQ ID NO:90, b is an integer of 15 to 738, where both a and b correspond to the positions of nucleotide residues shown in SEQ ID NO:90, and where b is greater than or equal to a+14.

Features of Protein Encoded by Gene No: 81

In specific embodiments, polypeptides of the invention comprise the following amino acid sequence: IFSCDSIAII-QIKHLAFP (SEQ ID NO:333). Polynucleotides encoding these polypeptides are also encompassed by the invention.

This gene is expressed primarily in prostate cancer.

Therefore, polynucleotides and polypeptides of the invention are useful as reagents for differential identification of the tissue(s) or cell type(s) present in a biological sample and for diagnosis of diseases and conditions which include, but are not limited to, prostate cancer, and other reproductive disorders and diseases. Similarly, polypeptides and antibodies directed to these polypeptides are useful in providing immunological probes for differential identification of the tissue(s) or cell type(s). For a number of disorders of the above tissues or cells, particularly of the prostate, expression of this gene at significantly higher or lower levels may be routinely detected in certain tissues or cell types (e.g., reproductive, prostate, and cancerous and wounded tissues) or bodily fluids (e.g., seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:187 as residues: Pro-25 to Pro-30.

The tissue distribution in prostate tissue indicates that polynucleotides and polypeptides corresponding to this gene are useful for the diagnosis and treatment of cancer and other proliferative disorders, particularly prostate cancer and disorders and conditions afflicting the male reproductive system. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:91 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 492 of SEQ ID NO:91, b is an integer of 15 to 506, where both a and b correspond to the positions of nucleotide residues shown in SEQ ID NO:91, and where b is greater than or equal to a+14.

Features of Protein Encoded by Gene No: 82

The translation product of this gene was found to have homology to the conserved human nitrilase homolog 1 (See Genbank Accession No. gi|3242978 (AF069984)) which is thought to play the role of a tumor suppressor, and may be useful in the modulation of cellular proliferation (See, for example, Proc Natl Acad Sci USA Jul. 21, 1998;95(15) :8744–9, which is hereby incorporated by reference herein). Such activities are known in the art and described elsewhere herein. Moreover, the translation product of this gene was shown to have homology to the conserved *Saccharomyces cerevisiae* protein YJL126w which is thought to be important in the decarbamylation of N-carbamoyl-D-alpha aminoacids (See Genebank Accession No.gi|1008324). In specific embodiments, polypeptides of the invention comprise the following amino acid sequence:

(SEQ ID NO:334)
GLWLSLGGFHERGQDWEQTQKIYNCHVLLNRKGQ, (SEQ ID NO:335)
AWPRLGADSENLQLSRAAEQKGAVVATYRKTHLCDVEIPGQGLCVKATL

PCLGPVLSHLSAHQQARLV, (SEQ ID NO:336)
RAAEQKGAVVATYRKTHLCDVEIPGQG, and/or (SEQ ID NO:337)
RRDSRAGA.

Polynucleotides encoding these polypeptides are also encompassed by the invention. The gene encoding the disclosed cDNA is believed to reside on chromosome 1. Accordingly, polynucleotides related to this invention are useful as a marker in linkage analysis for chromosome 1.

This gene is expressed primarily in fetal heart, brain, emangiopericytoma, human adrenal gland tumor, and B cell lymphoma.

Therefore, polynucleotides and polypeptides of the invention are useful as reagents for differential identification of the tissue(s) or cell type(s) present in a biological sample and for diagnosis of diseases and conditions which include, but are not limited to, reproductive, neural, immune or hematopoietic disorders and diseases, particularly emangiopericytoma, adrenal gland tumor, B cell lymphoma. Similarly, polypeptides and antibodies directed to these polypeptides are useful in providing immunological probes for differential identification of the tissue(s) or cell type(s). For a number of disorders of the above tissues or cells, particularly of the immune, heart, brain, expression of this gene at significantly higher or lower levels may be routinely detected in certain tissues or cell types (e.g., immune, developing, reproductive, neural, endocrine, or cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:188 as residues: Cys-2 to Pro-9, His-89 to Gly-96.

The tissue distribution in B cell lymphoma indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells.

This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types.

Alternatively, expression in the brain indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, soft-tissue cancers, or disorders of the cardiovascular system. The protein is also useful for the detection, treatment, and/or prevention of endocrine and metabolic disorders, particularly lethargy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:92 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1189 of SEQ ID NO:92, b is an integer of 15 to 1203, where both a and b correspond to the positions of nucleotide residues shown in SEQ ID NO:92, and where b is greater than or equal to a+14.

Features of Protein Encoded by Gene No: 83

When tested against PC12 cell lines, supernatants removed from cells containing this gene activated the EGR1 (early growth response gene 1) pathway. Thus, it is likely that this gene activates sensory neuron cells, or more generally, neural cells and tissues, in addition to other cells or cell-types, through the EGR1 signal transduction pathway. EGR1 is a separate signal transduction pathway from JAK-STAT, genes containing the EGR1 promoter are induced in various tissues and cell types upon activation, leading the cells to undergo differentiation and proliferation. In specific embodiments, polypeptides of the invention comprise the following amino acid sequence: LSAGNHDT (SEQ ID NO:338). Polynucleotides encoding these polypeptides are also encompassed by the invention.

This gene is expressed primarily in T cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders and diseases, particularly immunodeficiencies such as AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells indicates that polynucleotides and polypeptides corresponding to this gene are useful for the diagnosis and treatment of a variety of immune system disorders. Expression of this gene product combined with its observed utility as an activator for the early growth response promoter (EGR1) indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:93 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 696 of SEQ ID NO:93, b is an integer of 15 to 710, where both a and b correspond to the positions of nucleotide residues shown in SEQ ID NO:93, and where b is greater than or equal to a+14.

Features of Protein Encoded by Gene No: 84

The translation product of this gene was found to have homology to the conserved ATP(GTP)-binding protein which is thought to be important in development (See Genbank Accession No.gnl|PID|e1321523 (AJ010842)). When tested against PC12 cell lines, supernatants removed from cells containing this gene activated the EGR1 (early growth response gene 1) pathway. Thus, it is likely that this gene activates sensory neuron cells, or more generally, neural cells and tissues, in addition to other cells or cell-types, through the EGR1 signal transduction pathway. EGR1 is a separate signal transduction pathway from JAK-STAT, genes containing the EGR1 promoter are induced in various tissues and cell types upon activation, leading the cells to undergo differentiation and proliferation. In specific embodiments, polypeptides of the invention comprise the following amino acid sequence:

KQVKCAKVSYLLFLFQYCAIDSCIKFWNAGSSWLSSVTLWS, (SEQ ID NO:339)

IYVMDTSRSTNPV, (SEQ ID NO:340)

NMLYACSILYKTKL, (SEQ ID NO:341)

MNKTDIIDHSFAVEWMQDF, (SEQ ID NO:342)

AFQDALNQETTYV, (SEQ ID NO:343)

NLTRSMSLVLDEFYSSLRVVGVSAVLGTGLDELFVQVTSAA, (SEQ ID NO:344)

LKKSLANAES, (SEQ ID NO:345)

KDMGSVALDAGTAKDSLSPVLHPSDLILT, (SEQ ID NO:346)

AGSGKTTFVQRLTGHLHAQGTPPYVINL, (SEQ ID NO:347)

STWIQQYMKFPFLPILVMKFIEKAQNMSKYVLIDTPGQIEVFTWSASGT (SEQ ID NO:348)

IITEALASSFPTVXIYVMDTSRSTNPVTFMCNMLYACSILYKTKLAFIX

GMNKTDIIDHSFAVEWMQDFXAFQDALNQETTYVIT.

and/or

GFPRCLESRDYIRHNLTRSMSLVLDEFYSSLRVVGVSAVLGTGLDELFV (SEQ ID NO:349)

QVTSAAEEYEREYRPEYERLKKSLANAESQQQREQLERLRKDMGSVALD

AGTAKDSLSPVLHPSDLILTRGTLDEEDEEADSDTDDIDHRVTEESHEE

PAFQNFMQESMAQYWKRNNKHRVTEESHEEPAFQNFMQESMAQYWKRNNK.

Polynucleotides encoding these polypeptides are also encompassed by the invention. The gene encoding the disclosed cDNA is believed to reside on chromosome 2. Accordingly, polynucleotides related to this invention are useful as a marker in linkage analysis for chromosome 2.

This gene is expressed primarily in T cells and neutrophils.

Therefore, polynucleotides and polypeptides of the invention are useful as reagents for differential identification of the tissue(s) or cell type(s) present in a biological sample and for diagnosis of diseases and conditions which include, but are not limited to, hematopoietic or immune disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., hematopoietic, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:190 as residues: Ser-10 to Lys-15, Gly-25 to Asp-30, Phe-47 to Ser-52, Phe-66 to Tyr-75, Lys-89 to Thr-101.

The tissue distribution in T cells and neutrophils, combined with its observed activity as an activator of the early growth response promoter and homology to a conserved ATP(GTP)-binding protein indicates that polynucleotides and polypeptides corresponding to this gene are useful for the diagnosis and treatment of a variety of immune system disorders. Expression of this gene product indicates the protein may play a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:94 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1736 of SEQ ID NO:94, b is an integer of 15 to 1750, where both a and b correspond to the positions of nucleotide residues shown in SEQ ID NO:94, and where b is greater than or equal to a+14.

Features of Protein Encoded by Gene No: 85

The gene encoding the disclosed cDNA is believed to reside on chromosome 12. Accordingly, polynucleotides related to this invention are useful as a marker in linkage analysis for chromosome 12.

This gene is expressed primarily in spinal cord, and infant brain.

Therefore, polynucleotides and polypeptides of the invention are useful as reagents for differential identification of the tissue(s) or cell type(s) present in a biological sample and for diagnosis of diseases and conditions which include, but are not limited to, neural and/or developmental disorders and diseases. Similarly, polypeptides and antibodies directed to these polypeptides are useful in providing immunological probes for differential identification of the tissue(s) or cell type(s). For a number of disorders of the above tissues or cells, particularly of the central and peripheral nervous systems, expression of this gene at significantly higher or lower levels may be routinely detected in certain tissues or cell types (e.g., neural, and cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:191 as residues: Thr-14 to Thr-21.

The tissue distribution in spinal cord and infant brain indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system.

Expression within fetal tissue indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:95 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 592 of SEQ ID NO:95, b is an integer of 15 to 606, where both a and b correspond to the positions of nucleotide residues shown in SEQ ID NO:95, and where b is greater than or equal to a+14.

Features of Protein Encoded by Gene No: 86

The translation product of this gene was shown to have homology to the human TFIIE transcription factor subunit, which is known to be essential for the recruitment of TFIIH to the transcriptional initiating complex, and for the stimulation of the C-terminal domain kinase of RNA polymerase II, in addition to promoter clearance by RNA polymerase II (See Genebank Accession No. P29083). In specific embodiments, polypeptides of the invention comprise the following amino acid sequence:

```
                                              (SEQ ID NO:350)
LAPSSVGSAS, (SEQ ID NO:351)
REATKNPTHHRSTPHAAGSQLNVPPQPCFPLHHQIKTSP, (SEQ ID NO:352)
SQTIFKQSRHRCDSRQESTWLCSHEKDATKMMHLNDNS, and/or (SEQ ID NO:353)
VTGSPILQLALLQLPAWPLRGRLRGKRHCTGLNLAISGNGGEWGGRGE.
```

Polynucleotides encoding these polypeptides are also encompassed by the invention.

This gene is expressed primarily in brain tissue, such as the striatum.

Therefore, polynucleotides and polypeptides of the invention are useful as reagents for differential identification of the tissue(s) or cell type(s) present in a biological sample and for diagnosis of diseases and conditions which include, but are not limited to, neural disorders. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:192 as residues: Ile-17 to Asn-22.

The tissue distribution in brain striatum tissue indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:96 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 603 of SEQ ID NO:96, b is an integer of 15 to 617, where both a and b correspond to the positions of nucleotide residues shown in SEQ ID NO:96, and where b is greater than or equal to a+14.

Features of Protein Encoded by Gene No: 87

The translation product of this gene was shown to have homology to the Sus scrofa apolipoprotein C-III, which is the principal protein component of plasma high-density lipoprotein (HDL), an activator of lecithin:cholesterol acyltransferase exchanges between triglyceride-rich lipoproteins and HDL, and inhibits the lipolysis and uptake of triglyceride-rich lipoproteins (See Genebank Accession No.gb|M84133|PIGAC3A). In specific embodiments, polypeptides of the invention comprise the following amino acid sequence:

```
                                            (SEQ ID NO:354)
EFGTRSLDPSGRHRVGAAG, (SEQ ID NO:355)
AQGRCSRDGASAHGGLSVPRWTCPSSGSHNPLPLHYFTQVGTFP, (SEQ ID NO:356)
CRVSALRELKDSQRHQGSLAQRSNSQAPRRTAMERTETHLQWGL, (SEQ ID NO:357)
GTLPVPGVQSLPTPSLCLPPSKGGVTTSVAKHLLPGSLHPGHLSL, and/or (SEQ ID NO:358)
WSVCLSVPPSLNLLPPCPLLLAPGSPXPLLAAPSHLTQGSLRTLKWWI

HPE.
```

Polynucleotides encoding these polypeptides are also encompassed by the invention.

This gene is expressed primarily in smooth muscle cells, whole week old embryo, cerebellum, and Soares infant brain tissues.

Therefore, polynucleotides and polypeptides of the invention are useful as reagents for differential identification of the tissue(s) or cell type(s) present in a biological sample and for diagnosis of diseases and conditions which include, but are not limited to, vascular, developing, and neural disorders. Similarly, polypeptides and antibodies directed to these polypeptides are useful in providing immunological probes for differential identification of the tissue(s) or cell type(s). For a number of disorders of the above tissues or cells, particularly of the central and peripheral nervous system, expression of this gene at significantly higher or lower levels may be routinely detected in certain tissues or cell types (e.g., neural, developing, vascular, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:193 as residues: Pro-42 to Thr-52, Arg-58 to Ser-78.

The tissue distribution in cerebellum and infant brain tissues indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system.

Alternatively, expression in smooth muscle, in addition to its homology to a conserved lipoprotein, may suggest that polynucleotides and polypeptides corresponding to this gene are useful for the detection, treatment, and/or prevention of a variety of cardiovascular and metabolic disorders, particularly atherosclerosis, as well as conditions and pathologies of the cardiovascular system, such as heart disease, restenosis, atherosclerosis, stoke, angina, thrombosis, and wound healing. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:97 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 620 of SEQ ID NO:97, b is an integer of 15 to 634, where both a and b correspond to the positions of nucleotide residues shown in SEQ ID NO:97, and where b is greater than or equal to a+14.

Features of Protein Encoded by Gene No: 88

This gene is expressed primarily in stomach cancer tissue.

Therefore, polynucleotides and polypeptides of the invention are useful as reagents for differential identification of the tissue(s) or cell type(s) present in a biological sample and for diagnosis of diseases and conditions which include, but are not limited to, gastrointestinal disorders, particularly stomach ulcers and cancer. Similarly, polypeptides and antibodies directed to these polypeptides are useful in providing immunological probes for differential identification of the tissue(s) or cell type(s). For a number of disorders of the above tissues or cells, particularly of the digestive system, expression of this gene at significantly higher or lower levels may be routinely detected in certain tissues or cell types (e.g., gastrointestinal, or cancerous and wounded tissues) or bodily fluids (e.g., lymph, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:194 as residues: Thr-26 to Gly-37, Pro-43 to Lys-49.

The tissue distribution in stomach cancer tissues indicates that polynucleotides and polypeptides corresponding to this gene are useful for the diagnosis, treatment, and/or prevention of various gastrointesinal disorders and afflications, particularly stomach cancer and ulcers. The tissue distribution further indicates that the translation product of this gene is useful for the detection and/or treatment of cancers of other tissues where expression has been observed. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:98 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 498 of SEQ ID NO:98, b is an integer of 15 to 512, where both a and b correspond to the positions of nucleotide residues shown in SEQ ID NO:98, and where b is greater than or equal to a+14.

Features of Protein Encoded by Gene No: 89

The translation product of this gene was shown to have homology to the human KIAA0130 protein which is known to be related to a mouse genetic suppressor element which may implicate this gene as playing an integral role in development or the regulation of cellular proliferation (See Genebank Accession No. gnl|PID|d1010121). The translation product of this gene also shares sequence homology with thyroid hormone receptor-associated protein 100 (TRAP 100). TRAP100 contain an LXXLL domain found in other nuclear receptor-interacting proteins, and appears to reside in a single complex with other TRAPs (in the absence of TR) (See Genbank Accession No. gi|3319292). In specific embodiments, polypeptides of the invention comprise the following amino acid sequence:

```
                                           (SEQ ID NO:359)
SPGLXGIRHEQPSKLMRLLSSNEDDANILSSPTDRSMSSSLSASQLHT

VN, (SEQ ID NO:360)
QPSKLMRLLSSNEDDANILSSPTDR, (SEQ ID NO:361)
QLHTVNMRDPLNRVLANLFLLISSIL, (SEQ ID NO:362)
GSRTAGPHTQFVQWFME, and/or (SEQ ID NO:363)
KVSAMSSPKVVLAITD.
```

Polynucleotides encoding these polypeptides are also encompassed by the invention. The gene encoding the disclosed cDNA is thought to reside on chromosome 17. Accordingly, polynucleotides related to this invention are useful as a marker in linkage analysis for chromosome 17.

This gene is expressed primarily in skin tumor, prostate, and fetal brain tissues.

Therefore, polynucleotides and polypeptides of the invention are useful as reagents for differential identification of the tissue(s) or cell type(s) present in a biological sample and for diagnosis of diseases and conditions which include, but are not limited to, wound healing or neural disorders. Similarly, polypeptides and antibodies directed to these polypeptides are useful in providing immunological probes for differential identification of the tissue(s) or cell type(s). For a number of disorders of the above tissues or cells, particularly of the skin and neural systems, expression of this gene at significantly higher or lower levels may be routinely detected in certain tissues or cell types (e.g., neural, integumentary, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in skin tumor tissue indicates that polynucleotides and polypeptides corresponding to this gene are useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm).

Alternatively, expression in neural tissues indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:99 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 930 of SEQ ID NO:99, b is an integer of 15 to 944, where both a and b correspond to the positions of nucleotide residues shown in SEQ ID NO:99, and where b is greater than or equal to a+14.

Features of Protein Encoded by Gene No: 90

The translation product of this gene shares sequence homology with the human, mouse, and *S. cerevisiae* ubiquitin protein ligase, which is known to be an essential intermediate protein in the poly-ubiquitination of proteins. Disruption of the yeast homolog was shown to result in premature initiation into mitosis which strongly implicates the human homolog as playing an essential role in regulation of cellular division—the aberration of which may lead to cancer (See Genebank Accession Nos gi|2708329 (AF038564), gi|2827198 (AF037454), and g2842707). In specific embodiments, polypeptides of the invention comprise the following amino acid sequence:

DNYCLQINP, (SEQ ID NO:364)

KRILNKPVGLKDL, (SEQ ID NO:365)

GPQIAYVRDFKAKVQYFRFW, (SEQ ID NO:366)

YEVNHNTRITQWEDPRSQGQL, (SEQ ID NO:367)

IGRFIAMALFHGKFIDTGFSLPF, (SEQ ID NO:368)

KQIMWFWQFVKIEDNEKR, (SEQ ID NO:369)

FNRLDLPPYKSYEQLKE, (SEQ ID NO:370)

and/or (SEQ ID NO:371)
THASATRPGPLPPGWEKRTDSNGRVYFVNHNTRITQWEDPRSQGQLNEK

PLPEGWEMRFTVDGIPYFVDHNRRTTTYIDPRTGKSALDNGPQIAYVRD

FKAKVQYFRFWCQQLAMPQHIKITVTRKTLFEXSFQQXXSFSPQDLRXR

LWVIFPGEEGLDYGGVAREWFFLLSHEVLNPMYCLFEYAGKDNYCLQIN

PXSYINPDHLKYFRFIGRFIAMALFHGKFIDTGFSLPFXKRILNKPVGL

KDLESIDPEFYNSLIWVKENNIEECDLEMYFSVDKEILGEIKSHDLKPN

GGNILVTEENKEEYIRMVAEWRLSRGVEEQTQAFFEGFNEILPQQYLQY

FDAKELEVLLCGMQEIDLNDWQRHAIYRHYARTSKQIMWFWQFVKEIDN

EKRMRLLQFVTGTCRLPVGGFADLMGSNGPQKFCIXKVGKENWLPRSHT

CPNRLDLPPYKSYEQLKEKLLFAIEETEGFGQE.

Polynucleotides encoding these polypeptides are also encompassed by the invention.

This gene is expressed primarily in activated monocytes, whole brain, osteoclasts, colon, testes, and prostate tissues.

Therefore, polynucleotides and polypeptides of the invention are useful as reagents for differential identification of the tissue(s) or cell type(s) present in a biological sample and for diagnosis of diseases and conditions which include, but are not limited to, hematopoietic, skeletal, digestive, or neural disorders, particularly those involving proliferating tissues, such as cancers and tumors. Similarly, polypeptides and antibodies directed to these polypeptides are useful in providing immunological probes for differential identification of the tissue(s) or cell type(s). For a number of disorders of the above tissues or cells, particularly of the skeletal system and digestive system, expression of this gene at significantly higher or lower levels may be routinely detected in certain tissues or cell types (e.g., skeletal, neural, gastrointestinal, or cancerous and wounded tissues) or bodily fluids (e.g., lymph, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in monocytes indicates that polynucleotides and polypeptides corresponding to this gene are useful for the treatment and/or diagnosis of hematopoietic related disorders such as anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc.

In addition, this gene product may have commercial utility in the expansion of stem cells and committed progenitors of various blood lineages, and in the differentiation and/or proliferation of various cell types. Expression of this gene product in monocytes also strongly indicates a role for this protein in immune function and immune surveillance.

Alternatively, expression in neural tissues indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:100 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2337 of SEQ ID NO:100, b is an integer of 15 to 2351, where both a and b correspond to the positions of nucleotide residues shown in SEQ ID NO:100, and where b is greater than or equal to a+14.

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HBMSO46 | 209146 July 7, 1997 | Uni-ZAP XR | 11 | 975 | 132 | 846 | 273 | 273 | 107 | 1 | 19 | 20 | 36 |
| 2 | HBMWF85 | 209146 July 7, 1997 | Uni-ZAP XR | 12 | 2753 | 1121 | 1682 | 147 | 147 | 108 | 1 | 30 | 31 | 457 |
| 2 | HBMWF85 | 209146 July 7, 1997 | Uni-ZAP XR | 101 | 776 | 198 | 761 | 220 | 220 | 197 | 1 | 23 | 24 | 125 |
| 3 | HCDEJ37 | 209146 July 7, 1997 | Uni-ZAP XR | 13 | 1025 | 1 | 1025 | 556 | 556 | 109 | 1 | 30 | 31 | 103 |
| 3 | HCDEJ37 | 209146 July 7, 1997 | Uni-ZAP XR | 102 | 1065 | 1 | 1035 | 194 | 194 | 198 | 1 | 23 | 24 | 23 |
| 4 | HCE3L18 | 209146 July 7, 1997 | Uni-ZAP XR | 14 | 781 | 1 | 781 | 212 | 212 | 110 | 1 | 36 | 37 | 45 |
| 5 | HCYBI42 | 209146 July 7, 1997 | pBluescript SK- | 15 | 1040 | 620 | 1040 | 252 | 252 | 111 | 1 | 30 | 31 | 210 |
| 5 | HCYBI42 | 209146 July 7, 1997 | pBluescript SK- | 103 | 687 | 1 | 687 | 143 | 143 | 199 | 1 | 47 | 48 | 80 |
| 6 | HE6FB81 | 209146 July 7, 1997 | Uni-ZAP XR | 16 | 712 | 1 | 712 | 164 | 164 | 112 | 1 | 50 | 51 | 109 |
| 7 | HFAMB72 | 209146 July 7, 1997 | Uni-ZAP XR | 17 | 1323 | 509 | 1323 | 559 | 559 | 113 | 1 | 22 | 23 | 60 |
| 8 | HFCDW42 | 209146 July 7, 1997 | Uni-ZAP XR | 18 | 786 | 137 | 786 | 154 | 154 | 114 | 1 | 34 | 35 | 134 |
| 9 | HFPAE26 | 209146 July 7, 1997 | Uni-ZAP XR | 19 | 510 | 1 | 510 | 34 | 34 | 115 | 1 | 36 | 37 | 73 |
| 10 | HFXJM91 | 209146 July 7, 1997 | Lambda ZAP II | 20 | 750 | 186 | 721 | 306 | 306 | 116 | 1 | 20 | 21 | 87 |
| 11 | HHNAA05 | 209146 July 7, 1997 | pBluescript SK- | 21 | 838 | 1 | 838 | 36 | 36 | 117 | 1 | 16 | 17 | 36 |
| 12 | HJABX32 | 209146 July 7, 1997 | pBluescript SK- | 22 | 1061 | 454 | 1061 | 557 | 557 | 118 | 1 | 18 | 19 | 51 |
| 13 | HJMBW30 | 209146 July 7, 1997 | pCMVSport 3.0 | 23 | 884 | 1 | 874 | 110 | 110 | 119 | 1 | 18 | 19 | 42 |
| 14 | HSOAM40 | 209177 July 24, 1997 | Uni-ZAP XR | 24 | 711 | 1 | 711 | 168 | 168 | 120 | 1 | 20 | 21 | 32 |
| 15 | HSVAT02 | 209177 July 24, 1997 | Uni-ZAP XR | 25 | 507 | 1 | 507 | 141 | 141 | 121 | 1 | 20 | 21 | 45 |
| 16 | HSVBM90 | 209177 July 24, 1997 | Uni-ZAP XR | 26 | 2232 | 965 | 1654 | 105 | 105 | 122 | 1 | 37 | 38 | 178 |
| 17 | HSYBL17 | 209177 July 24, 1997 | pCMVSport 3.0 | 27 | 640 | 1 | 640 | 203 | 203 | 123 | 1 | 23 | 24 | 47 |
| 18 | HTEBI28 | 209177 July 24, 1997 | Uni-ZAP XR | 28 | 413 | 1 | 413 | 43 | 43 | 124 | 1 | 20 | 21 | 67 |
| 19 | HTPDS14 | 209177 July 24, 1997 | Uni-ZAP XR | 29 | 1122 | 70 | 885 | 205 | 205 | 125 | 1 | 37 | 38 | 74 |
| 20 | HTSGG36 | 209177 July 24, 1997 | pBluescript | 30 | 778 | 199 | 756 | 233 | 233 | 126 | 1 | 30 | 31 | 64 |
| 21 | HTTEU77 | 209177 July 24, 1997 | Uni-ZAP XR | 31 | 2476 | 1657 | 2476 | 1706 | 1706 | 127 | 1 | 46 | 47 | 60 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 22 | HTTFG10 | 209177 July 24, 1997 | Uni-ZAP XR | 32 | 691 | 1 | 691 | 308 | 308 | 128 | 1 | 28 | 29 | 31 |
| 23 | HTWEV82 | 209177 July 24, 1997 | pSport1 | 33 | 700 | 1 | 700 | 174 | 174 | 129 | 1 | 15 | 16 | 21 |
| 24 | HTXDB52 | 209177 July 24, 1997 | Uni-ZAP XR | 34 | 1722 | 696 | 1722 | 724 | 724 | 130 | 1 | 44 | 45 | 48 |
| 25 | HTXDP60 | 209177 July 24, 1997 | Uni-ZAP XR | 35 | 878 | 249 | 842 | 353 | 353 | 131 | 1 | 27 | 28 | 61 |
| 26 | HTXEB42 | 209177 July 24, 1997 | Uni-ZAP XR | 36 | 954 | 1 | 954 | 363 | 363 | 132 | 1 | 13 | 14 | 161 |
| 27 | HTXFB20 | 209177 July 24, 1997 | Uni-ZAP XR | 37 | 793 | 1 | 793 | 521 | 521 | 133 | 1 | 23 | 24 | 49 |
| 27 | HTXFB20 | 209177 July 24, 1997 | Uni-ZAP XR | 104 | 804 | 1 | 804 | 266 | 266 | 200 | 1 | 15 | 16 | 22 |
| 28 | HAIBX96 | 209177 July 24, 1997 | Uni-ZAP XR | 38 | 559 | 1 | 559 | 226 | 226 | 134 | 1 | 16 | 17 | 37 |
| 29 | HBAFZ29 | 209177 07/24/9.7 1997 | pSport1 | 39 | 1263 | 1 | 614 | 236 | 236 | 135 | 1 | 25 | 26 | 77 |
| 30 | HBAGY25 | 209177 July 24, 1997 | pSport1 | 40 | 455 | 1 | 455 | 122 | 122 | 136 | 1 | 16 | 17 | 30 |
| 31 | HBAHA77 | 209177 July 24, 1997 | pSport1 | 41 | 1128 | 524 | 1128 | 682 | 682 | 137 | 1 | 23 | 24 | 57 |
| 32 | HBJEW84 | 209177 July 24, 1997 | Uni-ZAP XR | 42 | 648 | 1 | 648 | 289 | 289 | 138 | 1 | 20 | 21 | 40 |
| 33 | HBJFE12 | 209177 July 24, 1997 | Uni-ZAP XR | 43 | 736 | 1 | 736 | 511 | 511 | 139 | 1 | 18 | 19 | 47 |
| 34 | HBZAJ83 | 209177 July 24, 1997 | pSport1 | 44 | 600 | 1 | 600 | 185 | 185 | 140 | 1 | 16 | 17 | 29 |
| 35 | HCFBM53 | 209177 July 24, 1997 | pSport1 | 45 | 687 | 232 | 687 | 322 | 322 | 141 | 1 | 42 | 43 | 45 |
| 36 | HCFBQ81 | 209177 July 24, 1997 | pSport1 | 46 | 697 | 1 | 697 | 154 | 154 | 142 | 1 | 40 | 41 | 85 |
| 37 | HCFCI07 | 209177 July 24, 1997 | pSport1 | 47 | 286 | 1 | 286 | 47 | 47 | 143 | 1 | 33 | 34 | 42 |
| 37 | HCFCI07 | 209177 July 24, 1997 | pSport1 | 105 | 373 | 1 | 373 | 128 | 128 | 201 | 1 | | | 8 |
| 38 | HCFDD76 | 209177 July 24, 1997 | pSport1 | 48 | 858 | 1 | 858 | 237 | 237 | 144 | 1 | 52 | 53 | 65 |
| 39 | HCFMJ81 | 209177 July 24, 1997 | pSport1 | 49 | 1307 | 1 | 1307 | 298 | 298 | 145 | 1 | 46 | 47 | 312 |
| 40 | HCFOG45 | 209177 July 24, 1997 | pSport1 | 50 | 606 | 115 | 603 | 359 | 359 | 146 | 1 | 56 | 57 | 58 |
| 40 | HCFOG45 | 209177 July 24, 1997 | pSport1 | 106 | 687 | 1 | 687 | 178 | 178 | 202 | 1 | | | 10 |
| 41 | HCUBN71 | 209177 July 24, 1997 | ZAP Express | 51 | 547 | 20 | 300 | 239 | 239 | 147 | 1 | 48 | 49 | 63 |
| 42 | HHEMA75 | 209179 July 24, 1997 | pCMVSport 3.0 | 52 | 865 | 229 | 865 | 569 | 569 | 148 | 1 | 35 | 36 | 84 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 43 | HHEPL34 | 209179 July 24, 1997 | pCMVSport 3.0 | 53 | 689 | 1 | 689 | 74 | 74 | 149 | 1 | 21 | 22 | 25 |
| 44 | HHPTJ65 | 209179 July 24, 1997 | Uni-ZAP XR | 54 | 515 | 1 | 515 | 247 | 247 | 150 | 1 | 32 | 33 | 48 |
| 45 | HHSDR11 | 209179 July 24, 1997 | Uni-ZAP XR | 55 | 747 | 85 | 747 | 464 | 464 | 151 | 1 | 34 | 35 | 63 |
| 46 | HHSDT26 | 209179 July 24, 1997 | Uni-ZAP XR | 56 | 676 | 1 | 676 | 42 | 42 | 152 | 1 | 26 | 27 | 33 |
| 47 | HJMAN03 | 209179 July 24, 1997 | pCMVSport 3.0 | 57 | 832 | 62 | 832 | 95 | 95 | 153 | 1 | 19 | 20 | 210 |
| 48 | HKGBS49 | 209179 July 24, 1997 | pSport1 | 58 | 1003 | 1 | 1003 | 193 | 193 | 154 | 1 | 30 | 31 | 114 |
| 49 | HKISA27 | 209179 July 24, 1997 | pBluescript | 59 | 702 | 1 | 702 | 22 | 22 | 155 | 1 | 16 | 17 | 227 |
| 50 | HKIXE06 | 209179 July 24, 1997 | pBluescript | 60 | 1095 | 348 | 1091 | 588 | 588 | 156 | 1 | 29 | 30 | 114 |
| 51 | HKMMV77 | 209179 July 24, 1997 | pBluescript | 61 | 867 | 1 | 867 | 684 | 684 | 157 | 1 | 15 | 16 | 46 |
| 52 | HLMIS23 | 209179 July 24, 1997 | Lambda ZAP II | 62 | 1134 | 85 | 1134 | 174 | 174 | 158 | 1 | 20 | 21 | 35 |
| 53 | HLWAT72 | 209179 July 24, 1997 | pCMVSport 3.0 | 63 | 1448 | 896 | 1448 | 933 | 933 | 159 | 1 | 24 | 25 | 37 |
| 54 | HILWAZ66 | 209179 July 24, 1997 | pCMVSport 3.0 | 64 | 756 | 1 | 756 | 59 | 59 | 160 | 1 | 18 | 19 | 29 |
| 55 | HLYAB80 | 209179 July 24, 1997 | pSport1 | 65 | 496 | 20 | 496 | 94 | 94 | 161 | 1 | 42 | 43 | 55 |
| 56 | HLYAG19 | 209179 July 24, 1997 | pSport1 | 66 | 557 | 1 | 557 | 173 | 173 | 162 | 1 | 43 | 44 | 69 |
| 57 | HLYBY48 | 209179 July 24, 1997 | pSport1 | 67 | 674 | 1 | 655 | 22 | 22 | 163 | 1 | 21 | 22 | 51 |
| 58 | HMUAW28 | 209179 July 24, 1997 | pCMVSport 3.0 | 68 | 794 | 1 | 794 | 195 | 195 | 164 | 1 | 24 | 25 | 103 |
| 59 | HMWHC36 | 209179 July 24, 1997 | Uni-Zap XR | 69 | 1915 | 506 | 1366 | 632 | 632 | 165 | 1 | 41 | 42 | 75 |
| 60 | HMWHS73 | 209179 July 24, 1997 | Uni-Zap XR | 70 | 733 | 1 | 733 | 75 | 75 | 166 | 1 | 21 | 22 | 37 |
| 61 | HNFIS82 | 209179 July 24, 1997 | pBluescript | 71 | 1266 | 568 | 1266 | 4 | 4 | 167 | 1 | 14 | 15 | 272 |
| 62 | HNGAZ20 | 209179 July 24, 1997 | Uni-ZAP XR | 72 | 485 | 1 | 485 | 78 | 78 | 168 | 1 | 19 | 20 | 25 |
| 63 | HNGBB17 | 209179 July 24, 1997 | Uni-ZAP XR | 73 | 639 | 1 | 639 | 105 | 105 | 169 | 1 | 23 | 24 | 25 |
| 64 | HNGBO16 | 209179 July 24, 1997 | Uni-ZAP XR | 74 | 532 | 1 | 532 | 75 | 75 | 170 | 1 | 47 | 48 | 132 |
| 65 | HNGBQ90 | 209179 July 24, 1997 | Uni-ZAP XR | 75 | 514 | 1 | 506 | 132 | 132 | 171 | 1 | 27 | 28 | 71 |
| 66 | HNGBV72 | 209179 July 24, 1997 | Uni-ZAP XR | 76 | 644 | 1 | 644 | 224 | 224 | 172 | 1 | 39 | 40 | 75 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 67 | HNGDQ52 | 209179 July 24, 1997 | Uni-ZAP XR | 77 | 1199 | 1 | 1199 | 15 | 15 | 173 | 1 | 24 | 25 | 31 |
| 68 | HNGEG08 | 209179 July 24, 1997 | Uni-ZAP XR | 78 | 660 | 1 | 660 | 94 | 94 | 174 | 1 | 35 | 36 | 66 |
| 69 | HNGFI02 | 209179 July 24, 1997 | Uni-ZAP XR | 79 | 524 | 1 | 524 | 95 | 95 | 175 | 1 | 35 | 36 | 128 |
| 70 | HNGGF85 | 209179 July 24, 1997 | Uni-ZAP XR | 80 | 434 | 1 | 434 | 51 | 51 | 176 | 1 | 33 | 34 | 45 |
| 71 | HNGHM75 | 209179 July 24, 1997 | Uni-ZAP XR | 81 | 735 | 1 | 735 | 261 | 261 | 177 | 1 | 28 | 29 | 41 |
| 72 | HNGIN84 | 209179 July 24, 1997 | Uni-ZAP XR | 82 | 722 | 1 | 722 | 210 | 210 | 178 | 1 | 36 | 37 | 72 |
| 73 | HNGJB81 | 209180 July 24, 1997 | Uni-ZAP XR | 83 | 785 | 1 | 785 | 69 | 69 | 179 | 1 | 22 | 23 | 30 |
| 74 | HNGJH08 | 209180 July 24, 1997 | Uni-ZAP XR | 84 | 570 | 1 | 570 | 88 | 88 | 180 | 1 | 18 | 19 | 72 |
| 75 | HNHAH01 | 209180 July 24, 1997 | Uni-ZAP XR | 85 | 905 | 1 | 905 | 328 | 328 | 181 | 1 | 42 | 43 | 54 |
| 76 | HNHET53 | 209180 July 24, 1997 | Uni-ZAP XR | 86 | 706 | 1 | 706 | 122 | 122 | 182 | 1 | 23 | 24 | 66 |
| 77 | HOABP21 | 209180 July 24, 1997 | Uni-ZAP XR | 87 | 1544 | 463 | 1544 | 647 | 647 | 183 | 1 | 50 | 51 | 73 |
| 78 | HODAA12 | 209180 July 24, 1997 | Uni-ZAP XR | 88 | 840 | 1 | 833 | 66 | 66 | 184 | 1 | | | 44 |
| 79 | HOEFO68 | 209180 July 24, 1997 | Uni-ZAP XR | 89 | 510 | 1 | 510 | 65 | 65 | 185 | 1 | 23 | 24 | 97 |
| 80 | HOVAP06 | 209180 July 24, 1997 | pSport1 | 90 | 738 | 1 | 738 | 153 | 153 | 186 | 1 | 25 | 26 | 61 |
| 81 | HPEAE34 | 209180 July 24, 1997 | Uni-ZAP XR | 91 | 506 | 1 | 506 | 282 | 282 | 187 | 1 | 26 | 27 | 40 |
| 82 | HPTRO86 | 209180 July 24, 1997 | pBluescript | 92 | 1203 | 158 | 944 | 163 | 163 | 188 | 1 | 46 | 47 | 153 |
| 83 | HSAXJ60 | 209180 July 24, 1997 | Uni-ZAP XR | 93 | 710 | 1 | 710 | 244 | 244 | 189 | 1 | 15 | 16 | 59 |
| 84 | HSAXM32 | 209180 July 24, 1997 | Uni-ZAP XR | 94 | 1750 | 1 | 1750 | 817 | 817 | 190 | 1 | 63 | 64 | 108 |
| 85 | HSDEW29 | 209180 July 24, 1997 | Uni-ZAP XR | 95 | 606 | 1 | 606 | 55 | 55 | 191 | 1 | 19 | 20 | 29 |
| 86 | HSDZR95 | 209180 July 24, 1997 | pBluescript | 96 | 617 | 1 | 617 | 32 | 32 | 192 | 1 | 18 | 19 | 22 |
| 87 | HSKND71 | 209180 July 24, 1997 | pBluescript | 97 | 634 | 1 | 634 | 58 | 58 | 193 | 1 | 20 | 21 | 105 |
| 88 | HSOAC84 | 209180 July 24, 1997 | Uni-ZAP XR | 98 | 512 | 1 | 512 | 318 | 318 | 194 | 1 | 34 | 35 | 53 |
| 89 | HSRAL66 | 209180 July 24, 1997 | Uni-ZAP XR | 99 | 944 | 1 | 909 | 151 | 151 | 195 | 1 | 21 | 22 | 97 |
| 90 | HSRFB56 | 209180 July 24, 1997 | Uni-ZAP XR | 100 | 2351 | 1543 | 2351 | 1774 | 1774 | 196 | 1 | 22 | 23 | 24 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X and the translated SEQ ID NO:Y are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs. Species homologs may be isolated and identified by making suitable probes or primers from the sequences provided herein and screening a suitable nucleic acid source for the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, prosequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified by the one-step method described in Smith and Johnson, Gene 67:31–40 (1988). Polypeptides of the invention also can be purified from natural or recombinant sources using antibodies of the invention raised against the secreted protein in methods which are well known in the art.

Signal Sequences

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. These polypeptides, and the polynucleotides encoding such polypeptides, are contemplated by the present invention.

Polynucleotide and Polypeptide Variants

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is becuase the FASTDB program does not account for N- and C-terminal truncations of the subject sequence when calculating global percent identity. For subject sequences truncated at the N- and C-termini, relative to the the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

In the present invention, a "polynucleotide fragment" refers to a short polynucleotide having a nucleic acid sequence contained in the deposited clone or shown in SEQ ID NO:X. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:X. These nucleotide fragments are useful as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Epitopes & Antibodies

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998–4002 (1983).)

Fragments which function as epitopes may be produced by any conventional means. (See, e.g., Houghten, R. A., Proc. Natl. Acad. Sci. USA 82:5131–5135 (1985) further described in U.S. Pat. No. 4,631,211.)

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., Cell 37:767–778 (1984); Sutcliffe, J. G. et al., Science 219:660–666 (1983).)

Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316–325 (1983).) Thus, these fragments are preferred, as well as the products of a FAB or other immunoglobulin expression library. Moreover, antibodies of the present invention include chimeric, single chain, and humanized antibodies.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination (see, e.g., U.S. Pat. No. 5,641, 670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Biological Activities

The polynucleotides and polypeptides of the present invention can be used in assays to test for one or more biological activities. If these polynucleotides and polypeptides do exhibit activity in a particular assay, it is likely that these molecules may be involved in the diseases associated with the biological activity. Thus, the polynucleotides and polypeptides could be used to treat the associated disease.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity, and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair color, eye color, skin, percentage of adipose tissue, pigmentation, size, and shape (e.g., cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1

Isolation of a Selected cDNA Clone from the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
| --- | --- |
| Lambda Zap | pBluescript (pBS) |
| Uni-Zap XR | pBluescript (pBS) |
| Zap Express | pBK |
| lafmid BA | pLafmid BA |
| pSport1 | pSport1 |
| pCMVSport 2.0 | pCMVSport 2.0 |
| pCMVSport 3.0 | pCMVSport 3.0 |
| pCR ® 2.1 | pCR ® 2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK–, KS+ and KS. The S and K refers to the orientation of the polylinker to the T7 and T3 primer sequences which flank the polylinker region ("S" is for SacI and "K" is for KpnI which are the first sites on each respective end of the linker). "+" or "–" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into E. coli strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into E. coli strain XL-1 Blue. Vector pCR®2.1, which is available from Invitrogen, 1600 Faraday Avenue, Carlsbad, Calif. 92008, contains an ampicillin resistance gene and may be transformed into E. coli strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 µl of reaction mixture with 0.5 ug of the above cDNA template. A convenient reaction mixture is 1.5–5 mM $MgCl_2$, 0.01% (w/v) gelatin, 20 µM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript: (Fromont-Racine et al., Nucleic Acids Res. 21(7) :1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3
Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Amp$^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the $E.$ $coli$ strain M15/rep4 (Qiagen, Inc.) which contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an $E.$ $coli$ origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in $E$ $coli$ when it is present in the form of inclusion bodies. Unless otherwise specified, all of the following steps are conducted at 4–10° C.

Upon completion of the production phase of the $E.$ $coli$ fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000× g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five μg of a plasmid containing the polynucleotide is co-transfected with 1.0 μg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One μg of BaculoGold™ virus DNA and 5 μg of the plasmid are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pC-MVSport 3.0. Mammalian host cells that could be used include, human Hela, 293, H9 and Jurkat cells, mouse NIH3T3 and C127 cells, Cos 1, Cos 7 and CV1, quail QC1–3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five μg of the expression plasmid pC6 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region: (SEQ ID NO:1)
GGGATCCGGAGCCCAAATCTTCTGACAAAACTCACACATGCCCACCGTG

CCCAGCACCTGAATTCGAGGGTGCACCGTCAGTCTTCCTCTTCCCCCCA

AAACCCAAGGACACCCTCATGATCTCCCGGACTCCTGAGGTCACATGCG

TGGTGGTGGACGTAAGCCACGAAGACCCTGAGGTCAAGTTCAACTGGTA

CGTGGACGGCGTGGAGGTGCATAATGCCAAGACAAAGCCGCGGGAGGAG

CAGTACAACAGCACGTACCGTGTGGTCAGCGTCCTCACCGTCCTGCACC

AGGACTGGCTGAATGGCAAGGAGTACAAGTGCAAGGTCTCCAACAAAGC

CCTCCCAACCCCCATCGAGAAAACCATCTCCAAAGCCAAAGGGCAGCCC

CGAGAACCACAGGTGTACACCCTGCCCCCATCCCGGGATGAGCTGACCA

AGAACCAGGTCAGCCTGACCTGCCTGGTCAAAGGCTTCTATCCAAGCGA

CATCGCCGTGGAGTGGGAGAGCAATGGGCAGCCGGAGAACAACTACAAG

ACCACGCCTCCCGTGCTGGACTCCGACGGCTCCTTCTTCCTCTACAGCA

AGCTCACCGTGGACAAGAGCAGGTGGCAGCAGGGGAACGTCTTCTCATG

CTCCGTGATGCATGAGGCTCTGCACAACCACTACACGCAGAAGAGCCTC

TCCCTGTCTCCGGGTAAATGAGTGCGACGGCCGCGACTCTAGAGGAT

Example 10

Production of an Antibody from a Polypeptide

The antibodies of the present invention can be prepared by a variety of methods. (See, Current Protocols, Chapter 2.) For example, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μ/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production of Secreted Protein for High-Throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at 2× $10^5$ cells/well in 0.5 ml DMEM (Dulbecco's Modified Eagle Medium) (with 4.5 G/L glucose and L-glutamine (12-604F Biowhittaker))/10% heat inactivated FBS (14-503F Biowhittaker)/1×Penstrep (17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1% BSA in DMEM with 1× penstrep, or CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$-$H_2O$; 71.02 mg/L of $Na_2HPO4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1×penstrep. (BSA (81-068-3 Bayer) 100 gm dissolved in 1L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37° C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| Ligand | JAKs tyk2 | Jak1 | Jak2 | Jak3 | STATS | GAS(elements) or ISRE |
|---|---|---|---|---|---|---|
| IFN family | | | | | | |
| IFN-a/B | + | + | − | − | 1,2,3 | ISRE |
| IFN-g | | + | + | − | 1 | GAS (IRFT>Lys6>IFP) |
| IL-10 | + | ? | ? | − | 1,3 | |
| gp130 family | | | | | | |
| IL-6 (Pleiotrophic) | + | + | + | ? | 1,3 | GAS (IRF1>Lys6>IFP) |
| I1-11(Pleiotrophic) | ? | + | ? | ? | 1,3 | |
| OnM(Pleiotrophic) | ? | + | + | ? | 1,3 | |
| LTF(Pleiotrophic) | ? | + | + | ? | 1,3 | |
| CNTF(Pleiotrophic) | −/+ | + | + | ? | 1,3 | |
| G-CSF(Pleiotrophic) | ? | + | ? | ? | 1,3 | |
| IL-12(Pleiotrophic) | + | − | + | + | 1,3 | |
| g-C family | | | | | | |
| IL-2 (lymphocytes) | − | + | − | + | 1,3,5 | GAS |
| IL-4 (lymph/myeloid) | − | + | − | + | 6 | GAS (IRF1 = IFP>>Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1>IFP>>Ly6) |
| IL-5 (myeloid) | − | − | + | − | 5 | GAS |
| GM-CSE (myeloid) | − | − | + | − | 5 | GAS |
| Growth hormone family | | | | | | |
| GH | ? | − | + | − | 5 | |
| PRL | ? | +/− | + | − | 1,3,5 | |
| EPO | ? | − | + | − | 5 | GAS(B-CAS>IRF1=IFP>>Ly6) |
| Receptor Tyrosine Kinases | | | | | | |
| EGF | ? | + | + | − | 1,3 | GAS(IRE1) |
| PDGF | ? | + | + | − | 1,3 | |
| CSE-1 | ? | + | + | − | 1,3 | GAS (not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:

(SEQ ID NO:3)
5':GCGCCTCGAGATTTCCCCGAAATCTAGACCCCGAAATGATTTCCC

CGAAATGATTTCCCCGAAATATCTGCCATCTCAATTAG:3'

The downstream primer is complementary to the SV40 promoter and is flanked with a Hind III site: 5':GCG-GCAAGCTTTTTGCAAAGCCTAGGC:3' (SEQ ID NO:4)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

(SEQ ID NO:5)
5':CTCGAGATTTCCCCGAAATCTAGATTTCCCCGAAATGATTTCCCCG

AAATGATTTCCCCGAAATATCTGCCATCTCAATTAGTCAGCAACCATAG

TCCCGCCCCTAACTCCGCCCATCCCGCCCCTAACTCCGCCCAGTTCCGC

CCATTCTCCGCCCCATGGCTGACTAATTTTTTTTATTTATGCAGAGGCC

GAGGCCGCCTCGGCCTCTGAGCTATTCCAGAAGTAGTGAGGAGGCTTTT

TTGGAGGCCTAGGCTTTTGCAAAAAGCTT:3'

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, Il-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13

High-Throughput Screening Assay for T-Cell Activity

The following protocol is used to assess T-cell activity by identifying factors, such as growth factors and cytokines, that may proliferate or differentiate T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI +10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI +10% serum, 1 mg/ml Genticin, and 1% Pen-Strep. These cells are treated with supernatants containing a polypeptide as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 17. The plates containing the remaining treated cells are placed at 4° C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14

High-Throughput Screening Assay Identifying Myeloid Activity

The following protocol is used to assess myeloid activity by identifying factors, such as growth factors and cytokines, that may proliferate or differentiate myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest $2 \times 10e^7$ U937 cells and wash with PBS. The U937 cells are usually grown in RPMI 1640 medium containing 10% heat-inactivated fetal bovine serum (FBES) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4 \cdot 7H_2O$, 1 mM $MgCl_2$, and 675 uM $CaCl_2$. Incubate at 37° C. for 45 min.

Wash the cells with RPMI 1640 medium containing 10% FBS and then resuspend in 10 ml complete medium and incubate at 37° C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS. Suspend the cells in 200 ml above described growth medium, with a final density of $5 \times 10^5$ cells/ml. Plate 200 ul cells per well in the 96-well plate (or $1 \times 10^5$ cells/well).

Add 50 ul of the supernatant prepared by the protocol described in Example 11. Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat pheno-chromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

(SEQ ID NO:6)
5' GCGCTCGAGGGATGACAGCGATAGAACCCCGG-3'

(SEQ ID NO:7)
5'GCGAAGCTTCGCGACTCCCCGGATCCGCCTC-3'

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 ul of the cell suspension to each well of 96-well plate (equivalent to $1 \times 10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-Throughput Screening Assay for T-Cell Activity

NF-κB (Nuclear Factor κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from apoptosis), B and T-cell development, anti-viral and antimicrobial responses, and multiple stress responses.

In non-stimulated conditions, NF-κB is retained in the cytoplasm with I-κB (Inhibitor κB). However, upon stimulation, I-κB is phosphorylated and degraded, causing NF-κB to shuttle to the nucleus, thereby activating transcription of target genes. Target genes activated by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 11. Activators or inhibitors of NF-kB would be useful in treating diseases. For example, inhibitors of NF-κB could be used to treat those diseases related to the acute or chronic activation of NF-kB, such as rheumatoid arthritis.

To construct a vector containing the NF-κB promoter element, a PCR based strategy is employed. The upstream primer contains four tandem copies of the NF-κB binding site (GGGGACTTTCCC) (SEQ ID NO:8), 18 bp of sequence complementary to the 5' end of the SV40 early promoter sequence, and is flanked with an XhoI site:

```
                                          (SEQ ID NO:9)
5':GCGGCCTCGAGGGGACTTTCCCGGGGACTTTCCGGGGACTTTCCGG

GACTTTCCATCCTGCCATCTCAATTAG:3'
```

The downstream primer is complementary to the 3' end of the SV40 promoter and is flanked with a Hind III site:

```
5':GCGGCAAGCTTTTTGCAAAGCCTAGGC-3'    (SEQ ID NO:4)
```

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confabs the insert contains the following sequence:

```
                                              (SEQ ID NO:10)
5':CTCGAGGGGACTTTCCCGGGGACTTTCCGGGGACTTTCCGGGACTT

TCCATCTGCCATCTCAATTAGTCAGCAACCATAGTCCCGCCCCTAACTC

CGCCCATCCCGCCCCTAACTCCGCCCAGTTCCGCCCATTCTCCGCCCCA

TGGCTGACTAATTTTTTTTATTTATGCAGAGGCCGAGGCCGCCTCGGCC

TCTGAGCTATTCCAGAAGTAGTGAGGAGGCTTTTTTGGAGGCCTAGGCT

TTTGCAAAAAGCTT:3'
```

Next, replace the SV40 minimal promoter element present in the pSEAP2-promoter plasmid (Clontech) with this NF-κB/SV40 fragment using XhoI and HindIII. However, this vector does not contain a neomycin resistance gene, and therefore, is not preferred for mammalian expression systems.

In order to generate stable mammalian cell lines, the NF-κB/SV40/SEAP cassette is removed from the above NF-κB/SEAP vector using restriction enzymes SalI and NotI, and inserted into a vector containing neomycin resistance. Particularly, the NF-κB/SV40/SEAP cassette was inserted into pGFP-1 (Clontech), replacing the GFP gene, after restricting pGFP-1 with SalI and NotI.

Once NF-κB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1, 1, 10 ng) is added to wells H9, H10, and H11, with a 5–10 fold activation typically observed.

Example 17

Assay for SEAP Activity

As a reporter molecule for the assays described in Examples 13–16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 μl of 2.5× dilution buffer into Optiplates containing 35 μl of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 μl Assay Buffer and incubate at room temperature 5 min. Empty the dispenser and prime with the Reaction Buffer (see the table below). Add 50 μl Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/ well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to $2-5\times10^6$ cells/ml with HBSS in a 50-ml conical tube. 4 ul of 1 mg/ml fluo-4 solution in 10% pluronic acid DMSO is added to each ml of cell suspension. The tube is then placed in a 37° C. water bath for 30–60 min. The cells are washed twice with HBSS, resuspended to $1\times10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular $Ca^{++}$ concentration.

Example 19

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4° C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$_{2+}$ (5 mM ATP/50 mM MgCl$_2$), then 10 ul of 5× Assay Buffer (40 mM imidazole hydrochloride, pH7.3, 40 mM beta-glycerophosphate, 1 mM EGTA, 100 mM MgCl$_2$, 5 mM MnCl$_2$, 0.5 mg/ml BSA), then 5 ul of Sodium Vanadate (1 mM), and then 5 ul of water. Mix the components gently and preincubate the reaction mix at 30° C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phosphotyrosine antibody conjugated to horse radish peroxidase (anti-P-Tyr-POD (0.5 u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSAIPBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95° C. for 30 seconds; 60–120 seconds at 52–58° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton, T. A. and Graham, M. W., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(-)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-mil vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 24

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 27

Method of Treatment Using Gene Therapy—in vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. N.Y. Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization. and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 28

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tall tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 29

Knock-Out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated polypeptide comprising amino acid residues 2 to 47 of SEQ ID NO:139.

2. The isolated polypeptide of claim 1 which comprises amino acid residues 1 to 47 of SEQ ID NO:139.

3. The isolated polypeptide of claim 1 which is fused to a polypeptide sequence heterologous to SEQ ID NO:139.

4. The composition comprising the isolated polypeptide of claim 1 and an acceptable carrier.

5. An isolated polypeptide produced by the method comprising:
   (a) expressing the polypeptide of claim 1 by a cell; and
   (b) recovering said polypeptide.

6. An isolated protein comprising the amino acid sequence of the complete polypeptide encoded by the HBJFE12 cDNA contained in ATCC Deposit No. 209177, excepting the N-terminal methionine.

7. The isolated protein of claim 6 which comprises the amino acid sequence of the complete polypeptide encoded by the HBJFE12 cDNA contained in ATCC Deposit No. 209177.

8. The protein of claim 6 which is fused to a polypeptide sequence heterologous to SEQ ID NO:139.

9. A composition comprising the protein of claim 6 and an acceptable carrier.

10. An isolated protein produced by the method comprising:
    (a) synthesizing the protein of claim 6 in a cell; and
    (b) recovering said protein.

11. An isolated polypeptide consisting of at least amino acid residues 19 to 47 of SEQ ID NO:139, wherein said isolated polypeptide is capable of being used to generate or select an antibody that specifically binds amino acid residues 19 to 47 of SEQ ID NO:139.

12. The isolated polypeptide of claim 11 which is fused to a polypeptide sequence heterologous to SEQ ID NO:139.

13. A composition comprising the isolated polypeptide claim 11 and an acceptable carrier.

14. An isolated polypeptide produced by the method comprising:
    (a) synthesizing the polypeptide of claim 11 in a cell; and
    (b) recovering said polypeptide.

15. An isolated protein consisting of at least the secreted portion of the polypeptide encoded by the HBJFE12 cDNA contained in ATCC Deposit No. 209177, wherein said isolated protein is capable of being used to generate or select an antibody that specifically binds the polypeptide encoded by the HBJFE12 cDNA contained in ATCC Deposit No. 209177.

16. The isolated protein of claim 15 which is fused to a polypeptide sequence heterologous to SEQ ID NO:139.

17. A composition comprising the isolated protein of claim 15 and an acceptable carrier.

18. An isolated protein produced by the method comprising:
    (a) synthesizing the protein of claim 15 in a cell; and
    (b) recovering said polypeptide.

19. An isolated protein consisting of at least 30 contiguous amino acid residues of amino acid residues 1 to 47 of SEQ ID NO:139, wherein said isolated protein is capable of being used to generate or select an antibody that specifically binds amino acid residues 1 to 47 of SEQ ID NO:139.

20. The isolated protein of claim 19 which is fused to a polypeptide sequence heterologous to SEQ ID NO:139.

21. A composition comprising the isolated protein of claim 19 and an acceptable carrier.

22. An isolated protein produced by the method comprising:
    (a) synthesizing the protein of claim 19 in a cell; and
    (b) recovering said protein.

23. An isolated protein consisting of at least 30 contiguous amino acid residues of the complete polypeptide encoded by the HBJFE12 cDNA contained in ATCC Deposit No. 209177, wherein said isolated protein is capable of being used to generate or select an antibody that specifically binds the complete polypeptide encoded by the HBJFE12 cDNA contained in ATCC Deposit No. 209177.

24. The isolated protein of claim 23 which is fused to a polypeptide sequence heterologous to SEQ ID NO:139.

25. A composition comprising the isolated protein of claim 23 and an acceptable carrier.

26. An isolated protein produced by the method comprising:
    (a) synthesizing the protein of claim 23 in a cell; and
    (b) recovering said protein.

* * * * *

SEQUENCE LISTING

<160> NUMBER OF SEQ ID NOS: 371

<210> SEQ ID NO 1
<211> LENGTH: 733
<212> TYPE: DNA
<213> ORGANISM: Homo sapiens

<400> SEQUENCE: 1

| gggatccgga | gcccaaatct | tctgacaaaa | ctcacacatg | cccaccgtgc | ccagcacctg | 60 |
| aattcgaggg | tgcaccgtca | gtcttcctct | tccccccaaa | acccaaggac | accctcatga | 120 |
| tctcccggac | tcctgaggtc | acatgcgtgg | tggtggacgt | aagccacgaa | gaccctgagg | 180 |
| tcaagttcaa | ctggtacgtg | gacggcgtgg | aggtgcataa | tgccaagaca | aagccgcggg | 240 |
| aggagcagta | caacagcacg | taccgtgtgg | tcagcgtcct | caccgtcctg | caccaggact | 300 |
| ggctgaatgg | caaggagtac | aagtgcaagg | tctccaacaa | agcccctccca | accccccatcg | 360 |
| agaaaaccat | ctccaaagcc | aaagggcagc | cccgagaacc | acaggtgtac | accctgcccc | 420 |
| catcccggga | tgagctgacc | aagaaccagg | tcagcctgac | ctgcctggtc | aaaggcttct | 480 |
| atcccagcga | catcgccgtg | gagtgggaga | gcaatgggca | gccggagaac | aactacaaga | 540 |
| ccacgcctcc | cgtgctggac | tccgacggct | ccttcttcct | ctacagcaag | ctcaccgtgg | 600 |
| acaagagcag | gtggcagcag | gggaacgtct | tctcatgctc | cgtgatgcat | gaggctctgc | 660 |
| acaaccacta | cacgcagaag | agcctctccc | tgtctccggg | taaatgagtg | cgacggccgc | 720 |
| gactctagag | gat | | | | | 733 |

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally
      ocurring L-amino acids

<400> SEQUENCE: 2

Trp Ser Xaa Trp Ser
 1               5

<210> SEQ ID NO 3
<211> LENGTH: 86
<212> TYPE: DNA
<213> ORGANISM: Homo sapiens

<400> SEQUENCE: 3

| gcgcctcgag | atttccccga | aatctagatt | tccccgaaat | gatttccccg | aaatgatttc | 60 |
| cccgaaatat | ctgccatctc | aattag | | | | 86 |

<210> SEQ ID NO 4
<211> LENGTH: 27
<212> TYPE: DNA
<213> ORGANISM: Homo sapiens

<400> SEQUENCE: 4

| gcggcaagct | ttttgcaaag | cctaggc | | | | 27 |

<210> SEQ ID NO 5
<211> LENGTH: 271

```
<212> TYPE: DNA
<213> ORGANISM: Homo sapiens

<400> SEQUENCE: 5
ctcgagattt ccccgaaatc tagatttccc cgaaatgatt tccccgaaat gatttccccg    60
aaatatctgc catctcaatt agtcagcaac catagtcccg cccctaactc cgcccatccc   120
gcccctaact ccgcccagtt ccgcccattc tccgcccat ggctgactaa ttttttttat    180
ttatgcagag gccgaggccg cctcggcctc tgagctattc cagaagtagt gaggaggctt   240
ttttggaggc ctaggctttt gcaaaaagct t                                  271

<210> SEQ ID NO 6
<211> LENGTH: 32
<212> TYPE: DNA
<213> ORGANISM: Homo sapiens

<400> SEQUENCE: 6
gcgctcgagg gatgacagcg atagaaccc gg                                   32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c                                   31

<210> SEQ ID NO 8
<211> LENGTH: 12
<212> TYPE: DNA
<213> ORGANISM: Homo sapiens

<400> SEQUENCE: 8
ggggactttc cc                                                        12

<210> SEQ ID NO 9
<211> LENGTH: 73
<212> TYPE: DNA
<213> ORGANISM: Homo sapiens

<400> SEQUENCE: 9
gcggcctcga ggggactttc cggggacttt ccggggactt tccatcctg               60 ccatctcaat tag                                                      73

<210> SEQ ID NO 10
<211> LENGTH: 256
<212> TYPE: DNA
<213> ORGANISM: Homo sapiens

<400> SEQUENCE: 10
ctcgagggga ctttcccggg gactttccgg gactttccgg gactttcca tctgccatct    60 caattagtca gcaaccatag tcccgcccct aactccgccc atcccgcccc taactccgcc   120
cagttccgcc cattctccgc cccatggctg actaatttt tttatttatg cagaggccga   180
ggccgcctcg gcctctgagc tattccagaa gtagtgagga ggcttttttg gaggcctagg   240
cttttgcaaa aagctt                                                   256

<210> SEQ ID NO 11
<211> LENGTH: 975
<212> TYPE: DNA
```

<213> ORGANISM: Homo sapiens
<220> FEATURE:
<221> NAME/KEY: SITE
<222> LOCATION: (970)
<223> OTHER INFORMATION: n equals a,t,g, or c
<221> NAME/KEY: SITE
<222> LOCATION: (973)
<223> OTHER INFORMATION: n equals a,t,g, or c

<400> SEQUENCE: 11

```
gggtcgaccc acgcgtcsgt gcttaccagc tctaggccag ggcagatggg atatgacgaa    60
tggactgcca gctggataca aggatgctca ccaagcacca agttctcaca agttatttta   120
tgtgactttg caggaactga ggcattatat ctgaggacac caggggaaaa gtgtggcatc   180
tcagggaaat acagccctgg gctgtgtcta cacacaccat gagagtgctg atgggggcgc   240
aatagtcttg aaaatgtata agtgtccag gaatggaagt gctctttgat tcattattat    300
tttcttcctt catattcccc tcccagagtc tcctatctag gacatcagca ttctcacaca   360
agcctaatgg cttatctgag taagcagggc ttagaaattc actttcttga tactcagtct   420
tgccttctaa acactccttg atcttgccta cctctcccct tttccacatg tctttcctg    480
taggaacact ttctccattt attcctgcct atccaattct tccctatatt tcctggacca   540
gctaaagtcc agtgtttcca gagacttttg aaagtcaact tacactttt  ccttcttcat   600
tcacaaagct cttcttccct gggccctggt atgtatgcct ttctctccta ctgtctaata   660
gcacctcgta aattgtcaat gaactttct aagggtatt cttgaattcc caactagatt    720
gtgagcttct ggaagacaag gctatgtctt tgattgttgt ctccctacc acagcccagt    780
actttagtta cagaaaataa taatatttta ctgattgatt gactttcctc ttgtccacta   840
gctttagggt ttggggggcca aattytaccc tgggatttk aaaaattcaa actgtgaaca   900
ccacaatgtt atagagcata ttaggtagta gccagcatga agggatgttt tcttcctgag   960
aaacagtgtn aangg                                                    975
```

<210> SEQ ID NO 12
<211> LENGTH: 2753
<212> TYPE: DNA
<213> ORGANISM: Homo sapiens

<400> SEQUENCE: 12

```
ggcacgaggg gacatggagg tgggaggccc ccactcccct gcagtcacta ggtccaacca    60
ctccctccct gccctcagtg gcagacctgt gccaggacgg gcatggtggc tgcagtgagc   120
acgccaactg tagccaggta ggaacaatgg tcacttgtac ctgcctgccc gactacgagg   180
gtgatggctg gagctgccgg gcccgcaacc cctgcacaga tggccaccgc gggggctgca   240
gcgagcacgc caactgcttg agcaccggcc tgaacacacg gcgctgtgag tgccacgcag   300
gctacgtagg cgatggactg cagtgtctgg aggagtcgga accacctgtg accgctgct   360
tgggccagcc accgccctgc cactcagatg ccatgtgmac tgacctgcac ttccaggaga   420
aacgggctgg cgtttccac ctccaggcca ccagcggccc ttatggtctg aacttttcgg   480
aggctgaggc ggcatgcgaa gcacagggag ccgtccttgc ttcattccct cagctctctg   540
ctgcccagca gctgggcttc cacctgtgcc tcatgggctg gctggccaat ggctccactg   600
cccaccctgt ggttttccct gtggcggact gtggcaatgg tcgggtgggc rtagtcagcc   660
tgggtgcccg caagaacctc tcagaacgct gggatgccta ctgcttccgt gtgcaagatg   720
tggcctgccg atgccgaaat ggcttcgtgg gtgacgggat cagcacgtgc aatgggaagc   780
```

```
tgctggatgt gctggctgcc actgccaact tctccacctt ctatgggatg ctattgggct    840
atgccaatgc cacccagcgg ggtctcgact tcctggactt cctggatgat gagctcacgt    900
ataagacact cttcgtccct gtcaatgaag gctttgtgga caacatgacg ctgagtggcc    960
cagacttgga gctgcatgcc tccaacgcca ccctcctaag tgccaacgcc agccagggga   1020
agttgcttcc ggcccactca ggcctcagcc tcatcatcag tgacgcaggc cctgacaaca   1080
gttcctgggc ccctgtggcc ccagggacag ttgtggttag ccgtatcatt gtgtgggaca   1140
tcatggcctt caatggcatc atccatgctc tggccagccc cctcctggca cccccacagc   1200
cccaggcagt gctggcgcct gaagccccac ctgtggcggc aggcgtgggg gctgtgcttg   1260
ccgctggagc actgcttggc ttggtggccg gagctctcta cctccgtgcc cgaggcaagc   1320
ccatgggctt tggcttctct gccttccagg cggaagatga tgctgatgac gacttctcac   1380
cgtggcaaga agggaccaac cccacccctg tctctgtccc caaccctgtc tttggcagcg   1440
acacctttg tgaacccttc gatgactcac tgctggagga ggacttccct gacacccaga   1500
ggatcctcac agtcaagtga cgaggctggg gctgaaagca gaagcatgca cagggaggag   1560
accacttta ttgcttgtct gggtggatgg ggcaggaggg gctgagggcc tgtcccagac   1620
aataaaggtg ccctcagcgg atgtgggcca tgtcaccaag gaagggggtc ttcatgcagc   1680
cggtgcagag ctggtccatc cagaggggtg cctcgtgctg cagcggcgta cggcgtgggt   1740
agaaggtgaa gtccacgcgg tagttgagca ggcagctgag ggaggccatg tagaggtcag   1800
agaagcgcac gaggcgcctt gagaagtagg tggggttgtg gaaggtgcgg aagatgctgc   1860
cgaactgcgc attgaacagg gccttggtga tgcacctcag ctcctgccgc tctttcatcc   1920
aggcagccag cacctgcctc gactccgcgt cctgataggt ctgcatgcgc tccagcagcc   1980
ccgtgagcgc ctgctgccac gtcagcgagt gcatgtactg ctccgtgttg atgatgcgga   2040
tctcacgctc cagctcgggg atgatggcgc ctgtgcgcca gccgtgccgc agcatgagat   2100
ccgccagatc actatagagg tggtccccga agtagagcac gcgggggcca cgccattccg   2160
tcaagcgtaa gaagtcaaac aggtttccct gccgatagat cttgcccttt tccaagcggg   2220
tgatccggtc ccactgaagt gagcccttct catcgagttt tctgaaagct tgcgccggtc   2280
agtgaagaag ctgggcttgt ctgcctggac aatgaccaca tcgaagagct ggcgccaatc   2340
gggacccacc atgtgccgca tccccttgtc tacgaagctg aaaggactgt tggtgatgag   2400
gaacagctgt ttcccatggg ccaccaggcg gctcaggaca gcaaacgtct catcccctct   2460
caggatgtac ttctccatgt cctgctcgat ccactggtac atgaggccct tcacatgcac   2520
gtctcggatg gcgtccgtca cgtccttgta gagatgtgct tggtcaaact ccaggctgtg   2580
gcccagaaag tagtccacca cacaggacag cagagccatc tccggtagcg agaagatgtc   2640
catgaactgc ttaatggagg gacccttgcc atagaagcca ctcatctggt atagtgggat   2700
gtgctgggta cccccataca gctcaatcac ctcctcgtct ggcacaggct ggc           2753

<210> SEQ ID NO 13
<211> LENGTH: 1025
<212> TYPE: DNA
<213> ORGANISM: Homo sapiens

<400> SEQUENCE: 13
tttttttttt tttttttttt tttttttttt tttttcaaa tccaactttt atttattaaa     60
ttaaaaaaaa aagactccac aaagggcatg atccccttcca ttccacaatg ttctctcccc   120
aagctccagc ggctttaacc ctttaacttg gggccttgag acagcagggg acagaaaagg   180
```

-continued

```
aggatccaac gttacaggaa aggcacgaag cggctttaaa agtcactgga ggtggagatg      240
ggagcatcca aagtcccagg gtgggggtgc gtggatgcac caccagatca gcttgggggc      300
ctctgtcctc ctagctcttt aagttctttc tcagggcttc taggcaccag atctagcata      360
gtgccttgca cagagtaggc actcaataca tacttgattt atttgaatct gatcctagag      420
aaagccttcc ccacccattc ttcaggaggt gcacccccaa accaatgtcc tcctgttaga      480
tgggcttccc caaagagcac atctaagatg gcagctgcaa gctctccata accatggcaa      540
caggggatta acctgatggg gtcatggtgt ctaaggggtg gggcagtgga ggaacctgct      600
ctgcagtcaa gggagatggg gtacattcca gtccttctcc cctccatagg acttgaggtt      660
tcacagcttc tggctgggc tggggatatt agggatcccc ctaatcaaga gatacccat       720 caactgttta gcagagatgt agctaaccca atttgtagag acttcattac aagagaaacc      780
ctatcaactg agattctgat gatagacatt ctattaacaa gatcttctcc actaacattt      840
tgtctataca gagatgcatt tgactagaat ttccttagca gaaatggatc cacttccctc      900
cccagctcac tctacctgac ccgtcatcat aacttacata aatagaatta ttactattca      960
ttactcctgg tacataggg ttaaatatac aggcctgggg gcagcctccc tgaccctctc      1020
gtgcc                                                                 1025
```

<210> SEQ ID NO 14
<211> LENGTH: 781
<212> TYPE: DNA
<213> ORGANISM: Homo sapiens

<400> SEQUENCE: 14

```
gaattcggca cgagaagagt atcatatgca gagtttccct tggtaaacat atttaaaata       60
aataaatctg gaagtgtctg agagtcaaaa atgtggtgca tgcaatatat gatgtaaaac      120
aaaggcgggt ggtttacgta gctcagcaga caagacgcca gatggtatgt atgcttgatt      180
gaaagtaccc acctgttatt ctgcgaacac aatgggagga acagaatcct acatttcctc      240
atccccttta ctgaggactc tccttctttc atacttagta tttttatatt acctgtatct      300
attattctac gtggcaagaa gtccttttgg gaaggcagag tataaataat gtagttttat      360
taatagataa gtattagtaa aactttgcat tagaagatgt atgactgacg ttgcatagag      420
ttgtgtgatg tagagtaata ttccatggtg tacacatcca taattatgtt tgccgaaaca      480 tgaatacct actacaggtc tttgtgatag acatcaggt ggggatgcat aggggacaaa      540
aatgtacaca attttgtgtc tgctctcaga gagattacat agtaggagag aagacccag       600 tattaaaaaa tagaataaag gcaagtgccc caaatctttg tcattaattt tractggaag      660
agaggcttag gaaagatgag acatttaagc attgcatgga ggaaaaaaga agtagatctc      720
cttggcaggt ggataggcta ggacattcca aactgagaaa aaaaaaaaaa aaacgscacg      780
a                                                                     781
```

<210> SEQ ID NO 15
<211> LENGTH: 1040
<212> TYPE: DNA
<213> ORGANISM: Homo sapiens
<220> FEATURE:
<221> NAME/KEY: SITE
<222> LOCATION: (33)
<223> OTHER INFORMATION: n equals a,t,g, or c

<400> SEQUENCE: 15

-continued

```
cctggcaggt accggctccg gtaattcccg ggntcgaccc acgcgtccgc ggcgcccgta      60
agcggacgct gttaggggtg gcgggggggtt ggcggcggtt cgagaggctc tgggccggca    120
gtctaagctc tcgcagcctg gctcttgcag ccgcaccctc aagcaacgga tccccatggc    180
gcttgttggg cgcgttgtgc ctgcagcggc cacctgtagt ctccaagccg ttgaccccat    240
tgcaggaaga gatggcgtct ctactgcagc agattgagat agagagaagc ctgtattcag    300
accacgagct tcgtgctctg gatgaaaacc agcgactggc aaagaagaaa gctgaccttc    360
atgatgaaga agatgaacag gatatattgc tggcgcaaga tttggaagat atgtgggagc    420
agaaatttct acagttcaaa cttggagctc gcataacaga agctgatgaa agaatgacc     480 gaacatccct gaacaggaag ctagacagga accttgtcct gttagtcaga gagaagtttg    540
gagaccagga tgtttggata ctgccccagg cagagtggca gcctgggggag acccttcgag    600 gaacagctga acgaaccctg gccacactct cagaaaacaa catggaagcc aagttcctag    660
gaaatgcacc ctgtgggcac tacacattca agttccccca gcaatgcgg acagagagta    720 acctcggagc caaggtgttc ttcttcaaag cactgctatt aactggagac ttttcccagg    780
ctgggaataa gggccatcat gtgtgggtca ctaaggatga gctgggtgac tatttgaaac    840
caaaatacct ggcccaagtt aggaggtttg tttcagacct ctgatgggcc gagctgcctg    900
tggacggtgc tcagacaagt ctgggattag agcctcaagg acattgtgtg attgcctcac    960
atttgcaggt aatatcaagc agcaaactaa attctgagaa ataaacgagt ctattacwaa   1020
aaaaaaaaaa aaaaatcgca                                               1040
```

<210> SEQ ID NO 16
<211> LENGTH: 712
<212> TYPE: DNA
<213> ORGANISM: Homo sapiens

<400> SEQUENCE: 16

```
gaattcggca cgagagcycc ctctccatgg gatacctgt ggggcacttc agagtcccca     60
ccagcaagaa ggctctctct caccagatgt gcccccccgcc aaccttggat gtctcagtct   120
ccagaactca gatgagccag ctcccttgtg aagctgtaag aacatggtac ttacaggagt   180
aaggctcatg aagtggagag atgagaagac tttcgggaca gattgtgtgg aggctgtcat   240
tctcctcgtg acattgctgt gggagaagaa ggaggcattc catgttggct tcagtgaaga   300
acttcagtat tttccagaga gaagtactga gaagcttaaa gtatttgaat gggaggagga   360
gaagcaaact acagctactt cagaggataa cactaaacac ctagtccact ctgtatacac   420
tagaggtgct gttaattttc ttgtggaaa ggaactgtct ttagaaaaat atctcaaaaa    480
gccactgaag tagaaagttt cagcatgctg aagatgaac ttgagaagat agaaagttct    540
gggtccttag tggcatgact gagtcgctgg accactgttg gaaccaccct atgtcttagt    600
ttttaaatct ctttactgtc taagacattt ttagtggaag tatttatctc tggcatccaa    660
taagaccttt aaggatttgc agttttaaaa aaaaaaaaa aaaaaaactc ga             712
```

<210> SEQ ID NO 17
<211> LENGTH: 1323
<212> TYPE: DNA
<213> ORGANISM: Homo sapiens
<220> FEATURE:
<221> NAME/KEY: SITE
<222> LOCATION: (1086)
<223> OTHER INFORMATION: n equals a,t,g, or c
<221> NAME/KEY: SITE
<222> LOCATION: (1087)

<223> OTHER INFORMATION: n equals a,t,g, or c

<400> SEQUENCE: 17

| | | | | | |
|---|---|---|---|---|---|
| gctgaagatg | gggtccctcg | cacggcacgg | tccatgtccc | tcacgctggg | aaagaatatg | 60 |
| cctcgccgga | ggtcagcgtt | gctgtggttc | ctaagtttaa | tgccctgaat | ctgcctggcc | 120 |
| aaactcccag | ctcatcatcc | attccctcct | taccagcctt | gtcggaatca | cccaatggga | 180 |
| aaggcagcct | acctgtcact | tcagcactgc | ctgcactttt | ggaaaatgga | agacaaatg | 240 |
| gggacccaga | ttgtgaagcc | tctgctcctg | cgctgaccct | gagctgcctg | ggaggagctt | 300 |
| agtcaggaga | ccaaggccag | gatggaggaa | gaagcctaca | gcaagggatt | ccaagaaggt | 360 |
| ytaaagaaga | ccaaagaact | tcaagacctg | aaggaggagg | aggaagaaca | gaagagtgag | 420 |
| agtcctgagg | aacctgaaga | ggtagaagaa | actgaggaag | aggaaaaggg | cccaagaagc | 480 |
| agcaaacttg | aagaattggt | ccatttctta | caagtcatgt | atcccaaact | gtgtcagcac | 540 |
| tggcaagtga | tctggatgat | ggctgcagtg | atgctggtct | tgactgttgt | gctgggctc | 600 |
| tacaattcct | ataactcttg | tgcagagcag | gctgatgggc | ccttggaag | atccacttgc | 660 |
| tcggcagccc | cagggactcc | tggtggagct | caggactcca | gcatgagcag | cctacagagc | 720 |
| agtaggaaac | ctcacaccta | gccagtgccc | tgctctgaga | cactcagact | accaccctt | 780 |
| ccccaagtat | aacgtcaggc | ccaagtgtgg | acacactgcc | gcccatccca | tcaggtcatg | 840 |
| aggaagggtt | cttttaacac | tcggcacttc | tgtgggagct | attcatacac | agtgacttga | 900 |
| tgttcttgga | ggatcaacaa | aactgccctg | ggaaagcatc | cagtggatga | agaagtcacc | 960 |
| ttcaccaagg | aactctattg | gaagggaagg | tctcctgccc | ctagctcagg | tggctgggga | 1020 |
| gaactaaaac | accttcactg | gtggttgggg | gtaaggagcg | gggcacgggg | gaggaggagg | 1080 |
| tagggnncag | taaaaaactt | actctctttt | ttcctctctg | taattggtta | tcaggaagaa | 1140 |
| tttgcttaat | gactaacacc | ctaagcatca | gacctggaat | ttggagttgc | aaagtgacta | 1200 |
| tcttcccatt | tcccatctca | ttttcaataa | cttcagcctc | ccattctttc | ctttggaatg | 1260 |
| agagtttctt | tttacagaag | taggaaaggc | ttctcagaaa | aaaaaaaaaa | aaaaaaaact | 1320 |
| cga | | | | | | 1323 |

<210> SEQ ID NO 18
<211> LENGTH: 786
<212> TYPE: DNA
<213> ORGANISM: Homo sapiens

<400> SEQUENCE: 18

| | | | | | |
|---|---|---|---|---|---|
| cccacccggg | gagggtcgtt | gtgcgcctgc | ccagggtggg | ggttgccgtc | gcgcctaggc | 60 |
| cttttccctca | ggttttcctc | ttccccactg | cggctcccca | gtcggcgctt | gcgggagaac | 120 |
| tcagcgctga | gattgtctaa | agccccagga | aaaatggtgg | aaaattcacc | gtcgccattg | 180 |
| ccagaaagag | cgatttatgg | ctttgttctt | ttcttaagct | cccaatttgg | cttcatactt | 240 |
| tacctcgtgt | gggccttat | tcctgaatct | tggctaaact | cttaggtttt | aacctattgg | 300 |
| cctcaaaaat | attgggcagt | tgcattacct | gtctacctcc | ttattgctat | agtaattggc | 360 |
| tacgtgctct | tgtttgggat | taacatgatg | agtacctctc | cactcgactc | catccataca | 420 |
| atcacagata | actatgcaaa | aaatcaacag | cagaagaaat | accaagagga | ggccattcca | 480 |
| gccttaagag | atatttctat | tagtgaagta | aaccaaatgt | tctttcttgc | agccaaagaa | 540 |
| ctttacacca | aaaactgaac | tgtgtgtaac | catagtaaca | ccaagcacgt | atttatttat | 600 |
| aagtttttgc | cattataatt | ttgaccataa | attaatttga | ccatctctct | tattaataga | 660 |

```
gaagtaaaaa atgtaagttg accttctctt agattatgtt caatgaatat tgtaaatgtt      720
caagtattgt taatgaatag aataaataca atattgcatt cccaaaaaaa aaaaaaaaaa      780
actcga                                                                786

<210> SEQ ID NO 19
<211> LENGTH: 510
<212> TYPE: DNA
<213> ORGANISM: Homo sapiens
<220> FEATURE:
<221> NAME/KEY: SITE
<222> LOCATION: (2)
<223> OTHER INFORMATION: n equals a,t,g, or c

<400> SEQUENCE: 19 gnaccccgg gctgcaggaa ttcggcmcga gaaatgaggc ttcagcctga catctgtaac       60
ctccccacca accctctgag tctgaagttg ggcttgatgc tgttatcact gacccttttgt    120 ttggagaaaa cagtccaagg tttgaaattg ggtctatgtt tattcaaact aagcttctct    180
gagcacatgg tctgtcccac tcatcctcag agtatccgtt ggttttactt catgttcaga    240
ctgcagtgtt gttaaagaaa taaagctaca gtgttttcag aaggatttgt tatattatac    300
ttcatgttcc cactgctcca ggctaagcgt ctcctctggg ctccattgtt taatgcagga    360
caaagccagg ttttctggca gcttcctttt catagcaatt ctcagtagag gtatagaatg    420
agacctgcct accttcttgg gtgtttatta ccccatttgt ggattttact ttaacttctg    480
ttaccttaaa aaaaaaaaaa aaaaactcga                                     510

<210> SEQ ID NO 20
<211> LENGTH: 750
<212> TYPE: DNA
<213> ORGANISM: Homo sapiens
<220> FEATURE:
<221> NAME/KEY: SITE
<222> LOCATION: (749)
<223> OTHER INFORMATION: n equals a,t,g, or c

<400> SEQUENCE: 20
gagctgcctg atggaaagaa gagaagaaag gtcctggcgc tccctcaca ccgaggcccc      60 aaaatcaggt tgcgggacaa aggcaaagtg aagcccgtcc atcccaaaaa gccaaagcca    120
cagataaacc agtggaagca ggagaagcag caattatcgt ccgagcaggt atctaggaaa    180
aaagctaagg gaataagac ggaaacccgc ttcaaccagc tggtcgaaca atataagcag    240
aaattattgg gaccttctaa aggagcacct cttgcaaaga ggagcaaatg gtttgatagt    300
tgatgatggc agcaggctgg gtaagaagct gggttgtgta cttttctggtg acactcctgg    360 gctcctcccc atccccgtg tctctcactg agggaaagaa aatccccaag ggcactgcca    420
ctgtgctcgg aggtgccctg gactgtgtac atctgaactt tggtccatcc tttgatgtgt    480
ggttcgttag ccacaaagag aaatatctga agtcaacat gatgcttctt gcatattatc    540
cagattattg tatgaagttg tgtctataat tattaccaat ttttattctt tatttctcaa    600
atggaaacac ctgaaaaagc attctggagt gctgaatttt taagatgtat attttgttaa    660
gcatattctc taaatgagat attgtgtggc tttttagtaa caacgtcatt tctaataaaa    720
aaaaaaaaaa aaaagaaaa gaaaaaaana                                      750

<210> SEQ ID NO 21
<211> LENGTH: 838
<212> TYPE: DNA
```

<213> ORGANISM: Homo sapiens

<400> SEQUENCE: 21

```
gaattcggca cgaggagcca ctgcggctgg ccaagatgct ttatattctt ttaaaaccat      60
tgttgtgtct atctgttaac tgcacaaata tttaccaaat gcttaccaag agccaaggac     120
tagacttggc actgggtaga aactagtaag gcatggtcct tcttctacat agaatcttag     180
cattttagag atgagttccc agacatggtc cagaaggtca cagttcacac cattaggcaa     240
ggcagtattt gaaataaaag tcatgtctaa tactaaatcc agtatgttct ctccttcagg     300
attttactct cattgctgcc ccttggtttg ctatgctctt ccccagacag ctgcacagct     360
catttaattt agatctcatt taatttagat ctctcaatta atttagatct ctgttaaaaa     420
aaaaaaaag ccctaggcag caaggtctaa catatcatcc tcaaattaaa gagaaagccc      480
tttggtgtta tttttcttta tagcacttac caactcccag tagaatgtaa actccagtag     540
ggcacatatc tttgcctctt ttatttactg ctctattccc agcaccagaa cagtccttgc     600
cacaaagtag gtgctcaata aacatttggt gaatgaatta acctagtgtt cttttttacct    660
acacatgcac acacagagcc atgacactcc tgccgaggaa gctcgcggct ctaagaggga    720
cattaaagaa aagccaattc agtgcctgcc aaagagtaga acatgttttg acagcaggat    780
cagcttgggt ggtggaccaa caatgggttg cagaccaaga aaaaaaaaaa aaactcga     838
```

<210> SEQ ID NO 22
<211> LENGTH: 1061
<212> TYPE: DNA
<213> ORGANISM: Homo sapiens
<220> FEATURE:
<221> NAME/KEY: SITE
<222> LOCATION: (138)
<223> OTHER INFORMATION: n equals a,t,g, or c
<221> NAME/KEY: SITE
<222> LOCATION: (460)
<223> OTHER INFORMATION: n equals a,t,g, or c
<221> NAME/KEY: SITE
<222> LOCATION: (473)
<223> OTHER INFORMATION: n equals a,t,g, or c
<221> NAME/KEY: SITE
<222> LOCATION: (1048)
<223> OTHER INFORMATION: n equals a,t,g, or c

<400> SEQUENCE: 22

```
acaccaatgg agacataatt gtgggcagac tatgacaacc gttgggtcag catcttctcc      60
cctgaggggc aagttcaaga ccaagattgg agctgggccg cctcatgggc ccaagggag     120
tggccgtaga ccggaatnga catatcattg tggtcgacaa caagtcttgc tgcgtcttta    180
ccttccagcc caatggcaaa ctggttggcc gttttggggg ccgtgggcc actgaccgcc     240
actttgcagg gccccatttt gtggctgtga acaacaagaa tgaaattgta gtaacggact    300
tccataacca ttcagtgaag gtgtacagtc ccgatggaga gttcctcttc aagtttggct    360
cccatggcga gggcaatggg cagttcaatg ccccacagg agtagctgtg gactccaatg    420
gaaacatcat tgtggctgac tggggcaaca gccgcatccn aggtattcga canctctggc    480
tccttcctgt cctatatcaa cacatctgca gaaccactgt atggtccaca gggcctggca    540
ctgacctcgg atggccatgt ggtggtggct gatgctggca accactgctt taaagcctat    600
cgctacctcc agtagctgta cagaggccct gcctggcttg tgagggaca gacattgggg    660
tgattggaca agagggtctg gctgggaggt gggccagacc tggcagcact gaatgtgggc    720
tgtgggcatg ggtgcacccg gtgccctccc tctcctaccc ccaccccac ggttgcactt     780
```

| | |
|---|---|
| tatttattcg gttcttgctt tggtgactgg gtgagcctgg actgtggtcc caaggatgtg | 840 |
| tgcagagctt caccctaccc ttcttacaca cctcccacc cctgtcagtc tgctccccat | 900 |
| cccccagcct ggggccagaa cagcctaccc caggacagga gtccctctag ttgtctccct | 960 |
| accaccctat acacactgac agagacagca atacccacc cccatatta aataaatgtc | 1020 |
| ttcaccaaga aaaaaaaaa aaaaaaanac tcgcggcacg a | 1061 |

<210> SEQ ID NO 23
<211> LENGTH: 884
<212> TYPE: DNA
<213> ORGANISM: Homo sapiens
<220> FEATURE:
<221> NAME/KEY: SITE
<222> LOCATION: (307)
<223> OTHER INFORMATION: n equals a,t,g, or c
<221> NAME/KEY: SITE
<222> LOCATION: (356)
<223> OTHER INFORMATION: n equals a,t,g, or c

<400> SEQUENCE: 23

| | |
|---|---|
| tcgacccacg cgtccgccgg atggttgcca cccctcctgc tgtaggatgg aagcagccat | 60 |
| ggagtgggag ggaggcgcaa taagacaccc ctccacagag cttggcatca tgggaagctg | 120 |
| gttctacctc ttcctggctc ctttgtttaa aggcctggct gggagccttc cttttgggtg | 180 |
| tctttctctt ctccaaccag cagaaaagac tgctcttcaa agtggaggt cttcatgaaa | 240 |
| cacagctgcc aggagcccag gcacaggctg ggggcctgga aaaggaggg cacacaggag | 300 |
| gagggangga gctggtaggg gagatgctgg gctttaccta agtctcgaaa caaggnggca | 360 |
| gaataggcag aggcctctcc gttccaggcc cattttgac aratggcggg acggaaatgc | 420 |
| aatagaccag cctgcaaraa aracatgtgt tttgatgaca ggcagtgtgg ccgggtggaa | 480 |
| caagcacagg ccttggaatc ccaatggact gaatcagaac cctaggcctg ccatctgtca | 540 |
| gccgggtgac ctgggtcaat tttagcctct aaaagcctca gtctccttat ctgcaaaatg | 600 |
| aggcttgtga tacctgtttt gaagggttgc tgagaaaatt aaagataagg gtatccaaaa | 660 |
| tagtctacgg ccataccacc ctgaacgtgc ctaatctcgt aagctaagca gggtcaggcc | 720 |
| tggttagtac ctggatgggg agagtatgga aaacatacct gcccgcagtt ggagttggac | 780 |
| tctgtcttaa cagtagcgtg gcacacagaa ggcactcagt aaatacttgt tgaataaatg | 840 |
| aagtagcgat ttggtgtgaa aaaaaaaaa aaaaaaaaa aaac | 884 |

<210> SEQ ID NO 24
<211> LENGTH: 711
<212> TYPE: DNA
<213> ORGANISM: Homo sapiens

<400> SEQUENCE: 24

| | |
|---|---|
| atagggcgat tggtacgggg cccccctcg agtttttttt tttttttttt tttagagaca | 60 |
| gagtcttgct ctgtcaccta ggctggagta cagtggcgtg atcatagctc actgtaacct | 120 |
| tgaactcctg ggcttgagca accctcctgg cacaatctcc ttgaatgatg ggtcccaaga | 180 |
| gccagacaga acggacttcc tcccttatgc ctcatcaagt tagagagaga agagctcaca | 240 |
| tccccaaat gcctatgaac ataactct actgattcct gacctgacct gccttggcct | 300 |
| caagagggcc aaatgctcaa ttccttgagt tcaaatcttt ttccctgtat ttctcacct | 360 |
| gtggggtcca cctctgtccc tctgactcac agaatgtgac tgcccccctc cttcttatga | 420 |
| tagtccttca gaggtctgaa gacagaaagc atatcttcct tgagtcttct ctaagttgaa | 480 |

-continued

```
tactcccaat cacccccaaac agagtagtgc agtgcaggaa aagtatagtt ttgtgatcag     540
agttgtattc aaaattccat atcacaactt actaactaca tgacctagag tatgttcttt     600
cacctcacag aggcaggagc attgtgagga ttaaagcgcc tagccaggaa taggccatag     660
tatgtgctca ataaatgata cttctcaaga taacaatctc gtgccgaatt c              711
```

<210> SEQ ID NO 25
<211> LENGTH: 507
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c
<221> NAME/KEY: SITE
<222> LOCATION: (10)
<223> OTHER INFORMATION: n equals a,t,g, or c
<221> NAME/KEY: SITE
<222> LOCATION: (48)
<223> OTHER INFORMATION: n equals a,t,g, or c

<400> SEQUENCE: 25

```
ctcgaantan ccccactaag ggaacaaagc tggagctcca cgcggtgncg gccgctctar      60
aactagtgga tcccccgggc tgcaggaatt cggcacgagc ttttccaaaa tggctgtact     120
aatttacatt cccaccaaca atgttcaagg atttcatatt cttgacattc ttaccaaaat     180
tgtcacagtt tgtaaaaggt agtctaataa gtggcctaag tgaatgtgac aacacttcat     240
tgaaagcaat cttaggtttt tccaactata gtcaataata acttaattgt acattctaaa     300
ataactcaaa gagtgtaatt ggattgcttg taacttaaag gataaatgct tgagggatg     360 gatgcctcat tctccatgat gtgcttattt cacattgcat gcctgtatca aaacattaca     420
tttatcccat aatatacaca cttactatgt accccaaaa aataaacatt aaaattaagt     480
tttcaaaaaa aaaaaaaaaa aactcga                                         507
```

<210> SEQ ID NO 26
<211> LENGTH: 2232
<212> TYPE: DNA
<213> ORGANISM: Homo sapiens
<220> FEATURE:
<221> NAME/KEY: SITE
<222> LOCATION: (715)
<223> OTHER INFORMATION: n equals a,t,g, or c

<400> SEQUENCE: 26

```
ctcccaggcc cgcgaacttg gccattcagc cgccgctgtc cccgctgcgc gccctcgcgc      60
ctctgcctga raagccaggc gctgttcccc caccccagaa gaggatggca aaggtggcta     120
aggacctcaa cccaggagtt aaaaagatgt ccctgggcca gctgcagtca gcaagaggtg     180
tggcatgttt gggatgcaag gggacgtgtt cgggcttcga gccacattca tggaggaaaa     240
tatgcaagtc ttgcaaatgc agccaagagg accactgcct aacatctgac ctagaagacg     300
atcggaaaat tggccgcttg ctgatggact ccaagtattc caccctcact gctcgggtga     360
aaggcgggga cggcatccgg atttacaaga ggaaccggat gatcatgacc aaccctattg     420
ctactgggaa agatcccact tttgacacca tcacctacga gtgggctccc cctggagtca     480
cccagaaact gggactgcag tacatggagc tcatccccaa ggagaagcag ccagtgacag     540
gcacagaggg tgcttttacc gccgccgcca gctcatgcac cagctcccca tctatgacca     600
ggatccctcg cgctgccgtg gacttttgga gaatgagttg aaactgatgg aagaatttgt     660
caagcaatat aagagcgagg ccctcggcgt gggagaagtg gccctcccgg ggcangggtg     720
```

```
gcttgccaag gaggagggga agcagcagga aaagccagag ggggcagaga ccaytgctgy      780
taccaccaac ggcaktytca gtgacccgtc caaagaagaa gcgtgctagc cagtcccact      840
cgtgtgataa cccattaatc tattaagcca taagtggatt aatccattcc tgaggacctg      900
agccctcacg acccaatcat ctcttaaagg ccccacctct caatactgcc atgcagagga      960
ttatgtttca acctgagtgt ttggagggga tgttcaaccc ataggaagtg gcagtgtgga     1020
agaagtgctg ctgaggagtg agtcactggg ggccattttg agaaaacaga aaggagaagc     1080
cagagttggg gagatgaaag cctcatggct tggtttgtct taaactgccc cacagaaggc     1140
gaaaggaatg cttgaggctg gaccacgtgg gtctagcgtg tactgcgttt ctggtcccca     1200
gcccctgttt tacctttttgc tcctcctgcc ccatcaacca agtgtcttca tttgtttcta     1260
tggcaattaa ctttttggaga tagaagtccc agcacacgag atccccaagc acattatcta     1320
ccttgctgaa caggctggca gtcacacatg agccaggcga cccagggaaa tgccagccca     1380
aacgaagctg ctgccacatc cagagagggc cggactcttt ctcccttgta gtcactcaag     1440
ctaatcatcc aaaacctgca tcctccatct ccaagcccca tcttattagc accatctggg     1500
attgccaacc aagaaactgt tttatctgag aactctaaga ccaaagaaca agatttattt     1560
cctctactac agatttggca gtgacgcata aaaggcccat ttctcaggaa gaatacatgt     1620
cctaaggatg taaaaaaaaa aaaaatatta gatctagtta ccatggkcta taaactggtc     1680
ttttcccgcc ccaccctgat cctggcttct gtccacctc aaatagctgt ttgktcataa      1740
accctaaata ctagataatt ctaagttgga aggagacctc taagtcactg tagcatttcc     1800
aaatcgccat tcccaagaga catgtggatc tgacatcgtg ttttattctt gactgagcct     1860
cgcayatttg ttctgtgtgg aacaaaggca aaggcagccc aagaacccgg gtccttgcct     1920
acagtcagct ttaggaaatg attgtgaact tgggaagcat ttaaatagca atactagaca     1980
gtaaatggaa aaggccaaag tcagaaaata agtagggatt ccaaaggaag cctttattgg     2040
ttgggctagg ctgggctagc tgtggaagat agacttctat gtccctgccc caaccacaat     2100
tttactttaa ttattatgta attagtgaat cgatgtctgt caccgtctgt agatgctgag     2160
gtcttgttca tctcttttatt tgcattgata tacatagcca ttgctcaata aatatgtgac     2220
ccatgaaaaa aa                                                         2232

<210> SEQ ID NO 27
<211> LENGTH: 640
<212> TYPE: DNA
<213> ORGANISM: Homo sapiens
<220> FEATURE:
<221> NAME/KEY: SITE
<222> LOCATION: (1)
<223> OTHER INFORMATION: n equals a,t,g, or c
<221> NAME/KEY: SITE
<222> LOCATION: (4)
<223> OTHER INFORMATION: n equals a,t,g, or c
<221> NAME/KEY: SITE
<222> LOCATION: (15)
<223> OTHER INFORMATION: n equals a,t,g, or c
<221> NAME/KEY: SITE
<222> LOCATION: (17)
<223> OTHER INFORMATION: n equals a,t,g, or c
<221> NAME/KEY: SITE
<222> LOCATION: (21)
<223> OTHER INFORMATION: n equals a,t,g, or c

<400> SEQUENCE: 27
nggngtgacc tatanangta nccttcagta ccgtccggaa ttcccgggtc gacccacgcg       60
```

-continued

| | |
|---|---|
| tccgaggaga tgcttcaaaa tgtcaattgc tttaaactta aattacctct caagagacca | 120 |
| aggtacattt acctcattgt gtatataatg tttaatattt gtcagagcat tctccaggtt | 180 |
| tgcagtttta tttctataaa gtatgggtat tatgttgctc agttactcaa atggtactgt | 240 |
| attgtttata tttgtacccc aaataacatc gtctgtactt tctgttttct gtattgtatt | 300 |
| tgtgcaggat tctttaggct ttatcagtgt aatctctgcc ttttaagata tgtacagaaa | 360 |
| atgtccatat aaatttccat tgaagtcgaa tgatactgag aagcctgtaa agaggagaaa | 420 |
| aaaacataag ctgtgtttcc ccataagttt tttaaattg tatattgtat ttgtagtaat | 480 |
| attccaaaag aatgtaaata ggaaatagaa gagtgatgct tatgttaagt cctaacacta | 540 |
| cagtagaaga atggaagcag tgcaaataaa ttacattttt cccaaaaaaa aaaaaaaaa | 600 |
| aaaaaagggc ggccgctcta gaggatccct cgagggccc | 640 |

<210> SEQ ID NO 28
<211> LENGTH: 413
<212> TYPE: DNA
<213> ORGANISM: Homo sapiens
<220> FEATURE:
<221> NAME/KEY: SITE
<222> LOCATION: (407)
<223> OTHER INFORMATION: n equals a,t,g, or c
<221> NAME/KEY: SITE
<222> LOCATION: (408)
<223> OTHER INFORMATION: n equals a,t,g, or c
<221> NAME/KEY: SITE
<222> LOCATION: (409)
<223> OTHER INFORMATION: n equals a,t,g, or c

<400> SEQUENCE: 28

| | |
|---|---|
| gaattcggca cgagtgcagc ttcattttgg gctgccttag ccatgaagct cctttttgctg | 60 |
| actttgactg tgctgctgct cttatcccag ctgactccag gtggcaccca agatgctgg | 120 |
| aatctttatg gcaaatgccg ttacagatgc tccaagaagg aaagagtcta tgtttactgc | 180 |
| ataaataata aaatgtgctg cgtgaagccc aagtaccagc caaaagaaag gtggtggcca | 240 |
| ttttaactgc tttgaagcct gaagccatga aaatgcagat gaagctccca gtggattccc | 300 |
| acactccatc aataaacacc tctggctgaa aaaaaaaaaa aaraaaaaaa araraaaaaa | 360 |
| aagaaaaaaa actcaagggg gggcccggta cccattcgcc ctatgtnnnt cgt | 413 |

<210> SEQ ID NO 29
<211> LENGTH: 1122
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<221> NAME/KEY: SITE
<222> LOCATION: (948)
<223> OTHER INFORMATION: n equals a,t,g, or c
<221> NAME/KEY: SITE
<222> LOCATION: (1107)
<223> OTHER INFORMATION: n equals a,t,g, or c
<221> NAME/KEY: SITE
<222> LOCATION: (1116)
<223> OTHER INFORMATION: n equals a,t,g, or c
<221> NAME/KEY: SITE
<222> LOCATION: (1121)
<223> OTHER INFORMATION: n equals a,t,g, or c

<400> SEQUENCE: 29

| | |
|---|---|
| ggcanagcta accgcagtct ctactacttc ctcttcgccc ccaccttgtg ctacgagctc | 60 |
| aactttcccc gctctcccg catccggaag cgctttctgc tgcgacggat ccttgagatg | 120 |

```
ctgttcttca cccagctcca ggtggggctg atccagcagt ggatggtccc caccatccag      180
aactccatga agcccttcaa ggacatggac tactcacgca tcatcgagcg cctcctgaag      240
ctggcggtcc ccaatcacct catctggctc atcttcttct actggctctt ccactcctgc      300
ctgaatgccg tggctgagct catgcagttt ggagaccggg agttctaccg ggactggtgg      360
aactccgagt ctgtcaccta cttctggcag aactggaaca tccctgtgca caagtggtgc      420
atcaggtagg tggggtgtgt gtgtgtgtga tgtggaacat ggctgtgaac ctgaaccgct      480
ttccatgccc cctcctctgc agacacttct acaagcccat gcttcgacgg ggcagcagca      540
agtggatggc caggacaggg gtgttcctgg cctcggcctt cttccacgag tacctggtga      600
gcgtccctct gcgaatgttc cgcctctggg ckttcacggg catgatggct cagatcccac      660
tggcctggtt cgtgggccgc ttttccagg gcaactatgg caacgcagct gtgtggctgt      720
cgctcatcat cggacagcca atagccgtcc tcatgtacgt ccacgactac tacgtgctca      780
actatgaggc cccagcggca gaggcctgag ctgcacctga gggcctggct tctcactgcc      840
acctcacacc cgctgccaga gcccacctct cctcctaggc ctcgagtgct ggggatgggc      900
ctggctgcac agcatcctcc tctggtccca gggaggcctc tctgcccnta tgggctctg      960 tcctgcaccc ctcagggatg cgacagcag gccagacaca gtctgatgcc agctgggagt     1020
cttgctgacc ctgccccggg tccgagggtg tcaataaagt gctgtccagt gaaaaaaaaa     1080
aaaaaaaaac tcgagggggg gcccggnacc caattngccc na                       1122
```

<210> SEQ ID NO 30
<211> LENGTH: 778
<212> TYPE: DNA
<213> ORGANISM: Homo sapiens

<400> SEQUENCE: 30

```
ggttctctgg ccaagaggag caattttcgt gccatcagca aaaagctgaa tttgatccca       60
cgtgtggacg gcgagtatga tctgaaagtg ccccgagaca tggcttacgt cttcrgtggt      120
gcttatgtgc ccctgagctg ccgaatcatt gagcaggtgc tagagcggcg astgcaggg      180 ccttgatgag gtggtacggc tgctcaactg magtgacttt gcattcacag atatgactaa      240
ggaagacaag gcttccagtg agtccctgcg cctcatcttg gtggtgttct tgggtggttg      300
tacattctct gagatctcag ccctccggtt cctgggcaga gagaaaggct acaggttcat      360
tttcctgacg acagcagtca caaacagcgc tcgccttatg gaggccatga gtgaggtgaa      420
agcctgatgt ttttcccggc cagtgttgac atcttccctg aacacattcc tcagtgagat      480
gcaggcatct ggcacccagc tgctataacc aagtgtccac caactacctg ctaagagccg      540
ggagcatgga acgtgttggg atttagagaa cattatctga gaaaagagtt cacttcctgc      600
tcccaggata tttctctttt ctgtttatga agtacaaccc atgctgctaa gatgcgagca      660
ggaagaggca tcctttgcta aatcctgttt gaatgtcatt gtaaataaag cctctgctct      720
cagatgtaaa aaaaaaaaa aaaaaaaaa aaaaaaaaa aaaaaagggg ggggggc           778
```

<210> SEQ ID NO 31
<211> LENGTH: 2476
<212> TYPE: DNA
<213> ORGANISM: Homo sapiens
<220> FEATURE:
<221> NAME/KEY: SITE
<222> LOCATION: (853)
<223> OTHER INFORMATION: n equals a,t,g, or c
<221> NAME/KEY: SITE
<222> LOCATION: (2227)
<223> OTHER INFORMATION: n equals a,t,g, or c

<400> SEQUENCE: 31

| | | | | | |
|---|---|---|---|---|---|
| actcaagacc | ctgtgcacct | ctcagcaggc | ctttgctgga | cagatgaaga | gtgacttgtt | 60 |
| tctggatgat | tctaagaggt | tatcaatact | ctggctgacc | atcgtcatcg | tgggactgac | 120 |
| tttggtggaa | gtccttggtt | acttatcatt | actgtgtttc | tgagaagtta | taaatttgcc | 180 |
| atctccctct | gcacaagtta | cctttgtgtg | tctttcctga | agactatctt | cccgtctcaa | 240 |
| aatggacatg | atggatccac | ggatgtacag | cagagagcca | ggaggtccaa | cygccgtaga | 300 |
| caggaaggaa | ttaaaattgt | cctggaagac | atctttactt | tatggagaca | ggtggaaacc | 360 |
| aaagttcgag | ctaaaatccg | taagatgaag | gtgacaacaa | aagtcaaccg | tcatgacaaa | 420 |
| atcaatggaa | agaggaagac | cgccaaagaa | catctgagga | aactaagcat | gaaagaacgt | 480 |
| gagcacggag | aaaaggagag | gcaggtgtca | gaggcagagg | aaaatgggaa | attggatatg | 540 |
| aaagaaatac | acacctacat | ggaaatgttt | caacgtgcgc | aagtttgcgg | cggcgggcag | 600 |
| aggactacta | cagatgcaaa | atcaccccti | ctgcaagaaa | gcctctttgc | aaccgggtaa | 660 |
| gtttgcttgt | tttccttgct | tttggacata | gtctgccagg | tcaggacatg | gatacatttt | 720 |
| tctccctacg | gctctgtgct | caagccctgc | agagggagat | ggcagagagg | aaggctgcct | 780 |
| acaagcatca | cagtcccatc | cctgttggta | accgtgttgc | gcaaaaacac | cttcatcccc | 840 |
| acccagtggg | gcncccccatc | taatattcta | agtgtcagag | gttccgtatt | tgtaatarca | 900 |
| aatgggccct | gactgtaaat | tagtgaagag | tgaatgtaac | ttattaccca | cagggacaat | 960 |
| tccaaatgag | ggccttaaat | gatgctcagc | taagctggtt | cttgtgtggc | ctctgtacct | 1020 |
| tcaaaagctg | ccgagtccta | tgattrcacg | cgatgggact | tgtacacttg | aagtgaaaca | 1080 |
| cagttttaaa | acttgctttg | tttagaattc | ccacctcatt | tttccatgga | caaaagtatt | 1140 |
| ctttatgtcc | tagtgcactt | acaatttggt | attacctggg | agtgaaaaga | atattacag | 1200 |
| ccatgcctaa | ctgacttctt | gaggtaagat | tgttctgtca | gaaaaccctc | tcccagttcc | 1260 |
| cctgcagctc | ttcaggaatc | cacatctctc | cagagctctt | tgttctcatg | ggtggcacct | 1320 |
| ccagagtgaa | gaagatcctt | tgtcaagaag | ggaaacagag | gggaaatgag | agggtcctgc | 1380 |
| aggcagagct | ggaatcaact | tccactctgc | ctcttgcaag | ctgtgtgacc | ctgggcacaa | 1440 |
| tttctccttc | ctctggaaac | ctctgttttc | ttagatttgg | agcaggrtgg | tcacactgac | 1500 |
| cttgcagagt | tctgagaatc | agagacagaa | cataaaaggc | ctggaaaaca | ttctccaaaa | 1560 |
| agaagctgca | acatgtgtgg | acaatgggct | tttcatgcct | ctcttactgt | ctcttactgt | 1620 |
| ctattgacct | ggtgcaagaa | acatgctctg | gtgatggctg | tgagggagga | atgaggatag | 1680 |
| acatagacac | tcctgtgtct | caaacatgct | tctttattac | tctgttatga | ctctgtcttc | 1740 |
| cctggggcag | gacccagcc | tgcctacatt | tgcagacaga | cacagtggca | tgtgagaca | 1800 |
| acagtgtgtc | ccartgactt | ttctttaccc | cccagctgtc | ggcagtactc | agtggaaggg | 1860 |
| tgatatgaca | ctgatactgc | tattttgaaa | cctggaggat | ggaaaggtgc | aaaaatctat | 1920 |
| caccagcaac | agaaggtgca | gacygtgttg | gtggcggtaa | ttttgtccat | caaatgaata | 1980 |
| tgtgtgaaaa | cattccctcc | tttgccccta | caggtcagaa | tggcggcagy | ggagcatcgt | 2040 |
| cattcttcag | gattgccctr | ctggccctac | ctcacagctg | aaactttaaa | aaacaggatg | 2100 |
| ggccaccagc | cacctcctcc | aactcaacaa | cattctataa | ytgataactc | cctgagcctc | 2160 |
| aagacacctg | csgagtgtct | gctctatccc | cttccaccct | cagcgatgA | taatctcaag | 2220 |

```
acacctnccg agtgtctgct cactcccctt ccaccctcag ctccaccctc agcggatgat    2280
aatctcaaga cacctcccga gtgtgtctgc tcactcccct tccaccctca gctccaccct    2340
cagcggatga taatctcaag acacctccca agtgtgtctg ctcactcccc ttccaccctc    2400
agtggatgat aatctsaaga aactaasgaa gaataaataa ataatataaa aataaaaaaa    2460
aaaaaaaaaa actcga                                                   2476
```

<210> SEQ ID NO 32
<211> LENGTH: 691
<212> TYPE: DNA
<213> ORGANISM: Homo sapiens

<400> SEQUENCE: 32

```
gaattcggca cgagctcgtg ccgaaaaatt attatttaag attaaaccat agcatcacat      60
tttcagtaat ggcaaataaa acttgaatat cataatgagt ttatattcat catcattcac     120
tgaaacagta taaaaacaag atctttacat taagagattc tacattttc tgtttacttc      180 ttgaatattg tcctaatcta ttttatattt gaacatattt tgttgatttc tgctaataga    240
aagttaccaa aaacttagaa ataagacaaa tttatcattg catgttttcc tttttcatac    300
tgaagtaatg tctaaaagat tcaccttgga ttatttgttt ctttctgaga ttgtactttg    360
tttgttttac tacttattac ttattagggc cttggctctg tgaagttgga tgttaactta    420
taaatggtat tcatagagat acgtgattta tttcaggtag aaaaaacaac cctacaagat    480
tttttttttc cagcaaaaca ttaaacagct ttgcctcaaa cttagcaaat gtatttcatc    540
atgactttct taaactgaca acataacaac catttgaatt ttcctttgaa ccagctttac    600
cacctgtggt tttcctcatt atttcccaca ttattgagtt aaataaatat ttgacgtgtg    660
ttcactttaa aaaaaaaaaa aaaaaactcg a                                   691
```

<210> SEQ ID NO 33
<211> LENGTH: 700
<212> TYPE: DNA
<213> ORGANISM: Homo sapiens

<400> SEQUENCE: 33

```
ggtcgaccca cgcgtccgga atatttaagg gtaaaatttt tctacttta aagcttaaaa      60 aaatgttttt ttactactgt aaaagtaatg cagagaaatg ttcacttacc aaacacatac    120
ctttgtaaaa atcaccactt aaagtttgtt tctaaagatt ttaggacacc aagatgcaaa    180
taatattttt ggctgttacc tgctctttca ctactgctga gtctgcagtg gcaagatagc    240
tacacagtac ctcagccctc ctgctcagtt tttaacatct attgataata ctaattacaa    300
gaaaatttaa aatgtctttt tgcaaaaaga taccataagc agtcaaaaca caattaaaaa    360
aaaaaaagag agagatgtaa acaattactt tccggccggg tgcggtggct cacacctgta    420
atcccagcat tttgggagac caaggcggga ggattgcctg aggtcaggag ttcaagacca    480
gcctggctaa catggtgaaa acccatctct actaaaaata caaaaaaata gccaggcgtg    540
gtgacgcatg cctgtagtcc caggtactcg ggaggctgag gcaggagaat cgcctgaacc    600
caggagatgg aggttgcggt gagccaagat cacgccactg cactccagcc tgggtgatag    660
agcaagactc tgtttccaaa aaaaaaaaaa aagggcggcc                          700
```

<210> SEQ ID NO 34
<211> LENGTH: 1722
<212> TYPE: DNA
<213> ORGANISM: Homo sapiens
<220> FEATURE:
<221> NAME/KEY: SITE
<222> LOCATION: (2)
<223> OTHER INFORMATION: n equals a,t,g, or c
<221> NAME/KEY: SITE
<222> LOCATION: (413)
<223> OTHER INFORMATION: n equals a,t,g, or c

<400> SEQUENCE: 34

| | | | | | |
|---|---|---|---|---|---|
| tnactatgcc | ctgcgcactg | gggcctttga | acctgctgag | gcctcagtta | atccccaaga | 60 |
| cctccaagga | tccttgcagg | agttgaagga | gagggctctg | agccgataca | acctcgtgcg | 120 |
| gggccagggt | ccagagaggc | tggtgtctgg | ctccgacgac | ttcaccttat | tcctgtggtc | 180 |
| cccagcagag | grcaaaaagc | ctctcactcg | gatgacagga | caccaagctc | tcatcaacca | 240 |
| ggtgctcttc | tctcctgact | cccgcatcgt | ggctagtgcc | tcctttgaca | agtccatcaa | 300 |
| gctgtgggat | ggcaggacgg | gcaagtacct | ggcttccta | cgcggccacg | tggctgccgt | 360 |
| gtaccagatt | gcgtggtcag | ctgacagtcg | gctcctggtc | agcggcagca | gtngacagca | 420 |
| cactgaaggt | gtgggatgtg | aaggcccaga | agctggccat | ggacctgccc | ggccacgcgg | 480 |
| atgaggtata | tgctgttgac | tggagtccag | atggccagag | agtggcaagt | ggtgggaagg | 540 |
| acaaatgcyt | ccggatatgg | aggagatgag | acggcccgaa | gttctctctg | accccacct | 600 |
| cgactcggcc | tctgccagct | gccttccctg | ccagagaaca | aaggctgaga | tggcagtgca | 660 |
| cacaccctcc | ccaccagtgg | ggacctgaga | atgcgtgtgg | cctgctgtcc | tcgatagacc | 720 |
| ggaatggggt | tttcccacag | atccccgcct | gtggcacacc | ccagagccag | aaatcgaagg | 780 |
| tcacaggaag | ttgtcactga | acttggcccg | tgtctgctac | tctgtacctt | gctggtacag | 840 |
| acagggtgg | tgggcagcca | ggctctatga | gtgggcccct | agtgtcagct | ctgtacaggg | 900 |
| tcagatccca | ggttctatga | ccaaataagt | aacttaagtt | ttgtgtgttg | ggttctaatt | 960 |
| ccttgtccta | gaatcccat | gactcaatca | aggactgtgc | taaatgagat | tgtccagccc | 1020 |
| ccgcccttgc | actggactac | gccaaaacca | cactgaccag | gcacttgcct | tccctctctt | 1080 |
| cccccgtgtt | ggtaagagag | aggccagttg | tgatagtggc | caaggagaat | ctagggctgt | 1140 |
| attgttgtcc | actgcagtag | gcaccggcca | catgtgactg | ctggcatgaa | atagaagtgc | 1200 |
| agttcctcca | tcgcactggg | taaggcctcc | agtattggac | agcacacaga | aaggttttca | 1260 |
| tcatcaagag | agttctgctg | gtcagccctg | ctccaggga | tgcctctgcc | ttcgcatagc | 1320 |
| acactgcttg | aggccctgcc | aggcaccaag | cactgccctg | gcccatggg | atagagcggg | 1380 |
| gaaggtgatg | gctcttccag | aggattccct | cagatgggga | ggcagcagta | tgagctctga | 1440 |
| gcagaagtgg | gtattgttga | tacagaggaa | gttctttgcc | acgagaactt | tcaagcagtg | 1500 |
| aaaggaattc | ccatcaggac | tcagacccca | ggccgagatc | ttgccctgaa | tgtaccctgc | 1560 |
| ctctgctttc | tcctgcatcc | catgctaagc | agggtcatgg | tctgaactac | tcagattgga | 1620 |
| tttccaaacc | atccttgtat | aaactgctca | gaactaraaa | aaaaaaaaa | aaaaaaactc | 1680 |
| gagggggggc | ccgtacccaa | ttcgccctat | agtgagtcgt | at | | 1722 |

<210> SEQ ID NO 35
<211> LENGTH: 878
<212> TYPE: DNA
<213> ORGANISM: Homo sapiens

<400> SEQUENCE: 35

| | | | | | |
|---|---|---|---|---|---|
| gcccacgcgt | ccgcccacgc | gtccggagta | cgctcgggag | ccctgcccat | ggcgaattgt | 60 |
| ggatgattgc | ggtggagcct | tcactatggg | tgtcatcggt | ggcggagtct | tccaggccat | 120 |

```
caagggtttc cgcaatgccc ctgttggaat tcggcaccgg ttgagaggta gtgccaatgc      180
tgtgaggatc cgagccccca agattggagg tagcttcgca gtgtggggg gcctgttctc      240 caccatygac tgtggcctgg tgcggcttcg gggcaaggag gatccctgga actctatcac      300
cagtggagca ttgaccgggg ctgtgctggc tgcccgcagt ggcccactgg ccatggtggg      360
ctcagcaatg atggggggca tcctgttggc cctcattgag ggcgttggca tcctcctcac      420
tcgctacaca gcccagcagt tccgaaatgc gcccccattc ctggaggacc ccagccagct      480
gccccctaag gatggcaccc cggccccagg ctaccccagc tatcagcagt accactgagg      540
aagccactgc caccatggga gctacttctc ggttccctcc ccgatggtct acctcgaagg      600
gagggctggc tcccagttag ccctgggacc ctccagagag ggtttctact ctgctcccta      660
gtcccagggt gggggtgggg caccccagct gccctgacag atgggtcccc ttttctctc       720 tcagggcacc ccagcccac actcacatgt acgaagttct cacccagct cctttgtgtg        780 gcaccctgat gagtatttaa agcccgtttt gaaatgccwa aaaaaaaaaa aaaaaaytc        840 gggggggggc cccttaaccc atttgggcct taaggggg                              878
```

<210> SEQ ID NO 36
<211> LENGTH: 954
<212> TYPE: DNA
<213> ORGANISM: Homo sapiens

<400> SEQUENCE: 36

```
gaattcggca cgagaggaag agcgccagag cctgctgccc attaacaggg gcacagagga       60
ggggccaggc acttcccaca ccgagggcag ggcctggcca ctccccagct ccagtcgccc      120
ccagcgcacc ccaagaggat gggggttcac cacctgcacc gcaaggacag cctgacccag      180
gcccaggagc agggcaacct gctcaactag ggcccctgct ggccttcctg ccattgctgc      240
accaggactg caaggagtcc ccacaccttg gcagctcagg gtccccagtc caagcccttg      300
acctctcctc tatccagacc cgcacagctg tttcctgtgt ggatggggtc aggttgtggg      360
ccatgccagg cctgtcagct gcgttgactg actgcagcag cttgcctcat ggttttccct      420 tttctagga atatttattc ttcagaggta acatgcagtt gggtctcaag acctttcctc      480
caatcagccc aacccagccc agactgggct tttctgggga gctgaggagt ttatcagtat      540
tcatcttcca tcctttcata gtcacaagtt ttgttatttt gtttttttt gggggtgatg      600 gtgtaattgt taacctcatt tccgtttcct acctgtttgc ttcccccccc agtcctccgc      660
atgagctgtt gccctccagg ggcctggcac agctggcctt ggggacgagg gagaggactg      720 attcaggggcc ccctcagctg tctcctccct ccctctggaa aggagggtgg ggctcagggg      780
cctcaagctg ggctctgtgt gaggcctggc ccccactccc aaccttggct ctagactgtt      840
actcttaagc tttgagaaat tttcacattg atgactatat taaatcaaa taaaactatt       900 ttactggtaa aaaaaaaaaa aaaaaactcg aggggggccc gtacccaatc gcct            954
```

<210> SEQ ID NO 37
<211> LENGTH: 793
<212> TYPE: DNA
<213> ORGANISM: Homo sapiens

<400> SEQUENCE: 37

```
ggcacgagat tttcttcatg cagtattctc agattggaaa catgcttcat gtttcttata       60
aataaccctc aattatgagg gcgtactttt cactttgaag aaaattgact tgcattaaag       120
```

```
tggctaacaa ttctttcctg ggcaggatgt aaaattttcc tctcctctaa taccagtact      180
gttgagctca cattctccca cttttcctct tttcaggtgg ttcacgtatt tgggatttta      240
tgaaacctca gaagcagaca tgttaacttt tcttatcttt ttattccctg aggtagtcct      300
ggggctctta agagattaca gttcttaaaa cctggaaagt gacaccagag aggtagatct      360
tagttcccaa aattaaagtt actttctagg gcataaaacc ttttcagaat tcagattaaa      420
ttttatttat tttttctttt ttctgtaacc ttatatttga ggggaaaatt ttattttcaa      480
cttttgcata tatctaattt aacatttggg aaaactgtaa atgggccaaa gtttctccct      540
ttatatgatt ttccagattt ttaccacttt cttagtgcca cttgatgcta ggcattgtct      600
attggagact cactggtacg taactgcagg ttttaccatg gaaccacata tacacatgtc      660
ttggaattga gggttagggt ttccagaagg acttagttgt cctgtgcttt tgtctgcccc      720
atgccaaaga ccactaagaa cagttttgta agtgaaactt gggtctacac gttaaaaaaa      780
aaaaaaaaaa aaa                                                        793

<210> SEQ ID NO 38
<211> LENGTH: 559
<212> TYPE: DNA
<213> ORGANISM: Homo sapiens
<220> FEATURE:
<221> NAME/KEY: SITE
<222> LOCATION: (3)
<223> OTHER INFORMATION: n equals a,t,g, or c
<221> NAME/KEY: SITE
<222> LOCATION: (9)
<223> OTHER INFORMATION: n equals a,t,g, or c
<221> NAME/KEY: SITE
<222> LOCATION: (35)
<223> OTHER INFORMATION: n equals a,t,g, or c
<221> NAME/KEY: SITE
<222> LOCATION: (42)
<223> OTHER INFORMATION: n equals a,t,g, or c

<400> SEQUENCE: 38
ccntgattnc gccaagctcg aaattacccc tcacnaaggg ancaaaagct ggagctccac       60
gcggtggcgg ccgctctaga actagtggat ccccgggct gcaggaattc ggcacgasca      120
cacttgtacg ctgtaaccte atctacttct gatgttttta aaaatgact tttaacaagg      180 agagggaaaa gaaacccact aaattttgct ttgtttcctt gaagaatgtg gcaacactgt      240
tttgtgattt tatttgtgca ggtcatgcac acagttttga taaagggcag taacaagtat      300
tggggcctat tttttttttt tccacaaggc attctctaaa gctatgtgaa atttctctg       360 caccctctgta cagagaatac acctgcccct gtatatcctt ttttccctc ccctccctcc     420 cagtggtact tctactaaat tgttgtcttg ttttttattt tttaataaa ctgacaaatg      480 acaaaaaaaa aaaaaaaaa aactcgaggg ggggcccggt acccaattcg ccctatagtg      540
agtcgtatta caattcact                                                   559

<210> SEQ ID NO 39
<211> LENGTH: 1263
<212> TYPE: DNA
<213> ORGANISM: Homo sapiens
<220> FEATURE:
<221> NAME/KEY: SITE
<222> LOCATION: (1091)
<223> OTHER INFORMATION: n equals a,t,g, or c

<400> SEQUENCE: 39
ggccgccctt tttttttttt tttttttaa aaacaaaaca ggttttaatg gttaaaacag        60
```

```
atgaattaat aggtttataa taaccattaa ctaagggaag ccctagaaca agaaataagg      120 attttttaatt gcatgcaaaa cctagttacc ataaaaacca atgcaatacc aaaatatctc     180
agcttcctag catagactcc aggtctttc atttccaata cttggcagtc ataatatgta      240
cactttcata tgcacctggt tgtggaggga taagctcatt cacataggac tacaaatatc     300
tctcacaggt aggagggcac aaaagaacaa tatcttcctc cacttttttg ggtccatctt     360
gaaaaacaaa aaaggcactc ccaaaggttc cttggtaaca cctttgttag gtttcttaat     420
tactaacata atctttacat gtaaggttaa tggtccactc atttcataga tctgggaacc     480
atcaggcatt ggaactgcct ttaactcaca tgccaaacaa ctggctttct taaacaatga     540
caaaaactgt atacttgttt taaaaacatt tgggctttgt ttccykgaca acttatatat     600
gcttaatcac tggactttgg catgcagagc caaacatatc atggaactga agaaccaca     660 atatgacatg gtgacagaag actctttgaa tcattattct gttttccact atcagctgct    720
ccagctccct tatactaatc caactttgtc cctcagagca cccatgctct gaacctaggt    780
ttaatctctc tgctgaaaga tttattaaag atacttagat aaattaccaa gtctttctct    840
acgatcatca aagagtaagg gaagtcaaat gctcatgggc agttgtccac tattcacaga    900
atctttagaa actatttgcc tgaggccaag gagaatttgc tttatcacta aatctgaccc    960
atgttgagcc atactaaaac tgcacttggg tactagtctc aaatcaaatt gagcttatgt   1020
attgctctac atttattgca tcccatgctg tgtgcaattt ctgatgctga ataagagaaa   1080
tacggcaatt naaaggcttc accacaagcg tcacattcca tgggtttcct tgggttttca   1140
cctctgcatg gatcttctga tggttgacaa gatgcgctgt tgactgaaac ttttgtcgca   1200
cttctcacac ttataaggtt tctctcctgt gtgtattctc tgatgctgaa taagacccga   1260
gtt                                                                 1263

<210> SEQ ID NO 40
<211> LENGTH: 455
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c

<400> SEQUENCE: 40
ggaattnccg gggtcgaccc acgcgtccgc ccacgcgtcc gcccacgcgt ccgcaaatat      60
attggcagga gattatccag aacatctagg tgcaggtaaa cagttctaag tccaagaagt    120
tatggaggga ttgatgctac cacttctaag tgttatttat tctgaaggaa ctgtatggga    180
ggagatcatt gtttctggaa gacagtacta ttagttatat agatggttct ttctggttct    240
gaatgactaa tcagtcattc agtcaataac actgaccacc tactatatgg tagtcattgt    300
tctaggtatt gagcatgtaa tggtggaaga taaatggcag atgagaatcc tgcatttaga    360
accttaagtc tgattggatg gcggaagaaa tatagttgat aagcataatt ttaggtagtg    420
attcatttcc aaaaaaaaaa aaaaaaaggg cggcc                              455

<210> SEQ ID NO 41
<211> LENGTH: 1128
<212> TYPE: DNA
<213> ORGANISM: Homo sapiens

<400> SEQUENCE: 41
ttacaaatga ttactacagg aatagtggcc acttaatgtc agttactccg gtggaagaat      60
```

```
ttatctagtt tttttttttt tcttttttgg aaggatggtg tgaaaaatag caagattaga      120
gaatgagttg tatagttttt tctatcacat ttcatctaaa atgatttgaa ggacttttga      180
agatttttac caacatcctt aaatcaactc caggttggat gaacaactga tttaaaacaa      240
actaagagaa cattaactag atgtgggctt tttaaaatat ataggtattg catttcctac      300
cttgttattt attccacttt gaatacttta gagggcttaa ctttcaactc tttaaggtag      360
taatggatag ttttatactt gttctcacaa aattgttatg gtcagtttat atcattgctc      420
catgcattga ttataaaaat tcagtattaa tttttttctga tcttataagc tttataggag      480 ttttctttc tcttataaag tgtttcacct tatgtaaaac aaatgcctgc ttgcatattg        540
gaagatgttg aaattagttt tagacaaaag tggtccatca attcagacac tctgcttgga      600
tgccttaccc ttttcattag tgcattcttt gcttctgaaa cttggcagaa actcgttagc      660
cagtccactg cctttctgac aatgtgtgga gtcacgtatg cttggtatat gcctttacta      720
cttttaaagt tctacagttt attacttgcc caagtgttac taaatccttt tcttatgtgt      780
actggatgga gaaaaaatta tagccagcac tttgagagga aagttttcag aaacaatatt      840
aactggcact actaactgaa ggccacagga gatgctatca atgttatttg taatctgaag      900
attgaacaag gctgtgaggc tcatttcaaa ctattttgag gtgttaaaat atatatatgc      960
tgtttctcag ctgttccact caaaccgtgt taggactctc aaaggtaaaa tgtcacaggg     1020
gcttttcagt tgttacagag ctcagcagct gtggttgccc ctgttctaca ccaatttcag     1080
ttcaataaaa atgttaactt tgcaaaaaaa aaaaaaaaaa gggcggcc                  1128

<210> SEQ ID NO 42
<211> LENGTH: 648
<212> TYPE: DNA
<213> ORGANISM: Homo sapiens

<400> SEQUENCE: 42
gaattcggca cgaggcaata tttgcctcac ccaacaccac aaagattttc ttctgttttc       60
ttctagaact ttttagtttt tagggtttat atttaggtct gtgatccatt ttgaatcaat      120
attagcatat gaggcaaagt ggagatcgaa gttttatttt ttccttatga ataccccagtt     180 gttccaacac cacttattaa aaacactata ctttatccac tgagtttgtt ttgtaccttc      240
atcaaaaacc agttttcaat atatctgtgg attaaatttt ttatttttat gtttattttt      300
agagacggtc tcactatgtt ttccaggctg gtctcaaact cttgtcctca agtgatcctc      360
ccatcttggc ctcctgagtc gctgggagga tcaggcagga ggatttcttg agcctgggag      420
gttgaggctg cagtgagccg agattgctcc actgcacttc agcccgggca atagagtgag      480
atcctatctc aaagaaaaaa agagttattg tgttatatct ttttttaatcc attttctttt     540 aacccttttat atccttatat ttaaactaga gtttctgtca agtgcactcc agcctggtga     600
caaagcaaga ctccgcctca aacacaaaaa aaaaaaaaaa aaactcga                   648

<210> SEQ ID NO 43
<211> LENGTH: 736
<212> TYPE: DNA
<213> ORGANISM: Homo sapiens

<400> SEQUENCE: 43
tcgagttttt tttttttttt ttttgagac tgaatttcac tcttgttgcc caggctggag        60
tgtaatggtg caatctcggc ctgggcgaca gagcgagact ccgtctcaaa aaaaaataaa      120
```

-continued

```
taaataaaat aaaattaaat taaaaaaaaa aaaaaaaagt ctgctttgaa aaccagtatc      180
catagacttc tggcagtcat ttctggggtt taattttgga tgtgacaaag gtttgtttcc      240
actggactta attttttcac atcgctctaa cttttgaaaa cacagataca gtccttttgc      300
tgaataaaat gaaaactcga gcctaaattt aaaggcatag atatttcctg gacttccagg      360
acagtaatat catgtactac tttgtcaaaa aaattttctg gaggttttc tagaggaaga       420 aactaagata acaacaacaa aaaagacaaa tccaaatgca ttacttgaag agcgactact      480
catgtttcta gagaattttt tggtcatact atgtcatggg gttatttcct gggggcttca      540
gttctgcttc agaatttctt tagtagttat ctactgaccc catctggtaa aattatagag      600
gaagttacag tcgttaaagc ttctgtcaac tcgatttcta aaaattttat gtaaagagat      660
attttaagag aaataagaaa ataggagatc agggcaaatg aatctaaaga tctttagctt      720
tactcgtgcc gaattc                                                      736
```

<210> SEQ ID NO 44
<211> LENGTH: 600
<212> TYPE: DNA
<213> ORGANISM: Homo sapiens
<220> FEATURE:
<221> NAME/KEY: SITE
<222> LOCATION: (547)
<223> OTHER INFORMATION: n equals a,t,g, or c
<221> NAME/KEY: SITE
<222> LOCATION: (549)
<223> OTHER INFORMATION: n equals a,t,g, or c

<400> SEQUENCE: 44

```
gggtcgaccc acgcgtccgc caaatcccag tctttaccat ttcatatcag gatcgttgtg      60
tgagggaata acttggtttt ctgtcctcag ttttctcaa tttcaatcca tcttataaat       120
cccagcaaaa ttaattttcc taaagacact tttagaattt ctgcaatagc tccttgagat      180
caggatgcca gggatattca ttctgttcat gacactagct agcacatttg atcagcgctt      240
gttaaacgat tctcaaccca agatcactc ctagggaaaa agtctccaa tggcttcccg        300 ttgccttcat ggtattaaac ctgcaattcc agagctcgat atttaaattt tttaggggc      360 tggaatttct cataatactc cttggctatc tactaaacac taagtactag gcatacagaa      420
ataacagata cacttgggtc aggcacggtg gctcacgcct gtaatcctaa cactttggga     480
ggccaaggtg ggtggatcgc atgagctcaa gagttcaaga ctagcccagg caacaaagga     540
tcctgtntnt acaaaaaaaa aaaaaaaaa aaaaaaaaaa aaaaaaaaa aagggcggcc       600
```

<210> SEQ ID NO 45
<211> LENGTH: 687
<212> TYPE: DNA
<213> ORGANISM: Homo sapiens
<220> FEATURE:
<221> NAME/KEY: SITE
<222> LOCATION: (57)
<223> OTHER INFORMATION: n equals a,t,g, or c

<400> SEQUENCE: 45

```
aattcggcac gagaaaaaat aaaaaaaata agccaggtgt ggtggtgggc acctgtnatc      60
tcagctacgt gggaggctga ggcaggagaa tctyttgaac ctaggaggca gaggttgcag     120
tgagccaaga ttgtsccagc ctgggcgaca ggtgaggctc ttgtctcaaa aaaaaagtc      180 cacatcttca tgaaccctca gactctggag ttgggtgtcg gcttttttag ccagcttttg     240
tgggaattgc ctttgaccta ttaaagaagg aaagtgggta atggagtccc agccactcaa     300
```

| | | |
|---|---|---|
| gagactggat atccccgag aatggcttgg gttaccagct atggacccct ggaagatgaa | 360 | |
| tctaatcctt ctcactggtt tttctttgca aattcatttg cttttatttt tctaataaca | 420 | |
| ataaactcta ttttccatgt tctcagggcc cctgggtaga cagacacagc ttgatttcag | 480 | |
| agcagacata ggcgaagaaa acatggcatt gagtgtgctg agtccagaca aatgttattt | 540 | |
| atatacacat ccaaatttga agagaaaatg tatttcttta ggtttcaaac actgtaatag | 600 | |
| atataaagca aaaataaaaa cctgttgcaa agttcaaaaa aaaaaaaaaa aaaaaaaaa | 660 | |
| aaaaaaaaaa aaaaaaaaag ggcggcc | 687 | |

<210> SEQ ID NO 46
<211> LENGTH: 697
<212> TYPE: DNA
<213> ORGANISM: Homo sapiens
<220> FEATURE:
<221> NAME/KEY: SITE
<222> LOCATION: (97)
<223> OTHER INFORMATION: n equals a,t,g, or c
<221> NAME/KEY: SITE
<222> LOCATION: (394)
<223> OTHER INFORMATION: n equals a,t,g, or c

<400> SEQUENCE: 46

| | | |
|---|---|---|
| ggccgccctt tttttttttt tttgataaaa gaaaagattg gtcttgtctc tgtaaaactg | 60 | |
| aggaacaatt actttagata actggtgtta gttttcnctt tctttcttga cggaagcaaa | 120 | |
| acagatatgg gttctaccct caagaagctt tagatgaatc agagatatag acataaaata | 180 | |
| aagaactata aaacaattca ttcgcttat gatagctgta ataataaaaa agtacaggga | 240 | |
| acaataatat catataacag agggataaca tcacacaggg aacaacagta tcacatagca | 300 | |
| gggatatata caaggatcct aggtaacctg gtctggatat atacaaggat cccgggtgac | 360 | |
| ccggtctggc tggtaagagg tttccctgag aaancgatca gtgagagctg agagagaagc | 420 | |
| aggcagagca agktgatggg gcaggggtgg ggagagagca gaagcgtgac ccaagagggt | 480 | |
| cccaggccaa aacctttgca ctcagtgact ctgaaagaat gcagaggggc tgtggctcaa | 540 | |
| agctgcagct ggaaaggtaa gaggggccag gcactcagc accatgtgga tcacactata | 600 | |
| aactttgaat atcatcctaa gagaaatggg aaaccaatta tggattttta aaaggaaata | 660 | |
| ttttattttc catttaacc ggacgcgtgg gtcgacc | 697 | |

<210> SEQ ID NO 47
<211> LENGTH: 286
<212> TYPE: DNA
<213> ORGANISM: Homo sapiens
<220> FEATURE:
<221> NAME/KEY: SITE
<222> LOCATION: (1)
<223> OTHER INFORMATION: n equals a,t,g, or c
<221> NAME/KEY: SITE
<222> LOCATION: (3)
<223> OTHER INFORMATION: n equals a,t,g, or c

<400> SEQUENCE: 47

| | | |
|---|---|---|
| ntnctagcac tcaggagtcc aaaccattgc ttttgggtta gaatgcatga agaacatgca | 60 | |
| cgtctatctg aactacaata actttctgct tartctactt aggctaatgt tgaacatttg | 120 | |
| ttcattcaca caaccactgg tggcagaaga agagagacct cttacaccac tatagcatag | 180 | |
| gagctgcaat gtcacatgag ttttaaaga tgctytttaa agaaaaaaaa aaacamgrag | 240 | |
| sargaaaaaa aaaaaaaaaa aaaaaaaaaa aaaaaaaaaa aaaggg | 286 | |

<210> SEQ ID NO 48
<211> LENGTH: 858
<212> TYPE: DNA
<213> ORGANISM: Homo sapiens
<220> FEATURE:
<221> NAME/KEY: SITE
<222> LOCATION: (843)
<223> OTHER INFORMATION: n equals a,t,g, or c
<221> NAME/KEY: SITE
<222> LOCATION: (847)
<223> OTHER INFORMATION: n equals a,t,g, or c

<400> SEQUENCE: 48

```
ggccgccctt tttttttttt tttgataaat acaaagatac atgtaaagtt ttacttacct      60
gattttaaaa acaggctacc aaaatttatc caaatatatt aaaaaatgag actgttttaa     120
aaacctttcg tttccatatt gtgactccac taagcgggta aaaagttcag gacagagatg     180
gaaaggaaag aaggaaacag gaagaagtga actaggaag gtggtgccag tggcacatgg      240
atgaagaaag agagatcatc agccatggag aattttgtaa tgtaagtaga gagagagatt     300
gggtaggaag acaggcttca cagtttgtaa agtgtaaggg aactacccat cgtaccctgt     360
cattgactag ggctgtgagt tatgtagttc tgtctcctct tgcaaaagac ttaccacttc     420
tggcaagtga ttaaccactt ctggcaactc ttcatttctt cttatccttg aatattcatc     480
tacatcactc taaacagcac agccccagaa gcatggaaag gggagttatt agtatggaaa     540
ggggagttac tcttctggtg tagtggtccg attgagtcca tggcttccca gccttaccag     600
agctgataaa aatgtcaatt cctttggggc caatcttgct cctccagtgt gttttagccc     660
taatgaggtc atggttattt ctagacttct gagacttact gtggctttga attgacacaa     720
acactaattt tctgtcaaag gctagagtga tggatgttat atgcctgcgg acgcgtgggt     780
cgacccggga attccggacc ggtacctgca ggcgtaccag ctttccacta tccgtgcgtc     840
agncgcnact gtaaccct                                                  858
```

<210> SEQ ID NO 49
<211> LENGTH: 1307
<212> TYPE: DNA
<213> ORGANISM: Homo sapiens

<400> SEQUENCE: 49

```
ggtcgaccca cgcgtccgga gccgcgaggg agaggccgcg gccccttccc gttgcctgcg      60
gccaccggcc ggcattcaga gcccctcgcc tggcgctaaa tttaaaaacg taacacgagc     120
agcaggctgg tctcggaaac gaaacgaaat tcggtccctg gcctcctcc cgggcgctgc     180
cggtccctca gcgcgccgcg ccacccggaa cagacccttc tcccgccatt ttcggcgggg     240
ctgggagact gaggccgcg gcgctgagcc tgcggcgccc cggaagaggc gggcggcatg      300
gccgctggcg tggactgcgg ggacggggtt ggcgcccggc agcacgtgtt cctggtttca     360
gaatatttaa aagatgcttc aaagaagatg aaaaatgggc taatgtttgt aaaactggtt     420
aaccctgtt caggagaagg agccatttac ttgttcaata tgtgtctaca gcagctgttt     480
gaagtaaaag ttttcaagga aaacaccat tcttggttta taaatcaatc agttcaatca     540
ggaggtcttc tccattttgc cacacctgtg gatcctctat ttctgcttct ccactacctc     600
ataaaggctg ataaggaggg gaagtttcag ccccttgatc aagttgtggt ggataacgtg     660
tttccaaatt gcatcttgtt gctgaaactt cctggacttg agaagttact tcatcatgtg     720
acagaggaaa aagtaatcc agaaatagac aacaagaaat attacaagta cagcaaagag     780
aagacattaa agtggctgga aaaaaggtt aatcaaactg tggcagcatt aaaaaccaat     840
```

```
aatgtgaatg tcagttcccg ggtacagtca actgcatttt tctctggtga ccaagcttcc      900
actgacaagg aagaggatta tattcgttat gcccatggtc tgatatctga ctacatccct      960
aaagaattaa gtgatgactt atctaaatac ttaaagcttc cagaaccttc agcctcattg     1020
ccaaatcctc catcaaagaa aataaagtta tcagatgagc ctgtagaagc aaaagaagat     1080
tacactaagt ttaatactaa agatttgaag actgaaaaga aaaatagcaa aatgactgca     1140
gctcagaagg ctttggctaa agttgacaag agtggaatga aagtattga tacctttttt      1200 ggggtaaaaa ataaaaaaaa aattggaaag gtttgaaact ttgaaaataa aatctagcaa     1260
aaataaaaaa aaaaaaaaaa aaaaaaaaa aaaaaaaag ggcggcc                     1307

<210> SEQ ID NO 50
<211> LENGTH: 606
<212> TYPE: DNA
<213> ORGANISM: Homo sapiens
<220> FEATURE:
<221> NAME/KEY: SITE
<222> LOCATION: (606)
<223> OTHER INFORMATION: n equals a,t,g, or c

<400> SEQUENCE: 50
aaaaattgga gacactgttt aacttctgtg catggactcc atcagcakct acaaagccay       60
tgggaggctg aggatcactt gagcccagaa gtttgaggct gtagtaagct tcaaaggcca      120
ctgcactcta gcttgggtga ggcaagaccc tttcaagcag taagctgcat gcttgcttgt      180
tgtggtcatt aaaaacccta gtttaggata acaggtctgc ctgcatttct tcaatcatga      240
attctgagtc ctttgcttct ttaaaacttg ctccacacag tgtagtcaag ccgactctcc      300
atacctttaa aaggtatgac aggaactgtc ttcatgtcct tacccaagca agtcatccat      360
ggataaaaac gttaccagga gcagaaccat taagctggtc caggcaagtt ggactccacc      420
atttcaactt ccagctttct gtctaatgcc tgtgtgccaa tggcttgagt taggcttgct      480
ctttaggact tcagtagcta ttctcatcct tccttgggga cacaactgtc cataaggtgc      540
tatccagagc cacactgcat ctgcacccag caccatacct cacaggagtc gactcctact      600 cttagn                                                                606

<210> SEQ ID NO 51
<211> LENGTH: 547
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<221> NAME/KEY: SITE
<222> LOCATION: (22)
<223> OTHER INFORMATION: n equals a,t,g, or c

<400> SEQUENCE: 51 gggcnccca aaaattcccc cnrggttttt tttttttttt tttgttttca agaagaaga        60 agcaatgcag caaagtggtg cagaacacag gagctggagc cattcagacc caagtccaac     120
tcttgacctc gcccactttc tctacagtcc tgagcaatta cacctgccaa gcaccttccc     180
aatggacaga ctggcaggcc ctactcccaa caggcatcca gactgagcat caccaaggat     240
gggacaaaca gaagcaatgc aagaggaaat gcgaacacga acatgcacca ctacaccaca     300
acctatggaa acaatcaggc aaaacaagac taggagacat atgacaagaa acaggcctg      360 gacgcttcaa aaatgccaat gtcacgaaag acaaaaactg ggcatgctct tctggatcaa     420
```

```
aggagactaa agagatataa caaccaaaca caataaaact atcctagatt acatcctgga    480 tttttttaaaa gcaaaaaaga acaatttggt aacaactggg gaaagtgtta atgtggctac   540
attttaa                                                              547
```

<210> SEQ ID NO 52
<211> LENGTH: 865
<212> TYPE: DNA
<213> ORGANISM: Homo sapiens
<400> SEQUENCE: 52

```
gctgaatata aggaaatatg tctaatggac accagttaat acttttaaaa actactcttt    60
aaaaaaaaaa tacgttcccc ttggttaact gattttttaa tccagggtgg acattttttc   120
aacctttatt aaaaagacaa ataaactatt ttgtagaaga tcagactcct acttaactgg   180
aagagaaatg tctattaaat gtctctcctc tttctctggg tcaagaccat gtaatttat   240 gcttcagaga tgaagatact gtttgtttac aaagagttta gtttttaaga catccaaaac   300
tctatgctag agcaaaaatc aaatagcaaa ggacactagc cagaaaatac agtgtgtgtg   360
tgtgcacctg tgtgcctgct gaacaacttg acagtgtaac agataaggta actgaagatg   420
gtggatattt gaattgtatt agcttaatgt ctacatatct ttggccaaaa ctctattgtc   480
atattagaaa catgttatct ttttcatgtt tattagtaat ttattttga ttcttttgttt   540 tcttttcgt ccaactaaaa caactgtaat gtacttgata catttatatc aagttctaaa    600
gtatttagac aaatccaaat actttgtttt tagtttttc ctccttccca tcctgttaac   660
cacagtgaaa cgctgcagta tttgatttg gtcagtgcta cggaggaaga ccatgaaagc   720
tgaattggtc tgtgccaccc agagtaaacc tcttctcttc ttctggaaag atggcgtgat   780 gttttttcaag gattctaata aatatcccgc agtcatctcc tgaaaaaaaa aaaaaaaaaa   840
aaaaaaaaaa aaaaaaggg cggcc                                          865
```

<210> SEQ ID NO 53
<211> LENGTH: 689
<212> TYPE: DNA
<213> ORGANISM: Homo sapiens
<220> FEATURE:
<221> NAME/KEY: SITE
<222> LOCATION: (309)
<223> OTHER INFORMATION: n equals a,t,g, or c
<400> SEQUENCE: 53

```
tcgacccacg cgtccgattt tctgataaga cgattactaa gacaaacttc tatcctttca    60
cttagtaagc atcatgacat catatataat caacctatct ttcttcttac ctttggcaac   120
tcggaaggtc agtgctaagc cttgtggtta accctagtag tgacatccct tcttatgtct   180
tagtaatcgt cttatcagaa aatatcatat aaaataaaca caaagtaaac ttttactta    240 aaaagatctg tagatattc actaactcta ttaatgcttt ggtaatagct atttaatcta   300
taatcctgnc ctagatcaag ttttgaggcc tcagtgttat tcattccttg ggctaagagc   360
cactgaaatg ggataattat tggtacagtt acttcctcct tttaaatggt ttctgttctg   420
ccatttactc tttatttgaa attgccttct tttaaagtt attcttaata ttgtaagcta   480
tttgaaaata ggtgagccat aaaaataaat attaataatg tatttctaat tatccttatct   540 aacaaaata ataataaata tccactttag aaaatttgga aaatcatgaa ggtataaata   600
ctaaaatcga aattctctat aagatcaata ttcagatttg acctcaggca aacacagaaa   660
```

```
ttaaagttaa aaaaaaaaaa agggcggcc                                    689
```

<210> SEQ ID NO 54
<211> LENGTH: 515
<212> TYPE: DNA
<213> ORGANISM: Homo sapiens
<220> FEATURE:
<221> NAME/KEY: SITE
<222> LOCATION: (3)
<223> OTHER INFORMATION: n equals a,t,g, or c
<221> NAME/KEY: SITE
<222> LOCATION: (4)
<223> OTHER INFORMATION: n equals a,t,g, or c
<221> NAME/KEY: SITE
<222> LOCATION: (7)
<223> OTHER INFORMATION: n equals a,t,g, or c
<221> NAME/KEY: SITE
<222> LOCATION: (20)
<223> OTHER INFORMATION: n equals a,t,g, or c

<400> SEQUENCE: 54

```
tanntgnatc cccccgggcn tgccaggaat tcggcacgag ttacaactgg tggaccacac    60
accaggcact aatcacctgg tgaggatttg gcatatccac caaaaaatgc atccgattta   120
accaacatct ccaccagcgc tacggactcc tcccaattct gacatctctt gcagacaata   180
ctatgctctc tacacactgt ttagaaatgg aaaggtgatc tgcactgtat cttgggtttg   240
ttggctatgc ttcctttgat gacatatatt atacagtata tatatacata tatttwwwww   300
gttagagttc tagccatttt atttctccgc agggtccttt ctcagacatt actgcatgct   360
gtatatggcg ttagctgtgt gttgatcttc taaaagatga tagagtttac tggtaattgt   420
gtaatcagct cctgcctttt tattttcttg ggttatttac atgtcagaga catttataaa   480
aagtgaaagg ataaaaaaaa aaaaaaaaaa ctcga                              515
```

<210> SEQ ID NO 55
<211> LENGTH: 747
<212> TYPE: DNA
<213> ORGANISM: Homo sapiens

<400> SEQUENCE: 55

```
aaaaaggaag aaaagaaaaa aaggaaacca gccctgtcat ggaatttctc tccttccctg    60
cacagtaaag acttttgggt tttcatggat aaaatcaatg tcagtactga aactcctact   120
ctcccctccc gccccactct cccccgttgc ccgagatggc caagttcagg cctgtgcaat   180
gccgcttccc tctgagcctc cctctcaagg gccacgcagg cagctgcagc agggccagct   240
gcaggatggg gctgccggtc actgaattgt cgttcaaatg catcatcttt gtggcgtctt   300
tctcatgcga gcaaagccac gtgctctcct gtctgctgtc acatctgtgc ctggattgct   360
taaatattgt ttgtgatggg gaggttttaa tctggtgatg cagagggaag cagggctgtg   420
ggggcacgtt taattggctc ccagcagcgt ggggagtgct tctatggtgt gtggggtttt   480
ttgttgcctc cctctagaag tgttaccgtt ttcacgtcct attaatgtcc tctggttgtt   540
aaattacagc agcacattac agtgcactgg gttccctcct ggagtgaata caaacggagg   600
gcatctactt gtattttag aagtttggg agaatttagt gatttgtggc twtgatcaat    660
cctgttgact ggtgtatgtc tgcgcaaacc tgtttcaaat aaatctttg ttaaagtaaa    720
aaaaaaaaaa aaaaaaaaa aactcga                                       747
```

<210> SEQ ID NO 56
<211> LENGTH: 676
<212> TYPE: DNA

```
<213> ORGANISM: Homo sapiens

<400> SEQUENCE: 56
gaattcggca cgaggacgag gtaaaattat tagaatggag tatgtcatca ggtcttttcc      60
tagtcctttt ctgcttcctg tgtgtctttg taggtttctt tgatttccat tgttggtgtg    120
atattttggt aaaaagcagc tgactcacat cccatccaaa tccccagtgc ccttcagatc    180
cttcacaaat ttggcattca gcccactcct tgccaattgc ttcctttcct cccaattccc    240
acatgtctcc ttcctacgcc atctgcttct cctcccttcc ttcgattagt gctttcgtct    300
gctcttccaa tttctttcat tgttcaatgt cttttgcttc ctcttccccc tcctctcccc    360
tagaggaaat taacatactt aatacagctg atgtcataaa gccccttttc cctaagaagt    420
taaatttctg tttctgcaaa ataaatacat agctctgttg tgtgaaggtc aaaggaaacc    480
tgagtagtaa acctgaaata gattttttg gggttcatct tacataaagt gtcaatgcat     540
attatgtatt ctatttattt tccaaaataa attttctatt tgggatttaa atatggtaag    600
tcaacacaac tttattgtac cagtcattgg attgaataaa tgacttaaaa ataaaaaaaa    660
aaaaaaaaaa actcga                                                     676

<210> SEQ ID NO 57
<211> LENGTH: 832
<212> TYPE: DNA
<213> ORGANISM: Homo sapiens

<400> SEQUENCE: 57
aacccgctgg cccaatggca gcgtcctaca gtgtagcctc cgcctcccga ttgactggcc      60
tgcttggcaa ggcaagtagc ggcggcgctt caagatgcgc tgcctgacca cgcctatgct    120
gctgcgggcc ctggcccagg ctgcacgtgc aggacctcct ggtggccgga gcctccacag    180
cagtgcagtg gcagccacct acaagtatgt gaacatgcag gatcccgaga tggacatgaa    240
gtcagtgact gaccgggcag cccgcaccct gctgtggact gagctcttcc gaggcctggg    300
catgaccctg agctacctgt tccgggaacc ggccaccatc aactaccgt tcgagaaggg     360 cccgctgagc cctcgcttcc gtggggagca tgcgctgcgc cggtacccat ccggggagga    420
gcgttgcatt gcctgcaagc tctgcgaggc catctgcccc gcccaggcca tcamcatcga    480
ggctgagcca agagctgatg gcagccgccg gaccaccgc tatgacatcg acatgaccaa      540
gtgcatctac tgcggcttct gccaggagcc ctgtcccgtg gatgccatcg tcgagggccc    600
caactttgag ttctccacgg agaccatga ggagctgctg tacaacaagg agaagttgct      660
caacaacggg gacaagtggg aggccgagat cgccgccaac atccaggctg actacttgta    720
tcggtgacgc cccaccggcc tgcagcccct gctgcccaat aaaaccactc cgaccccaaa    780
aaaaaaaaaa aaaaaaaaaa aaaaaaaaaa aaaaaaaaaa aaagggcgg cc              832

<210> SEQ ID NO 58
<211> LENGTH: 1003
<212> TYPE: DNA
<213> ORGANISM: Homo sapiens
<220> FEATURE:
<221> NAME/KEY: SITE
<222> LOCATION: (422)
<223> OTHER INFORMATION: n equals a,t,g, or c
<221> NAME/KEY: SITE
<222> LOCATION: (700)
<223> OTHER INFORMATION: n equals a,t,g, or c
<221> NAME/KEY: SITE
<222> LOCATION: (758)
<223> OTHER INFORMATION: n equals a,t,g, or c
```

-continued

```
<400> SEQUENCE: 58
ggtcgaccca cgcgtccgga ggcccgcagc ccgggcggcg cagggtagag cgccgcggac      60
ccggccacgc agcccgggga ctcccgggcc ctcccggagc cccgcggggt ccccgccgtg     120
catccggcgg gctcagggag cgagtgggag cgccctcccc ccgctgcccc ctcccccgag     180
catcgagaca agatgctgcc cgggctcagg cgcctgctgc aagctcccgc ctcggcctgc     240
ctcctgctga tgctcctggc cctgcccctg gcggccccca gctgyc ccat gctctgcacc     300 tgctactcat ccccgcccac cgtgaagctg ccaggccaac aacttctcct ctgtgccgct     360
gtccctgcca cccagcactc agcgactctt cctgcagaac aacctcatcc gcacgctgcg     420
gncaggcacc tttgggtcca acctgctcac cctgtggctc ttctccaaca acctctccac     480
catctacccg ggcactttcc gccacttgca agccctggag gatctggacc tcggtgacaa     540
ccggtacctg cgctcgctgg agcccgacac cttccarggc ctggagcggc tgcagtcgct     600
gcatttgtac cgtgccagct cagcarcstg cccggcaaca tcttccgagg cctggtcagc     660
ctgcagtacg tctacctcca ggagaacagc ctgctccacn tacaggatga cttgttcgcg     720
gacttggcca acctgagcca cctcttcctc cacgggganag cctgcggctg ctcacagagc     780
acgtgtttcg cggcctgggc agcctggacc ggctgctgct gcacgggaac cggctgcagg     840
gcgtgcaccg cgcggccttc cgcggcctca gccgcctcac catcctctac ctgttcaaca     900
acagcctggc ctcgytgccc ggcgaggcgs tcgccgacct gccctcgctc gagttrctgc     960
ggctcaacgc taaccccctgg gcgtgcgact gccgcgcgcg gcc                     1003

<210> SEQ ID NO 59
<211> LENGTH: 702
<212> TYPE: DNA
<213> ORGANISM: Homo sapiens

<400> SEQUENCE: 59
gaattcggca cgagctgggt catggatttt gagaatcttt tctcaaaacc ccccaacccg      60
gccctcggca aaacggccac ggactctgac gaaagaatcg atgatgaaat agatacagaa     120
gttgaagaaa cacaagaaga gaaaattaaa ctggagtgcg agcaaattcc caaaaaattt     180
agacactctg caatatcacc aaaaagttcg ctgcatagaa aatcaagaag taaggactat     240
gatgtatata gtgataatga tatctgcagt caggaatcag aagataattt tgccaaagag     300
cttcaacagt acatacaagc cagagaaatg gcaaatgctg ctcaacctga gaatctaca      360 aagaaagaag gagtaaaaga taccccacag gctgctaaac aaaaaaataa aaatcttaaa     420
gctggtcaca agaatggcaa acagaagaaa atgaagcgaa aatggcctgg ccctggaaac     480
aaaggatcaa atgctttgct gaggaacagc ggctcacagg aagaggatgg taaacctaaa     540
gagaagcagc agcatttgag tcaggcattc atcaaccaac atacagtgga acgcaaggga     600
aaacaaattt gtaaatattt tcttgaaagg aaatgtatta agggagacca gtgtaaattt     660
gatcatgatg cagagataga aaaaaaaaaa aaaaaactc ga                         702

<210> SEQ ID NO 60
<211> LENGTH: 1095
<212> TYPE: DNA
<213> ORGANISM: Homo sapiens
<220> FEATURE:
<221> NAME/KEY: SITE
<222> LOCATION: (107)
<223> OTHER INFORMATION: n equals a,t,g, or c
<221> NAME/KEY: SITE
```

```
<222> LOCATION: (202)
<223> OTHER INFORMATION: n equals a,t,g, or c
<221> NAME/KEY: SITE
<222> LOCATION: (556)
<223> OTHER INFORMATION: n equals a,t,g, or c

<400> SEQUENCE: 60
cccgggcagg agggtcaggg ccagatggag gggccaccaa ggacatgggg aagatgctgg      60
ggggtgacga ggagaaggtt ttgcttctta cgaacgccac ggccgtnttc acttctaaac    120
taaaggaaac aaagcaatag gtttggggga cgcccagccc ccaccccgt cacccgctc      180 ttcccaagtc ctcgccccc gnccggcctc ctagcctctc cgcccacgcg gctgctgctt     240
ctccctgggg aggaccctg ccctcggcca ttgaacactg caccctccac aggagccgca    300
gaggcccgag gcaccggacg ctggagaccc tgcgcccctg cccagcacct cctccgtggg   360
cagctcctcg ggtggggcct gcggggttcc ctgcgcgcac tggcgcgtgt gtggcctaat   420
ccacctggtg gccctgcggg gcggcatccg agccctgtt tctcctccat tcatgtttaa    480
tttgcatcac aatttgttga atctcaggta aatgaggtct ttgcatttaa tgagttttat  540
cttgacaggc gccgcntcgc ccccgggccc tttcgtccac akcaaaaatg catcaagtct  600
ccacgtgttt cgggccaggg cgtggcttgg cattgacctt catgacctta catagcttta  660
gagaagccat aacgttagac tgcaatacta acgaccgacg cccctccggg cagagaccac   720
cgcgcccctc tgcgcccag cgacgcggcc cgcggggacg tcgctgtccg tcctgctcgc    780
cctgtgccct ctcactgact tctcccgggt cgtgtctttt aaaaactcct gttttcacac   840
cttacaaagc cagctctgag cagacagggc gtcctctcgt agaacctgcg caccccgttc    900
ccagcgcatg gcgcccggg ccgcgagctt agcttagacc gtggtgtcct ctgtccgtct   960
gtcctgcgcc tgcgcctcct cctgcatgtc ggggcccctg cgtgtgttct ctccggatgg  1020
aatcacagcc aataaacacc agtgatttca aaaaaaaaa aaaaaaaaa aaaaaaaaa     1080 aaaaaaaaaa aaaaa                                                    1095

<210> SEQ ID NO 61
<211> LENGTH: 867
<212> TYPE: DNA
<213> ORGANISM: Homo sapiens
<220> FEATURE:
<221> NAME/KEY: SITE
<222> LOCATION: (831)
<223> OTHER INFORMATION: n equals a,t,g, or c

<400> SEQUENCE: 61
tcgagttttt ttttttttt tttttaagta gagatggggt ttcaccgtgt tagccaggat      60
ggtctcgaac tcctgacctc gtgatccgcc cgcctcggcc tcccaaagtg ctggattac    120 aggcatgagc cactgcgccc agccggtctt tttaaacatt ccccaggact gtacagccaa  180
cccatactca cctgacattt gggaactccc ccccacggcc ataactgatc tgcagaggta  240
agaccaagag caagaatggg ggattcacat ctaaggtctg gtgatggctg atgaaggaag  300
aagaatcagc gaacaaaagc ctctaggtct ttcttaccac aaacacctct ctgcccacct  360
gctttgaaag gggcagaagt atagtgggcg agctgcccac ctgctacagt gaagggatct  420 ggagaaaatac tcacactttg aggtgctcgc cctcttcatc agccagctct aacttaagcc  480
aatgacccca cgggagctta cacaagtyca aacaggccca aatgcattca tgagcagggg  540
gaggccaaag gactccggag gagagaggcc caataaggct ggtgctattt ccgatccata  600
gagagagcag aggtgggcag gcccttttga ttaatgtatc attcttgaat gcaagcttca  660
```

```
aaatccggt  atgccgggtg  agaatgagca  ggactaacac  ctgggtgtca  tggcaagcct      720
ccagggccga  ctggccagag  acagatccgc  aagaggctct  gcagccagct  ctggtgccaa     780
gccactcgga  tttgaacccc  ggctcctcaa  ggtcagctgt  gtagccttga  ntgaaycacc     840
tgctatgacc  aatctcgtgc  cgaattc                                            867
```

<210> SEQ ID NO 62
<211> LENGTH: 1134
<212> TYPE: DNA
<213> ORGANISM: Homo sapiens

<400> SEQUENCE: 62

```
tctgaaggtc  tcagcttcct  agatgttcta  cactcttcct  gaccattttc  actgaaccct      60
atttgattta  ctgaaagcat  atttactaat  tgtttgcact  taaaggtgct  tttatcctag     120
aataaacaat  gcttttaaaa  caattcacta  ttctaaattg  atactggctt  aagatgttgt     180
tccagtgtca  ggtattgtta  tcgattttt   ctttcctaga  acctgtcctt  tccagtggct     240
ccagtagact  tgtatttat   aatctttcaa  atattatgta  gcttgttaaa  cttcccatca     300
tgatcttgtt  cagtttctca  actcatttgc  aaaagagatg  actagcatgg  gagcctggat     360
tccagtatct  gttttagtgc  cttattagtg  cctcttagct  taggttcttt  tgatgattca     420
gcgtccagat  aatccaaggg  agtgactgta  atcataggg   tttctagtag  aatgcaatca     480 tgagccctt   aggaagtttt  ggtcaataat  aaaccacaca  tagggtggtg  gtcccctaag     540
attataatga  agctagaaaa  ttcctcttcc  ctagtgagtt  gtagccatcc  cacactatag     600
tagtgcaacg  cgttactcac  tgtgtttgtg  atgatgctgg  tgtcaacaaa  cccgcactac     660
cagttgtata  aaagtatagc  atgtacatac  atttatatgt  agtacatata  ttgataataa     720
atggctgtgt  tactggctta  tgtatttact  atgttttta   attgttattt  tacagagtac     780
atcttctact  tattaaaaga  agttaactgt  aaaacatcct  caggcaggtc  cttcaggggg     840
tattccagaa  aaaggcattg  ttatcgtagg  tgatgacagc  cctatgcacg  ttttcacca      900 gtgggatgaa  atatggagat  ggaagacagt  gatattgatg  atcctgatct  ttgcaggcct     960
aggctaatgt  gtgtttgtgt  cttataagaa  aaaggattaa  aaagaaaga   attttaaat     1020 ggaaaaaagc  ttatagaata  tgaatataag  gaaagaaaat  attttgtac   aactatacaa    1080 tgtgttggtg  ttgtaaacta  aatgttatta  caaaaaaaaa  aaaaaaaaac  tcga          1134
```

<210> SEQ ID NO 63
<211> LENGTH: 1448
<212> TYPE: DNA
<213> ORGANISM: Homo sapiens

<400> SEQUENCE: 63

```
ctcaggggta  cagtaccaaa  ccaaggttga  tggtaccact  taaaatggac  tctatcacag      60
tgcacataag  gagcaccaac  ggacctatcg  atgtctattt  gtgtgaagtg  gagcagggtc     120
agaccagtaa  caaaaggtct  gaaggtgtcg  ggacctcttc  atctgagagc  actcatccag     180
aaggccctga  ggaagaagaa  atcctcagc   aaagtgaaga  attgcttgaa  gtaagcaact     240
gatggcattt  gagaatttat  gtatcactga  gttttttggg  aatatcttcg  tggagaatta     300
cgcatcaaat  ttgattctca  gagcaataaa  ttatccatga  agtgctctcg  ttctcagtag     360
cggcatcatg  gccagtagtg  tctttgagga  gttcaccact  tagattactg  agtaattgtg     420
gtttccacat  ttgaaaacaa  ctccttttat  aattattcac  tgcttttgt   cagtgaaata     480
```

```
gacatcttgc ctcctgaagt agcttcatca cagagtgtca tgaagacaga cagtcaggct      540
gaaatggaca gttctttgtg gactctaccc ttcccttcaa ggagtatgtc atatatcaca      600
aaagaaattg ccttacactg gttcatgttt gcagttactg ttgtacattg catagatgta      660
cacacgaatt taaatgtgat gtctttgtat atatctgtat aatgttgaga ttacttacga      720
aatatgtctg agtgacactt ttcacccttg tacagccaaa ataatgtata tatggaaagt      780
gacagacaaa ttctctaatc tctttggtay ctataactta ttagaatcct ctggatgagg      840
gttagaagag acttttttcca aacttctaca tgtagaagta tcataaatgt gctacacatt     900
tatgtttgtg gatttaatta aagtatttta atatggtttt cagtgctaaa attggagtca      960
gatacttctt ggttttaagc tgtctaccta attgctgtct cccagcagac tggtggcatg     1020
cccagtggct ttgggggcaa ggatagaaat gccatcagga aatagctgaa ttcattgtga     1080
aacatgaatt cagtcatggt gataattgga aactcctttc aggttttttgc aagtagattt    1140 tgtaatgttt gtgtatgcag ccttgctgtt gagtcagtcc aagggtttt acttaggaca      1200 agttgtacct tgccctctct ccagctctgc tcccacattt tcacatacct agctgtttct    1260
acctcattgg gtaagtcatt taccactctg tgcctcagtt tactctgtag tttaccatta   1320
gactgtgagc tccttgaggg actttgtcat aatcactgtt acatcccagt gcctcacacc   1380
atgcctggcc cttaagaagt gctcaataaa tgtctgaaca ataaaaaaaa aaaaaaaaa    1440 gggcggcc                                                            1448

<210> SEQ ID NO 64
<211> LENGTH: 756
<212> TYPE: DNA
<213> ORGANISM: Homo sapiens
<220> FEATURE:
<221> NAME/KEY: SITE
<222> LOCATION: (354)
<223> OTHER INFORMATION: n equals a,t,g, or c

<400> SEQUENCE: 64
tcgacccacg cgtccgagca tattaggatt atatgtagat ttgtatgtat tttgcattat       60
gtacttcagt ctcctagttt tattattctc accttccgtt ttattcttgg cgaggaaaaa     120
atgcactaga aataatacat taaactgact cttagtctta atgtacgctt gctgtcttaa     180 ataggtgat tgagtccaac agactcaatc atacatgtca tacatgttta tgattaagag      240
atattctttt tgtgtgctag ttgattttgc cgagaaaaaa tgaagaagaa ttcaagaaga    300
gatgagggta ggtaagctct cagagcattt ctgtctgccc atttggttct atgncttatg    360
tgggctgcta atgtgactaa ttcagagtgt tgtatttcca catctgtgga ttccaccatg    420
gaaaaggtgg gctaccattg gtccttatat ggctttatta gaaaatagaa cattctatcg   480
tttgtctgcc cagtggccag agtcctggtg aacaacagag ctcatgggaa aycagcctct   540
ctcagggcac cccgctatga ggatattgaa atatgttcaa tcatttctca tctcccttgg    600
aatgtaattc cctgccctat acaaaatagg atattccaat gcgctatttg aatctaggga    660
ttgaggattt gtagttgagt tttggggtaa aggcttggct cattgccatg gaagaataaa    720
agttatttat taaaaaaaaa aaaaaaaagg gcggcc                               756

<210> SEQ ID NO 65
<211> LENGTH: 496
<212> TYPE: DNA
<213> ORGANISM: Homo sapiens
<220> FEATURE:
<221> NAME/KEY: SITE
```

<222> LOCATION: (22)
<223> OTHER INFORMATION: n equals a,t,g, or c
<221> NAME/KEY: SITE
<222> LOCATION: (472)
<223> OTHER INFORMATION: n equals a,t,g, or c
<221> NAME/KEY: SITE
<222> LOCATION: (479)
<223> OTHER INFORMATION: n equals a,t,g, or c
<221> NAME/KEY: SITE
<222> LOCATION: (493)
<223> OTHER INFORMATION: n equals a,t,g, or c

<400> SEQUENCE: 65

| | | | | | |
|---|---|---|---|---|---|
| ccgtgatgtg | gcgcctgcac | antcctttcc | ctttcggatt | cccgacgctg | tggttgctgt | 60 |
| aaggggtcct | ccctgcgcca | cacggccgtc | gccatggtga | agctgagcaa | agaggccaag | 120 |
| cagagactac | agcagctctt | caaggggagc | cagtttgcca | ttcgctgggg | ctttatccct | 180 |
| cttgtgattt | acctgggatt | taagagdggt | gcagatcccg | gaatgcctga | accaactgtt | 240 |
| ttgagcctac | tttggggata | aaggattatt | tggtcttctg | gatttggagg | caatcagcgg | 300 |
| acagcatgga | agatgtgtgc | tctggctcgg | ataagagatg | ggacatcatt | cagtcactag | 360 |
| ttggatggca | caaggctctt | cacagacgca | tctgtagcag | agtggawctt | gtactaactt | 420 |
| atgatagaat | gtatcagaat | aaatgttttt | aacagtgtwa | aaaaaaaaa | rnaggrggng | 480 |
| agtgggtggg | gtngag | | | | | 496 |

<210> SEQ ID NO 66
<211> LENGTH: 557
<212> TYPE: DNA
<213> ORGANISM: Homo sapiens
<220> FEATURE:
<221> NAME/KEY: SITE
<222> LOCATION: (16)
<223> OTHER INFORMATION: n equals a,t,g, or c

<400> SEQUENCE: 66

| | | | | | |
|---|---|---|---|---|---|
| gcaggtaccc | ggtccngga | ttcccgggtc | gacccacgcg | tccggtattt | ttttattggg | 60 |
| gtggggaaag | gggcaaaaag | aatgatctta | gtgtctttac | ctttctcata | ttaactcacc | 120 |
| tctttattct | gtggtctttt | ctgaatagaa | atgtatgccc | taggaagaaa | tcatgctggg | 180 |
| ttttgctttt | agagataaaa | ggtggtggat | ttattttgcc | tgcagtaaag | attctcaggg | 240 |
| tgtcagagca | gcatattgtc | aaatcctgct | tctgttttat | gtttcagtgt | attcactttc | 300 |
| attttcttac | ttactagacc | atttctgcag | tttgcccaaa | cctctactgt | ttgggacagt | 360 |
| aagccaaata | cctcattttt | aaaagaagt | tttcatggca | tcagtgttaa | taagtacat | 420 |
| ttttaactga | gtcttaatct | ctatttgaag | aaaaagtaga | gacaaaagta | atgtcaatgt | 480 |
| aatccccagg | atcatgaaat | gtatacaaaa | taaataaagt | aggagagtta | aaaaaaaaaa | 540 |
| aaaaaaaag | ggcggcc | | | | | 557 |

<210> SEQ ID NO 67
<211> LENGTH: 674
<212> TYPE: DNA
<213> ORGANISM: Homo sapiens

<400> SEQUENCE: 67

| | | | | | |
|---|---|---|---|---|---|
| ggtcgaccca | cgcgtccgat | aatgtgtagc | tactgtatgc | cttatttaat | tattttttg | 60 |
| agtgtcattc | acaatcacaa | aacgataccc | ttactgaaag | tgttagtgga | taaacttaat | 120 |
| tgcataatta | cggacctgtg | tatttccaga | gatgatgttt | tccccactac | atgttaagat | 180 |
| gtacgtattt | aatgacaatg | ctgtttgttg | tatgagaact | tgagacagaa | gatttagtag | 240 |

```
gattatccag tgacagtcag tacagggtgc gattaagctg tccttctggc tcttggcctg      300
gtatatgttt gtctctggcc atgcagttac agaatagggc aggtggcatg tttatatatg      360
cctttgattt cacagaagtt ggtgagcttt cctaagtgga aattttttaga gctagatagg     420 attgttgtgg gagaggggc agggaatgga gagttgattc ttcactcttc tgtggtgcag       480
ttgaatttac atgtagctgg aactgatttt ccaaggatt atgatggcaa tgagcttaga      540
agattggttg ggttttagca cttcagaatt ggatcccttg ccggaaccct tgctaagagg      600
gagtggactt gtatttggta cagagaccaa aaaaaaaaaa aaaaaagggg sggcccccc      660 caaggggggcc ccaa                                                       674
```

\<210\> SEQ ID NO 68
\<211\> LENGTH: 794
\<212\> TYPE: DNA
\<213\> ORGANISM: Homo sapiens
\<220\> FEATURE:
\<221\> NAME/KEY: SITE
\<222\> LOCATION: (345)
\<223\> OTHER INFORMATION: n equals a,t,g, or c

\<400\> SEQUENCE: 68

```
tcgacccacg cgtccgagat cttcagcaga aagatattgg tgtgaaaccg gagttcagct      60
ttaacatacc tcgtgccaaa agagagctgg ctcagctgaa caaatgcacc tccccacagc     120
agaagcttgt ctgcttgcga aaagtggtgc agctcattac acagtctcca agccagagag     180
tgaacctgga gaccatgtgt gctgatgatc tgctatcagt cctgttatac ttgcttgtga     240
aaacggagat ccctaattgg atggcaaatt tgagttacat caaaaacttc aggtttagca     300
gcttggcaaa ggatgaactg gggatactgc ctgacctcat tcgangctgc ccattgaata     360
ttcggcaagg aagcctctct gctaaacccc ctgagtctga gggatttgga gacaggctgt     420
tccttaagca gagaatgagc ttactctctc agatgacttc gtctcccacc gactgcctgt     480
ttaaggctga tgctctatta gaataaaaga ggatccccta gtccatagca agtataaaaa      540
taataataaa taaaaaaata acaagatgaa gctgggcatg gtggtgtgca cttgtagtcc     600
cagctatatg ggaggctgag gtgggaggat cacttgagcc cgagaggttg aggctgcagt     660
gagctctgat tgtgccactc tactccagcc tgggcaacat agcaagacct tgtttctaaa     720
aaaataaata aataaattct gttatttgtc accctgtagg gattcactga aaaaaaaaa     780 aaaaaagggc ggcc                                                       794
```

\<210\> SEQ ID NO 69
\<211\> LENGTH: 1915
\<212\> TYPE: DNA
\<213\> ORGANISM: Homo sapiens

\<400\> SEQUENCE: 69

```
gaattcggca cgagcttaaa tgttcgacag ctcaaagctg ggaccaaatt agtgtcctca     60
ctagcagaat gtggggctca aggagttaca ggactgctac aagcaggagt gatcagtgga     120
ttatttgaac ttctgtttgc tgatcacgta tcatcttctc ttaagttaaa tgcttttaaa     180
gctttggaca gtgtcattag tatgacagaa ggaatggaag cttttttttaa gaggtaggca     240 gaatgaaaaa agtggttatc aaaagcttct ggaactcata cttttagatc agactgtgag     300
ggttgttact gctggttcag ctattctcca aaaatgccat ttctatgaag tcttgtcaga     360
gattaaaaga cttggtgacc atttagcaga gaagacttca wctcttccta accacagtga     420
```

| | |
|---|---|
| acctgatcac gacacagatg ctggacttga gagaacaaac ccagaatatg aaaatgaggt | 480 |
| ggaagcttct atggatatgg atcttttgga atcctcaaat ataagtgaag gggaaataga | 540 |
| aaggcttatt aacctcctag aagaagtttt tcatttaatg gaaactgccc ctcatacaat | 600 |
| gatccaacaa cctgttaagt ctttcccaac gatggcacga attactggac ctccagagag | 660 |
| ggatgatcca tacctgttc tctttagata tcttcacagt catcacttct tggagttggt | 720 |
| taccttgctt ctgtcaattc cagtaacaag tgctcaccct ggtgtgctgc aagccacaaa | 780 |
| agatgttttg aagtttcttg cacagtcaca gaagggtctt ctttttttta tgtcggaata | 840 |
| tgaagcaaca atttattgat ccgagctctg tgtcactttt atgatcaaga tgaggaggaa | 900 |
| ggtctccaat ctgatggtgt tattgatgat gcatttgcct tgtggctaca ggactcaaca | 960 |
| cagacattgc aatgtattac agaactgttc agccattttc agcgttgtac agccagtgaa | 1020 |
| gaaacagacc attcagatct cttgggaacc ctgcacaatc tttatttgat tacttytaat | 1080 |
| cctgtgggaa gatcagctgt tggccatgtt tttagtctgg agaaaaatct ccaaagtctt | 1140 |
| attactctaa tggagtacta ttcctcaaga tggaatacct ccaccaaaac ggccactcaa | 1200 |
| agtatcacag aagatttctt cccgtggtgg gttttcaggc aatagaggag gacggggtgc | 1260 |
| tttccacagt cagaataggt ttttcacacc acctgcttca aaaggaaact acagtcgtcg | 1320 |
| ggaaggaaca agaggctcca gttggagtgc tcagaatact cctcgaggaa attacaatga | 1380 |
| aagtcgtgga ggccagagca attttaacag aggccctctt ccaccattac gaccccttag | 1440 |
| ttctacaggt taccgcccaa gtcctcggga ccgtgcttct agaggtcgtg ggggacttgg | 1500 |
| accttcctgg gctagtgcaa atagcggcag tggaggctca agaggaaagt ttgttagtgg | 1560 |
| aggcagtggt agaggtcgtc atgtacgctc ctttacacga taaaaatcct tttgggaaca | 1620 |
| tcttaactgt atatgaacat ttcacgagga caataaaaat aagacattga aggaccaatt | 1680 |
| tagacttagc agttatctgg agacatctga gagaatattt ttatctgaag aaagcagaat | 1740 |
| ttgtttgata cctaacaaga tttcaataaa aatccaaact ttgtatgtac gtttgtatat | 1800 |
| attttccctt ttttgtatga ctatttattt agaaaatttc taggtgaaaa actaaatgat | 1860 |
| gttttgtatt tttcttgcct atagcacaga tattctcaaa ctttctcagc tcatg | 1915 |

<210> SEQ ID NO 70
<211> LENGTH: 733
<212> TYPE: DNA
<213> ORGANISM: Homo sapiens
<220> FEATURE:
<221> NAME/KEY: SITE
<222> LOCATION: (3)
<223> OTHER INFORMATION: n equals a,t,g, or c

<400> SEQUENCE: 70

| | |
|---|---|
| gcnggtggcg gccrcrtcgt agaactagtg gatcccccckg ggctgcagga attcggcacg | 60 |
| agggcggatt catcatgaag caaacgcggc tgaacccccc agtggtcttc attcttctcc | 120 |
| aacccctttc aagacccagg gatgggctca gcaattctgt tttaataatt ttgcattctg | 180 |
| tcccttaaat cataaagaga gccccccaatc tgtaaagctt ctgatcccac acaacctctc | 240 |
| agggctccag ggtcctgagg aggatggcca ggtcactgtg ggcctgtggt ggagccagcg | 300 |
| ggcacccagg gcttcctggt gggccaggtc cctggtcata gactgagcca gammagcatc | 360 |
| agcytccgat ctccaggccc ctgcggtgag ggccccaatg cccctgataa ggctctgctc | 420 |
| ctaagggct gttggccttg aacaagctgc tctcctgcct cagtttccam ttcaggatgg | 480 |
| agacatgaat gagagaagtg tccctgaaac tcctgatggc tttccatttc ctggtttcct | 540 |

```
gtctttcctg aggctgaatt cttcgcctgc tttctctgag atccctcact ttcctgccaa      600
gaaatttcct ctttagtctg ttcagagtga agtgcaaatc aaaataaaaa agtgcaagtt      660
caaagtgcaa tcaaaacaaa caaacaaact ttggctaagg caaaaccaaa ccaaaaaaaa      720
aaaaaaaaaa ctc                                                        733
```

<210> SEQ ID NO 71
<211> LENGTH: 1266
<212> TYPE: DNA
<213> ORGANISM: Homo sapiens

<400> SEQUENCE: 71

```
cccatgtcgg ccctgaggcg ctcgggctac ggccccagtg acggtccgtc ctacggccgc       60
tactacgggc ctggggtgg agatgtgccg gtacacccac ctccacccctt atatcctctt      120 cgccctgaac ctccccagcc tcccatttcc tggcgggtgc gcggggcgg cccggcggag      180 accacctggc tgggagaagg cggaggaggc gatggctact atccctcggg aggcgcctgg      240
ccagagcctg gtcgagccgg aggaagccac cagagtttga attcttatac aaatggagcg      300
tatggtccaa catacccccc aggccctggg gcaaatactg ccttcatact cagggcgtta      360
wtatgcacct ggttatactc agaccagtta ctycacagaa ttccaagtac ttaccgttca      420
tctggcaaca gcccaactcc agtctctcgt tggatctatc cccagcagga ctgtcagact      480
gaagcamccc ctcttagggg caaggttcca ggatatccgc cttcamagaa mcctggaatg      540
amcctgcccc attatcctta tggagatggt aatcgtagtg ttccacaatc aggaccgact      600
gtacgaccac aagaagatgc gtgggcttct cctggtgctt atggaatggg tggccgttat      660
ccctggcctt catcagcgcc ctcagcacca cccggcaatc tctacatgac tgaagtactt      720
caccatggcc tagcagtggc tctccccagt cacccccttc accccagtc cagcagccca      780 aggattcttc ataccccctat agccaatcag atcaaagcat gaaccggcac aactttcctt      840
gcagtgtcca tcagtacgaa tcctcgggga cagtgaacaa tgatgattca gatcttttgg      900
attcccaagt ccagtatagt gctgagcctc agctgtatgg taatgccacc agtgaccatc      960
ccaacaatca agatcaaagt agcagtcttc ctgaagaatg tgtaccttca gatgaaagta     1020
ctcctccgag tattaaaaaa atcatacatg tgctggagaa ggtccagtat cttgaacaag     1080
aagtagaaga atttgtagga aaaaagacag acaaagcata ctggcttctg gaagaaatgc     1140
taaccaagga acttttggaa ctggattcag ttgaaactgg gggccaggac tctgtacggc     1200
aggccagaaa agaggctgtt tgtaagattc aggccatact ggaaaaaaaa aaaaaaaaa     1260 actcga                                                              1266
```

<210> SEQ ID NO 72
<211> LENGTH: 485
<212> TYPE: DNA
<213> ORGANISM: Homo sapiens

<400> SEQUENCE: 72

```
gaattcggca cgagtaccct gttctaatac agttcagtgt gtcttataga aaatcattta       60
tcttttgcct ccctgaaatg atttaactt tttgtgtttt tctcctttc tcatttcata      120 atgcaattaa atctaccccct tttctcaaat tttaaaaaca catgaataaa atatcttta      180 cttaaggtca acacaaatg gagtggcgta ggctggtcat ggtggctgac acctataatc      240
ccaacactgt gggaggccga ggcaggtgga tcacttgagc tcacaagttt cagagccgcg      300
```

```
tgagcaacat ggcaaaaccc cgtctctaca aaagaataaa aaacttagcc aggcatggta    360
gctactcagg gaggatggct tgagcctggg aggcagtggt tgcaatgagc caagatcgca    420
ccactgcact ccagcctggg stataaagcc agaacttgtc tcaaaaaaaa aaaaaaaaa    480 ctcga                                                                485
```

<210> SEQ ID NO 73
<211> LENGTH: 639
<212> TYPE: DNA
<213> ORGANISM: Homo sapiens

<400> SEQUENCE: 73

```
gaattcggca cgagtattaa gtcaaattgc tgtattctac gtgttagagt gagttcaaaa    60
gatccattgt attactgaat aggcaaaagt tttaatttca gaggatgaaa ctgatatatt    120
actgccacct tgtggatatt ctgttattac aggctattat aaaargcaat gcgggtatgt    180
aatctgttct aacaagaagc atttcctttt tttgtcgttt ttattattgt tattattaca    240
ttttaagttc tgagatacat gtacagaacg tggaggtttg ttacataggt atacacatgc    300
catggtggtt tactgcaccc atcaacccat catctacatt aggtatttct cctaatgcta    360
tccctccccc agcctccac cccttgacag gccccggtat gtgatgttcc cctccctgtg    420
tccatgtgtt ctcattgttc aactcaaaag aaaaacagaa gcattttctg ctttcccaat    480
ttcttaaata caatgcaact ttatgtttaa tttaactaac ttaattttttt gagacaaggt    540 ctagctctgt tgcccaggct ggagtggcgt ggcgtgaata tggttcagtg aaacctccac    600
ctccctggct caagtgatcc tccttcctca gcctctcga                           639
```

<210> SEQ ID NO 74
<211> LENGTH: 532
<212> TYPE: DNA
<213> ORGANISM: Homo sapiens

<400> SEQUENCE: 74

```
atggctgctt tcaacccgaa cgcgtccatc cttcaagatc aagacccatt ccatagttca    60
acaagtagtt ggtgatgata gagtgccctg actgggccag aacagcctct ttagccaaac    120
agcgcaggaa agtctttaaa cagatgctca gctcctttct tcattttcac tttaattcca    180
tgatgcctct gtgtccctct gacgacatct ctcctggggt ctgggactct gctggtcttc    240
catgcctact gagaaggctt cctggccatc atcaggcagg aaaacctcaa agccctccgt    300
cctcaacgtg ggatccctgg gccagcagca tcagcctcac caggaaacct gttcttctgc    360
tcattcttgg gccccacccc aggcctattc aaagaaagac tccagggggca gcgcttggca    420 gcctgtgttt ccaccagatc tgtgtgaaaa ctcaaatgaa ccagcccagg tgatgtgacg    480
caggaagtgc aaggctgaga gccagtgtct aaggcaacct cgtgccgaat tc            532
```

<210> SEQ ID NO 75
<211> LENGTH: 514
<212> TYPE: DNA
<213> ORGANISM: Homo sapiens
<220> FEATURE:
<221> NAME/KEY: SITE
<222> LOCATION: (507)
<223> OTHER INFORMATION: n equals a,t,g, or c

<400> SEQUENCE: 75

```
aggcagacgt agaactagtg gatccccmgg gctgcaggaa ttcggcacga gccccagcta    60
ggaagaaaga atggcactct tgggcttggc ccagaattag agttattaga gcaagagaga    120
```

```
gcttaggaag catgagggca actatagtga ggccttattg ccaggaggga gggttttggt        180
tgctggcgct tgtgtataaa ggggcaagag cagctccttt ggactattcc tgggaggact        240
ctgatgcagg gcgtctgttg ctcccctggg tcacctcctc cctgctcgct gacatctggg        300
gctttgaccc tttctttttt aatctacttt tgctaagatg catttaataa aaaaaaagag        360
agagagagag aggtgtgagg gacaaaatgc aaacctattt cccttgcctc ataggcttct        420
gggatgtcat cacctccagt ttgttggttt tgtttccaac tgttaataaa gcattgaaac        480
agtaaaaaaa aaaaaaaaaa acaaaanaaa aaaa                                    514
```

<210> SEQ ID NO 76
<211> LENGTH: 644
<212> TYPE: DNA
<213> ORGANISM: Homo sapiens

<400> SEQUENCE: 76

```
tcgagttttt ttttttttt tatttattat tttactttaa gttctgggat acatgtgctg         60
aatgtgcagg tttgttacat aggtatacat gtgccatggt ggtttgctgc acctatcaac       120
ccgtcatcta ggttttatgc cccgcatgca ttaggtattt gtcctaatgc tctcccgccc       180 cttcccact aacaccctcc tgagtttatg aatccttgca gatatgtttt atgtatatga        240
tcatagtatg tatgtagaca cacacacaca cacacgtt ccctctctct acacaaatgg         300
taacatacta aagatactct tctgtacctt cacagtacaa gtaccatatt ccccacttag       360
cacttggcaa aggccaaagc cagttaaggg cagggtgagc acttggcctc caagctctat       420
gtccagtgct cgctccccac agggcccta actcacccac agaagcggac tcagccccag        480
gctacgtcta acaaccacac acaaaagcag caagaaatgg cccatgctgc cttctgggca       540
ggacattcca tcctgcagaa ggaaccttta ggctcactcc gccacctggg aagccaggct       600
gccaggggat ggggcaggcg gttggactca ctcgtgccga attc                        644
```

<210> SEQ ID NO 77
<211> LENGTH: 1199
<212> TYPE: DNA
<213> ORGANISM: Homo sapiens
<220> FEATURE:
<221> NAME/KEY: SITE
<222> LOCATION: (469)
<223> OTHER INFORMATION: n equals a,t,g, or c
<221> NAME/KEY: SITE
<222> LOCATION: (582)
<223> OTHER INFORMATION: n equals a,t,g, or c
<221> NAME/KEY: SITE
<222> LOCATION: (630)
<223> OTHER INFORMATION: n equals a,t,g, or c

<400> SEQUENCE: 77

```
gaatggcacg agcaatggct ctgttagtcc tgactctgta ttgcattctt tttttaaaaa        60
tctacatgcc tgtcccatct cactgtgagc aattcaaagg caggaattaa gtcttattaa       120
tttctctctt ccgttgccca gcatagtgac cagaacagga ctcaataaaa tgtgttgaat       180
agataaatgg gctgttaaga gaaaacttt agcagaatta aatttaaagg agtttaattg       240
agcaatgaat gattcacgga tcaggcagcc cccagaatta ctgcarattc agagaggctc       300
cagggtacct catggtcaga acaaaaaaag ggaagtgacg tacagaaatc agaggtgagg      360
tgcaraaaca gctggattgg ttacagcttg gcatttgtgt tatttgaaca cagtctgaac      420
actcagcact gtatgaatgg ttgaagtgtg gctgctgaaa ttggctgana ctcagctatt      480
```

-continued

```
gttacaggct gtaatcctaa attagggttt caatcttgtc tgcacactaa ggtaggttgc      540
agttcgtcca caaggactta aatacagaag tatggagtcc tnctcaggcc atatttagtt      600
tgctttaaca aggcatagca gtgataagtn ccagagagag gtggtcagca cgattcatca      660
ctgtcctcag acaagaagag gatgaggagg gatgagccat tgtgcctat tttgkaccttt     720 tttggcaaag tcatgattac ttagtcatgt wacatgtaac ttagcatgac ccatgggtac      780
agaaactagg tttaattttt ttatccaaca gtgamgtttt ccatacttca ctcaagtact      840
tagtaattgc tgtagctttg cttcattgca gcggcttcat agatcatggc tgttgttcat      900
cgcttgtggc gtgcctggga aatcaatagc taaaaaygtt ttgtgaaccc ttagtagttg      960
ttacctgggt aggtttggaa tgttccagga gaattaatga acamtcaggt gatmgttttg     1020
tcattttaca gggaataata agcaaatgcg tgtttggaag tgtgattcta tcaaatctgt     1080
ttataaataa gtgcatattt gccatttaaa gtaatttttt tatctgtgac ttgggcttca     1140
tgggattagc tataatgaca cgtctgggag tctcctcaca attagaatga aatcctcga      1199
```

<210> SEQ ID NO 78
<211> LENGTH: 660
<212> TYPE: DNA
<213> ORGANISM: Homo sapiens

<400> SEQUENCE: 78

```
gaattcggca cgagcagagg cccggtacct ttaagctcta cctcgccaat gccctctcgc       60
ctagtaatcc gtgcacacag cctgctgttt gccatgcaga atgatggcct caagttcatg      120
gaaatggtgc tccatgtcct tcaggcaagt ataggtgttc tgttgcttat ggtggatgtg      180
ctcgagcatt tccttgccat gctcattggc aatgcagggg ctcctttgcc actgctggat      240
gtgctgggga aggatgttat tgatgtggct gaaagaagag agagcaagaa atgaaatggg      300
tagatgggga catcagagga atgagaaaga tgagctacca aatggtgact ctataaggta      360
ctgagtggtg gatgagtgca cgttggtgaa tgggtggttg aacagtggac gggtgggtgg      420
atgggtggag gggcaggtgg gtgagtggct ataaggtgg atgagcaggt gggtgagtgg      480
ctatgagggt gaatgagcag gtggatgagt ggctataagg gtggatgagc atcctggtgg      540
atgtaatgtg gatgggcagt tcagtgagtg ggtgactatg acggtggatg ggtgggtggc      600
tgagtggaat tacagatggc atagatcaca ccttactttg cctttgtccc ttaacctcga      660
```

<210> SEQ ID NO 79
<211> LENGTH: 524
<212> TYPE: DNA
<213> ORGANISM: Homo sapiens

<400> SEQUENCE: 79

```
tcgagccccg gctggcgggc ctggctgctg ggtctttgtc ttctaggttc ctctttctcc       60
caagaagggc taagtggatc ctgtgaaggg agggatgcag tgggggaag gagctggccc      120 cagctgggtt tacattctca gctgggacag cagagcctca ctgtgtatgt gtgcagccag      180
cagatacctg tgcacaggca cagacccacc aactcgtggg gacacttcaa caccgcacaa      240
agccattttg ccactagacc catgcccca aattagcaga actgctcgtg ccgaattcct       300
gcagcccggg ggatccacta gttctagagc ggccgccacc gcggtggagc tccagctttt      360
gttcccttta gtgagggtta atttcgagct tggcgtaatc atggtcatag ctgtttcctg      420
tgtgaaattg ttatccgctc acaattccac acaacatacg agccgaaagc ataaagtgta      480
aagcctgggg tgcctaatga gtgagctaac tcacattaat tgcg                       524
```

<210> SEQ ID NO 80
<211> LENGTH: 434
<212> TYPE: DNA
<213> ORGANISM: Homo sapiens

<400> SEQUENCE: 80

| | | | | | |
|---|---|---|---|---|---|
| gaattcggca | cgagcggcac | gagctcgtgc | cgaattcggc | acgagatttc | atgggcagtg | 60 |
| tctggaactg | cctttagca | ttacttgaaa | acatttaat | tactttgtac | aaattaataa | 120 |
| taacagtgct | actagatttg | ctcagtgcca | ggcataagtg | ctttacatct | gtgaactcat | 180 |
| ttaactgaat | tggtcccggg | gttgggatag | aacagctgcc | cctccttcag | cagcggttcc | 240 |
| agccgtccta | gctctgcggc | ctggccactt | tgttttcccc | aatccctggy | ctccaggagc | 300 |
| agggctctca | gctcccctgg | ctctcacgtc | ctcacctgag | ctgaggagag | gacagggtgg | 360 |
| ctctctccag | ctccamamtg | gtctgtatcc | aggctattyc | amcctcattc | aaaaaaaaaa | 420 |
| aaaaaaaact | tcga | | | | | 434 |

<210> SEQ ID NO 81
<211> LENGTH: 735
<212> TYPE: DNA
<213> ORGANISM: Homo sapiens

<400> SEQUENCE: 81

| | | | | | |
|---|---|---|---|---|---|
| gaattcggca | cgagcttctt | ataacctaat | ctctgaagtg | atatcatcac | ttctgctata | 60 |
| tcctgttcat | tagatgtgag | tcagtaagtc | cagcccactc | tcaagggaag | gggtgtgaat | 120 |
| atcaggaagt | ggggaatcac | tggggttatc | ttagaggctg | ctaccataac | ggaggaatat | 180 |
| tggcatcttt | attttcatta | acctctaact | ggctttagtg | tcacattcta | caataaatgt | 240 |
| aggcaacaag | tcactgtggt | atgaacagca | cctgtggttt | tgtaaccagt | ataaatcaga | 300 |
| tatttcttat | tattttatgg | tkgttgtacc | tgcctctact | taccactact | ttggaaatat | 360 |
| gggagttatt | agmcctactg | cactagattt | tgttatttaa | tatataaaaa | gaaattcaca | 420 |
| ttactataca | acaacttaaa | aaatgcttgg | acaaaactat | tttatttgta | acttttgta | 480 |
| ttttgtttta | tgagatgtaa | aatattattc | tgagaggtga | tccacaggta | ttaccaaact | 540 |
| gttaaggcgt | ttgtgacaca | aaaatattaa | gaatccctaa | gcaagtgata | ttcaaagtgt | 600 |
| ggttctggga | acagcagcat | caacatcacc | tgggaactag | tctgaaacgc | aaattatcag | 660 |
| gaggttcctt | ccctgaccta | ctgagtcaga | aactctggcg | gagggaccca | gcaatctgtt | 720 |
| caaatacacc | ctcga | | | | | 735 |

<210> SEQ ID NO 82
<211> LENGTH: 722
<212> TYPE: DNA
<213> ORGANISM: Homo sapiens
<220> FEATURE:
<221> NAME/KEY: SITE
<222> LOCATION: (697)
<223> OTHER INFORMATION: n equals a,t,g, or c
<221> NAME/KEY: SITE
<222> LOCATION: (717)
<223> OTHER INFORMATION: n equals a,t,g, or c

<400> SEQUENCE: 82

| | | | | | |
|---|---|---|---|---|---|
| gaattcggca | cgagcatgag | ccactgcacc | cagccgatac | tactatatcc | ccattttaca | 60 |
| gatgagcaca | tggcaaaatt | gagggtaagg | cactgaccca | tgatcataca | gctgagaagt | 120 |
| ggcaaaggca | ggatttgaac | ctagaacctc | tggctccaca | cactagtaat | ctaaaccact | 180 |

```
ctccctacaa tacaacatac gtggtaaaga tgtgtggtgg gcacgcaatc aacgtaggtc      240
ccttcacagt tgctgggaga ggcaggaatt tgcagttcct ccgcgttctc ctcctccgct      300
gcccacctgt cctgggtcat tcctgcagcs tgccctgccc tgcctggtct caccctccct      360
ctgccaacag aagtctgggc agggttttat gggctctgat aaggccctgg cagggccgaa      420
gttcatgagc acttcctctt tgcaggaggg cgtaggggag gggacccagg tgatttgggt      480
cctggctggt caccagggaa gctggcaagg gaagggagac tagggtgcgc tctaggagaa      540
gccgacagcc tgagagtccc agaagaggag ccctgtggac cctccctgc cagccactcc      600 cttaccctgg gtataagagc caccaccgcc tgccatccgc caccatctcc cactcctgca      660
gctcttctca cagaccagcc actagcgcag cctcganggg gggcccgtcc caatttncct      720
ct                                                                    722

<210> SEQ ID NO 83
<211> LENGTH: 785
<212> TYPE: DNA
<213> ORGANISM: Homo sapiens

<400> SEQUENCE: 83
gaattcggca cgagcttgtt cacactcagt aaacacatta gttgaattcc tctgattgtc       60
aattagcaat ggttttgcca agaatactgg tattgatgct gtttttagca ctgaaaaatc      120
ctgtgggaga aatgaggaat ttaacacatt gtaggtgtta agattcctgg gtgtctgaca      180
gtatccctgg aaccattatc attaattaac ttttcaatca gaaaggcaaa ctactttgct      240
gttaggcttc cagatgaggt tttttgaaaa aacagtaaga taataaaggc ttggattgct      300
cctacttcct gaggcaagtc acatctcata ttattcagaa cttggactga agagctcata      360
gggcaagtga ggccaaggtc aggagtcttc agacatcttg gccaagtgc cattctagaa       420 gaaatgattc tcttcctcag tcaccatcta tctatgcccc caggtttgac tcgctctttt      480
cccaaggagt gctgttcatt cctgacacaa gggagaccag aaaagagatc atgaatgaca      540
gtgaaaacct ttatgacact gacataaagc agagagttag actgaatatg agttggtagc      600
ttttcctttg tatctgtgta agttgaatca tacaaaattg tcattttggt gattcaaaag      660
tgtaaaacaa aagcaagttc atatgattca agcttacatt ttttctcac tataagaaag      720 aggatttaaa gaattgtatt aggttagcga atctgatttc tttcatgcaa atacagctcc      780
tccga                                                                 785

<210> SEQ ID NO 84
<211> LENGTH: 570
<212> TYPE: DNA
<213> ORGANISM: Homo sapiens

<400> SEQUENCE: 84
aaacgacggc cagtgaattg taatacgact cactataggc cgaattggtt accggccccc       60
ccctcgagtt gaattagaga aaacgacatg gacacacgtg gagtggtttt aaggagcgga      120
gagtttaata ggcaagaagg aagggagaag acagaaggaa gaagctcctc catatggaga      180
cagagggagg gggctccaa agccaaaaga ggaggtcccc aagtgcagtg gacaccagcc      240
aagtatatat gcagaggctg gaaggggcga tgtctgattt acatagggct cagggggattg      300 gtttgaccac gcatgttatt cacatagccc actaaaaagc tggctctccc accctagtct      360
tttaatatgc aaatgcaggg agccatggat gttctacaca tgtggggata tttggggatg      420
```

| | |
|---|---:|
| ttctacacat gtggggcggc catgttgcca ggaacatgtg aggcaagggt aagaaggcct | 480 |
| tgggaattgc catgttgggt ggacccagtt tctaatggcc tgcatttgca tatcaaaggt | 540 |
| tgctcgtgcc gaattcctgc agcccggggg | 570 |

<210> SEQ ID NO 85
<211> LENGTH: 905
<212> TYPE: DNA
<213> ORGANISM: Homo sapiens

<400> SEQUENCE: 85

| | |
|---|---:|
| gaattcggca cgaggtgatg aataaataaa tcaacagaga ttttaccatg ttttttttta | 60 |
| aactgatcta gtttatcact ctcttatctc tacaatttat ctttcactca aagaactaaa | 120 |
| gttatcttcc aaaacacag aatgaatcag ctcactctcc tcaagactct taaatggtcc | 180 |
| ttcattactt gttgagaaaa gcccagactt gtttagtgga gcaattaaac tccccacaat | 240 |
| ttatctgcca gaagactttc tggaaccatg tatggttttt tgccctcca acttacagtc | 300 |
| ttattggtcc attatttttt tctcatcatg ccacacattt ttgtgtcagg taattttagt | 360 |
| cttttggcct tgttcttact atcagccaac ttcatagttg aagtccagag ttggttgttg | 420 |
| ttgttgttgt tttttatcka tttaggtagg agttacaatt tttatttgct ttgtgacagc | 480 |
| attattttct gacacatttt cttcatattc tttttaaagag tttctttttt aaacccatgt | 540 |
| tattcaaggt taaacaaata acgagtttct ttgtttggat gttatgctta cacttacttg | 600 |
| aatatgttgt ttttttttcca gactagccat tagcaagatt cctgtggagt gagggagtgc | 660 |
| ccagggtagt tctccagatt attctgctca aattcttcct cttctcatgc tgcagtgatg | 720 |
| aattatttct tcaaaactat gaccccactg tgtagctcca cctttccttg ttctcacaag | 780 |
| agtgtacaaa atcgttgagt cttctgagcc atggctaaca agaatcctag ctactgcctt | 840 |
| ccactatatc tttcccttt taaaggagc attttctgag tttagtcatc tcaggccttc | 900 |
| ctcga | 905 |

<210> SEQ ID NO 86
<211> LENGTH: 706
<212> TYPE: DNA
<213> ORGANISM: Homo sapiens

<400> SEQUENCE: 86

| | |
|---|---:|
| gaattcggca cgagcaaaga tgaggctgtc tacaaactta tgtatcattc taataaatat | 60 |
| tttaatacag aatgttctaa attttaatag gaaaataata tttaagttcc ttccatgtgc | 120 |
| catgcataat cttatatcaa gtataatttc atttttatat aatttctgtg ccttacctct | 180 |
| tgcttctccc caattcacaa atgaagaaag tagttacacc gcccttcgtt catgtacaag | 240 |
| gggagggttt gaatccaggt ctctaggaac ccaaaagtca tgcaccttcc aaggcaaagg | 300 |
| agattaccat gttacagcat agataaaaac ataatagaat taggaattgg ataagtatag | 360 |
| agggttcaat agtgttcccc caaaattcct ctcaacactg aagctcagaa tgtgaccta | 420 |
| tttggagata ggatctccaa aggtaatgca gatgtaatca gttaagatga ggtcataccg | 480 |
| gattaatttg ggtcctaaat ctaatgactg gtatcctttt aagaagaaga gaaaacacag | 540 |
| gacacagaca caaggaagca gcaaacgtga agacagaggc tgggggtgta gtgatgcagc | 600 |
| tataaggcat ggggccaccg gaggctggga agggataagg agggacccct ccccaaagcc | 660 |
| ttcagaggga gcagctgaca ctttgaattt ggacttctag cctcga | 706 |

-continued

```
<210> SEQ ID NO 87
<211> LENGTH: 1544
<212> TYPE: DNA
<213> ORGANISM: Homo sapiens
<220> FEATURE:
<221> NAME/KEY: SITE
<222> LOCATION: (1)
<223> OTHER INFORMATION: n equals a,t,g, or c
<221> NAME/KEY: SITE
<222> LOCATION: (8)
<223> OTHER INFORMATION: n equals a,t,g, or c

<400> SEQUENCE: 87
natgcttnca actatttata atgcatcaat ttgaacttag arggtrggag atcrgatcat     60
atgtgggaaa atgtaaaagc agggatatca gtgggcatta gaataaaaac tagggataca    120
ataacttctt tgcatatgac aatacttatt tgtatataag agaaagaacg aaataacctt    180
tattgaaata agatactat gcaagaaaat gtacagttgt cgaagtggag aaaatgagga     240
tatattcttg cagacgagct ataggtcata catgaatgtc tagtgagaca ttcaaaattc    300
gtataggttg cagagtaatt tcttattgtg aggaactgtc caatgtattg caagatgttc    360
tgcatacttg gctctcacat actaaatgct agtagcgccc ccaccccac gcccagtcac     420
ggtgacaacc acaaacccta tcagatctat tcacctttttt cagagcagat attttgtaac   480
attctcttttg ctgacctgaa atgactcata gataatacaa tctacttaca cacatgaatt   540
tcttaaaaaa atcaatttaa tgccctaact ctcttattaa ggagaaatag aaaagaagaa    600
atttataatg aaaagaagat gaatttcatt atgtaaacgc tcaggcatga ctacgctgtt    660
tgaaacagac agatgtttac tcttccttgt aatgagtagg tttggattta agagccgatt    720
agaggctact tcctgtaaac aagtacagga aaatgaaact agacgggtgg gggacactag    780
aatgaaaacc agtgttaggg taaagacaaa acagactatg tacataatct gtatatggga    840
aaagaaagag cgaaattacc ttacttaagg ataataggac aagacaaatt acagattgtc    900
tcagagaaaa caaatgagtt actctctcgg acaagctgta ggtcctacct aaatgtccag    960
caggacatta gacagtcgta cagggtacag aataattctt cgttgtgtgg cactaaccca   1020
cacactgcag gacatcgttc tccctggctg catccactca gtgctgggag tagtccccag   1080
ttattatgaa accaccaata acccactgac cacagtgaga accactgatt ttttccactg   1140
acctactgaa tatctagcat ccttagattg gctcaactgt tactttccta aggagtcctt   1200
ctacagaata ggtcagatct tggcctccca aacccttat ttttaaaata ctttgcgcct    1260
tgctttgata atttgtatta tgtatccaaa ctgaaattat ctgctttctg cattagaatg   1320
taagcccccct gagggttgag tcagtctgtc ttgtttgctg tgccacgcct gatgcccagc   1380
ccagcagcat gctttgtaca ctgatatatt gggtaaattt tgttgaataa attaagctca   1440
actatttgta tttcaatagt tgagttgtat tgcttcctgt tcttcaagct taatttgaac   1500
tgtctaataa aaagaagtaa ttaaaaaaaa aaaaaaaac tcga                     1544

<210> SEQ ID NO 88
<211> LENGTH: 840
<212> TYPE: DNA
<213> ORGANISM: Homo sapiens
<220> FEATURE:
<221> NAME/KEY: SITE
<222> LOCATION: (326)
<223> OTHER INFORMATION: n equals a,t,g, or c

<400> SEQUENCE: 88
gaattcggca cgagcttttt cattatcttt accttaatct cttagcatat gatttatgga     60
```

```
ctggaatggt gagtgatatc agtgggcaaa acaatcatt agaggctgtt aaggaacatt      120
tattgtttat ttggctacct gtctataaaa gtacacatga aggccctaat agcaaaatat     180
caaattatca agtgctttaa agcagaaaat gtcatttgtt tctcaaaact gcaccaactt     240
tatataattg cccttttaat tatccctagt ggcccgtgaa atttgcaaaa tagagcatca     300
aagcttgatt tacttacagt tgcacnttgg cgggatctta atgaatattg tttagtacta     360
atgctgagat ggaatcgtaa atgtttatag tgagggactt acttagaaga gtggggaggc     420
cagtaatgaa actgaatcaa ctgggttctt caagatggaa caatatgcc atattcttgg      480 gcctaacatt ttgaaaaatt cttttttatag tggaattta tttttaattc aggtctagat      540
gaatacacat taagtttagt tttgcagaat cttttttttt ctgcctagct atcttattac     600
tttccaaggg cttttgagga gtaatttgtt tcctggcaat ttcggattaa aatcacctgt     660
ttcttcataa attgtcatct tcaaggtaac actgagaact ggatctctga atctcatgt      720 tttcgagatg atttttatag ctgcagacct gtgggctgat tccagactga gagttgaagt    780
tttgtgtgca tcatcatgtg ccattaaatg aaaaaaaaaa aaaaaaaacy cgggggggggg  840

<210> SEQ ID NO 89
<211> LENGTH: 510
<212> TYPE: DNA
<213> ORGANISM: Homo sapiens

<400> SEQUENCE: 89
gaactastgg atccccggg ctgcaggaat tcggcackag gctgcgctcg gccaggccgg       60
caccatgcgg ccctgctct gcgcgctgac cggactggcc ctgctccgcg ccgcgggctc     120
tttggccgct gccgaaccct tcagccctcc gcgaggagac tcagctcaga gcacagcgtg     180
tgacagacac atggctgtgc aacgccgtct agatgtcatg gaggagatgg tagagaagac     240
cgtggatcac ctggggacag aggtgaaagg cctgctgggc ctgctggagg agctggcctg     300
gaacctgccc ccgggaccct tcagcccccgc tcccgacctt tcggagatg gcttctgagc      360 cctggagctg gagcccagca gttggaggtg gtgcacctgc cagcagcgcc cacagaacca     420
gccctgtcct ctcgacttcc ttccttagct tcatgtgaaa taaaagctat tctggtcaaa     480
aaaaaaaaaa aaaaaaaaaaa aaaaactcga                                     510

<210> SEQ ID NO 90
<211> LENGTH: 738
<212> TYPE: DNA
<213> ORGANISM: Homo sapiens
<220> FEATURE:
<221> NAME/KEY: SITE
<222> LOCATION: (1)
<223> OTHER INFORMATION: n equals a,t,g, or c
<221> NAME/KEY: SITE
<222> LOCATION: (14)
<223> OTHER INFORMATION: n equals a,t,g, or c
<221> NAME/KEY: SITE
<222> LOCATION: (66)
<223> OTHER INFORMATION: n equals a,t,g, or c

<400> SEQUENCE: 90
ncggaagtcg gcgncacgta gtagggaaac ctgggacgcc gtgcaggtac cgggccggaa       60
ttcccngggt cgacccacgc gtccggtcaa taactgtcat agtgaaaatg tggtttttaa     120
gagtagtagc tacttatggg ggtgtagaaa gaatggcctc tctcttagac aatttcatt      180 taaacatcat agtcatcttt tgcatagtga ttgactccta tctttgtggt ttcatgtatt     240
```

-continued

| | |
|---|---|
| tctttgtgat tgattcccca gtgcctgcct gcagtccatt gcaactctcc caaactttaa | 300 |
| tcctgcagct tcagcccact gctagatatt tccattgatg acctgtcatc tgaaacctag | 360 |
| cattcatcat gtgctgtgtt gtataattgt atgtctgtgt tattgtatta ctttcccaag | 420 |
| taaagttttt gtgtaaggac ttaacactgc tttgaatccc ctgtacctat tatactgctg | 480 |
| tgtacaaagt aggagttcaa atacatgtga tcacaatagt cttccattca taactcatca | 540 |
| gcagctcagt ccttcttatg tctagtctca gttcattcag ccaaagctca tttttgtcct | 600 |
| atccaaagta gaaagggttc ttttagaaaa cttgaagaat gtgcctcctc ttagcatctg | 660 |
| tttctgactc ccagttattt ttaaaataaa tgatgaataa aatgccaaaa aaaaaaaaaa | 720 |
| aaaaaaaaaa gggcggcc | 738 |

<210> SEQ ID NO 91
<211> LENGTH: 506
<212> TYPE: DNA
<213> ORGANISM: Homo sapiens

<400> SEQUENCE: 91

| | |
|---|---|
| tccgagtttt ttgtaccact gattgttctt tcggtggtgt tgttagaatt gagctagtta | 60 |
| tttatagttc tctgttgaaa gagcccacag ggaggagagg tgagctgagc atttgaaatt | 120 |
| caggatctgg ttaakgttgt cagctcagtg gatttgagaa tattcacaga taagcaactc | 180 |
| agaaggatca tacttgtatt gtaggccctc aggtattcag gaaatagatc ttctcttgtg | 240 |
| attcaatagc cataatccaa attaaacatc tggcttttcc aatgtgtatt tttgaatgta | 300 |
| tgtgtcattt cttcatagac atatcaaatc attactatgt ggtaagattt tatccagaag | 360 |
| attctcttcc taaaaccttt atatatgacc cttttaaagc ataaaattat tttaggtgtg | 420 |
| agttttatt atgcaataca aggatacagt ctttaatttt ctacctttaa gctcgtgccg | 480 |
| aattcctgca gcccggggga tccact | 506 |

<210> SEQ ID NO 92
<211> LENGTH: 1203
<212> TYPE: DNA
<213> ORGANISM: Homo sapiens
<220> FEATURE:
<221> NAME/KEY: SITE
<222> LOCATION: (1165)
<223> OTHER INFORMATION: n equals a,t,g, or c

<400> SEQUENCE: 92

| | |
|---|---|
| gtggactctg gctgtccttg ggtggtttcc atgagcgtgg ccaagactgg gagcagactc | 60 |
| agaaaatcta caattgtcac gtgctgctga acagaaaggg gcagtagtgg ccacttacag | 120 |
| gaagacacat ctgtgtgacg tagagattcc agggcagggg ctatgtgtga aagcaactct | 180 |
| accatgcctg ggcccagtct tgagtcacct gtcagcacac cagcaggcaa gattggtcta | 240 |
| gctgtctgct atgacatgcg gttccctgaa ctctctctgg cattggctca agctggagca | 300 |
| gagatactta cctatccttc agcttttgga tccattacag gcccagccca ctgggaggtg | 360 |
| ttgctgcggg cccgtgctat cgaaacccag tgctatgtag tggcagcagc acagtgtgga | 420 |
| cgccaccatg agaagagagc aagttatggc cacagcatgg tggtagaccc ctggggaaca | 480 |
| gtggtggccc gctgctctga ggggccaggc ctctgccttg cccgaataga cctcaactat | 540 |
| ctgcgacagt tgcgccgaca cctgcctgtg ttccagcacc gcaggcctga cctctatggc | 600 |
| aatctgggtc acccactgtc ttaagacttg acttctgtga gtttagacct gcccctccca | 660 |
| cccccaccct gccactatga gctagtgctc atgtgacttg gaggcaggat ccaggcacag | 720 |

```
ctcccctcac ttggagaacc ttgactctct tgatggaaca cagatgggct gcttgggaaa      780
gaaactttca cctgagcttc acctgaggtc agactgcagt ttcagaaagg tggaatttta      840
tatagtcatt gtttatttca tggaaactga agttctgctg agggctgagc agcactggca      900
ttgaaaaata taataatcat aaagtctgtg tctggacatc gcctttggga actagaaggg      960
gagttggtat tgtaccagct ggactaagct ccagttctag acctcctggc tcattcaaca     1020
tgcctcccta cctaaataaa agtgcaacac tcagtgcatg tcccagcccc attctcccaa     1080
gcatgggagt gggcgtagga gtggaggagg gggaaggaaa aaggaattac ttcacttaca     1140
cctatgatgc cctttgccca agccngaaga aagcaaaggg gaaaaggggc tgcagggtac     1200
att                                                                   1203
```

<210> SEQ ID NO 93
<211> LENGTH: 710
<212> TYPE: DNA
<213> ORGANISM: Homo sapiens

<400> SEQUENCE: 93

```
gaattcggca caggtttcac catgttggcc aggctggtct caaactcctg accgcagkga       60
tcccaaagtg ctgggattac aggtatgarc ctcccaaagt gctgggatta caggcatgag      120
ccactgtccc cagcaggatt atcttactat attgtgccac agaatatttt attagcgttt      180
gattggaatt acatagaatt ataaatttgg tatttgtgac tttctgctgg aaatcatgat      240
accatgaaca ttctgatgtt tgcgtttatg ataattttca tgggagctaa atttcaagaa      300
gtagaatttt gggtcagagg atatgatcat ttaaaagcaa cattgtttga tcagattggc      360
agatacttaa agatgggtgg acaggagcca ttgctggcaa aggtttgggt aagggcact      420 tgagtatgct gctagtgaca gggaattcta cgcatttgtg catagaatct gggaatgact      480
attaagattt atttattccc tctctaggta aaatccctct ctaggtatat aaataaataa      540
taaataataa ataaataatc agtttcagcc aggcacaatg gctcacacct gtaatcccag      600
cactttggga ggccaaggcc gatggatcac ttgaggtcaa ggagtttgag accagtctgg      660
ccaacgtggt gaaaccccat ctctactaaa aaaaaaaaaa aaaaactcga                 710
```

<210> SEQ ID NO 94
<211> LENGTH: 1750
<212> TYPE: DNA
<213> ORGANISM: Homo sapiens
<220> FEATURE:
<221> NAME/KEY: SITE
<222> LOCATION: (24)
<223> OTHER INFORMATION: n equals a,t,g, or c
<221> NAME/KEY: SITE
<222> LOCATION: (34)
<223> OTHER INFORMATION: n equals a,t,g, or c
<221> NAME/KEY: SITE
<222> LOCATION: (1287)
<223> OTHER INFORMATION: n equals a,t,g, or c
<221> NAME/KEY: SITE
<222> LOCATION: (1392)
<223> OTHER INFORMATION: n equals a,t,g, or c

<400> SEQUENCE: 94

```
agaaagtgaa agctgtttgc aatnatataa attnctaatt tggaaatcat gacaagcagt       60
cttaagaaca aagttaaaat taaaagtct ttatccaagt caccaatgaa acaggattct      120
gattcattaa tcatgtcttg cccactttt tcaacaaacc tgacgtccta taatgagcta      180
tacagtgtga ggcatatttc atagcaacgt tggttgattg ccaaggagac tctgccaccg      240
```

```
ttctggataa gctcatgttt ccctttttcct tggctgctaa tagaagggca acttacagtg    300
cagggtcaag agcaagaagc tgggggagta gaggctatac atctagccta ataatagaga    360
tctgaggtgg tyaccaggag actacgttct tttgattcca ttcctcagca gcaaaagtac    420
ttgagttcaa atgataaaac ttgaagttgt aggcttggaa gagtatcagc tcagtatatc    480
cttccttgca taaatacaag ggaaaggcca aggaataatc agcattaacc tgccaggtcc    540
aagggtcttc tatccctgac ttcatctgag tcacaagatt tctctaataa gagaaacttt    600
gctactctga ggaaaattat ccctatggga agccccagt tcagaggtaa gaacagttct    660
ttcacgtgga ggtccaaaat tctggacttc tagaaacaag tgaagtgtgc taaagtctcc    720
tatttattgt ttctcttcca gtattgtgcc atcgattctt gcataaaatt ctggaatgct    780
ggctcttcat ggctttcctc tgtaactctg tggtcaatgt catcagtatc gctgtctgct    840
tcctcatcct cttcatccaa ggttcctcga gtcaggatca aatcagaagg gtgcagcaca    900
ggagataagc tgtctttggc agtccctgca tccaaggcta cagaacccat atctttcga    960
aggcgttcca gttgttctct ctgctgttgg ctctctgcgt tggccagtga ttttttcaga   1020
cgttcatatt caggacgata ctcccttcca tattcttcgg cagcactggt aacttgcaca   1080
aagagttcat ctaatccagt acccagaaca gcagagacac ccaccaccct gagtgagctg   1140
taaaactcat ctaacaccag gctcattgaa cgagtcaggt tatgacgtat gtagtctctt   1200
gattcaaggc atcttggaaa gcctyaaaat cctgcatcca ttccactgca aagctgtggt   1260
caatgatgtc agttttattc atgcccncaa tgaaagccac cttggttttg tataagatgc   1320
tgcaggcata gagcatgttg cacatgaagg tcactgggtt ggtacttctc gatgtgtcca   1380
ttacatagat gncaactgtt ggaaatgagg atgcaagggc ttcagtgata attgtcccag   1440
aagctgacca ggtgaatacc tcaatctgtc caggtgtgtc aatcaacaca tatttggaca   1500
tgttctgggc cttctcaata aatttcatca ccaatattgg caggaaaggg aacttcatgt   1560
actgctggat ccaggttgat cacatacggt ggagtgcctt gggcatgcag gtgtcctgtg   1620
agcctctgta caaaagtggt tttcccggat cccgccattc ccaacaccaa cagacacact   1680
gggtgccgcg gacccccaga agcctggagc tcagcggcag ctgcggacgc cgccatcttc   1740
ctcctggcaa                                                          1750
```

<210> SEQ ID NO 95
<211> LENGTH: 606
<212> TYPE: DNA
<213> ORGANISM: Homo sapiens
<220> FEATURE:
<221> NAME/KEY: SITE
<222> LOCATION: (272)
<223> OTHER INFORMATION: n equals a,t,g, or c

<400> SEQUENCE: 95

```
ggaattcggc acgaggaaat aaggtgacag atccccagct gctgaagaac tagaatgtct     60
attacactca tacaattgat gttttatttt aatacaccag agctaccaca caaaacttcc    120
ttccatgtga aaggctccag ataaaattct gccatccctc ctctcctcat gtcctcctgc    180
tcagacccac cttcatgccc ctaaaccaat ctgcatcatg cctgtttcag agagtcatgg    240
gaagatgggc agtgcctcca ttgtcaccat tnccccacac ctctgcacac ttctgcccct    300
tccctctag acgccacaac ttcacagtct tactgttgta atattcctg cacagttagt     360
aatgatcaaa tgatcctgtg gtcagaggcc tctttggcag tgtcttctta cccttaagaa    420
```

-continued

```
aggtcatgaa atccagaagg ggcaacctttt ccaggagagc tttggagtca tttctgtgtg    480
agacactatt gcataatcct gtaagattgc ttttatattt aaggaatgat gttacttaac    540
aaatgaacaa aaaaaattgc aaataaattt tttaacaatg tttaaaaaaa aaaaaaaaa     600 actcga                                                              606
```

<210> SEQ ID NO 96
<211> LENGTH: 617
<212> TYPE: DNA
<213> ORGANISM: Homo sapiens

<400> SEQUENCE: 96

```
gaattcggca cgaggcggaa gatagattaa aatgtctcta cttctctttt taaaagttca    60 tcttttttagc ccttctacaa ttttcaaaag aaataattag atggtcgctg taacattttat  120 atgaagaaaa tagtttgaga caacctaaat atgtcaatac trgawtaatt attaaaataa   180
wtcatggccc tgtcatataa twgaatacta tggagtttgg aagaaagcat gatgtagaat   240
atttaattat atgggaaaat aatcagtaaa tcttttttaaa acagaaggta aaactataca   300
tagttcaata tagtaaagag ggccgggcac agtgctcacg cctgtaatcc cagcactttg   360
ggaggccaag acaggtggat cacctgaggt tgggagttcc agactagcct ggccaacatg   420
gctagtctct actaaaaata caaaaatcag ccaggcatgg tagcaggcac ctgtaatcca   480
agctacttgg cagggaaggc aggagaatta cctgaaccca gaaggcagag gttgcggtga   540
gccaaaatca tgccactgca ctccagcctg ggcaccagag tgaaactctg tctcaaaaaa   600
aaaaaaaaaa aactcga                                                  617
```

<210> SEQ ID NO 97
<211> LENGTH: 634
<212> TYPE: DNA
<213> ORGANISM: Homo sapiens

<400> SEQUENCE: 97

```
gaattcggca cgagatccct tgacccctcg ggtaggcaca gggtaggtgc agcagggatg    60
gggccagcgc tcatggtggc ctctctgtgc ctcggtggac ctgccccagc agtgggagcc   120
ataaccccct ccccctttcat tacttcactc aggtgggcac cttcccctgc agggtgtctg   180
ccctcaggga actcaaggac tctcagagac accagggcag cctggcccag aggagcaaca   240
gccaggcccc caggaggaca gccatggaga gaactgagac ccacttacag tggggtctgg   300
gaaccctgcc tgtacctggg gtycagtccc tcccaactcc ctccttgtgt cttccccccca   360 gcaaaggtgg ggtgaccact tctgtagcta agcacctgct ccccggctct cttcacccag   420
gacatctgtc tctctggagt gtctgtctgt ctgtccctcc ctctctgaac ctgcttcctc   480
cgtgtcccct gctcctcgcc cctgggagcc camtcccmct ccttgcggct ccctcccatc   540
tcactcaagg ttctctgagg acattaaagt ggtggattca ccctgaaaaa aaaaaaaaaa   600
aaaaaaaaaa aaaaaaaaaa aaaaaaaac tcga                                 634
```

<210> SEQ ID NO 98
<211> LENGTH: 512
<212> TYPE: DNA
<213> ORGANISM: Homo sapiens
<220> FEATURE:
<221> NAME/KEY: SITE
<222> LOCATION: (483)
<223> OTHER INFORMATION: n equals a,t,g, or c
<221> NAME/KEY: SITE
<222> LOCATION: (487)

<223> OTHER INFORMATION: n equals a,t,g, or c

<400> SEQUENCE: 98

| | | | | | |
|---|---|---|---|---|---|
| gtggatcccc | cgggctgcag | gattcggcac | gagtctgact | ggaagggtg | aggtgtgcag | 60 |
| ataattttac | ttttcaacta | cagaaaagat | gtatctgggt | aaagaaaatc | atgcatttaa | 120 |
| ctacatcaat | gcagcctatg | aacaatagcc | tgtgaccata | actagatatc | tcaccaacgt | 180 |
| ggcagctctt | cctaaccaaa | agatcaaatc | aaaactctag | tggcatttc | ctatcactca | 240 |
| cagaacaggc | taagcttccc | acctggagta | gacccggagc | ctagaactca | taaaaatttt | 300 |
| taaaaatcaa | acaaaacatg | aaagtacaaa | gtttctacaa | aactcttatc | cctctcctga | 360 |
| caatatttat | gatggtggca | ttagtgaatt | ttactggaaa | aaaaaattcc | caaaactatc | 420 |
| cagctggraa | tataagctca | cttccaaagg | ataaaacagt | taagacgaga | ttaggataaa | 480 |
| ttnactnaca | aaaaaaaaaa | aaaaaaactc | ga | | | 512 |

<210> SEQ ID NO 99
<211> LENGTH: 944
<212> TYPE: DNA
<213> ORGANISM: Homo sapiens
<220> FEATURE:
<221> NAME/KEY: SITE
<222> LOCATION: (13)
<223> OTHER INFORMATION: n equals a,t,g, or c
<221> NAME/KEY: SITE
<222> LOCATION: (486)
<223> OTHER INFORMATION: n equals a,t,g, or c
<221> NAME/KEY: SITE
<222> LOCATION: (934)
<223> OTHER INFORMATION: n equals a,t,g, or c

<400> SEQUENCE: 99

| | | | | | |
|---|---|---|---|---|---|
| tcccccggac | tgncaggaat | tcggcacgag | cagccttcga | agttgatgcg | actgctgagc | 60 |
| tctaatgagg | acgatgccaa | catcctttcg | agcccacag | accgatccat | gagcagctcc | 120 |
| ctctcagcct | ctcagctcca | cacggtcaac | atgcgggacc | ctctgaaccg | agtcctggcc | 180 |
| aacctgttcc | tgctcatctc | ctccatcctg | gggtctcgca | ccgctggccc | ccacacccag | 240 |
| ttcgtgcagt | ggttcatgga | ggagtgtgtg | gactgcctgg | agcagggtgg | ccgtggcagc | 300 |
| gtcctgcagt | tcatgccctt | caccaccgtg | tcggaactgg | tgaaggtgtc | agccatgtcc | 360 |
| agccccaagg | tggttctggc | catcacggac | ctcagcctgc | ccctgggccg | ccaggtggct | 420 |
| gctaaagcca | ttgctgcact | ctgaggggct | tggcatggcc | gcagtggggg | ctggggactg | 480 |
| gcgcanccc | aggcgcctcc | aagggaagca | gtgaggaaag | atgaggcatc | gtgcctcaca | 540 |
| tccgctccac | atggtgcaag | agcctctagc | ggcttccagt | tccccgctcc | tgactcctga | 600 |
| cctccaggat | gtctcccggt | ttcttctttc | aaaatttcct | ctccatctgc | tggcacctga | 660 |
| ggagtgtgag | caacctggac | cacaagccca | gtggtcaccc | ctgtgtgcgc | ccgccccagc | 720 |
| ccaggagtag | tcttacctct | gaggaacttt | ctagatgcaa | agtgtgtata | tgtgtgtgtg | 780 |
| tgtgtgtgtg | tgtgtgtgtg | tgtgtttatg | tgtattttgt | aatatgtgag | ggaaatctac | 840 |
| cttcgttcat | gtataaataa | agctcctcgt | ggctcccta | aaaaaaaaa | aaaaaaactc | 900 |
| gagggggggc | ccgtacccag | cttttttccc | tttngtgagg | ttgg | | 944 |

<210> SEQ ID NO 100
<211> LENGTH: 2351
<212> TYPE: DNA
<213> ORGANISM: Homo sapiens
<220> FEATURE:
<221> NAME/KEY: SITE
<222> LOCATION: (593)
<223> OTHER INFORMATION: n equals a,t,g, or c

<400> SEQUENCE: 100

```
acccacgcgt ccgccacgcg tccgggtcca ttgccacctg gatgggagaa gagaacagac    60
agcaatggca gagtatattt cgtcaaccac aacacacgaa ttacacaatg ggaagacccc   120
agaagtcaag gtcaattaaa tgaaaagccc ttacctgaag gttgggaaat gagattcaca   180
gtggatggaa ttccatattt tgtggaccac aatagaagaa ctaccaccta tatagatccc   240
cgcacaggaa aatctgccct agacaatgga cctcagatag cctatgttcg ggacttcaaa   300
gcaaaggttc agtatttccg gttctggtgt cagcaactgg ccatgccaca gcacataaag   360
attacagtga caagaaaaac attgtttgag grttcctttc aacagwtawt gagcttcagt   420
ccccaagatc tgcgargacg tttgtgggtg atttttccag gagaagaagg tttagattat   480
ggaggtgtag caagagaatg gttctttctt ttgtcacatg aagtgttgaa cccaatgtat   540
tgcctgtttg aatatgcagg gaaggataac tactgcttgc agataaaccc cgnttcttac   600
atcaatccag atcacctgaa atattttcgt tttattggca gatttattgc catggctctg   660
ttccatggga aattcataga cacgggtttt tctttaccat tckakaagcg tatcttgaac   720
aaaccagttg gactcaagga tttagaatct attgatccag aattttacaa ttctctcatc   780
tgggttaagg aaaacaatat tgaggaatgt gatttggaaa tgtacttctc cgttgacaaa   840
gaaattctag gtgaaattaa gagtcatgat ctgaaaccta atggtggcaa tattcttgta   900
acagaagaaa ataagagga atacatcaga atggtagctg agtggaggtt gtctcgaggt   960
gttgaagaac agacacaagc tttctttgaa ggctttaatg aaattcttcc ccagcaatat  1020
ttgcaatact ttgatgcaaa ggaattagag gtccttttat gtggaatgca agagattgat  1080
ttgaatgact ggcaaagaca tgccatctac cgtcattatg caaggaccag caaacaaatc  1140
atgtggtttt ggcagtttgt taaagaaatt gataatgaga agagaatgag acttctgcag  1200
tttgttactg gaacctgccg attgccagta ggaggatttg ctgatctcat ggggagcaat  1260
ggaccacaga aattctgcat ykaaaaagtt gggaaagaaa attggctacc cagaagtcat  1320
acctgtttta atcgcctgga cctgccacca tacaagagct atgagcaact gaaggaaaag  1380
ctgttgtttg ccatagaaga aacagaagga tttggacaag agtaacttct gagaacttgc  1440
accatgaatg ggcaagaact tatttgcmat gtttgtcctt ctctgcctgt tgcacatctt  1500
gtaaaattgg acaatggctc tttagagagt tatctgagtg taagtaaatt aatgttctca  1560
tttagattta tctcccagtg atttctactc agcgtttcca gaaatcaggt ctgcaaatga  1620
ctagtcagaa ccttgcttaa catgagattt taacacaaca atgaaatttg ccttgtctta  1680
ttccactagt ttattccttt aacaacaata ttttatgtgt gtcaaaagtc tcacttggga  1740
gtagtgtttt tttcttttag acattctgca gacatgcagg gaagtccttt ggtaactgca  1800
atatacaaga ttttcctatt aagcctcttg gtaagaggca tttgttaaaa gtgcaagctt  1860
actcctgctt ctggggatgt gagcaaaatc gggcttgtgt tctccctctc attttagtct  1920
gacttgacta ttgttttttcc tttctggcgc atgaatccat acatcattcc tggaagtgag  1980
gcaagactct tgcatctcta caaagtagtt ttgtcaattt gaattcaggg aaaagttggt  2040
cacagcctgc aaatgacttc atttggaagt ctgattgttt cagttgcctg acaaatacta  2100
cactttacaa acaatgttaa cactgtgatt ccttccattgt tttaagaagt taacctaggg  2160
ccgggcatgg tggctcatac ctgtaatcct agcactctgg gaggccgagg caggaggatc  2220
```

| | |
|---|---|
| cctttagccc aggagttaaa gaccagcctg ggcaacatag ggagaccctg tcttttttt | 2280 |
| gggcagcgtg gtgggggata aataaaaaaa aaaaaaaaaa actcgagggg gggcccgtac | 2340 |
| ccaatcgcct g | 2351 |

<210> SEQ ID NO 101
<211> LENGTH: 776
<212> TYPE: DNA
<213> ORGANISM: Homo sapiens
<220> FEATURE:
<221> NAME/KEY: SITE
<222> LOCATION: (775)
<223> OTHER INFORMATION: n equals a,t,g, or c
<221> NAME/KEY: SITE
<222> LOCATION: (776)
<223> OTHER INFORMATION: n equals a,t,g, or c

<400> SEQUENCE: 101

| | |
|---|---|
| aatgaaggct tgtggacaa catgacgctg agtggcccag acttggagct gcatgcctcc | 60 |
| aacgccaccc tcctaagtgc caacgccagc caggggaagt tgcttccggc ccactcaggc | 120 |
| ctcagcctca tcatcagtga cgcaggccct gacaacagtt cctgggcccc tgtggcccma | 180 |
| gggacagttg tggttagccg tatcattgtg tgggacatca tggccttcaa tggcatcatc | 240 |
| catgctctgg ccagccccct cctggcaccc cacagcccc aggcagtgct ggcgcctgaa | 300 |
| gccccacctg tggcggcagg cgtggggct gtgcttgccg ctggagcact gcttggcttg | 360 |
| gtggccggag ctctctacct ccgtgcccga ggcaagccca tgggctttgg cttctctgcc | 420 |
| ttccaggcgg aagatgatgc tgatgacgac ttctcaccgt ggcaagaagg gaccaacccc | 480 |
| accctggtct ctgtccccaa ccctgtcttt ggcagcgaca ccttttgtga acccttcgat | 540 |
| gactcactgc tggaggagga cttccctgac acccagagga tcctcacagt caagtgacga | 600 |
| ggctggggct gaaagcagaa gcatgcacag ggaggagacc acttttattg cttgtctggg | 660 |
| tggatggggc aggaggggct gagggcctgt cccagacaat aaaggtgccc tcagcggatg | 720 |
| tgggccatgt caccaaraaa aaaaaaaaa aaaaaaaaa aaaaaaaaa aaaann | 776 |

<210> SEQ ID NO 102
<211> LENGTH: 1065
<212> TYPE: DNA
<213> ORGANISM: Homo sapiens

<400> SEQUENCE: 102

| | |
|---|---|
| gaattcggca cgagagggtc agggaggctg cccccaggcc tgtatattta acccctatgt | 60 |
| accaggagta atgaatagta ataattctat ttatgtaagt tatgatgacg ggtcaggtag | 120 |
| agtgagctgg ggagggaagt ggatccattt ctgctaagga aattctagtc aaatgcatct | 180 |
| ctgtatagac aaaatgttag tggagaagat cttgttaata gaatgtctat catcagaatc | 240 |
| tcagttgata gggtttctct tgtaatgaag tctctacaaa ttgggttagc tacatctctg | 300 |
| ctaaacagtt gatggggtat ctcttgatta gggggatccc taatatcccc agccccagcc | 360 |
| agaagctgtg aaacctcaag tcctatggag gggagaagga ctggaatgta ccccatctyc | 420 |
| cttgactgma gagcaggttc ctccactgcc ccacccctta gacaccatgm ccccatcagg | 480 |
| ttaatcccct gttgccatgg ttatggagac ttgcagctgc catcttagat gtgctctttg | 540 |
| gggaagccca tctaacagga ggacattggt ttggggtgc acctcctgaa gaatgggtgg | 600 |
| ggaaggcttt ctctaggatc agattcaaat aaatcaagta tgtattgagt gcctactctg | 660 |
| tgcaaggcac tatgctagat ctggtgccta gaagccctga gaaagaactt aaagagctag | 720 |

```
gaggacagag ccccccaagc tgatctggtg gtgcatccac gcaccccac cctgggactt      780 tggatgctcc catctccacc tccagtgact tttaaagccg cttcgtgcct ttcctgtaac     840
gttggatcct cctttcctgt ccctgctgt ctcaaggccc caagttaaag ggttaaagcc      900
gctggagctt ggggagagaa cattgtgaa tggaagggat catgcccttt gtggagtctt      960
ttttttttaa tttaataaat aaagttgga tttgaaaaaa aaaaaaaaaa aaaaaaaaa      1020 aaaaaaaaaa ctcgcagggg gggcccgtac ccgaatcgcc ctatg                    1065
```

<210> SEQ ID NO 103
<211> LENGTH: 687
<212> TYPE: DNA
<213> ORGANISM: Homo sapiens
<220> FEATURE:
<221> NAME/KEY: SITE
<222> LOCATION: (28)
<223> OTHER INFORMATION: n equals a,t,g, or c
<221> NAME/KEY: SITE
<222> LOCATION: (34)
<223> OTHER INFORMATION: n equals a,t,g, or c
<221> NAME/KEY: SITE
<222> LOCATION: (55)
<223> OTHER INFORMATION: n equals a,t,g, or c
<221> NAME/KEY: SITE
<222> LOCATION: (657)
<223> OTHER INFORMATION: n equals a,t,g, or c
<221> NAME/KEY: SITE
<222> LOCATION: (660)
<223> OTHER INFORMATION: n equals a,t,g, or c
<221> NAME/KEY: SITE
<222> LOCATION: (664)
<223> OTHER INFORMATION: n equals a,t,g, or c

<400> SEQUENCE: 103

```
aaaccagctt ttgccctgat tacgccangc tcgnaattam cctcactaaa gggancaaag       60
ctggagctcc accgcggtgg cggccgctct agaactagtg gatccccgg gctgcaggaa       120 ttcggcacga gcagaaaaca acatggaagc caagttccta ggaaatgcac cctgtgggca     180
ctacacattc aagttccccc aggcaatgcg gacagagagt aacctcggag ccaaggtgtt     240
cttcttcaaa gcactgctat taactggaga cttttcccag gctgggaata agggccatca     300
tgtgtgggtc actaaggatg agctgggtga ctatttgaaa ccaaaatacc tggcccaagt     360
taggaggttt gtttcagacc tctgatgggc cgagctgcct gtggacggtg ctcagacaag    420
tctgggatta gagcctcaag gacattgtgt gattgcctca catttgcagg taatatcaag     480
cagcaaacta aattctgaga aataaacgag tctattacaa aaaaaaaaaa aaaaactcg     540 agggggggcc cggtacccaa tttcgcccta tagtgagtcg tattacaatt cactggccgt     600
cgttttacaa cgtcgtgact ggggaaaccc tggcgttacc caacttaatc gccttgnagn    660
aacntcccct ttcggcagct gggtaa                                          687
```

<210> SEQ ID NO 104
<211> LENGTH: 804
<212> TYPE: DNA
<213> ORGANISM: Homo sapiens

<400> SEQUENCE: 104

```
gaattcggca cgagattttc ttcatgcagt attctcagat tggaaacatg cttcatgttt       60
cttataaata accctcaatt atgagggcgt acttttcact ttgaagaaaa ttgacttgca     120
ttaaagtggc taacaattct ttcctgggca ggatgtaaaa ttttcctctc ctctaatacc    180
agtactgttg agctcacatt ctcccacttt tcctcttttc aggtggttca cgtatttggg     240
```

-continued

```
attttatgaa acctcagaag cagacatgtt aacttttctt atcttttat tccctgaggt    300 agtcctgggg ctcttaagag attacagttc ttaaaacctg aaagtgaca ccagagaggt    360 agatcttagt tcccaaaatt aaagttactt tctagggcat aaaacctttt cagaattcag    420
attaaatttt atttatttt tctttttct gtaaccttat atttgagggg aaaattttat     480
tttcaacttt tgcatatatc taatttaaca tttgggaaaa ctgtaaatgg gccaaagttt    540
ctccctttat atgattttcc agattttac cactttctta gtgccacttg atgctaggca    600
ttgtctattg gagactcact ggtacgtaac tgcaggtttt accatggaac cacatataca    660
catgtcttgg aattgagggt tagggttttcc agaaggactt agttgtcctg tgcttttgtc   720
tgccccatgc caaagaccac taagaacagt tttgtaagtg aaacttgggt ctacacgtta    780
aaaaaaaaaa aaaaaaaaac tcga                                          804
```

<210> SEQ ID NO 105
<211> LENGTH: 373
<212> TYPE: DNA
<213> ORGANISM: Homo sapiens

<400> SEQUENCE: 105

```
ccacgcgtcc ggttctttga ttgcttcata agaaaccggt gtattgctct gtgctgaggt     60
cttagatatg ttctagcact caggagtcca aaccattgct tttgggttag aaatgcatga    120
aagaaacatg cacgtctatc tgaactacaa ataaactttc tgcttaagtc tacttaggct    180
aatgttgaaa catttgttca ttcaacacaa accacatggt ggcagaagaa gagagaccct    240 cattcacca catagtagca ataggagctg caatgtcaca atgagtttta aaaagaatgc     300
ctctttaaaa gaaaaaaaaa aacaagaaag aaagaaaaaa aaaaaaaaaa aaaaaaaaa     360 aaaaaaaaaa aaa                                                      373
```

<210> SEQ ID NO 106
<211> LENGTH: 687
<212> TYPE: DNA
<213> ORGANISM: Homo sapiens

<400> SEQUENCE: 106

```
ccacgcgtcc gctcctgtga ggtatggtgc tgggtgcaga tgcagtgtgg ctctggatag      60
caccttatgg acagttgtgt ccccaaggaa ggatgagaat agctactgaa gtcctaaaga    120
gcaagcctaa ctcaagccat tggcacacag gcattagaca gaaagctgga agttgaaatg    180
gtggagtcca acttgcctgg accagcttaa tggttctgct cctggtaacg ttttatcca    240 tggatgactt gcttgggtaa ggacatgaag acagttcctg tcatacctttt taaaggtatg    300 gagagtcggc ttgactacac tgtgtggagc aagtttaaa gaagcaaagg actcagaatt     360
catgattgaa gaaatgcagg cagacctgtt atcctaaact agggttttta atgaccacaa    420
caagcaagca tgcagcttac tgcttgaaag ggtcttgcct cacccaagct agagtgcagt    480
ggcctttgaa gcttactaca gcctcaaact tctgggctca agtgatcctc agcctcccag    540
tggtctttgt agactgcctg atggagtctc atggcacaag aagattaaaa cagtgtctcc    600
aattttaata aattttttgca atccaaaaaa aaaaaaaaa aaaaaaaaa aaaaaaaaa      660 aaaaaaaaaa aaaaaaaaa aaaaaaa                                         687
```

<210> SEQ ID NO 107
<211> LENGTH: 37
<212> TYPE: PRT
<213> ORGANISM: Homo sapiens

```
<220> FEATURE:
<221> NAME/KEY: SITE
<222> LOCATION: (37)
<223> OTHER INFORMATION: Xaa equals stop translation

<400> SEQUENCE: 107

Met Glu Val Leu Phe Asp Ser Leu Leu Phe Ser Ser Phe Ile Phe Pro
1               5                   10                  15

Ser Gln Ser Leu Leu Ser Arg Thr Ser Ala Phe Ser His Lys Pro Asn
            20                  25                  30

Gly Leu Ser Glu Xaa
        35

<210> SEQ ID NO 108
<211> LENGTH: 457
<212> TYPE: PRT
<213> ORGANISM: Homo sapiens
<220> FEATURE:
<221> NAME/KEY: SITE
<222> LOCATION: (84)
<223> OTHER INFORMATION: Xaa equals any of the naturally occurring L-
      amino acids
<221> NAME/KEY: SITE
<222> LOCATION: (169)
<223> OTHER INFORMATION: Xaa equals any of the naturally occurring L-
      amino acids

<400> SEQUENCE: 108

Met Val Thr Cys Thr Cys Leu Pro Asp Tyr Glu Gly Asp Gly Trp Ser
1               5                   10                  15

Cys Arg Ala Arg Asn Pro Cys Thr Asp Gly His Arg Gly Gly Cys Ser
            20                  25                  30

Glu His Ala Asn Cys Leu Ser Thr Gly Leu Asn Thr Arg Arg Cys Glu
        35                  40                  45

Cys His Ala Gly Tyr Val Gly Asp Gly Leu Gln Cys Leu Glu Glu Ser
    50                  55                  60

Glu Pro Pro Val Asp Arg Cys Leu Gly Gln Pro Pro Cys His Ser
65                  70                  75                  80

Asp Ala Met Xaa Thr Asp Leu His Phe Gln Glu Lys Arg Ala Gly Val
                85                  90                  95

Phe His Leu Gln Ala Thr Ser Gly Pro Tyr Gly Leu Asn Phe Ser Glu
            100                 105                 110

Ala Glu Ala Ala Cys Glu Ala Gln Gly Ala Val Leu Ala Ser Phe Pro
        115                 120                 125

Gln Leu Ser Ala Ala Gln Leu Gly Phe His Leu Cys Leu Met Gly
    130                 135                 140

Trp Leu Ala Asn Gly Ser Thr Ala His Pro Val Val Phe Pro Val Ala
145                 150                 155                 160

Asp Cys Gly Asn Gly Arg Val Gly Xaa Val Ser Leu Gly Ala Arg Lys
                165                 170                 175

Asn Leu Ser Glu Arg Trp Asp Ala Tyr Cys Phe Arg Val Gln Asp Val
            180                 185                 190

Ala Cys Arg Cys Arg Asn Gly Phe Val Gly Asp Gly Ile Ser Thr Cys
        195                 200                 205

Asn Gly Lys Leu Leu Asp Val Leu Ala Ala Thr Ala Asn Phe Ser Thr
    210                 215                 220

Phe Tyr Gly Met Leu Leu Gly Tyr Ala Asn Ala Thr Gln Arg Gly Leu
225                 230                 235                 240

Asp Phe Leu Asp Phe Leu Asp Asp Glu Leu Thr Tyr Lys Thr Leu Phe
```

```
                         245                 250                 255
Val Pro Val Asn Glu Gly Phe Val Asp Asn Met Thr Leu Ser Gly Pro
                 260                 265                 270

Asp Leu Glu Leu His Ala Ser Asn Ala Thr Leu Leu Ser Ala Asn Ala
             275                 280                 285

Ser Gln Gly Lys Leu Leu Pro Ala His Ser Gly Leu Ser Leu Ile Ile
         290                 295                 300

Ser Asp Ala Gly Pro Asp Asn Ser Ser Trp Ala Pro Val Ala Pro Gly
305                 310                 315                 320

Thr Val Val Val Ser Arg Ile Ile Val Trp Asp Ile Met Ala Phe Asn
                 325                 330                 335

Gly Ile Ile His Ala Leu Ala Ser Pro Leu Leu Ala Pro Pro Gln Pro
             340                 345                 350

Gln Ala Val Leu Ala Pro Glu Ala Pro Val Ala Ala Gly Val Gly
         355                 360                 365

Ala Val Leu Ala Ala Gly Ala Leu Leu Gly Leu Val Ala Gly Ala Leu
         370                 375                 380

Tyr Leu Arg Ala Arg Gly Lys Pro Met Gly Phe Gly Phe Ser Ala Phe
385                 390                 395                 400

Gln Ala Glu Asp Asp Ala Asp Asp Phe Ser Pro Trp Gln Glu Gly
                 405                 410                 415

Thr Asn Pro Thr Leu Val Ser Val Pro Asn Pro Val Phe Gly Ser Asp
             420                 425                 430

Thr Phe Cys Glu Pro Phe Asp Asp Ser Leu Leu Glu Glu Asp Phe Pro
         435                 440                 445

Asp Thr Gln Arg Ile Leu Thr Val Lys
    450                 455

<210> SEQ ID NO 109
<211> LENGTH: 103
<212> TYPE: PRT
<213> ORGANISM: Homo sapiens

<400> SEQUENCE: 109

Met Gly Ser Trp Cys Leu Arg Gly Gly Ala Val Glu Pro Ala Leu
1               5                   10                  15

Gln Ser Arg Glu Met Gly Tyr Ile Pro Val Leu Leu Pro Ser Ile Gly
            20                  25                  30

Leu Glu Val Ser Gln Leu Leu Ala Gly Ala Gly Asp Ile Arg Asp Pro
        35                  40                  45

Pro Asn Gln Glu Ile Pro His Gln Leu Phe Ser Arg Asp Val Ala Asn
    50                  55                  60

Pro Ile Cys Arg Asp Phe Ile Thr Arg Glu Thr Leu Ser Thr Glu Ile
65                  70                  75                  80

Leu Met Ile Asp Ile Leu Leu Thr Arg Ser Ser Pro Leu Thr Phe Cys
                85                  90                  95

Leu Tyr Arg Asp Ala Phe Asp
            100

<210> SEQ ID NO 110
<211> LENGTH: 46
<212> TYPE: PRT
<213> ORGANISM: Homo sapiens
<220> FEATURE:
<221> NAME/KEY: SITE
<222> LOCATION: (46)
<223> OTHER INFORMATION: Xaa equals stop translation
```

<400> SEQUENCE: 110

Met Gly Gly Thr Glu Ser Tyr Ile Ser Ser Pro Leu Leu Arg Thr
1               5                   10                  15

Leu Leu Leu Ser Tyr Leu Val Phe Leu Tyr Tyr Leu Tyr Leu Phe
                20                  25                  30

Tyr Val Ala Arg Ser Pro Phe Gly Lys Ala Glu Tyr Lys Xaa
            35                  40                  45

<210> SEQ ID NO 111
<211> LENGTH: 210
<212> TYPE: PRT
<213> ORGANISM: Homo sapiens

<400> SEQUENCE: 111

Met Ala Ser Leu Leu Gln Gln Ile Glu Ile Glu Arg Ser Leu Tyr Ser
1               5                   10                  15

Asp His Glu Leu Arg Ala Leu Asp Glu Asn Gln Arg Leu Ala Lys Lys
                20                  25                  30

Lys Ala Asp Leu His Asp Glu Glu Asp Glu Gln Asp Ile Leu Leu Ala
            35                  40                  45

Gln Asp Leu Glu Asp Met Trp Glu Gln Lys Phe Leu Gln Phe Lys Leu
        50                  55                  60

Gly Ala Arg Ile Thr Glu Ala Asp Glu Lys Asn Asp Arg Thr Ser Leu
65                  70                  75                  80

Asn Arg Lys Leu Asp Arg Asn Leu Val Leu Val Arg Glu Lys Phe
                85                  90                  95

Gly Asp Gln Asp Val Trp Ile Leu Pro Gln Ala Glu Trp Gln Pro Gly
            100                 105                 110

Glu Thr Leu Arg Gly Thr Ala Glu Arg Thr Leu Ala Thr Leu Ser Glu
        115                 120                 125

Asn Asn Met Glu Ala Lys Phe Leu Gly Asn Ala Pro Cys Gly His Tyr
    130                 135                 140

Thr Phe Lys Phe Pro Gln Ala Met Arg Thr Glu Ser Asn Leu Gly Ala
145                 150                 155                 160

Lys Val Phe Phe Phe Lys Ala Leu Leu Leu Thr Gly Asp Phe Ser Gln
                165                 170                 175

Ala Gly Asn Lys Gly His His Val Trp Val Thr Lys Asp Glu Leu Gly
            180                 185                 190

Asp Tyr Leu Lys Pro Lys Tyr Leu Ala Gln Val Arg Arg Phe Val Ser
        195                 200                 205

Asp Leu
    210

<210> SEQ ID NO 112
<211> LENGTH: 110
<212> TYPE: PRT
<213> ORGANISM: Homo sapiens
<220> FEATURE:
<221> NAME/KEY: SITE
<222> LOCATION: (110)
<223> OTHER INFORMATION: Xaa equals stop translation

<400> SEQUENCE: 112

Met Val Leu Thr Gly Val Arg Leu Met Lys Trp Arg Asp Glu Lys Thr
1               5                   10                  15

Phe Gly Thr Asp Cys Val Glu Ala Val Ile Leu Leu Val Thr Leu Leu
                20                  25                  30

```
Trp Glu Lys Lys Glu Ala Phe His Val Gly Phe Ser Glu Glu Leu Gln
        35                  40                  45

Tyr Phe Pro Glu Arg Ser Thr Glu Lys Leu Lys Val Phe Glu Trp Glu
    50                  55                  60

Glu Glu Lys Gln Thr Thr Ala Thr Ser Glu Asp Asn Thr Lys His Leu
65                  70                  75                  80

Val His Ser Val Tyr Thr Arg Gly Ala Val Asn Phe Leu Val Glu Lys
                85                  90                  95

Glu Leu Ser Leu Glu Lys Tyr Leu Lys Lys Pro Leu Lys Xaa
            100                 105                 110

<210> SEQ ID NO 113
<211> LENGTH: 61
<212> TYPE: PRT
<213> ORGANISM: Homo sapiens
<220> FEATURE:
<221> NAME/KEY: SITE
<222> LOCATION: (61)
<223> OTHER INFORMATION: Xaa equals stop translation

<400> SEQUENCE: 113

Met Ala Ala Val Met Leu Val Leu Thr Val Val Leu Gly Leu Tyr Asn
1               5                   10                  15

Ser Tyr Asn Ser Cys Ala Glu Gln Ala Asp Gly Pro Leu Gly Arg Ser
            20                  25                  30

Thr Cys Ser Ala Ala Pro Gly Thr Pro Gly Gly Ala Gln Asp Ser Ser
        35                  40                  45

Met Ser Ser Leu Gln Ser Ser Arg Lys Pro His Thr Xaa
    50                  55                  60

<210> SEQ ID NO 114
<211> LENGTH: 135
<212> TYPE: PRT
<213> ORGANISM: Homo sapiens
<220> FEATURE:
<221> NAME/KEY: SITE
<222> LOCATION: (135)
<223> OTHER INFORMATION: Xaa equals stop translation

<400> SEQUENCE: 114

Met Val Glu Asn Ser Pro Ser Pro Leu Pro Glu Arg Ala Ile Tyr Gly
1               5                   10                  15

Phe Val Leu Phe Leu Ser Ser Gln Phe Gly Phe Ile Leu Tyr Leu Val
            20                  25                  30

Trp Ala Phe Ile Pro Glu Ser Trp Leu Asn Ser Leu Gly Leu Thr Tyr
        35                  40                  45

Trp Pro Gln Lys Tyr Trp Ala Val Ala Leu Pro Val Tyr Leu Leu Ile
    50                  55                  60

Ala Ile Val Ile Gly Tyr Val Leu Leu Phe Gly Ile Asn Met Met Ser
65                  70                  75                  80

Thr Ser Pro Leu Asp Ser Ile His Thr Ile Thr Asp Asn Tyr Ala Lys
                85                  90                  95

Asn Gln Gln Gln Lys Lys Tyr Gln Glu Glu Ala Ile Pro Ala Leu Arg
            100                 105                 110

Asp Ile Ser Ile Ser Glu Val Asn Gln Met Phe Phe Leu Ala Ala Lys
        115                 120                 125

Glu Leu Tyr Thr Lys Asn Xaa
    130                 135
```

-continued

<210> SEQ ID NO 115
<211> LENGTH: 74
<212> TYPE: PRT
<213> ORGANISM: Homo sapiens
<220> FEATURE:
<221> NAME/KEY: SITE
<222> LOCATION: (74)
<223> OTHER INFORMATION: Xaa equals stop translation

<400> SEQUENCE: 115

Met Arg Leu Gln Pro Asp Ile Cys Asn Leu Pro Thr Asn Pro Leu Ser
 1               5                  10                  15

Leu Lys Leu Gly Leu Met Leu Leu Ser Leu Thr Leu Cys Leu Glu Lys
            20                  25                  30

Thr Val Gln Gly Leu Lys Leu Gly Leu Cys Leu Phe Lys Leu Ser Phe
        35                  40                  45

Ser Glu His Met Val Cys Pro Thr His Pro Gln Ser Ile Arg Trp Phe
    50                  55                  60

Tyr Phe Met Phe Arg Leu Gln Cys Cys Xaa
65                  70

<210> SEQ ID NO 116
<211> LENGTH: 88
<212> TYPE: PRT
<213> ORGANISM: Homo sapiens
<220> FEATURE:
<221> NAME/KEY: SITE
<222> LOCATION: (88)
<223> OTHER INFORMATION: Xaa equals stop translation

<400> SEQUENCE: 116

Met Ala Ala Gly Trp Val Arg Ser Trp Val Val Tyr Phe Leu Val Thr
 1               5                  10                  15

Leu Leu Gly Ser Ser Pro Ser Pro Val Ser Leu Thr Glu Gly Lys Lys
            20                  25                  30

Ile Pro Lys Gly Thr Ala Thr Val Leu Gly Gly Ala Leu Asp Cys Val
        35                  40                  45

His Leu Asn Phe Gly Pro Ser Phe Asp Val Trp Phe Val Ser His Lys
    50                  55                  60

Glu Lys Tyr Leu Lys Val Asn Met Met Leu Leu Ala Tyr Tyr Pro Asp
65                  70                  75                  80

Tyr Cys Met Lys Leu Cys Leu Xaa
                85

<210> SEQ ID NO 117
<211> LENGTH: 37
<212> TYPE: PRT
<213> ORGANISM: Homo sapiens
<220> FEATURE:
<221> NAME/KEY: SITE
<222> LOCATION: (37)
<223> OTHER INFORMATION: Xaa equals stop translation

<400> SEQUENCE: 117

Met Leu Tyr Ile Leu Leu Lys Pro Leu Leu Cys Leu Ser Val Asn Cys
 1               5                  10                  15

Thr Asn Ile Tyr Gln Met Leu Thr Lys Ser Gln Gly Leu Asp Leu Ala
            20                  25                  30

Leu Gly Arg Asn Xaa
            35

-continued

```
<210> SEQ ID NO 118
<211> LENGTH: 52
<212> TYPE: PRT
<213> ORGANISM: Homo sapiens
<220> FEATURE:
<221> NAME/KEY: SITE
<222> LOCATION: (52)
<223> OTHER INFORMATION: Xaa equals stop translation

<400> SEQUENCE: 118

Met Trp Trp Trp Leu Met Leu Ala Thr Thr Ala Leu Lys Pro Ile Ala
 1               5                  10                  15

Thr Ser Ser Ser Cys Thr Glu Ala Leu Pro Gly Leu Trp Arg Asp Arg
            20                  25                  30

His Trp Gly Asp Trp Thr Arg Gly Ser Gly Trp Glu Val Gly Gln Thr
        35                  40                  45

Trp Gln His Xaa
    50

<210> SEQ ID NO 119
<211> LENGTH: 43
<212> TYPE: PRT
<213> ORGANISM: Homo sapiens
<220> FEATURE:
<221> NAME/KEY: SITE
<222> LOCATION: (43)
<223> OTHER INFORMATION: Xaa equals stop translation

<400> SEQUENCE: 119

Met Gly Ser Trp Phe Tyr Leu Phe Leu Ala Pro Leu Phe Lys Gly Leu
 1               5                  10                  15

Ala Gly Ser Leu Pro Phe Gly Cys Leu Ser Leu Leu Gln Pro Thr Glu
            20                  25                  30

Lys Thr Ala Leu Gln Ser Gly Gly Ser Ser Xaa
        35                  40

<210> SEQ ID NO 120
<211> LENGTH: 32
<212> TYPE: PRT
<213> ORGANISM: Homo sapiens

<400> SEQUENCE: 120

Met Gly Pro Lys Ser Gln Thr Glu Arg Thr Ser Ser Leu Met Pro His
 1               5                  10                  15

Gln Val Arg Glu Arg Arg Ala His Ile Pro Gln Met Pro Met Asn Thr
            20                  25                  30

<210> SEQ ID NO 121
<211> LENGTH: 46
<212> TYPE: PRT
<213> ORGANISM: Homo sapiens
<220> FEATURE:
<221> NAME/KEY: SITE
<222> LOCATION: (46)
<223> OTHER INFORMATION: Xaa equals stop translation

<400> SEQUENCE: 121

Met Phe Lys Asp Phe Ile Phe Leu Thr Phe Leu Pro Lys Leu Ser Gln
 1               5                  10                  15

Phe Val Lys Gly Ser Leu Ile Ser Gly Leu Ser Glu Cys Asp Asn Thr
            20                  25                  30

Ser Leu Lys Ala Ile Leu Gly Phe Ser Asn Tyr Ser Gln Xaa
        35                  40                  45
```

-continued

```
<210> SEQ ID NO 122
<211> LENGTH: 178
<212> TYPE: PRT
<213> ORGANISM: Homo sapiens

<400> SEQUENCE: 122
```

Met Ala Lys Val Ala Lys Asp Leu Asn Pro Gly Val Lys Lys Met Ser
 1               5                  10                  15

Leu Gly Gln Leu Gln Ser Ala Arg Gly Val Ala Cys Leu Gly Cys Lys
             20                  25                  30

Gly Thr Cys Ser Gly Phe Glu Pro His Ser Trp Arg Lys Ile Cys Lys
         35                  40                  45

Ser Cys Lys Cys Ser Gln Glu Asp His Cys Leu Thr Ser Asp Leu Glu
     50                  55                  60

Asp Asp Arg Lys Ile Gly Arg Leu Leu Met Asp Ser Lys Tyr Ser Thr
 65                  70                  75                  80

Leu Thr Ala Arg Val Lys Gly Gly Asp Gly Ile Arg Ile Tyr Lys Arg
                 85                  90                  95

Asn Arg Met Ile Met Thr Asn Pro Ile Ala Thr Gly Lys Asp Pro Thr
            100                 105                 110

Phe Asp Thr Ile Thr Tyr Glu Trp Ala Pro Pro Gly Val Thr Gln Lys
        115                 120                 125

Leu Gly Leu Gln Tyr Met Glu Leu Ile Pro Lys Glu Lys Gln Pro Val
    130                 135                 140

Thr Gly Thr Glu Gly Ala Phe Thr Ala Ala Ser Ser Cys Thr Ser
145                 150                 155                 160

Ser Pro Ser Met Thr Arg Ile Pro Arg Ala Ala Val Asp Phe Trp Arg
                165                 170                 175

Met Ser

```
<210> SEQ ID NO 123
<211> LENGTH: 48
<212> TYPE: PRT
<213> ORGANISM: Homo sapiens
<220> FEATURE:
<221> NAME/KEY: SITE
<222> LOCATION: (48)
<223> OTHER INFORMATION: Xaa equals stop translation

<400> SEQUENCE: 123
```

Met Gly Ile Met Leu Leu Ser Tyr Ser Asn Gly Thr Val Leu Phe Ile
 1               5                  10                  15

Phe Val Pro Gln Ile Thr Ser Ser Val Leu Ser Val Phe Cys Ile Val
             20                  25                  30

Phe Val Gln Asp Ser Leu Gly Phe Ile Ser Val Ile Ser Ala Phe Xaa
         35                  40                  45

```
<210> SEQ ID NO 124
<211> LENGTH: 68
<212> TYPE: PRT
<213> ORGANISM: Homo sapiens
<220> FEATURE:
<221> NAME/KEY: SITE
<222> LOCATION: (68)
<223> OTHER INFORMATION: Xaa equals stop translation

<400> SEQUENCE: 124
```

Met Lys Leu Leu Leu Leu Thr Leu Thr Val Leu Leu Leu Ser Gln
 1               5                  10                  15

```
Leu Thr Pro Gly Gly Thr Gln Arg Cys Trp Asn Leu Tyr Gly Lys Cys
             20                  25                  30

Arg Tyr Arg Cys Ser Lys Lys Glu Arg Val Tyr Val Tyr Cys Ile Asn
         35                  40                  45

Asn Lys Met Cys Cys Val Lys Pro Lys Tyr Gln Pro Lys Glu Arg Trp
     50                  55                  60

Trp Pro Phe Xaa
 65

<210> SEQ ID NO 125
<211> LENGTH: 75
<212> TYPE: PRT
<213> ORGANISM: Homo sapiens
<220> FEATURE:
<221> NAME/KEY: SITE
<222> LOCATION: (75)
<223> OTHER INFORMATION: Xaa equals stop translation

<400> SEQUENCE: 125

Met Asp Tyr Ser Arg Ile Ile Glu Arg Leu Leu Lys Leu Ala Val Pro
 1               5                  10                  15

Asn His Leu Ile Trp Leu Ile Phe Phe Tyr Trp Leu Phe His Ser Cys
             20                  25                  30

Leu Asn Ala Val Ala Glu Leu Met Gln Phe Gly Asp Arg Glu Phe Tyr
         35                  40                  45

Arg Asp Trp Trp Asn Ser Glu Ser Val Thr Tyr Phe Trp Gln Asn Trp
     50                  55                  60

Asn Ile Pro Val His Lys Trp Cys Ile Arg Xaa
 65                  70                  75

<210> SEQ ID NO 126
<211> LENGTH: 65
<212> TYPE: PRT
<213> ORGANISM: Homo sapiens
<220> FEATURE:
<221> NAME/KEY: SITE
<222> LOCATION: (65)
<223> OTHER INFORMATION: Xaa equals stop translation

<400> SEQUENCE: 126

Met Thr Lys Glu Asp Lys Ala Ser Ser Glu Ser Leu Arg Leu Ile Leu
 1               5                  10                  15

Val Val Phe Leu Gly Gly Cys Thr Phe Ser Glu Ile Ser Ala Leu Arg
             20                  25                  30

Phe Leu Gly Arg Glu Lys Gly Tyr Arg Phe Ile Phe Leu Thr Thr Ala
         35                  40                  45

Val Thr Asn Ser Ala Arg Leu Met Glu Ala Met Ser Glu Val Lys Ala
     50                  55                  60

Xaa
 65

<210> SEQ ID NO 127
<211> LENGTH: 61
<212> TYPE: PRT
<213> ORGANISM: Homo sapiens
<220> FEATURE:
<221> NAME/KEY: SITE
<222> LOCATION: (37)
<223> OTHER INFORMATION: Xaa equals any of the naturally occurring L-
      amino acids
<221> NAME/KEY: SITE
<222> LOCATION: (61)
<223> OTHER INFORMATION: Xaa equals stop translation
```

-continued

```
<400> SEQUENCE: 127

Met Leu Leu Tyr Tyr Ser Val Met Thr Leu Ser Ser Leu Gly Gln Asp
  1               5                  10                  15

Pro Ser Leu Pro Thr Phe Ala Asp Arg His Ser Gly Met Trp Arg Gln
             20                  25                  30

Gln Cys Val Pro Xaa Thr Phe Leu Tyr Pro Pro Ala Val Gly Ser Thr
         35                  40                  45

Gln Trp Lys Gly Asp Met Thr Leu Ile Leu Leu Phe Xaa
     50                  55                  60

<210> SEQ ID NO 128
<211> LENGTH: 31
<212> TYPE: PRT
<213> ORGANISM: Homo sapiens

<400> SEQUENCE: 128

Met Ser Lys Arg Phe Thr Leu Asp Tyr Leu Phe Leu Ser Glu Ile Val
  1               5                  10                  15

Leu Cys Leu Phe Tyr Tyr Leu Leu Leu Ile Arg Ala Leu Ala Leu
             20                  25                  30

<210> SEQ ID NO 129
<211> LENGTH: 22
<212> TYPE: PRT
<213> ORGANISM: Homo sapiens
<220> FEATURE:
<221> NAME/KEY: SITE
<222> LOCATION: (22)
<223> OTHER INFORMATION: Xaa equals stop translation

<400> SEQUENCE: 129

Met Gln Ile Ile Phe Leu Ala Val Thr Cys Ser Phe Thr Thr Ala Glu
  1               5                  10                  15

Ser Ala Val Ala Arg Xaa
             20

<210> SEQ ID NO 130
<211> LENGTH: 49
<212> TYPE: PRT
<213> ORGANISM: Homo sapiens
<220> FEATURE:
<221> NAME/KEY: SITE
<222> LOCATION: (49)
<223> OTHER INFORMATION: Xaa equals stop translation

<400> SEQUENCE: 130

Met Gly Phe Ser His Arg Ser Pro Val Ala His Pro Arg Ala Arg
  1               5                  10                  15

Asn Arg Arg Ser Gln Glu Val Val Thr Glu Leu Gly Pro Cys Leu Leu
             20                  25                  30

Leu Cys Thr Leu Leu Val Gln Thr Gly Val Val Gly Ser Gln Ala Leu
         35                  40                  45

Xaa

<210> SEQ ID NO 131
<211> LENGTH: 62
<212> TYPE: PRT
<213> ORGANISM: Homo sapiens
<220> FEATURE:
<221> NAME/KEY: SITE
<222> LOCATION: (62)
```

<223> OTHER INFORMATION: Xaa equals stop translation

<400> SEQUENCE: 131

Met Val Gly Ser Ala Met Met Gly Gly Ile Leu Leu Ala Leu Ile Glu
1               5                   10                  15

Gly Val Gly Ile Leu Leu Thr Arg Tyr Thr Ala Gln Gln Phe Arg Asn
            20                  25                  30

Ala Pro Pro Phe Leu Glu Asp Pro Ser Gln Leu Pro Pro Lys Asp Gly
        35                  40                  45

Thr Pro Ala Pro Gly Tyr Pro Ser Tyr Gln Gln Tyr His Xaa
    50                  55                  60

<210> SEQ ID NO 132
<211> LENGTH: 161
<212> TYPE: PRT
<213> ORGANISM: Homo sapiens

<400> SEQUENCE: 132

Met Pro Gly Leu Ser Ala Ala Leu Thr Asp Cys Ser Ser Leu Pro His
1               5                   10                  15

Gly Phe Pro Phe Leu Glu Tyr Leu Phe Phe Arg Gly Asn Met Gln
            20                  25                  30

Leu Gly Leu Lys Thr Phe Pro Pro Ile Ser Pro Thr Gln Pro Arg Leu
        35                  40                  45

Gly Phe Ser Gly Glu Leu Arg Ser Leu Ser Val Phe Ile Phe His Pro
    50                  55                  60

Phe Ile Val Thr Ser Phe Val Ile Leu Phe Phe Gly Gly Asp Gly
65                  70                  75                  80

Val Ile Val Asn Leu Ile Ser Val Ser Tyr Leu Phe Ala Ser Pro Pro
                85                  90                  95

Ser Pro Pro His Glu Leu Leu Pro Ser Arg Gly Leu Ala Gln Leu Ala
            100                 105                 110

Leu Gly Thr Arg Glu Arg Thr Asp Ser Gly Pro Pro Gln Leu Ser Pro
        115                 120                 125

Pro Ser Leu Trp Lys Gly Gly Trp Gly Ser Gly Ala Ser Ser Trp Ala
    130                 135                 140

Leu Cys Glu Ala Trp Pro Pro Leu Pro Thr Leu Ala Leu Asp Cys Tyr
145                 150                 155                 160

Ser

<210> SEQ ID NO 133
<211> LENGTH: 49
<212> TYPE: PRT
<213> ORGANISM: Homo sapiens

<400> SEQUENCE: 133

Met Gly Gln Ser Phe Ser Leu Tyr Met Ile Phe Gln Ile Phe Thr Thr
1               5                   10                  15

Phe Leu Val Pro Leu Asp Ala Arg His Cys Leu Leu Glu Thr His Trp
            20                  25                  30

Tyr Val Thr Ala Gly Phe Thr Met Glu Pro His Ile His Met Ser Trp
        35                  40                  45

Asn

<210> SEQ ID NO 134
<211> LENGTH: 38
<212> TYPE: PRT

```
<213> ORGANISM: Homo sapiens
<220> FEATURE:
<221> NAME/KEY: SITE
<222> LOCATION: (38)
<223> OTHER INFORMATION: Xaa equals stop translation

<400> SEQUENCE: 134

Met Trp Gln His Cys Phe Val Ile Leu Phe Val Gln Val Met His Thr
 1               5                  10                  15

Val Leu Ile Lys Gly Ser Asn Lys Tyr Trp Gly Leu Phe Phe Phe Phe
            20                  25                  30

Pro Gln Gly Ile Leu Xaa
            35

<210> SEQ ID NO 135
<211> LENGTH: 77
<212> TYPE: PRT
<213> ORGANISM: Homo sapiens

<400> SEQUENCE: 135

Met Tyr Thr Phe Ile Cys Thr Trp Leu Trp Arg Asp Lys Leu Ile His
 1               5                  10                  15

Ile Gly Leu Gln Ile Ser Leu Thr Gly Arg Arg Ala Gln Lys Asn Asn
            20                  25                  30

Ile Phe Leu His Phe Phe Gly Ser Ile Leu Lys Asn Lys Lys Gly Thr
        35                  40                  45

Pro Lys Gly Ser Leu Val Thr Pro Leu Leu Gly Phe Leu Ile Thr Asn
 50                  55                  60

Ile Ile Phe Thr Cys Lys Val Asn Gly Pro Leu Ile Ser
65                  70                  75

<210> SEQ ID NO 136
<211> LENGTH: 31
<212> TYPE: PRT
<213> ORGANISM: Homo sapiens
<220> FEATURE:
<221> NAME/KEY: SITE
<222> LOCATION: (31)
<223> OTHER INFORMATION: Xaa equals stop translation

<400> SEQUENCE: 136

Met Glu Gly Leu Met Leu Pro Leu Leu Ser Val Ile Tyr Ser Glu Gly
 1               5                  10                  15

Thr Val Trp Glu Glu Ile Ile Val Ser Gly Arg Gln Tyr Tyr Xaa
            20                  25                  30

<210> SEQ ID NO 137
<211> LENGTH: 58
<212> TYPE: PRT
<213> ORGANISM: Homo sapiens
<220> FEATURE:
<221> NAME/KEY: SITE
<222> LOCATION: (58)
<223> OTHER INFORMATION: Xaa equals stop translation

<400> SEQUENCE: 137

Met Cys Gly Val Thr Tyr Ala Trp Tyr Met Pro Leu Leu Leu Leu Lys
 1               5                  10                  15

Phe Tyr Ser Leu Leu Leu Ala Gln Val Leu Leu Asn Pro Phe Leu Met
            20                  25                  30

Cys Thr Gly Trp Arg Lys Asn Tyr Ser Gln His Phe Glu Arg Lys Val
        35                  40                  45
```

-continued

```
Phe Arg Asn Asn Ile Asn Trp His Tyr Xaa
     50                  55

<210> SEQ ID NO 138
<211> LENGTH: 40
<212> TYPE: PRT
<213> ORGANISM: Homo sapiens

<400> SEQUENCE: 138

Met Phe Ile Phe Arg Asp Gly Leu Thr Met Phe Ser Arg Leu Val Ser
1               5                  10                  15

Asn Ser Cys Pro Gln Val Ile Leu Pro Ser Trp Pro Pro Glu Ser Leu
            20                  25                  30

Gly Gly Ser Gly Arg Arg Ile Ser
        35                  40

<210> SEQ ID NO 139
<211> LENGTH: 47
<212> TYPE: PRT
<213> ORGANISM: Homo sapiens

<400> SEQUENCE: 139

Met Ser Trp Gly Tyr Phe Leu Gly Ala Ser Val Leu Leu Gln Asn Phe
1               5                  10                  15

Phe Ser Ser Tyr Leu Leu Thr Pro Ser Gly Lys Ile Ile Glu Glu Val
            20                  25                  30

Thr Val Val Lys Ala Ser Val Asn Ser Ile Ser Lys Asn Phe Met
        35                  40                  45

<210> SEQ ID NO 140
<211> LENGTH: 30
<212> TYPE: PRT
<213> ORGANISM: Homo sapiens
<220> FEATURE:
<221> NAME/KEY: SITE
<222> LOCATION: (30)
<223> OTHER INFORMATION: Xaa equals stop translation

<400> SEQUENCE: 140

Met Pro Gly Ile Phe Ile Leu Phe Met Thr Leu Ala Ser Thr Phe Asp
1               5                  10                  15

Gln Arg Leu Leu Asn Asp Ser Gln Pro Lys Asp His Ser Xaa
            20                  25                  30

<210> SEQ ID NO 141
<211> LENGTH: 46
<212> TYPE: PRT
<213> ORGANISM: Homo sapiens
<220> FEATURE:
<221> NAME/KEY: SITE
<222> LOCATION: (46)
<223> OTHER INFORMATION: Xaa equals stop translation

<400> SEQUENCE: 141

Met Ala Trp Val Thr Ser Tyr Gly Pro Leu Glu Asp Glu Ser Asn Pro
1               5                  10                  15

Ser His Trp Phe Phe Ala Asn Ser Phe Ala Phe Ile Phe Leu Ile
            20                  25                  30

Thr Ile Asn Ser Ile Phe His Val Leu Arg Ala Pro Gly Xaa
        35                  40                  45

<210> SEQ ID NO 142
<211> LENGTH: 85
```

```
<212> TYPE: PRT
<213> ORGANISM: Homo sapiens
<220> FEATURE:
<221> NAME/KEY: SITE
<222> LOCATION: (81)
<223> OTHER INFORMATION: Xaa equals any of the naturally occurring L-
      amino acids

<400> SEQUENCE: 142

Met Asn Gln Arg Tyr Arg His Lys Ile Lys Asn Tyr Lys Thr Ile His
 1               5                  10                  15

Tyr Ala Tyr Asp Ser Cys Asn Asn Lys Lys Val Gln Gly Thr Ile Ile
                20                  25                  30

Ser Tyr Asn Arg Gly Ile Thr Ser His Arg Glu Gln Gln Tyr His Ile
            35                  40                  45

Ala Gly Ile Tyr Thr Arg Ile Leu Gly Asn Leu Val Trp Ile Tyr Thr
        50                  55                  60

Arg Ile Pro Gly Asp Pro Val Trp Leu Val Arg Gly Phe Pro Glu Lys
 65                 70                  75                  80

Xaa Ile Ser Glu Ser
                85

<210> SEQ ID NO 143
<211> LENGTH: 42
<212> TYPE: PRT
<213> ORGANISM: Homo sapiens
<220> FEATURE:
<221> NAME/KEY: SITE
<222> LOCATION: (16)
<223> OTHER INFORMATION: Xaa equals any of the naturally occurring L-
      amino acids

<400> SEQUENCE: 143

Met Lys Asn Met His Val Tyr Leu Asn Tyr Asn Asn Phe Leu Leu Xaa
 1               5                  10                  15

Leu Leu Arg Leu Met Leu Asn Ile Cys Ser Phe Thr Gln Pro Leu Val
                20                  25                  30

Ala Glu Glu Glu Arg Pro Leu Thr Pro Leu
            35                  40

<210> SEQ ID NO 144
<211> LENGTH: 65
<212> TYPE: PRT
<213> ORGANISM: Homo sapiens

<400> SEQUENCE: 144

Met Asp Glu Glu Arg Glu Ile Ile Ser His Gly Glu Phe Cys Asn Val
 1               5                  10                  15

Ser Arg Glu Arg Asp Trp Val Gly Arg Gln Ala Ser Gln Phe Val Lys
                20                  25                  30

Cys Lys Gly Thr Thr His Arg Thr Leu Ser Leu Thr Arg Ala Val Ser
            35                  40                  45

Tyr Val Val Leu Ser Pro Leu Ala Lys Asp Leu Pro Leu Leu Ala Ser
        50                  55                  60

Asp
 65

<210> SEQ ID NO 145
<211> LENGTH: 312
<212> TYPE: PRT
<213> ORGANISM: Homo sapiens
```

-continued

```
<400> SEQUENCE: 145

Met Ala Gly Val Asp Cys Gly Asp Val Gly Ala Arg Gln His
  1               5                  10                  15

Val Phe Leu Val Ser Glu Tyr Leu Lys Asp Ala Ser Lys Lys Met Lys
             20                  25                  30

Asn Gly Leu Met Phe Val Lys Leu Val Asn Pro Cys Ser Gly Glu Gly
             35                  40                  45

Ala Ile Tyr Leu Phe Asn Met Cys Leu Gln Gln Leu Phe Glu Val Lys
     50                  55                  60

Val Phe Lys Glu Lys His His Ser Trp Phe Ile Asn Gln Ser Val Gln
 65                 70                  75                  80

Ser Gly Gly Leu Leu His Phe Ala Thr Pro Val Asp Pro Leu Phe Leu
                 85                  90                  95

Leu Leu His Tyr Leu Ile Lys Ala Asp Lys Glu Gly Lys Phe Gln Pro
            100                 105                 110

Leu Asp Gln Val Val Asp Asn Val Phe Pro Asn Cys Ile Leu Leu
            115                 120                 125

Leu Lys Leu Pro Gly Leu Glu Lys Leu Leu His His Val Thr Glu Glu
130                 135                 140

Lys Gly Asn Pro Glu Ile Asp Asn Lys Lys Tyr Tyr Lys Tyr Ser Lys
145                 150                 155                 160

Glu Lys Thr Leu Lys Trp Leu Glu Lys Lys Val Asn Gln Thr Val Ala
            165                 170                 175

Ala Leu Lys Thr Asn Asn Val Asn Val Ser Ser Arg Val Gln Ser Thr
            180                 185                 190

Ala Phe Phe Ser Gly Asp Gln Ala Ser Thr Asp Lys Glu Glu Asp Tyr
            195                 200                 205

Ile Arg Tyr Ala His Gly Leu Ile Ser Asp Tyr Ile Pro Lys Glu Leu
            210                 215                 220

Ser Asp Asp Leu Ser Lys Tyr Leu Lys Leu Pro Glu Pro Ser Ala Ser
225                 230                 235                 240

Leu Pro Asn Pro Pro Ser Lys Lys Ile Lys Leu Ser Asp Glu Pro Val
                245                 250                 255

Glu Ala Lys Glu Asp Tyr Thr Lys Phe Asn Thr Lys Asp Leu Lys Thr
            260                 265                 270

Glu Lys Lys Asn Ser Lys Met Thr Ala Ala Gln Lys Ala Leu Ala Lys
            275                 280                 285

Val Asp Lys Ser Gly Met Lys Ser Ile Asp Thr Phe Phe Gly Val Lys
290                 295                 300

Asn Lys Lys Lys Ile Gly Lys Val
305                 310

<210> SEQ ID NO 146
<211> LENGTH: 58
<212> TYPE: PRT
<213> ORGANISM: Homo sapiens

<400> SEQUENCE: 146

Met Asp Lys Asn Val Thr Arg Ser Arg Thr Ile Lys Leu Val Gln Ala
  1               5                  10                  15

Ser Trp Thr Pro Pro Phe Gln Leu Pro Ala Phe Cys Leu Met Pro Val
             20                  25                  30

Cys Gln Trp Leu Glu Leu Gly Leu Leu Phe Arg Thr Ser Val Ala Ile
             35                  40                  45
```

-continued

Leu Ile Leu Pro Trp Gly His Asn Cys Pro
            50                  55

<210> SEQ ID NO 147
<211> LENGTH: 63
<212> TYPE: PRT
<213> ORGANISM: Homo sapiens

<400> SEQUENCE: 147

Met Gly Gln Thr Glu Ala Met Gln Glu Glu Met Arg Thr Arg Thr Cys
1               5                   10                  15

Thr Thr Thr Pro Gln Pro Met Glu Thr Ile Arg Gln Asn Lys Thr Arg
            20                  25                  30

Arg His Met Thr Arg Lys Gln Ala Trp Thr Leu Gln Lys Cys Gln Cys
        35                  40                  45

His Glu Arg Gln Lys Leu Gly Met Leu Phe Trp Ile Lys Gly Asp
    50                  55                  60

<210> SEQ ID NO 148
<211> LENGTH: 85
<212> TYPE: PRT
<213> ORGANISM: Homo sapiens
<220> FEATURE:
<221> NAME/KEY: SITE
<222> LOCATION: (85)
<223> OTHER INFORMATION: Xaa equals stop translation

<400> SEQUENCE: 148

Met Tyr Leu Ile His Leu Tyr Gln Val Leu Lys Tyr Leu Asp Lys Ser
1               5                   10                  15

Lys Tyr Phe Val Phe Ser Phe Phe Leu Leu Ser Ile Leu Leu Thr Thr
            20                  25                  30

Val Lys Arg Cys Ser Ile Leu Ile Trp Ser Val Leu Arg Arg Lys Thr
        35                  40                  45

Met Lys Ala Glu Leu Val Cys Ala Thr Gln Ser Lys Pro Leu Leu Phe
    50                  55                  60

Phe Trp Lys Asp Gly Val Met Phe Phe Lys Asp Ser Asn Lys Tyr Pro
65                  70                  75                  80

Ala Val Ile Ser Xaa
            85

<210> SEQ ID NO 149
<211> LENGTH: 26
<212> TYPE: PRT
<213> ORGANISM: Homo sapiens
<220> FEATURE:
<221> NAME/KEY: SITE
<222> LOCATION: (26)
<223> OTHER INFORMATION: Xaa equals stop translation

<400> SEQUENCE: 149

Met Thr Ser Tyr Ile Ile Asn Leu Ser Phe Phe Leu Pro Leu Ala Thr
1               5                   10                  15

Arg Lys Val Ser Ala Lys Pro Cys Gly Xaa
            20                  25

<210> SEQ ID NO 150
<211> LENGTH: 49
<212> TYPE: PRT
<213> ORGANISM: Homo sapiens
<220> FEATURE:
<221> NAME/KEY: SITE
<222> LOCATION: (17)

-continued

```
<223> OTHER INFORMATION: Xaa equals any of the naturally occurring L-
      amino acids
<221> NAME/KEY: SITE
<222> LOCATION: (18)
<223> OTHER INFORMATION: Xaa equals any of the naturally occurring L-
      amino acids
<221> NAME/KEY: SITE
<222> LOCATION: (49)
<223> OTHER INFORMATION: Xaa equals stop translation

<400> SEQUENCE: 150

Met Leu Pro Leu Met Thr Tyr Ile Ile Gln Tyr Ile Tyr Thr Tyr Ile
 1               5                  10                  15

Xaa Xaa Val Arg Val Leu Ala Ile Leu Phe Leu Arg Arg Val Leu Ser
             20                  25                  30

Gln Thr Leu Leu His Ala Val Tyr Gly Val Ser Cys Val Leu Ile Phe
         35                  40                  45
    Xaa

<210> SEQ ID NO 151
<211> LENGTH: 63
<212> TYPE: PRT
<213> ORGANISM: Homo sapiens

<400> SEQUENCE: 151

Met Val Cys Gly Val Phe Cys Cys Leu Pro Leu Glu Val Leu Pro Phe
 1               5                  10                  15

Ser Arg Pro Ile Asn Val Leu Trp Leu Leu Asn Tyr Ser Ser Thr Leu
             20                  25                  30

Gln Cys Thr Gly Phe Pro Pro Gly Val Asn Thr Asn Gly Gly His Leu
         35                  40                  45

Leu Val Phe Leu Glu Val Leu Gly Glu Phe Ser Asp Leu Trp Leu
     50                  55                  60

<210> SEQ ID NO 152
<211> LENGTH: 34
<212> TYPE: PRT
<213> ORGANISM: Homo sapiens
<220> FEATURE:
<221> NAME/KEY: SITE
<222> LOCATION: (34)
<223> OTHER INFORMATION: Xaa equals stop translation

<400> SEQUENCE: 152

Met Ser Ser Gly Leu Phe Leu Val Leu Phe Cys Phe Leu Cys Val Phe
 1               5                  10                  15

Val Gly Phe Phe Asp Phe His Cys Trp Cys Asp Ile Leu Val Lys Ser
             20                  25                  30

Ser Xaa

<210> SEQ ID NO 153
<211> LENGTH: 211
<212> TYPE: PRT
<213> ORGANISM: Homo sapiens
<220> FEATURE:
<221> NAME/KEY: SITE
<222> LOCATION: (127)
<223> OTHER INFORMATION: Xaa equals any of the naturally occurring L-
      amino acids
<221> NAME/KEY: SITE
<222> LOCATION: (211)
<223> OTHER INFORMATION: Xaa equals stop translation

<400> SEQUENCE: 153

Met Arg Cys Leu Thr Thr Pro Met Leu Leu Arg Ala Leu Ala Gln Ala
```

```
                1               5              10              15
Ala Arg Ala Gly Pro Pro Gly Gly Arg Ser Leu His Ser Ser Ala Val
                   20                  25                  30

Ala Ala Thr Tyr Lys Tyr Val Asn Met Gln Asp Pro Glu Met Asp Met
                   35                  40                  45

Lys Ser Val Thr Asp Arg Ala Ala Arg Thr Leu Leu Trp Thr Glu Leu
         50                  55                  60

Phe Arg Gly Leu Gly Met Thr Leu Ser Tyr Leu Phe Arg Glu Pro Ala
 65                  70                  75                  80

Thr Ile Asn Tyr Pro Phe Glu Lys Gly Pro Leu Ser Pro Arg Phe Arg
                   85                  90                  95

Gly Glu His Ala Leu Arg Arg Tyr Pro Ser Gly Glu Glu Arg Cys Ile
                  100                 105                 110

Ala Cys Lys Leu Cys Glu Ala Ile Cys Pro Ala Gln Ala Ile Xaa Ile
                  115                 120                 125

Glu Ala Glu Pro Arg Ala Asp Gly Ser Arg Arg Thr Thr Arg Tyr Asp
                  130                 135                 140

Ile Asp Met Thr Lys Cys Ile Tyr Cys Gly Phe Cys Gln Glu Ala Cys
145                 150                 155                 160

Pro Val Asp Ala Ile Val Glu Gly Pro Asn Phe Glu Phe Ser Thr Glu
                  165                 170                 175

Thr His Glu Glu Leu Leu Tyr Asn Lys Glu Lys Leu Leu Asn Asn Gly
                  180                 185                 190

Asp Lys Trp Glu Ala Glu Ile Ala Ala Asn Ile Gln Ala Asp Tyr Leu
                  195                 200                 205

Tyr Arg Xaa
    210

<210> SEQ ID NO 154
<211> LENGTH: 115
<212> TYPE: PRT
<213> ORGANISM: Homo sapiens
<220> FEATURE:
<221> NAME/KEY: SITE
<222> LOCATION: (77)
<223> OTHER INFORMATION: Xaa equals any of the naturally occurring L-
      amino acids
<221> NAME/KEY: SITE
<222> LOCATION: (115)
<223> OTHER INFORMATION: Xaa equals stop translation

<400> SEQUENCE: 154

Met Leu Pro Gly Leu Arg Arg Leu Leu Gln Ala Pro Ala Ser Ala Cys
 1               5                  10                  15

Leu Leu Leu Met Leu Leu Ala Leu Pro Leu Ala Ala Pro Ser Cys Pro
                   20                  25                  30

Met Leu Cys Thr Cys Tyr Ser Ser Pro Pro Thr Val Lys Leu Pro Gly
                   35                  40                  45

Gln Gln Leu Leu Leu Cys Ala Ala Val Pro Ala Thr Gln His Ser Ala
         50                  55                  60

Thr Leu Pro Ala Glu Gln Pro His Pro His Ala Ala Xaa Arg His Leu
 65                  70                  75                  80

Trp Val Gln Pro Ala His Pro Val Ala Leu Gln Gln Pro Leu His
                   85                  90                  95

His Leu Pro Gly His Phe Pro Pro Leu Ala Ser Pro Gly Gly Ser Gly
                  100                 105                 110

Pro Arg Xaa
```

<210> SEQ ID NO 155
<211> LENGTH: 227
<212> TYPE: PRT
<213> ORGANISM: Homo sapiens

<400> SEQUENCE: 155

Met Asp Phe Glu Asn Leu Phe Ser Lys Pro Pro Asn Pro Ala Leu Gly
1               5                   10                  15

Lys Thr Ala Thr Asp Ser Asp Glu Arg Ile Asp Asp Glu Ile Asp Thr
            20                  25                  30

Glu Val Glu Glu Thr Gln Glu Glu Lys Ile Lys Leu Glu Cys Glu Gln
        35                  40                  45

Ile Pro Lys Lys Phe Arg His Ser Ala Ile Ser Pro Lys Ser Ser Leu
    50                  55                  60

His Arg Lys Ser Arg Ser Lys Asp Tyr Asp Val Tyr Ser Asp Asn Asp
65                  70                  75                  80

Ile Cys Ser Gln Glu Ser Glu Asp Asn Phe Ala Lys Glu Leu Gln Gln
                85                  90                  95

Tyr Ile Gln Ala Arg Glu Met Ala Asn Ala Ala Gln Pro Glu Glu Ser
            100                 105                 110

Thr Lys Lys Glu Gly Val Lys Asp Thr Pro Gln Ala Ala Lys Gln Lys
        115                 120                 125

Asn Lys Asn Leu Lys Ala Gly His Lys Asn Gly Lys Gln Lys Lys Met
    130                 135                 140

Lys Arg Lys Trp Pro Gly Pro Gly Asn Lys Gly Ser Asn Ala Leu Leu
145                 150                 155                 160

Arg Asn Ser Gly Ser Gln Glu Glu Asp Gly Lys Pro Lys Glu Lys Gln
                165                 170                 175

Gln His Leu Ser Gln Ala Phe Ile Asn Gln His Thr Val Glu Arg Lys
            180                 185                 190

Gly Lys Gln Ile Cys Lys Tyr Phe Leu Glu Arg Lys Cys Ile Lys Gly
        195                 200                 205

Asp Gln Cys Lys Phe Asp His Asp Ala Glu Ile Glu Lys Lys Lys Lys
    210                 215                 220

Lys Thr Arg
225

<210> SEQ ID NO 156
<211> LENGTH: 114
<212> TYPE: PRT
<213> ORGANISM: Homo sapiens

<400> SEQUENCE: 156

Met His Gln Val Ser Thr Cys Phe Gly Pro Gly Arg Gly Leu Ala Leu
1               5                   10                  15

Thr Phe Met Thr Leu His Ser Phe Arg Glu Ala Ile Thr Leu Asp Cys
            20                  25                  30

Asn Thr Asn Asp Arg Arg Pro Ser Gly Gln Arg Pro Arg Pro Arg Ser
        35                  40                  45

Ala Pro Gln Arg Arg Gly Pro Arg Gly Arg Arg Cys Pro Ser Cys Ser
    50                  55                  60

Pro Cys Ala Leu Ser Leu Thr Ser Pro Gly Ser Cys Leu Leu Lys Thr
65                  70                  75                  80

Pro Val Phe Thr Pro Tyr Lys Ala Ser Ser Glu Gln Thr Gly Arg Pro

```
                85                  90                  95
Leu Val Glu Pro Ala His Pro Val Pro Ser Ala Trp Arg Pro Gly Pro
            100                 105                 110
Arg Ala
```

<210> SEQ ID NO 157
<211> LENGTH: 46
<212> TYPE: PRT
<213> ORGANISM: Homo sapiens

<400> SEQUENCE: 157

```
Met Ser Arg Thr Asn Thr Trp Val Ser Trp Gln Ala Ser Arg Ala Asp
  1               5                  10                  15
Trp Pro Glu Thr Asp Pro Gln Glu Ala Leu Gln Pro Ala Leu Val Pro
             20                  25                  30
Ser His Ser Asp Leu Asn Pro Gly Ser Ser Arg Ser Ala Val
         35                  40                  45
```

<210> SEQ ID NO 158
<211> LENGTH: 36
<212> TYPE: PRT
<213> ORGANISM: Homo sapiens
<220> FEATURE:
<221> NAME/KEY: SITE
<222> LOCATION: (36)
<223> OTHER INFORMATION: Xaa equals stop translation

<400> SEQUENCE: 158

```
Met Leu Phe Gln Cys Gln Val Leu Leu Ser Ile Phe Ser Phe Leu Glu
  1               5                  10                  15
Pro Val Leu Ser Ser Gly Ser Ser Arg Leu Val Phe Tyr Asn Leu Ser
             20                  25                  30
Asn Ile Met Xaa
         35
```

<210> SEQ ID NO 159
<211> LENGTH: 38
<212> TYPE: PRT
<213> ORGANISM: Homo sapiens
<220> FEATURE:
<221> NAME/KEY: SITE
<222> LOCATION: (38)
<223> OTHER INFORMATION: Xaa equals stop translation

<400> SEQUENCE: 159

```
Met Val Phe Ser Ala Lys Ile Gly Val Arg Tyr Phe Leu Val Leu Ser
  1               5                  10                  15
Cys Leu Pro Asn Cys Cys Leu Pro Ala Asp Trp Trp His Ala Gln Trp
             20                  25                  30
Leu Trp Gly Gln Gly Xaa
         35
```

<210> SEQ ID NO 160
<211> LENGTH: 30
<212> TYPE: PRT
<213> ORGANISM: Homo sapiens
<220> FEATURE:
<221> NAME/KEY: SITE
<222> LOCATION: (30)
<223> OTHER INFORMATION: Xaa equals stop translation

<400> SEQUENCE: 160

```
Met Tyr Phe Ser Leu Leu Val Leu Leu Phe Ser Pro Ser Val Leu Phe
```

```
                1               5              10              15
Leu Ala Arg Lys Lys Cys Thr Arg Asn Asn Thr Leu Asn Xaa
            20              25              30
```

<210> SEQ ID NO 161
<211> LENGTH: 56
<212> TYPE: PRT
<213> ORGANISM: Homo sapiens
<220> FEATURE:
<221> NAME/KEY: SITE
<222> LOCATION: (56)
<223> OTHER INFORMATION: Xaa equals stop translation

<400> SEQUENCE: 161

```
Met Val Lys Leu Ser Lys Glu Ala Lys Gln Arg Leu Gln Gln Leu Phe
 1               5              10              15

Lys Gly Ser Gln Phe Ala Ile Arg Trp Gly Phe Ile Pro Leu Val Ile
            20              25              30

Tyr Leu Gly Phe Lys Arg Gly Ala Asp Pro Gly Met Pro Glu Pro Thr
        35              40              45

Val Leu Ser Leu Leu Trp Gly Xaa
        50              55
```

<210> SEQ ID NO 162
<211> LENGTH: 70
<212> TYPE: PRT
<213> ORGANISM: Homo sapiens
<220> FEATURE:
<221> NAME/KEY: SITE
<222> LOCATION: (70)
<223> OTHER INFORMATION: Xaa equals stop translation

<400> SEQUENCE: 162

```
Met Leu Gly Phe Ala Phe Arg Asp Lys Arg Trp Trp Ile Tyr Phe Ala
 1               5              10              15

Cys Ser Lys Asp Ser Gln Gly Val Arg Ala Ala Tyr Cys Gln Ile Leu
            20              25              30

Leu Leu Phe Tyr Val Ser Val Tyr Ser Leu Ser Phe Ser Tyr Leu Leu
        35              40              45

Asp His Phe Cys Ser Leu Pro Lys Pro Leu Leu Phe Gly Thr Val Ser
    50              55                  60

Gln Ile Pro His Phe Xaa
65              70
```

<210> SEQ ID NO 163
<211> LENGTH: 52
<212> TYPE: PRT
<213> ORGANISM: Homo sapiens
<220> FEATURE:
<221> NAME/KEY: SITE
<222> LOCATION: (52)
<223> OTHER INFORMATION: Xaa equals stop translation

<400> SEQUENCE: 163

```
Met Cys Ser Tyr Cys Met Pro Tyr Leu Ile Ile Phe Leu Ser Val Ile
 1               5              10              15

His Asn His Lys Thr Ile Pro Leu Leu Lys Val Leu Asp Lys Leu
            20              25              30

Asn Cys Ile Ile Thr Asp Leu Cys Ile Ser Arg Asp Asp Val Phe Pro
        35              40              45

Thr Thr Cys Xaa
        50
```

<210> SEQ ID NO 164
<211> LENGTH: 104
<212> TYPE: PRT
<213> ORGANISM: Homo sapiens
<220> FEATURE:
<221> NAME/KEY: SITE
<222> LOCATION: (51)
<223> OTHER INFORMATION: Xaa equals any of the naturally occurring L-
      amino acids
<221> NAME/KEY: SITE
<222> LOCATION: (104)
<223> OTHER INFORMATION: Xaa equals stop translation

<400> SEQUENCE: 164

Met Cys Ala Asp Asp Leu Leu Ser Val Leu Leu Tyr Leu Leu Val Lys
 1               5                  10                  15

Thr Glu Ile Pro Asn Trp Met Ala Asn Leu Ser Tyr Ile Lys Asn Phe
                20                  25                  30

Arg Phe Ser Ser Leu Ala Lys Asp Glu Leu Gly Ile Leu Pro Asp Leu
            35                  40                  45

Ile Arg Xaa Cys Pro Leu Asn Ile Arg Gln Gly Ser Leu Ser Ala Lys
        50                  55                  60

Pro Pro Glu Ser Glu Gly Phe Gly Asp Arg Leu Phe Leu Lys Gln Arg
 65                  70                  75                  80

Met Ser Leu Leu Ser Gln Met Thr Ser Ser Pro Thr Asp Cys Leu Phe
                85                  90                  95

Lys Ala Asp Ala Leu Leu Glu Xaa
            100

<210> SEQ ID NO 165
<211> LENGTH: 76
<212> TYPE: PRT
<213> ORGANISM: Homo sapiens
<220> FEATURE:
<221> NAME/KEY: SITE
<222> LOCATION: (76)
<223> OTHER INFORMATION: Xaa equals stop translation

<400> SEQUENCE: 165

Met Ala Arg Ile Thr Gly Pro Pro Glu Arg Asp Asp Pro Tyr Pro Val
 1               5                  10                  15

Leu Phe Arg Tyr Leu His Ser His His Phe Leu Glu Leu Val Thr Leu
                20                  25                  30

Leu Leu Ser Ile Pro Val Thr Ser Ala His Pro Gly Val Leu Gln Ala
            35                  40                  45

Thr Lys Asp Val Leu Lys Phe Leu Ala Gln Ser Gln Lys Gly Leu Leu
        50                  55                  60

Phe Phe Met Ser Glu Tyr Glu Ala Thr Ile Tyr Xaa
 65                  70                  75

<210> SEQ ID NO 166
<211> LENGTH: 38
<212> TYPE: PRT
<213> ORGANISM: Homo sapiens
<220> FEATURE:
<221> NAME/KEY: SITE
<222> LOCATION: (38)
<223> OTHER INFORMATION: Xaa equals stop translation

<400> SEQUENCE: 166

Met Lys Gln Thr Arg Leu Asn Pro Pro Val Val Phe Ile Leu Leu Gln
 1               5                  10                  15

```
Pro Leu Ser Arg Pro Arg Asp Gly Leu Ser Asn Ser Val Leu Ile Ile
            20                  25                  30

Leu His Ser Val Pro Xaa
            35

<210> SEQ ID NO 167
<211> LENGTH: 272
<212> TYPE: PRT
<213> ORGANISM: Homo sapiens
<220> FEATURE:
<221> NAME/KEY: SITE
<222> LOCATION: (120)
<223> OTHER INFORMATION: Xaa equals any of the naturally occurring L-
      amino acids
<221> NAME/KEY: SITE
<222> LOCATION: (162)
<223> OTHER INFORMATION: Xaa equals any of the naturally occurring L-
      amino acids
<221> NAME/KEY: SITE
<222> LOCATION: (175)
<223> OTHER INFORMATION: Xaa equals any of the naturally occurring L-
      amino acids
<221> NAME/KEY: SITE
<222> LOCATION: (176)
<223> OTHER INFORMATION: Xaa equals any of the naturally occurring L-
      amino acids
<221> NAME/KEY: SITE
<222> LOCATION: (180)
<223> OTHER INFORMATION: Xaa equals any of the naturally occurring L-
      amino acids

<400> SEQUENCE: 167

Met Ser Ala Leu Arg Arg Ser Gly Tyr Gly Pro Ser Asp Gly Pro Ser
 1               5                  10                  15

Tyr Gly Arg Tyr Tyr Gly Pro Gly Gly Asp Val Pro Val His Pro
            20                  25                  30

Pro Pro Pro Leu Tyr Pro Leu Arg Pro Glu Pro Pro Gln Pro Pro Ile
            35                  40                  45

Ser Trp Arg Val Arg Gly Gly Pro Ala Glu Thr Thr Trp Leu Gly
     50                  55                  60

Glu Gly Gly Gly Gly Asp Gly Tyr Tyr Pro Ser Gly Gly Ala Trp Pro
 65                  70                  75                  80

Glu Pro Gly Arg Ala Gly Gly Ser His Gln Ser Leu Asn Ser Tyr Thr
                85                  90                  95

Asn Gly Ala Tyr Gly Pro Thr Tyr Pro Pro Gly Pro Gly Ala Asn Thr
            100                 105                 110

Ala Phe Ile Leu Arg Gly Leu Xaa Cys Thr Trp Leu Tyr Ser Asp Gln
        115                 120                 125

Leu Leu His Arg Ile Pro Ser Thr Tyr Arg Ser Ser Gly Asn Ser Pro
    130                 135                 140

Thr Pro Val Ser Arg Trp Ile Tyr Pro Gln Gln Asp Cys Gln Thr Glu
145                 150                 155                 160

Ala Xaa Pro Leu Arg Gly Lys Val Pro Gly Tyr Pro Pro Ser Xaa Xaa
                165                 170                 175

Pro Gly Met Xaa Leu Pro His Tyr Pro Tyr Gly Asp Gly Asn Arg Ser
            180                 185                 190

Val Pro Gln Ser Gly Pro Thr Val Arg Pro Gln Glu Asp Ala Trp Ala
        195                 200                 205

Ser Pro Gly Ala Tyr Gly Met Gly Gly Arg Tyr Pro Trp Pro Ser Ser
    210                 215                 220

Ala Pro Ser Ala Pro Pro Gly Asn Leu Tyr Met Thr Glu Val Leu His
```

-continued

```
                225                 230                 235                 240
His Gly Leu Ala Val Ala Leu Pro Ser His Pro Leu His Pro Gln Ser
                    245                 250                 255
Ser Ser Pro Arg Ile Leu His Thr Pro Ile Ala Asn Gln Ile Lys Ala
                260                 265                 270

<210> SEQ ID NO 168
<211> LENGTH: 26
<212> TYPE: PRT
<213> ORGANISM: Homo sapiens
<220> FEATURE:
<221> NAME/KEY: SITE
<222> LOCATION: (26)
<223> OTHER INFORMATION: Xaa equals stop translation

<400> SEQUENCE: 168

Met Ile Leu Thr Phe Cys Val Phe Leu Phe Ser Phe His Asn Ala
  1               5                  10                  15

Ile Lys Ser Thr Pro Phe Leu Lys Phe Xaa
                20                  25

<210> SEQ ID NO 169
<211> LENGTH: 26
<212> TYPE: PRT
<213> ORGANISM: Homo sapiens
<220> FEATURE:
<221> NAME/KEY: SITE
<222> LOCATION: (21)
<223> OTHER INFORMATION: Xaa equals any of the naturally occurring L-
      amino acids
<221> NAME/KEY: SITE
<222> LOCATION: (26)
<223> OTHER INFORMATION: Xaa equals stop translation

<400> SEQUENCE: 169

Met Lys Leu Ile Tyr Tyr Cys His Leu Val Asp Ile Leu Leu Leu Gln
  1               5                  10                  15

Ala Ile Ile Lys Xaa Asn Ala Gly Met Xaa
                20                  25

<210> SEQ ID NO 170
<211> LENGTH: 132
<212> TYPE: PRT
<213> ORGANISM: Homo sapiens

<400> SEQUENCE: 170

Met Ile Glu Cys Pro Asp Trp Ala Arg Thr Ala Ser Leu Ala Lys Gln
  1               5                  10                  15

Arg Arg Lys Val Phe Lys Gln Met Leu Ser Ser Phe Leu His Phe His
                20                  25                  30

Phe Asn Ser Met Met Pro Leu Cys Pro Ser Asp Asp Ile Ser Pro Gly
            35                  40                  45

Val Trp Asp Ser Ala Gly Leu Pro Cys Leu Leu Arg Arg Leu Pro Gly
     50                  55                  60

His His Gln Ala Gly Lys Pro Gln Ser Pro Ser Ser Thr Trp Asp
 65                  70                  75                  80

Pro Trp Ala Ser Ile Ser Leu Thr Arg Lys Pro Val Leu Leu Leu
                 85                  90                  95

Ile Leu Gly Pro His Pro Arg Pro Ile Gln Arg Lys Thr Pro Gly Ala
            100                 105                 110

Ala Leu Gly Ser Leu Cys Phe His Gln Ile Cys Val Lys Thr Gln Met
        115                 120                 125
```

Asn Gln Pro Arg
    130

<210> SEQ ID NO 171
<211> LENGTH: 72
<212> TYPE: PRT
<213> ORGANISM: Homo sapiens
<220> FEATURE:
<221> NAME/KEY: SITE
<222> LOCATION: (72)
<223> OTHER INFORMATION: Xaa equals stop translation

<400> SEQUENCE: 171

Met Arg Ala Thr Ile Val Arg Pro Tyr Cys Gln Glu Gly Gly Phe Trp
1               5                   10                  15

Leu Leu Ala Leu Val Tyr Lys Gly Ala Arg Ala Ala Pro Leu Asp Tyr
            20                  25                  30

Ser Trp Glu Asp Ser Asp Ala Gly Arg Leu Leu Pro Trp Val Thr
        35                  40                  45

Ser Ser Leu Leu Ala Asp Ile Trp Gly Phe Asp Pro Phe Phe Phe Asn
    50                  55                  60

Leu Leu Leu Leu Arg Cys Ile Xaa
65                  70

<210> SEQ ID NO 172
<211> LENGTH: 75
<212> TYPE: PRT
<213> ORGANISM: Homo sapiens

<400> SEQUENCE: 172

Met Phe Tyr Val Tyr Asp His Ser Met Tyr Val Asp Thr His Thr His
1               5                   10                  15

Thr His Val Pro Ser Leu Tyr Thr Asn Gly Asn Ile Leu Lys Ile Leu
            20                  25                  30

Phe Cys Thr Phe Thr Val Gln Val Pro Tyr Ser Pro Leu Ser Thr Trp
        35                  40                  45

Gln Arg Pro Lys Pro Val Lys Gly Arg Val Ser Thr Trp Pro Pro Ser
    50                  55                  60

Ser Met Ser Ser Ala Arg Ser Pro Gln Gly Pro
65                  70                  75

<210> SEQ ID NO 173
<211> LENGTH: 32
<212> TYPE: PRT
<213> ORGANISM: Homo sapiens
<220> FEATURE:
<221> NAME/KEY: SITE
<222> LOCATION: (32)
<223> OTHER INFORMATION: Xaa equals stop translation

<400> SEQUENCE: 173

Met Ala Leu Leu Val Leu Thr Leu Tyr Cys Ile Leu Phe Leu Lys Ile
1               5                   10                  15

Tyr Met Pro Val Pro Ser His Cys Glu Gln Phe Lys Gly Arg Asn Xaa
            20                  25                  30

<210> SEQ ID NO 174
<211> LENGTH: 67
<212> TYPE: PRT
<213> ORGANISM: Homo sapiens
<220> FEATURE:
<221> NAME/KEY: SITE
<222> LOCATION: (67)
<223> OTHER INFORMATION: Xaa equals stop translation

<400> SEQUENCE: 174

Met Gln Asn Asp Gly Leu Lys Phe Met Glu Met Val Leu His Val Leu
1               5                   10                  15

Gln Ala Ser Ile Gly Val Leu Leu Met Val Asp Val Leu Glu His
            20                  25                  30

Phe Leu Ala Met Leu Ile Gly Asn Ala Gly Ala Pro Leu Pro Leu Leu
        35                  40                  45

Asp Val Leu Gly Lys Asp Val Ile Asp Val Ala Glu Arg Arg Glu Ser
    50                  55                  60

Lys Lys Xaa
65

<210> SEQ ID NO 175
<211> LENGTH: 128
<212> TYPE: PRT
<213> ORGANISM: Homo sapiens

<400> SEQUENCE: 175

Met Gln Trp Gly Glu Gly Ala Gly Pro Ser Trp Val Tyr Ile Leu Ser
1               5                   10                  15

Trp Asp Ser Arg Ala Ser Leu Cys Met Cys Ala Ala Ser Arg Tyr Leu
            20                  25                  30

Cys Thr Gly Thr Asp Pro Pro Thr Arg Gly Asp Thr Ser Thr Pro His
        35                  40                  45

Lys Ala Ile Leu Pro Leu Asp Pro Cys Pro Gln Ile Ser Arg Thr Ala
    50                  55                  60

Arg Ala Glu Phe Leu Gln Pro Gly Gly Ser Thr Ser Ser Arg Ala Ala
65                  70                  75                  80

Ala Thr Ala Val Glu Leu Gln Leu Leu Phe Pro Leu Val Arg Val Asn
                85                  90                  95

Phe Glu Leu Gly Val Ile Met Val Ile Ala Val Ser Cys Val Lys Leu
            100                 105                 110

Leu Ser Ala His Asn Ser Thr Gln His Thr Ser Arg Lys His Lys Val
        115                 120                 125

<210> SEQ ID NO 176
<211> LENGTH: 46
<212> TYPE: PRT
<213> ORGANISM: Homo sapiens
<220> FEATURE:
<221> NAME/KEY: SITE
<222> LOCATION: (46)
<223> OTHER INFORMATION: Xaa equals stop translation

<400> SEQUENCE: 176

Met Gly Ser Val Trp Asn Cys Leu Leu Ala Leu Leu Glu Lys His Leu
1               5                   10                  15

Ile Thr Leu Tyr Lys Leu Ile Ile Thr Val Leu Leu Asp Leu Leu Ser
            20                  25                  30

Ala Arg His Lys Cys Phe Thr Ser Val Asn Ser Phe Asn Xaa
        35                  40                  45

<210> SEQ ID NO 177
<211> LENGTH: 42
<212> TYPE: PRT
<213> ORGANISM: Homo sapiens
<220> FEATURE:

-continued

```
<221> NAME/KEY: SITE
<222> LOCATION: (21)
<223> OTHER INFORMATION: Xaa equals any of the naturally occurring L-
      amino acids
<221> NAME/KEY: SITE
<222> LOCATION: (38)
<223> OTHER INFORMATION: Xaa equals any of the naturally occurring L-
      amino acids
<221> NAME/KEY: SITE
<222> LOCATION: (42)
<223> OTHER INFORMATION: Xaa equals stop translation

<400> SEQUENCE: 177

Met Asn Ser Thr Cys Gly Phe Val Thr Ser Ile Asn Gln Ile Phe Leu
 1               5                  10                  15

Ile Ile Leu Trp Xaa Leu Tyr Leu Pro Leu Leu Thr Thr Thr Leu Glu
            20                  25                  30

Ile Trp Glu Leu Leu Xaa Leu Leu His Xaa
        35                  40

<210> SEQ ID NO 178
<211> LENGTH: 73
<212> TYPE: PRT
<213> ORGANISM: Homo sapiens
<220> FEATURE:
<221> NAME/KEY: SITE
<222> LOCATION: (41)
<223> OTHER INFORMATION: Xaa equals any of the naturally occurring L-
      amino acids
<221> NAME/KEY: SITE
<222> LOCATION: (73)
<223> OTHER INFORMATION: Xaa equals stop translation

<400> SEQUENCE: 178

Met Cys Gly Gly His Ala Ile Asn Val Gly Pro Phe Thr Val Ala Gly
 1               5                  10                  15

Arg Gly Arg Asn Leu Gln Phe Leu Arg Val Leu Leu Leu Arg Cys Pro
            20                  25                  30

Pro Val Leu Gly His Ser Cys Ser Xaa Pro Cys Pro Ala Trp Ser His
        35                  40                  45

Pro Pro Ser Ala Asn Arg Ser Leu Gly Arg Val Leu Trp Ala Leu Ile
    50                  55                  60

Arg Pro Trp Gln Gly Arg Ser Ser Xaa
 65                 70

<210> SEQ ID NO 179
<211> LENGTH: 31
<212> TYPE: PRT
<213> ORGANISM: Homo sapiens
<220> FEATURE:
<221> NAME/KEY: SITE
<222> LOCATION: (31)
<223> OTHER INFORMATION: Xaa equals stop translation

<400> SEQUENCE: 179

Met Val Leu Pro Arg Ile Leu Val Leu Met Leu Phe Leu Ala Leu Lys
 1               5                  10                  15

Asn Pro Val Gly Glu Met Arg Asn Leu Thr His Cys Arg Cys Xaa
            20                  25                  30

<210> SEQ ID NO 180
<211> LENGTH: 72
<212> TYPE: PRT
<213> ORGANISM: Homo sapiens

<400> SEQUENCE: 180
```

-continued

```
Met Asp Thr Arg Gly Val Val Leu Arg Ser Gly Glu Phe Asn Arg Gln
  1               5                  10                  15

Glu Gly Arg Glu Lys Thr Glu Gly Arg Ser Ser Ser Ile Trp Arg Gln
             20                  25                  30

Arg Glu Gly Gly Ser Lys Ala Lys Arg Gly Gly Pro Gln Val Gln Trp
         35                  40                  45

Thr Pro Ala Lys Tyr Ile Cys Arg Gly Trp Lys Gly Arg Cys Leu Ile
     50                  55                  60

Tyr Ile Gly Leu Arg Gly Leu Val
 65              70

<210> SEQ ID NO 181
<211> LENGTH: 55
<212> TYPE: PRT
<213> ORGANISM: Homo sapiens
<220> FEATURE:
<221> NAME/KEY: SITE
<222> LOCATION: (38)
<223> OTHER INFORMATION: Xaa equals any of the naturally occurring L-
      amino acids
<221> NAME/KEY: SITE
<222> LOCATION: (55)
<223> OTHER INFORMATION: Xaa equals stop translation

<400> SEQUENCE: 181

Met Pro His Ile Phe Val Ser Gly Asn Phe Ser Leu Leu Ala Leu Phe
  1               5                  10                  15

Leu Leu Ser Ala Asn Phe Ile Val Glu Val Gln Ser Trp Leu Leu Leu
             20                  25                  30

Leu Leu Phe Phe Ile Xaa Leu Gly Arg Ser Tyr Asn Phe Tyr Leu Leu
         35                  40                  45

Cys Asp Ser Ile Ile Phe Xaa
     50                  55

<210> SEQ ID NO 182
<211> LENGTH: 67
<212> TYPE: PRT
<213> ORGANISM: Homo sapiens
<220> FEATURE:
<221> NAME/KEY: SITE
<222> LOCATION: (67)
<223> OTHER INFORMATION: Xaa equals stop translation

<400> SEQUENCE: 182

Met His Asn Leu Ile Ser Ser Ile Ile Ser Phe Leu Tyr Asn Phe Cys
  1               5                  10                  15

Ala Leu Pro Leu Ala Ser Pro Gln Phe Thr Asn Glu Glu Ser Ser Tyr
             20                  25                  30

Thr Ala Leu Arg Ser Cys Thr Arg Gly Gly Phe Glu Ser Arg Ser Leu
         35                  40                  45

Gly Thr Gln Lys Ser Cys Thr Phe Gln Gly Lys Gly Asp Tyr His Val
     50                  55                  60

Thr Ala Xaa
 65

<210> SEQ ID NO 183
<211> LENGTH: 74
<212> TYPE: PRT
<213> ORGANISM: Homo sapiens
<220> FEATURE:
<221> NAME/KEY: SITE
<222> LOCATION: (74)
```

-continued

<223> OTHER INFORMATION: Xaa equals stop translation

<400> SEQUENCE: 183

```
Met Thr Thr Leu Phe Glu Thr Asp Arg Cys Leu Leu Phe Leu Val Met
 1               5                  10                  15

Ser Arg Phe Gly Phe Lys Ser Arg Leu Glu Ala Thr Ser Cys Lys Gln
            20                  25                  30

Val Gln Glu Asn Glu Thr Arg Arg Val Gly Asp Thr Arg Met Lys Thr
        35                  40                  45

Ser Val Arg Val Lys Thr Lys Gln Thr Met Tyr Ile Ile Cys Ile Trp
    50                  55                  60

Glu Lys Lys Glu Arg Asn Tyr Leu Thr Xaa
 65                  70
```

<210> SEQ ID NO 184
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 184

```
Met Val Ser Asp Ile Ser Gly Gln Lys Gln Ser Leu Glu Ala Val Lys
 1               5                  10                  15

Glu His Leu Leu Phe Ile Trp Leu Pro Val Tyr Lys Ser Thr His Glu
            20                  25                  30

Gly Pro Asn Ser Lys Ile Ser Asn Tyr Gln Val Leu Xaa
        35                  40                  45
```

<210> SEQ ID NO 185
<211> LENGTH: 98
<212> TYPE: PRT
<213> ORGANISM: Homo sapiens
<220> FEATURE:
<221> NAME/KEY: SITE
<222> LOCATION: (98)
<223> OTHER INFORMATION: Xaa equals stop translation

<400> SEQUENCE: 185

```
Met Arg Pro Leu Leu Cys Ala Leu Thr Gly Leu Ala Leu Leu Arg Ala
 1               5                  10                  15

Ala Gly Ser Leu Ala Ala Ala Glu Pro Phe Ser Pro Pro Arg Gly Asp
            20                  25                  30

Ser Ala Gln Ser Thr Ala Cys Asp Arg His Met Ala Val Gln Arg Arg
        35                  40                  45

Leu Asp Val Met Glu Glu Met Val Glu Lys Thr Val Asp His Leu Gly
    50                  55                  60

Thr Glu Val Lys Gly Leu Leu Gly Leu Leu Glu Glu Leu Ala Trp Asn
 65                  70                  75                  80

Leu Pro Pro Gly Pro Phe Ser Pro Ala Pro Asp Leu Leu Gly Asp Gly
                85                  90                  95

Phe Xaa
```

<210> SEQ ID NO 186
<211> LENGTH: 62
<212> TYPE: PRT
<213> ORGANISM: Homo sapiens
<220> FEATURE:
<221> NAME/KEY: SITE

```
<222> LOCATION: (62)
<223> OTHER INFORMATION: Xaa equals stop translation

<400> SEQUENCE: 186

Met Ala Ser Leu Leu Asp Asn Phe Ile Leu Asn Ile Ile Val Ile Phe
1               5                   10                  15

Cys Ile Val Ile Asp Ser Tyr Leu Cys Gly Phe Met Tyr Phe Phe Val
                20                  25                  30

Ile Asp Ser Pro Val Pro Ala Cys Ser Pro Leu Gln Leu Ser Gln Thr
            35                  40                  45

Leu Ile Leu Gln Leu Gln Pro Thr Ala Arg Tyr Phe His Xaa
        50                  55                  60

<210> SEQ ID NO 187
<211> LENGTH: 40
<212> TYPE: PRT
<213> ORGANISM: Homo sapiens

<400> SEQUENCE: 187

Met Cys Ile Phe Glu Cys Met Cys His Phe Phe Ile Asp Ile Ser Asn
1               5                   10                  15

His Tyr Tyr Val Val Arg Phe Tyr Pro Glu Asp Ser Leu Pro Lys Thr
                20                  25                  30

Phe Ile Tyr Asp Pro Phe Lys Ala
            35                  40

<210> SEQ ID NO 188
<211> LENGTH: 153
<212> TYPE: PRT
<213> ORGANISM: Homo sapiens

<400> SEQUENCE: 188

Met Cys Glu Ser Asn Ser Thr Met Pro Gly Pro Ser Leu Ser Pro
1               5                   10                  15

Val Ser Thr Pro Ala Gly Lys Ile Gly Leu Ala Val Cys Tyr Asp Met
                20                  25                  30

Arg Phe Pro Glu Leu Ser Leu Ala Leu Ala Gln Ala Gly Ala Glu Ile
            35                  40                  45

Leu Thr Tyr Pro Ser Ala Phe Gly Ser Ile Thr Gly Pro Ala His Trp
        50                  55                  60

Glu Val Leu Leu Arg Ala Arg Ala Ile Glu Thr Gln Cys Tyr Val Val
65                  70                  75                  80

Ala Ala Ala Gln Cys Gly Arg His Glu Lys Arg Ala Ser Tyr Gly
                85                  90                  95

His Ser Met Val Val Asp Pro Trp Gly Thr Val Val Ala Arg Cys Ser
                100                 105                 110

Glu Gly Pro Gly Leu Cys Leu Ala Arg Ile Asp Leu Asn Tyr Leu Arg
            115                 120                 125

Gln Leu Arg Arg His Leu Pro Val Phe Gln His Arg Arg Pro Asp Leu
        130                 135                 140

Tyr Gly Asn Leu Gly His Pro Leu Ser
145                 150

<210> SEQ ID NO 189
<211> LENGTH: 60
<212> TYPE: PRT
<213> ORGANISM: Homo sapiens
<220> FEATURE:
<221> NAME/KEY: SITE
```

```
<222> LOCATION: (60)
<223> OTHER INFORMATION: Xaa equals stop translation

<400> SEQUENCE: 189

Met Asn Ile Leu Met Phe Ala Phe Met Ile Ile Phe Met Gly Ala Lys
  1               5                  10                  15

Phe Gln Glu Val Glu Phe Trp Val Arg Gly Tyr Asp His Leu Lys Ala
             20                  25                  30

Thr Leu Phe Asp Gln Ile Gly Arg Tyr Leu Lys Met Gly Gly Gln Glu
         35                  40                  45

Pro Leu Leu Ala Lys Val Trp Val Arg Gly Thr Xaa
     50                  55                  60

<210> SEQ ID NO 190
<211> LENGTH: 108
<212> TYPE: PRT
<213> ORGANISM: Homo sapiens

<400> SEQUENCE: 190

Met Ser Ser Val Ser Leu Ser Ala Ser Ser Ser Ser Ser Ser Lys Val
  1               5                  10                  15

Pro Arg Val Arg Ile Lys Ser Glu Gly Cys Ser Thr Gly Asp Lys Leu
             20                  25                  30

Ser Leu Ala Val Pro Ala Ser Lys Ala Thr Glu Pro Ile Ser Phe Arg
         35                  40                  45

Arg Arg Ser Ser Cys Ser Leu Cys Cys Trp Leu Ser Ala Leu Ala Ser
     50                  55                  60

Asp Phe Phe Arg Arg Ser Tyr Ser Gly Arg Tyr Ser Leu Ser Tyr Ser
 65                  70                  75                  80

Ser Ala Ala Leu Val Thr Cys Thr Lys Ser Ser Ser Asn Pro Val Pro
                 85                  90                  95

Arg Thr Ala Glu Thr Pro Thr Thr Leu Ser Glu Leu
            100                 105

<210> SEQ ID NO 191
<211> LENGTH: 30
<212> TYPE: PRT
<213> ORGANISM: Homo sapiens
<220> FEATURE:
<221> NAME/KEY: SITE
<222> LOCATION: (30)
<223> OTHER INFORMATION: Xaa equals stop translation

<400> SEQUENCE: 191

Met Ser Ile Thr Leu Ile Gln Leu Met Phe Tyr Phe Asn Thr Pro Glu
  1               5                  10                  15

Leu Pro His Lys Thr Ser Phe His Val Lys Gly Ser Arg Xaa
             20                  25                  30

<210> SEQ ID NO 192
<211> LENGTH: 23
<212> TYPE: PRT
<213> ORGANISM: Homo sapiens
<220> FEATURE:
<221> NAME/KEY: SITE
<222> LOCATION: (23)
<223> OTHER INFORMATION: Xaa equals stop translation

<400> SEQUENCE: 192

Met Ser Leu Leu Leu Phe Leu Lys Val His Leu Phe Ser Pro Ser Thr
  1               5                  10                  15
```

```
Ile Phe Lys Arg Asn Asn Xaa
                20
```

<210> SEQ ID NO 193
<211> LENGTH: 106
<212> TYPE: PRT
<213> ORGANISM: Homo sapiens
<220> FEATURE:
<221> NAME/KEY: SITE
<222> LOCATION: (89)
<223> OTHER INFORMATION: Xaa equals any of the naturally occurring L-
      amino acids
<221> NAME/KEY: SITE
<222> LOCATION: (106)
<223> OTHER INFORMATION: Xaa equals stop translation

<400> SEQUENCE: 193

```
Met Gly Pro Ala Leu Met Val Ala Ser Leu Cys Leu Gly Gly Pro Ala
 1               5                  10                  15

Pro Ala Val Gly Ala Ile Thr Pro Ser Pro Phe Ile Thr Ser Leu Arg
                20                  25                  30

Trp Ala Pro Ser Pro Ala Gly Cys Leu Pro Ser Gly Asn Ser Arg Thr
            35                  40                  45

Leu Arg Asp Thr Arg Ala Ala Trp Pro Arg Gly Ala Thr Ala Arg Pro
        50                  55                  60

Pro Gly Gly Gln Pro Trp Arg Glu Leu Arg Pro Thr Tyr Ser Gly Val
 65                  70                  75                  80

Trp Glu Pro Cys Leu Tyr Leu Gly Xaa Ser Pro Ser Gln Leu Pro Pro
                85                  90                  95

Cys Val Phe Pro Pro Ala Lys Val Gly Xaa
            100                 105
```

<210> SEQ ID NO 194
<211> LENGTH: 54
<212> TYPE: PRT
<213> ORGANISM: Homo sapiens
<220> FEATURE:
<221> NAME/KEY: SITE
<222> LOCATION: (54)
<223> OTHER INFORMATION: Xaa equals stop translation

<400> SEQUENCE: 194

```
Met Lys Val Gln Ser Phe Tyr Lys Thr Leu Ile Pro Leu Leu Thr Ile
 1               5                  10                  15

Phe Met Met Val Ala Leu Val Asn Phe Thr Gly Lys Lys Asn Ser Gln
                20                  25                  30

Asn Tyr Pro Ala Gly Asn Ile Ser Ser Leu Pro Lys Asp Lys Thr Val
            35                  40                  45

Lys Thr Arg Leu Gly Xaa
        50
```

<210> SEQ ID NO 195
<211> LENGTH: 98
<212> TYPE: PRT
<213> ORGANISM: Homo sapiens
<220> FEATURE:
<221> NAME/KEY: SITE
<222> LOCATION: (98)
<223> OTHER INFORMATION: Xaa equals stop translation

<400> SEQUENCE: 195

```
Met Arg Asp Pro Leu Asn Arg Val Leu Ala Asn Leu Phe Leu Leu Ile
 1               5                  10                  15
```

```
Ser Ser Ile Leu Gly Ser Arg Thr Ala Gly Pro His Thr Gln Phe Val
            20                  25                  30

Gln Trp Phe Met Glu Glu Cys Val Asp Cys Leu Glu Gln Gly Gly Arg
            35                  40                  45

Gly Ser Val Leu Gln Phe Met Pro Phe Thr Thr Val Ser Glu Leu Val
            50                  55                  60

Lys Val Ser Ala Met Ser Ser Pro Lys Val Val Leu Ala Ile Thr Asp
 65                  70                  75                  80

Leu Ser Leu Pro Leu Gly Arg Gln Val Ala Ala Lys Ala Ile Ala Ala
                    85                  90                  95

Leu Xaa

<210> SEQ ID NO 196
<211> LENGTH: 25
<212> TYPE: PRT
<213> ORGANISM: Homo sapiens
<220> FEATURE:
<221> NAME/KEY: SITE
<222> LOCATION: (25)
<223> OTHER INFORMATION: Xaa equals stop translation

<400> SEQUENCE: 196

Met Gln Gly Ser Pro Leu Val Thr Ala Ile Tyr Lys Ile Phe Leu Leu
  1               5                  10                  15

Ser Leu Leu Val Arg Gly Ile Cys Xaa
            20                  25

<210> SEQ ID NO 197
<211> LENGTH: 126
<212> TYPE: PRT
<213> ORGANISM: Homo sapiens
<220> FEATURE:
<221> NAME/KEY: SITE
<222> LOCATION: (126)
<223> OTHER INFORMATION: Xaa equals stop translation

<400> SEQUENCE: 197

Met Ala Phe Asn Gly Ile Ile His Ala Leu Ala Ser Pro Leu Leu Ala
  1               5                  10                  15

Pro Pro Gln Pro Gln Ala Val Leu Ala Pro Glu Ala Pro Pro Val Ala
            20                  25                  30

Ala Gly Val Gly Ala Val Leu Ala Ala Gly Ala Leu Leu Gly Leu Val
            35                  40                  45

Ala Gly Ala Leu Tyr Leu Arg Ala Arg Gly Lys Pro Met Gly Phe Gly
            50                  55                  60

Phe Ser Ala Phe Gln Ala Glu Asp Ala Asp Asp Asp Phe Ser Pro
 65                  70                  75                  80

Trp Gln Glu Gly Thr Asn Pro Thr Leu Val Ser Val Pro Asn Pro Val
                    85                  90                  95

Phe Gly Ser Asp Thr Phe Cys Glu Pro Phe Asp Asp Ser Leu Leu Glu
                100                 105                 110

Glu Asp Phe Pro Asp Thr Gln Arg Ile Leu Thr Val Lys Xaa
                115                 120                 125

<210> SEQ ID NO 198
<211> LENGTH: 24
<212> TYPE: PRT
<213> ORGANISM: Homo sapiens
<220> FEATURE:
<221> NAME/KEY: SITE
<222> LOCATION: (24)
```

<223> OTHER INFORMATION: Xaa equals stop translation

<400> SEQUENCE: 198

Met Leu Val Glu Lys Ile Leu Leu Ile Glu Cys Leu Ser Ser Glu Ser
1               5                   10                  15

Gln Leu Ile Gly Phe Leu Leu Xaa
            20

<210> SEQ ID NO 199
<211> LENGTH: 81
<212> TYPE: PRT
<213> ORGANISM: Homo sapiens
<220> FEATURE:
<221> NAME/KEY: SITE
<222> LOCATION: (81)
<223> OTHER INFORMATION: Xaa equals stop translation

<400> SEQUENCE: 199

Met Glu Ala Lys Phe Leu Gly Asn Ala Pro Cys Gly His Tyr Thr Phe
1               5                   10                  15

Lys Phe Pro Gln Ala Met Arg Thr Glu Ser Asn Leu Gly Ala Lys Val
            20                  25                  30

Phe Phe Phe Lys Ala Leu Leu Leu Thr Gly Asp Phe Ser Gln Ala Gly
        35                  40                  45

Asn Lys Gly His His Val Trp Val Thr Lys Asp Glu Leu Gly Asp Tyr
    50                  55                  60

Leu Lys Pro Lys Tyr Leu Ala Gln Val Arg Arg Phe Val Ser Asp Leu
65                  70                  75                  80

Xaa

<210> SEQ ID NO 200
<211> LENGTH: 23
<212> TYPE: PRT
<213> ORGANISM: Homo sapiens
<220> FEATURE:
<221> NAME/KEY: SITE
<222> LOCATION: (23)
<223> OTHER INFORMATION: Xaa equals stop translation

<400> SEQUENCE: 200

Met Leu Thr Phe Leu Ile Phe Leu Phe Pro Glu Val Val Leu Gly Leu
1               5                   10                  15

Leu Arg Asp Tyr Ser Ser Xaa
            20

<210> SEQ ID NO 201
<211> LENGTH: 9
<212> TYPE: PRT
<213> ORGANISM: Homo sapiens
<220> FEATURE:
<221> NAME/KEY: SITE
<222> LOCATION: (9)
<223> OTHER INFORMATION: Xaa equals stop translation

<400> SEQUENCE: 201

Met His Val Tyr Leu Asn Tyr Lys Xaa
1               5

<210> SEQ ID NO 202
<211> LENGTH: 11
<212> TYPE: PRT
<213> ORGANISM: Homo sapiens
<220> FEATURE:
<221> NAME/KEY: SITE
<222> LOCATION: (11)
<223> OTHER INFORMATION: Xaa equals stop translation

<400> SEQUENCE: 202

Met Val Glu Ser Asn Leu Pro Gly Pro Ala Xaa
 1               5                  10

<210> SEQ ID NO 203
<211> LENGTH: 24
<212> TYPE: PRT
<213> ORGANISM: Homo sapiens

<400> SEQUENCE: 203

Thr Phe Lys Ser Leu Trp Lys His Trp Thr Leu Ala Gly Pro Gly Asn
 1               5                  10                  15

Ile Gly Lys Asn Trp Ile Gly Arg
            20

<210> SEQ ID NO 204
<211> LENGTH: 48
<212> TYPE: PRT
<213> ORGANISM: Homo sapiens

<400> SEQUENCE: 204

His Glu Gly Thr Trp Arg Trp Glu Ala Pro Thr Pro Leu Gln Ser Leu
 1               5                  10                  15

Gly Pro Thr Thr Pro Ser Leu Pro Ser Val Ala Asp Leu Cys Gln Asp
            20                  25                  30

Gly His Gly Gly Cys Ser Glu His Ala Asn Cys Ser Gln Val Gly Thr
        35                  40                  45

<210> SEQ ID NO 205
<211> LENGTH: 11
<212> TYPE: PRT
<213> ORGANISM: Homo sapiens

<400> SEQUENCE: 205

Leu Lys Val Pro Thr Cys Tyr Ser Ala Asn Thr
 1               5                  10

<210> SEQ ID NO 206
<211> LENGTH: 42
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring L-
      amino acids

<400> SEQUENCE: 206

Trp Gln Val Pro Ala Pro Val Ile Pro Gly Xaa Asp Pro Arg Val Arg
 1               5                  10                  15

Gly Ala Arg Lys Arg Thr Leu Leu Gly Val Ala Gly Gly Trp Arg Arg
            20                  25                  30

Phe Glu Arg Leu Trp Ala Gly Ser Leu Ser
        35                  40

<210> SEQ ID NO 207
<211> LENGTH: 41
<212> TYPE: PRT
<213> ORGANISM: Homo sapiens

<400> SEQUENCE: 207

```
Ser Arg Ser Leu Ala Leu Ala Ala Pro Ser Ser Asn Gly Ser Pro
 1               5                  10                  15

Trp Arg Leu Leu Gly Ala Leu Cys Leu Gln Arg Pro Pro Val Val Ser
                20                  25                  30

Lys Pro Leu Thr Pro Leu Gln Glu Glu
            35                  40
```

<210> SEQ ID NO 208
<211> LENGTH: 41
<212> TYPE: PRT
<213> ORGANISM: Homo sapiens

<400> SEQUENCE: 208

```
Met Glu Glu Ala Tyr Ser Lys Gly Phe Gln Glu Gly Leu Lys Lys
 1               5                  10                  15

Thr Lys Glu Leu Gln Asp Leu Lys Glu Glu Glu Glu Gln Lys Ser
                20                  25                  30

Glu Ser Pro Glu Glu Pro Glu Glu Val
            35                  40
```

<210> SEQ ID NO 209
<211> LENGTH: 37
<212> TYPE: PRT
<213> ORGANISM: Homo sapiens

<400> SEQUENCE: 209

```
Glu Glu Thr Glu Glu Glu Lys Gly Pro Arg Ser Ser Lys Leu Glu
 1               5                  10                  15

Glu Leu Val His Phe Leu Gln Val Met Tyr Pro Lys Leu Cys Gln His
                20                  25                  30

Trp Gln Val Ile Trp
            35
```

<210> SEQ ID NO 210
<211> LENGTH: 41
<212> TYPE: PRT
<213> ORGANISM: Homo sapiens

<400> SEQUENCE: 210

```
Ile Leu Tyr Leu Val Trp Ala Phe Ile Pro Glu Ser Trp Leu Asn Ser
 1               5                  10                  15

Leu Gly Leu Thr Tyr Trp Pro Gln Lys Tyr Trp Ala Val Ala Leu Pro
                20                  25                  30

Val Tyr Leu Leu Ile Ala Ile Val Ile
            35                  40
```

<210> SEQ ID NO 211
<211> LENGTH: 20
<212> TYPE: PRT
<213> ORGANISM: Homo sapiens

<400> SEQUENCE: 211

```
Tyr Gly Phe Val Leu Phe Leu Ser Ser Gln Phe Gly Phe Ile Leu Tyr
 1               5                  10                  15

Leu Val Trp Ala
            20
```

<210> SEQ ID NO 212
<211> LENGTH: 12
<212> TYPE: PRT

```
<213> ORGANISM: Homo sapiens

<400> SEQUENCE: 212

Thr Ser Pro Leu Asp Ser Ile His Thr Ile Thr Asp
 1               5                  10

<210> SEQ ID NO 213
<211> LENGTH: 20
<212> TYPE: PRT
<213> ORGANISM: Homo sapiens

<400> SEQUENCE: 213

Pro Leu Pro Glu Arg Ala Ile Tyr Gly Phe Val Leu Phe Leu Ser Ser
 1               5                  10                  15

Gln Phe Gly Phe
            20

<210> SEQ ID NO 214
<211> LENGTH: 51
<212> TYPE: PRT
<213> ORGANISM: Homo sapiens

<400> SEQUENCE: 214

Pro Thr Arg Gly Gly Ser Leu Cys Ala Cys Pro Gly Trp Gly Leu Pro
 1               5                  10                  15

Ser Arg Leu Gly Leu Ser Leu Arg Phe Ser Ser Pro Leu Arg Leu
                20                  25                  30

Pro Ser Arg Arg Leu Arg Glu Asn Ser Ala Leu Arg Leu Ser Lys Ala
            35                  40                  45

Pro Gly Lys
        50

<210> SEQ ID NO 215
<211> LENGTH: 10
<212> TYPE: PRT
<213> ORGANISM: Homo sapiens

<400> SEQUENCE: 215

Pro Pro Gly Cys Arg Asn Ser Ala Arg Glu
 1               5                  10

<210> SEQ ID NO 216
<211> LENGTH: 10
<212> TYPE: PRT
<213> ORGANISM: Homo sapiens

<400> SEQUENCE: 216

Pro Pro Gly Cys Arg Asn Ser Ala Arg Glu
 1               5                  10

<210> SEQ ID NO 217
<211> LENGTH: 44
<212> TYPE: PRT
<213> ORGANISM: Homo sapiens
<220> FEATURE:
<221> NAME/KEY: SITE
<222> LOCATION: (25)
<223> OTHER INFORMATION: Xaa equals any of the naturally occurring L-
      amino acids

<400> SEQUENCE: 217

Gly Ala Ser Ser Arg Pro Arg Leu Glu Leu Gly Arg Leu Met Gly Pro
 1               5                  10                  15
```

-continued

```
Lys Gly Val Ala Val Asp Arg Asn Xaa His Ile Ile Val Val Asp Asn
            20                  25                  30

Lys Ser Cys Cys Val Phe Thr Phe Gln Pro Asn Gly
        35                  40

<210> SEQ ID NO 218
<211> LENGTH: 44
<212> TYPE: PRT
<213> ORGANISM: Homo sapiens

<400> SEQUENCE: 218

Lys Leu Val Gly Arg Phe Gly Gly Arg Gly Ala Thr Asp Arg His Phe
  1               5                  10                  15

Ala Gly Pro His Phe Val Ala Val Asn Asn Lys Asn Glu Ile Val Val
            20                  25                  30

Thr Asp Phe His Asn His Ser Val Lys Val Tyr Ser
        35                  40

<210> SEQ ID NO 219
<211> LENGTH: 42
<212> TYPE: PRT
<213> ORGANISM: Homo sapiens

<400> SEQUENCE: 219

Ala Asp Gly Glu Phe Leu Phe Lys Phe Gly Ser His Gly Glu Gly Asn
  1               5                  10                  15

Gly Gln Phe Asn Ala Pro Thr Gly Val Ala Val Asp Ser Asn Gly Asn
            20                  25                  30

Ile Ile Val Ala Asp Trp Gly Asn Ser Arg
        35                  40

<210> SEQ ID NO 220
<211> LENGTH: 38
<212> TYPE: PRT
<213> ORGANISM: Homo sapiens
<220> FEATURE:
<221> NAME/KEY: SITE
<222> LOCATION: (2)
<223> OTHER INFORMATION: Xaa equals any of the naturally occurring L-
      amino acids
<221> NAME/KEY: SITE
<222> LOCATION: (6)
<223> OTHER INFORMATION: Xaa equals any of the naturally occurring L-
      amino acids

<400> SEQUENCE: 220

Ile Xaa Gly Ile Arg Xaa Leu Trp Leu Leu Pro Val Leu Tyr Gln His
  1               5                  10                  15

Ile Cys Arg Thr Thr Val Trp Ser Thr Gly Pro Gly Thr Asp Leu Gly
            20                  25                  30

Trp Pro Cys Gly Gly Gly
        35

<210> SEQ ID NO 221
<211> LENGTH: 16
<212> TYPE: PRT
<213> ORGANISM: Homo sapiens

<400> SEQUENCE: 221

Met Glu Trp Glu Gly Gly Ala Ile Arg His Pro Ser Thr Glu Leu Gly
  1               5                  10                  15

<210> SEQ ID NO 222
```

```
<211> LENGTH: 36
<212> TYPE: PRT
<213> ORGANISM: Homo sapiens

<400> SEQUENCE: 222

Arg Pro Thr Arg Pro Pro Asp Gly Cys His Pro Ser Cys Cys Arg Met
 1               5                  10                  15

Glu Ala Ala Met Glu Trp Glu Gly Gly Ala Ile Arg His Pro Ser Thr
            20                  25                  30

Glu Leu Gly Ile
        35

<210> SEQ ID NO 223
<211> LENGTH: 35
<212> TYPE: PRT
<213> ORGANISM: Homo sapiens

<400> SEQUENCE: 223

Glu Cys Gln Glu Tyr Glu Ile Leu Glu His Cys Trp Trp Glu Cys Lys
 1               5                  10                  15

Leu Val Gln Pro Phe Trp Lys Ser Ser Cys Arg Ile Pro Ala Ala Arg
            20                  25                  30

Gly Ile His
        35

<210> SEQ ID NO 224
<211> LENGTH: 15
<212> TYPE: PRT
<213> ORGANISM: Homo sapiens

<400> SEQUENCE: 224

His Cys Trp Trp Glu Cys Lys Leu Val Gln Pro Phe Trp Lys Ser
 1               5                  10                  15

<210> SEQ ID NO 225
<211> LENGTH: 6
<212> TYPE: PRT
<213> ORGANISM: Homo sapiens

<400> SEQUENCE: 225

Phe Thr Phe Pro Pro Thr
 1               5

<210> SEQ ID NO 226
<211> LENGTH: 127
<212> TYPE: PRT
<213> ORGANISM: Homo sapiens
<220> FEATURE:
<221> NAME/KEY: SITE
<222> LOCATION: (90)
<223> OTHER INFORMATION: Xaa equals any of the naturally occurring L-
      amino acids
<221> NAME/KEY: SITE
<222> LOCATION: (110)
<223> OTHER INFORMATION: Xaa equals any of the naturally occurring L-
      amino acids
<221> NAME/KEY: SITE
<222> LOCATION: (112)
<223> OTHER INFORMATION: Xaa equals any of the naturally occurring L-
      amino acids
<221> NAME/KEY: SITE
<222> LOCATION: (117)
<223> OTHER INFORMATION: Xaa equals any of the naturally occurring L-
      amino acids
<221> NAME/KEY: SITE
<222> LOCATION: (118)
<223> OTHER INFORMATION: Xaa equals any of the naturally occurring L-
``` amino acids

<400> SEQUENCE: 226

His His His Leu Arg Val Gly Ser Pro Trp Ser His Pro Glu Thr Gly
1               5                   10                  15

Thr Ala Val His Gly Ala His Pro Gln Gly Glu Ala Ala Ser Asp Arg
            20                  25                  30

His Arg Gly Cys Phe Tyr Arg Arg Gln Leu Met His Gln Leu Pro
        35                  40                  45

Ile Tyr Asp Gln Asp Pro Ser Arg Cys Arg Gly Leu Leu Glu Asn Glu
    50                  55                  60

Leu Lys Leu Met Glu Glu Phe Val Lys Gln Tyr Lys Ser Glu Ala Leu
65                  70                  75                  80

Gly Val Gly Glu Val Ala Leu Pro Gly Xaa Gly Trp Leu Ala Lys Glu
                85                  90                  95

Glu Gly Lys Gln Gln Glu Lys Pro Glu Gly Ala Glu Thr Xaa Ala Xaa
            100                 105                 110

Thr Thr Asn Gly Xaa Xaa Ser Asp Pro Ser Lys Glu Glu Ala Cys
        115                 120                 125

<210> SEQ ID NO 227
<211> LENGTH: 7
<212> TYPE: PRT
<213> ORGANISM: Homo sapiens

<400> SEQUENCE: 227

Thr Tyr Glu Trp Ala Pro Pro
1               5

<210> SEQ ID NO 228
<211> LENGTH: 7
<212> TYPE: PRT
<213> ORGANISM: Homo sapiens

<400> SEQUENCE: 228

Pro Lys Glu Lys Gln Pro Val
1               5

<210> SEQ ID NO 229
<211> LENGTH: 34
<212> TYPE: PRT
<213> ORGANISM: Homo sapiens

<400> SEQUENCE: 229

Pro Arg Pro Ala Asn Leu Ala Ile Gln Pro Pro Leu Ser Pro Leu Arg
1               5                   10                  15

Ala Leu Ala Pro Leu Pro Glu Lys Pro Gly Ala Val Pro Pro Pro Gln
            20                  25                  30

Lys Arg

<210> SEQ ID NO 230
<211> LENGTH: 163
<212> TYPE: PRT
<213> ORGANISM: Homo sapiens

<400> SEQUENCE: 230

Ala His Ala Val Trp Arg Pro Gly Val Leu Pro Gly Leu Val Glu Leu
1               5                   10                  15

Arg Val Cys His Leu Leu Leu Ala Glu Leu Glu His Pro Cys Ala Gln
            20                  25                  30

Val Val His Gln Val Gly Gly Val Cys Val Cys Val Met Trp Asn Met
         35                  40                  45

Ala Val Asn Leu Asn Arg Phe Pro Cys Pro Leu Leu Cys Arg His Phe
 50                  55                  60

Tyr Lys Pro Met Leu Arg Arg Gly Ser Ser Lys Trp Met Ala Arg Thr
 65                  70                  75                  80

Gly Val Phe Leu Ala Ser Ala Phe Phe His Glu Tyr Leu Val Ser Val
                 85                  90                  95

Pro Leu Arg Met Phe Arg Leu Trp Ala Phe Thr Gly Met Met Ala Gln
                100                 105                 110

Ile Pro Leu Ala Trp Phe Val Gly Arg Phe Gln Gly Asn Tyr Gly
                115                 120                 125

Asn Ala Ala Val Trp Leu Ser Leu Ile Ile Gly Gln Pro Ile Ala Val
        130                 135                 140

Leu Met Tyr Val His Asp Tyr Tyr Val Leu Asn Tyr Glu Ala Pro Ala
145                 150                 155                 160

Ala Glu Ala

<210> SEQ ID NO 231
<211> LENGTH: 8
<212> TYPE: PRT
<213> ORGANISM: Homo sapiens

<400> SEQUENCE: 231

Tyr Phe Leu Phe Ala Pro Thr Leu
 1               5

<210> SEQ ID NO 232
<211> LENGTH: 16
<212> TYPE: PRT
<213> ORGANISM: Homo sapiens

<400> SEQUENCE: 232

Asn Leu Asn Arg Phe Pro Cys Pro Leu Leu Cys Arg His Phe Tyr Lys
 1               5                  10                  15

<210> SEQ ID NO 233
<211> LENGTH: 16
<212> TYPE: PRT
<213> ORGANISM: Homo sapiens

<400> SEQUENCE: 233

Gln Gly Asn Tyr Gly Asn Ala Ala Val Trp Leu Ser Leu Ile Ile Gly
 1               5                  10                  15

<210> SEQ ID NO 234
<211> LENGTH: 17
<212> TYPE: PRT
<213> ORGANISM: Homo sapiens

<400> SEQUENCE: 234

Leu Tyr Tyr Phe Leu Phe Ala Pro Thr Leu Cys Tyr Glu Leu Asn Phe
 1               5                  10                  15
Pro

<210> SEQ ID NO 235
<211> LENGTH: 26
<212> TYPE: PRT
<213> ORGANISM: Homo sapiens -continued

```
<400> SEQUENCE: 235

Glu Met Leu Phe Phe Thr Gln Leu Gln Val Gly Leu Ile Gln Gln Trp
 1               5                  10                  15

Met Val Pro Thr Ile Gln Asn Ser Met Lys
             20                  25

<210> SEQ ID NO 236
<211> LENGTH: 18
<212> TYPE: PRT
<213> ORGANISM: Homo sapiens

<400> SEQUENCE: 236

Val Thr Tyr Phe Trp Gln Asn Trp Asn Ile Pro Val His Lys Trp Cys
 1               5                  10                  15

Ile Arg

<210> SEQ ID NO 237
<211> LENGTH: 60
<212> TYPE: PRT
<213> ORGANISM: Homo sapiens

<400> SEQUENCE: 237

Pro Phe Lys Asp Met Asp Tyr Ser Arg Ile Ile Glu Arg Leu Leu Lys
 1               5                  10                  15

Leu Ala Val Pro Asn His Leu Ile Trp Leu Ile Phe Tyr Trp Leu
             20                  25                  30

Phe His Ser Cys Leu Asn Ala Val Ala Glu Leu Met Gln Phe Gly Asp
         35                  40                  45

Arg Glu Phe Tyr Arg Asp Trp Trp Asn Ser Glu Ser
     50                  55                  60

<210> SEQ ID NO 238
<211> LENGTH: 48
<212> TYPE: PRT
<213> ORGANISM: Homo sapiens

<400> SEQUENCE: 238

Arg His Phe Tyr Lys Pro Met Leu Arg Arg Gly Ser Ser Lys Trp Met
 1               5                  10                  15

Ala Arg Thr Gly Val Phe Leu Ala Ser Ala Phe Phe His Glu Tyr Leu
             20                  25                  30

Val Ser Val Pro Leu Arg Met Phe Arg Leu Trp Ala Phe Thr Gly Met
         35                  40                  45

<210> SEQ ID NO 239
<211> LENGTH: 47
<212> TYPE: PRT
<213> ORGANISM: Homo sapiens

<400> SEQUENCE: 239

Met Ala Gln Ile Pro Leu Ala Trp Phe Val Gly Arg Phe Phe Gln Gly
 1               5                  10                  15

Asn Tyr Gly Asn Ala Ala Val Trp Leu Ser Leu Ile Ile Gly Gln Pro
             20                  25                  30

Ile Ala Val Leu Met Tyr Val His Asp Tyr Tyr Val Leu Asn Tyr
         35                  40                  45

<210> SEQ ID NO 240
<211> LENGTH: 23
<212> TYPE: PRT
```

-continued

```
<213> ORGANISM: Homo sapiens
<220> FEATURE:
<221> NAME/KEY: SITE
<222> LOCATION: (3)
<223> OTHER INFORMATION: Xaa equals any of the naturally occurring L-
      amino acids
<221> NAME/KEY: SITE
<222> LOCATION: (16)
<223> OTHER INFORMATION: Xaa equals any of the naturally occurring L-
      amino acids

<400> SEQUENCE: 240

Ser Gly Xaa Trp Gln Gly Leu Asp Glu Val Val Arg Leu Leu Asn Xaa
  1               5                  10                  15

Ser Asp Phe Ala Phe Thr Asp
            20

<210> SEQ ID NO 241
<211> LENGTH: 61
<212> TYPE: PRT
<213> ORGANISM: Homo sapiens
<220> FEATURE:
<221> NAME/KEY: SITE
<222> LOCATION: (39)
<223> OTHER INFORMATION: Xaa equals any of the naturally occurring L-
      amino acids
<221> NAME/KEY: SITE
<222> LOCATION: (58)
<223> OTHER INFORMATION: Xaa equals any of the naturally occurring L-
      amino acids

<400> SEQUENCE: 241

Gly Ser Leu Ala Lys Arg Ser Asn Phe Arg Ala Ile Ser Lys Lys Leu
  1               5                  10                  15

Asn Leu Ile Pro Arg Val Asp Gly Glu Tyr Asp Leu Lys Val Pro Arg
             20                  25                  30

Asp Met Ala Tyr Val Phe Xaa Gly Ala Tyr Val Pro Leu Ser Cys Arg
         35                  40                  45

Ile Ile Glu Gln Val Leu Glu Arg Arg Xaa Ala Gly Pro
     50                  55                  60

<210> SEQ ID NO 242
<211> LENGTH: 194
<212> TYPE: PRT
<213> ORGANISM: Homo sapiens
<220> FEATURE:
<221> NAME/KEY: SITE
<222> LOCATION: (73)
<223> OTHER INFORMATION: Xaa equals any of the naturally occurring L-
      amino acids

<400> SEQUENCE: 242

Glu Val Ile Asn Thr Leu Ala Asp His Arg His Arg Gly Thr Asp Phe
  1               5                  10                  15

Gly Gly Ser Pro Trp Leu Leu Ile Ile Thr Val Phe Leu Arg Ser Tyr
             20                  25                  30

Lys Phe Ala Ile Ser Leu Cys Thr Ser Tyr Leu Cys Val Ser Phe Leu
         35                  40                  45

Lys Thr Ile Phe Pro Ser Gln Asn Gly His Asp Gly Ser Thr Asp Val
     50                  55                  60

Gln Gln Arg Ala Arg Arg Ser Asn Xaa Arg Arg Gln Glu Gly Ile Lys
 65                  70                  75                  80

Ile Val Leu Glu Asp Ile Phe Thr Leu Trp Arg Gln Val Glu Thr Lys
             85                  90                  95
```

-continued

```
Val Arg Ala Lys Ile Arg Lys Met Lys Val Thr Thr Lys Val Asn Arg
            100                 105                 110

His Asp Lys Ile Asn Gly Lys Arg Lys Thr Ala Lys Glu His Leu Arg
            115                 120                 125

Lys Leu Ser Met Lys Glu Arg Glu His Gly Lys Glu Arg Gln Val
            130                 135                 140

Ser Glu Ala Glu Glu Asn Gly Lys Leu Asp Met Lys Glu Ile His Thr
145                 150                 155                 160

Tyr Met Glu Met Phe Gln Arg Ala Gln Val Cys Gly Gly Gln Arg
                165                 170                 175

Thr Thr Thr Asp Ala Lys Ser Pro Leu Leu Gln Glu Ser Leu Phe Ala
            180                 185                 190

Thr Gly

<210> SEQ ID NO 243
<211> LENGTH: 143
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring L-
      amino acids
<221> NAME/KEY: SITE
<222> LOCATION: (28)
<223> OTHER INFORMATION: Xaa equals any of the naturally occurring L-
      amino acids
<221> NAME/KEY: SITE
<222> LOCATION: (55)
<223> OTHER INFORMATION: Xaa equals any of the naturally occurring L-
      amino acids
<221> NAME/KEY: SITE
<222> LOCATION: (84)
<223> OTHER INFORMATION: Xaa equals any of the naturally occurring L-
      amino acids

<400> SEQUENCE: 243

Ile Cys Val Lys Thr Phe Pro Pro Leu Ala Leu Gln Val Arg Met Ala
 1               5                  10                  15

Ala Xaa Glu His Arg His Ser Ser Gly Leu Pro Xaa Trp Pro Tyr Leu
            20                  25                  30

Thr Ala Glu Thr Leu Lys Asn Arg Met Gly His Gln Pro Pro Pro Pro
            35                  40                  45

Thr Gln Gln His Ser Ile Xaa Asp Asn Ser Leu Ser Leu Lys Thr Pro
        50                  55                  60

Ala Glu Cys Leu Leu Tyr Pro Leu Pro Pro Ser Ala Asp Asn Leu
65                  70                  75                  80

Lys Thr Pro Xaa Glu Cys Leu Leu Thr Pro Leu Pro Pro Ser Ala Pro
                85                  90                  95

Pro Ser Ala Asp Asp Asn Leu Lys Thr Pro Glu Cys Val Cys Ser
            100                 105                 110

Leu Pro Phe His Pro Gln Leu His Pro Gln Arg Met Ile Ile Ser Arg
            115                 120                 125

His Leu Pro Ser Val Ser Ala His Ser Pro Ser Thr Leu Ser Gly
            130                 135                 140

<210> SEQ ID NO 244
<211> LENGTH: 20
<212> TYPE: PRT
<213> ORGANISM: Homo sapiens
<220> FEATURE:
<221> NAME/KEY: SITE
```

```
<222> LOCATION: (7)
<223> OTHER INFORMATION: Xaa equals any of the naturally occurring L-
      amino acids

<400> SEQUENCE: 244

Arg Ala Arg Arg Ser Asn Xaa Arg Arg Gln Glu Gly Ile Lys Ile Val
1               5                   10                  15

Leu Glu Asp Ile
            20

<210> SEQ ID NO 245
<211> LENGTH: 16
<212> TYPE: PRT
<213> ORGANISM: Homo sapiens

<400> SEQUENCE: 245

Leu Ser Leu Lys Thr Pro Ala Glu Cys Leu Leu Tyr Pro Leu Pro Pro
1               5                   10                  15

<210> SEQ ID NO 246
<211> LENGTH: 27
<212> TYPE: PRT
<213> ORGANISM: Homo sapiens

<400> SEQUENCE: 246

Phe Leu Leu Ile Glu Ser Tyr Gln Lys Leu Arg Asn Lys Thr Asn Leu
1               5                   10                  15

Ser Leu His Val Phe Leu Phe His Thr Glu Val
            20                  25

<210> SEQ ID NO 247
<211> LENGTH: 159
<212> TYPE: PRT
<213> ORGANISM: Homo sapiens
<220> FEATURE:
<221> NAME/KEY: SITE
<222> LOCATION: (63)
<223> OTHER INFORMATION: Xaa equals any of the naturally occurring L-
      amino acids
<221> NAME/KEY: SITE
<222> LOCATION: (137)
<223> OTHER INFORMATION: Xaa equals any of the naturally occurring L-
      amino acids

<400> SEQUENCE: 247

Tyr Ala Leu Arg Thr Gly Ala Phe Glu Pro Ala Glu Ala Ser Val Asn
1               5                   10                  15

Pro Gln Asp Leu Gln Gly Ser Leu Gln Glu Leu Lys Glu Arg Ala Leu
            20                  25                  30

Ser Arg Tyr Asn Leu Val Arg Gly Gln Gly Pro Glu Arg Leu Val Ser
        35                  40                  45

Gly Ser Asp Asp Phe Thr Leu Phe Leu Trp Ser Pro Ala Glu Xaa Lys
    50                  55                  60

Lys Pro Leu Thr Arg Met Thr Gly His Gln Ala Leu Ile Asn Gln Val
65                  70                  75                  80

Leu Phe Ser Pro Asp Ser Arg Ile Val Ala Ser Ala Ser Phe Asp Lys
                85                  90                  95

Ser Ile Lys Leu Trp Asp Gly Arg Thr Gly Lys Tyr Leu Ala Ser Leu
            100                 105                 110

Arg Gly His Val Ala Ala Val Tyr Gln Ile Ala Trp Ser Ala Asp Ser
        115                 120                 125

Arg Leu Leu Val Ser Gly Ser Ser Xaa Gln His Thr Glu Gly Val Gly
```

```
            130                 135                 140
Cys Glu Gly Pro Glu Ala Gly His Gly Pro Ala Arg Pro Arg Gly
145                 150                 155

<210> SEQ ID NO 248
<211> LENGTH: 21
<212> TYPE: PRT
<213> ORGANISM: Homo sapiens

<400> SEQUENCE: 248

Leu Lys Glu Arg Ala Leu Ser Arg Tyr Asn Leu Val Arg Gly Gln Gly
  1               5                  10                  15

Pro Glu Arg Leu Val
             20

<210> SEQ ID NO 249
<211> LENGTH: 137
<212> TYPE: PRT
<213> ORGANISM: Homo sapiens

<400> SEQUENCE: 249

Met Pro Thr Pro Ser Met Arg Ala Asn Arg Met Pro Pro Ile Ile Ala
  1               5                  10                  15

Glu Pro Thr Met Ala Ser Gly Pro Leu Arg Ala Ala Ser Thr Ala Pro
             20                  25                  30

Val Asn Ala Pro Leu Val Ile Glu Phe Gln Gly Ser Ser Leu Pro Arg
         35                  40                  45

Ser Arg Thr Arg Pro Gln Ser Met Val Glu Asn Arg Pro Pro His Thr
     50                  55                  60

Ala Lys Leu Pro Pro Ile Trp Gly Ala Arg Ile Leu Thr Ala Leu Ala
 65                  70                  75                  80

Leu Pro Leu Asn Arg Cys Arg Ile Pro Thr Gly Ala Leu Arg Lys Pro
                 85                  90                  95

Leu Met Ala Trp Lys Thr Pro Pro Met Thr Pro Ile Val Lys Ala
             100                 105                 110

Pro Pro Gln Ser Ser Thr Ile Arg His Gly Gln Gly Ser Arg Ala Tyr
             115                 120                 125

Ser Gly Arg Val Gly Gly Arg Val Gly
        130                 135

<210> SEQ ID NO 250
<211> LENGTH: 25
<212> TYPE: PRT
<213> ORGANISM: Homo sapiens

<400> SEQUENCE: 250

Gly Ala Arg Ile Leu Thr Ala Leu Ala Leu Pro Leu Asn Arg Cys Arg
  1               5                  10                  15

Ile Pro Thr Gly Ala Leu Arg Lys Pro
             20                  25

<210> SEQ ID NO 251
<211> LENGTH: 38
<212> TYPE: PRT
<213> ORGANISM: Homo sapiens

<400> SEQUENCE: 251

Pro Thr Arg Pro Pro Thr Arg Pro Glu Tyr Ala Arg Glu Pro Cys Pro
  1               5                  10                  15
```

```
Trp Arg Ile Val Asp Asp Cys Gly Gly Ala Phe Thr Met Gly Val Ile
                20                  25                  30

Gly Gly Gly Val Phe Gln
        35
```

<210> SEQ ID NO 252
<211> LENGTH: 39
<212> TYPE: PRT
<213> ORGANISM: Homo sapiens

<400> SEQUENCE: 252

```
Ala Ile Lys Gly Phe Arg Asn Ala Pro Val Gly Ile Arg His Arg Leu
 1               5                  10                  15

Arg Gly Ser Ala Asn Ala Val Arg Ile Arg Ala Pro Gln Ile Gly Gly
                20                  25                  30

Ser Phe Ala Val Trp Gly Gly
        35
```

<210> SEQ ID NO 253
<211> LENGTH: 40
<212> TYPE: PRT
<213> ORGANISM: Homo sapiens

<400> SEQUENCE: 253

```
Leu Phe Ser Thr Ile Asp Cys Gly Leu Val Arg Leu Arg Gly Lys Glu
 1               5                  10                  15

Asp Pro Trp Asn Ser Ile Thr Ser Gly Ala Leu Thr Gly Ala Val Leu
                20                  25                  30

Ala Ala Arg Ser Gly Pro Leu Ala
        35                  40
```

<210> SEQ ID NO 254
<211> LENGTH: 38
<212> TYPE: PRT
<213> ORGANISM: Homo sapiens

<400> SEQUENCE: 254

```
Ile Arg His Glu Arg Lys Ser Ala Arg Ala Cys Cys Pro Leu Thr Gly
 1               5                  10                  15

Ala Gln Arg Arg Gly Gln Ala Leu Pro Thr Pro Arg Ala Gly Pro Gly
                20                  25                  30

His Ser Pro Ala Pro Val
        35
```

<210> SEQ ID NO 255
<211> LENGTH: 38
<212> TYPE: PRT
<213> ORGANISM: Homo sapiens

<400> SEQUENCE: 255

```
Ala Pro Ser Ala Pro Gln Glu Asp Gly Gly Ser Pro Pro Ala Pro Gln
 1               5                  10                  15

Gly Gln Pro Asp Pro Gly Pro Gly Ala Gly Gln Pro Ala Gln Leu Gly
                20                  25                  30

Pro Leu Leu Ala Phe Leu
        35
```

<210> SEQ ID NO 256
<211> LENGTH: 44
<212> TYPE: PRT
<213> ORGANISM: Homo sapiens -continued

```
<400> SEQUENCE: 256

Pro Leu Leu His Gln Asp Cys Lys Glu Ser Pro His Leu Gly Ser Ser
 1               5                  10                  15

Gly Ser Pro Val Gln Ala Leu Asp Leu Ser Ser Ile Gln Thr Arg Thr
            20                  25                  30

Ala Val Ser Cys Val Asp Gly Val Arg Leu Trp Ala
        35                  40

<210> SEQ ID NO 257
<211> LENGTH: 15
<212> TYPE: PRT
<213> ORGANISM: Homo sapiens

<400> SEQUENCE: 257

His Arg Leu Gln Val Phe Ser Phe Pro Ile Leu Gly Ser His Asn
 1               5                  10                  15

<210> SEQ ID NO 258
<211> LENGTH: 52
<212> TYPE: PRT
<213> ORGANISM: Homo sapiens

<400> SEQUENCE: 258

Gly Lys Val Glu Ile Glu Val Phe Ile Phe Pro Tyr Glu Tyr Pro Val
 1               5                  10                  15

Val Pro Thr Pro Leu Ile Lys Asn Thr Ile Leu Tyr Pro Leu Ser Leu
            20                  25                  30

Phe Cys Thr Phe Ile Lys Asn Gln Phe Ser Ile Tyr Leu Trp Ile Lys
        35                  40                  45

Phe Phe Ile Phe
    50

<210> SEQ ID NO 259
<211> LENGTH: 14
<212> TYPE: PRT
<213> ORGANISM: Homo sapiens

<400> SEQUENCE: 259

Arg Ala Thr Thr His Val Ser Arg Glu Phe Phe Gly His Thr
 1               5                  10

<210> SEQ ID NO 260
<211> LENGTH: 41
<212> TYPE: PRT
<213> ORGANISM: Homo sapiens

<400> SEQUENCE: 260

Thr Leu Phe Ser Met Phe Ser Gly Pro Leu Gly Arg Gln Thr Gln Leu
 1               5                  10                  15

Asp Phe Arg Ala Asp Ile Gly Glu Glu Asn Met Ala Leu Ser Val Leu
            20                  25                  30

Ser Pro Asp Lys Cys Tyr Leu Tyr Thr
        35                  40

<210> SEQ ID NO 261
<211> LENGTH: 46
<212> TYPE: PRT
<213> ORGANISM: Homo sapiens

<400> SEQUENCE: 261
```

His Pro Asn Leu Lys Arg Lys Cys Ile Ser Leu Gly Phe Lys His Cys
1               5                   10                  15

Asn Arg Tyr Lys Ala Lys Ile Lys Thr Cys Cys Lys Val Gln Lys Lys
            20                  25                  30

Lys Lys Lys Lys Lys Lys Lys Lys Lys Lys Gly Arg
        35                  40                  45

<210> SEQ ID NO 262
<211> LENGTH: 13
<212> TYPE: PRT
<213> ORGANISM: Homo sapiens

<400> SEQUENCE: 262

His Ser Gly Val Gln Thr Ile Ala Phe Gly Leu Glu Cys
1               5                   10

<210> SEQ ID NO 263
<211> LENGTH: 25
<212> TYPE: PRT
<213> ORGANISM: Homo sapiens

<400> SEQUENCE: 263

Lys Val Gln Asp Arg Asp Gly Lys Glu Arg Lys Gln Glu Glu Val
1               5                   10                  15

Lys Leu Gly Arg Trp Cys Gln Trp His
            20                  25

<210> SEQ ID NO 264
<211> LENGTH: 10
<212> TYPE: PRT
<213> ORGANISM: Homo sapiens

<400> SEQUENCE: 264

Ala Cys Gly Ala Pro Glu Glu Ala Gly Gly
1               5                   10

<210> SEQ ID NO 265
<211> LENGTH: 35
<212> TYPE: PRT
<213> ORGANISM: Homo sapiens

<400> SEQUENCE: 265

Leu Phe Ser Ser Phe Leu Gly Asp Thr Thr Val His Lys Val Leu Ser
1               5                   10                  15

Arg Ala Thr Leu His Leu His Pro Ala Pro Tyr Leu Thr Gly Val Asp
            20                  25                  30

Ser Tyr Ser
        35

<210> SEQ ID NO 266
<211> LENGTH: 39
<212> TYPE: PRT
<213> ORGANISM: Homo sapiens

<400> SEQUENCE: 266

Asp Phe Ser Ser Tyr Ser His Pro Ser Leu Gly Thr Gln Leu Ser Ile
1               5                   10                  15

Arg Cys Tyr Pro Glu Pro His Cys Ile Cys Thr Gln His His Thr Ser
            20                  25                  30

Gln Glu Ser Thr Pro Thr Leu
        35

```
<210> SEQ ID NO 267
<211> LENGTH: 38
<212> TYPE: PRT
<213> ORGANISM: Homo sapiens
<220> FEATURE:
<221> NAME/KEY: SITE
<222> LOCATION: (7)
<223> OTHER INFORMATION: Xaa equals any of the naturally occurring L-
      amino acids

<400> SEQUENCE: 267

Ala Pro Gln Lys Phe Pro Xaa Gly Phe Phe Phe Phe Phe Leu Phe Ser
 1               5                  10                  15

Arg Arg Lys Lys Gln Cys Ser Lys Val Val Gln Asn Thr Gly Ala Gly
            20                  25                  30

Ala Ile Gln Thr Gln Val
        35

<210> SEQ ID NO 268
<211> LENGTH: 38
<212> TYPE: PRT
<213> ORGANISM: Homo sapiens

<400> SEQUENCE: 268

Gln Leu Leu Thr Ser Pro Thr Phe Ser Thr Val Leu Ser Asn Tyr Thr
 1               5                  10                  15

Cys Gln Ala Pro Ser Gln Trp Thr Asp Trp Gln Ala Leu Leu Pro Thr
            20                  25                  30

Gly Ile Gln Thr Glu His
        35

<210> SEQ ID NO 269
<211> LENGTH: 36
<212> TYPE: PRT
<213> ORGANISM: Homo sapiens

<400> SEQUENCE: 269

His Gln Gly Trp Asp Lys Gln Lys Gln Cys Lys Arg Lys Cys Glu His
 1               5                  10                  15

Glu His Ala Pro Leu His His Asn Leu Trp Lys Gln Ser Gly Lys Thr
            20                  25                  30

Arg Leu Gly Asp
        35

<210> SEQ ID NO 270
<211> LENGTH: 27
<212> TYPE: PRT
<213> ORGANISM: Homo sapiens

<400> SEQUENCE: 270

Lys His Val Ile Phe Phe Met Phe Ile Ser Asn Leu Phe Leu Ile Leu
 1               5                  10                  15

Cys Phe Leu Phe Arg Pro Thr Lys Thr Thr Val
            20                  25

<210> SEQ ID NO 271
<211> LENGTH: 11
<212> TYPE: PRT
<213> ORGANISM: Homo sapiens

<400> SEQUENCE: 271

Asp Lys Leu Leu Ser Phe His Leu Val Ser Ile
```

<210> SEQ ID NO 272
<211> LENGTH: 14
<212> TYPE: PRT
<213> ORGANISM: Homo sapiens

<400> SEQUENCE: 272

Lys Trp Lys Gly Asp Leu His Cys Ile Leu Gly Leu Leu Ala
 1               5                  10

<210> SEQ ID NO 273
<211> LENGTH: 10
<212> TYPE: PRT
<213> ORGANISM: Homo sapiens

<400> SEQUENCE: 273

Leu Ala Pro Ser Ser Val Gly Ser Ala Ser
 1               5                  10

<210> SEQ ID NO 274
<211> LENGTH: 39
<212> TYPE: PRT
<213> ORGANISM: Homo sapiens

<400> SEQUENCE: 274

Arg Glu Ala Thr Lys Asn Pro Thr His His Arg Ser Thr Pro His Ala
 1               5                  10                  15

Ala Gly Ser Gln Leu Asn Val Pro Pro Gln Pro Cys Phe Pro Leu His
            20                  25                  30

His Gln Ile Lys Thr Ser Pro
        35

<210> SEQ ID NO 275
<211> LENGTH: 38
<212> TYPE: PRT
<213> ORGANISM: Homo sapiens

<400> SEQUENCE: 275

Ser Gln Thr Ile Phe Lys Gln Ser Arg His Arg Cys Asp Ser Arg Gln
 1               5                  10                  15

Glu Ser Thr Trp Leu Cys Ser His Glu Lys Asp Ala Thr Lys Met Met
            20                  25                  30

His Leu Asn Asp Asn Ser
        35

<210> SEQ ID NO 276
<211> LENGTH: 48
<212> TYPE: PRT
<213> ORGANISM: Homo sapiens

<400> SEQUENCE: 276

Val Thr Gly Ser Pro Ile Leu Gln Leu Ala Leu Leu Gln Leu Pro Ala
 1               5                  10                  15

Trp Pro Leu Arg Gly Arg Leu Arg Gly Lys Arg His Cys Thr Gly Leu
            20                  25                  30

Asn Leu Ala Ile Ser Gly Asn Gly Gly Glu Trp Gly Gly Arg Gly Glu
        35                  40                  45

<210> SEQ ID NO 277
<211> LENGTH: 13
<212> TYPE: PRT

<213> ORGANISM: Homo sapiens

<400> SEQUENCE: 277

Ile Arg His Glu Asp Glu Val Lys Leu Leu Glu Trp Ser
1               5                   10

<210> SEQ ID NO 278
<211> LENGTH: 35
<212> TYPE: PRT
<213> ORGANISM: Homo sapiens

<400> SEQUENCE: 278

Ser Leu His Ser Ser Ala Val Ala Ala Thr Tyr Lys Tyr Val Asn Met
1               5                   10                  15

Gln Asp Pro Glu Met Asp Met Lys Ser Val Thr Asp Arg Ala Ala Arg
            20                  25                  30

Thr Leu Leu
        35

<210> SEQ ID NO 279
<211> LENGTH: 60
<212> TYPE: PRT
<213> ORGANISM: Homo sapiens

<400> SEQUENCE: 279

Trp Thr Glu Leu Phe Arg Gly Leu Gly Met Thr Leu Ser Tyr Leu Phe
1               5                   10                  15

Arg Glu Pro Ala Thr Ile Asn Tyr Pro Phe Lys Gly Pro Leu Ser
            20                  25                  30

Pro Arg Phe Arg Gly Glu His Ala Leu Arg Arg Tyr Pro Ser Gly Glu
        35                  40                  45

Glu Arg Cys Ile Ala Cys Lys Leu Cys Glu Ala Ile
    50                  55                  60

<210> SEQ ID NO 280
<211> LENGTH: 57
<212> TYPE: PRT
<213> ORGANISM: Homo sapiens

<400> SEQUENCE: 280

Cys Pro Ala Gln Ala Ile Ile Glu Ala Glu Pro Arg Ala Asp Gly Ser
1               5                   10                  15

Arg Arg Thr Thr Arg Tyr Asp Ile Asp Met Thr Lys Cys Ile Tyr Cys
            20                  25                  30

Gly Phe Cys Gln Glu Ala Cys Pro Val Asp Ala Ile Val Glu Gly Pro
        35                  40                  45

Asn Phe Glu Phe Ser Thr Glu Thr His
    50                  55

<210> SEQ ID NO 281
<211> LENGTH: 19
<212> TYPE: PRT
<213> ORGANISM: Homo sapiens

<400> SEQUENCE: 281

Gly Asp Lys Trp Glu Ala Glu Ile Ala Ala Asn Ile Gln Ala Asp Tyr
1               5                   10                  15

Leu Tyr Arg

<210> SEQ ID NO 282

```
<211> LENGTH: 48
<212> TYPE: PRT
<213> ORGANISM: Homo sapiens

<400> SEQUENCE: 282

Ser Ala Asp Pro Ala Thr Gln Pro Gly Asp Ser Arg Ala Leu Pro
 1               5                  10                  15

Glu Pro Arg Gly Val Pro Ala Val His Pro Ala Gly Ser Gly Ser Glu
                20                  25                  30

Trp Glu Arg Pro Pro Pro Ala Ala Pro Ser Pro Glu His Arg Asp Lys
             35                  40                  45

<210> SEQ ID NO 283
<211> LENGTH: 24
<212> TYPE: PRT
<213> ORGANISM: Homo sapiens

<400> SEQUENCE: 283

Asp Ser Arg Ala Leu Pro Glu Pro Arg Gly Val Pro Ala Val His Pro
 1               5                  10                  15

Ala Gly Ser Gly Ser Glu Trp Glu
                20

<210> SEQ ID NO 284
<211> LENGTH: 7
<212> TYPE: PRT
<213> ORGANISM: Homo sapiens

<400> SEQUENCE: 284

Glu Phe Gly Thr Ser Trp Val
 1               5

<210> SEQ ID NO 285
<211> LENGTH: 78
<212> TYPE: PRT
<213> ORGANISM: Homo sapiens

<400> SEQUENCE: 285

Thr Leu His Pro Pro Gln Glu Pro Gln Arg Pro Glu Ala Pro Asp Ala
 1               5                  10                  15

Gly Asp Pro Ala Pro Leu Pro Ser Thr Ser Ser Val Gly Ser Ser Ser
                20                  25                  30

Gly Gly Ala Cys Gly Val Pro Cys Ala His Trp Arg Val Cys Gly Leu
             35                  40                  45

Ile His Leu Val Ala Leu Arg Gly Gly Ile Arg Ala Pro Val Ser Pro
         50                  55                  60

Pro Phe Met Phe Asn Leu His Ser Asn Leu Leu Asn Leu Arg
 65                  70                  75

<210> SEQ ID NO 286
<211> LENGTH: 21
<212> TYPE: PRT
<213> ORGANISM: Homo sapiens

<400> SEQUENCE: 286

Glu Pro Gln Arg Pro Glu Ala Pro Asp Ala Gly Asp Pro Ala Pro Leu
 1               5                  10                  15

Pro Ser Thr Ser Ser
                20

<210> SEQ ID NO 287
```

<211> LENGTH: 15
<212> TYPE: PRT
<213> ORGANISM: Homo sapiens

<400> SEQUENCE: 287

Arg Val Cys Gly Leu Ile His Leu Val Ala Leu Arg Gly Gly Ile
1               5                   10                  15

<210> SEQ ID NO 288
<211> LENGTH: 79
<212> TYPE: PRT
<213> ORGANISM: Homo sapiens

<400> SEQUENCE: 288

Gln Gly Tyr Ser Thr Lys Pro Arg Leu Met Val Pro Leu Lys Met Asp
1               5                   10                  15

Ser Ile Thr Val His Ile Arg Ser Thr Asn Gly Pro Ile Asp Val Tyr
                20                  25                  30

Leu Cys Glu Val Glu Gln Gly Gln Thr Ser Asn Lys Arg Ser Glu Gly
            35                  40                  45

Val Gly Thr Ser Ser Ser Glu Ser Thr His Pro Glu Gly Pro Glu Glu
        50                  55                  60

Glu Glu Asn Pro Gln Gln Ser Glu Glu Leu Leu Glu Val Ser Asn
65                  70                  75

<210> SEQ ID NO 289
<211> LENGTH: 30
<212> TYPE: PRT
<213> ORGANISM: Homo sapiens

<400> SEQUENCE: 289

Asp Ser Ile Thr Val His Ile Arg Ser Thr Asn Gly Pro Ile Asp Val
1               5                   10                  15

Tyr Leu Cys Glu Val Glu Gln Gly Gln Thr Ser Asn Lys Arg
                20                  25                  30

<210> SEQ ID NO 290
<211> LENGTH: 25
<212> TYPE: PRT
<213> ORGANISM: Homo sapiens

<400> SEQUENCE: 290

Leu Met Val Pro Leu Lys Met Asp Ser Ile Thr Val His Ile Arg Ser
1               5                   10                  15

Thr Asn Gly Pro Ile Asp Val Tyr Leu
                20                  25

<210> SEQ ID NO 291
<211> LENGTH: 26
<212> TYPE: PRT
<213> ORGANISM: Homo sapiens

<400> SEQUENCE: 291

Gln Gly Gln Thr Ser Asn Lys Arg Ser Glu Gly Val Gly Thr Ser Ser
1               5                   10                  15

Ser Glu Ser Thr His Pro Glu Gly Pro Glu
                20                  25

<210> SEQ ID NO 292
<211> LENGTH: 19
<212> TYPE: PRT
<213> ORGANISM: Homo sapiens

<400> SEQUENCE: 292

Arg Pro Thr Arg Pro Ser Ile Leu Gly Leu Tyr Val Asp Leu Tyr Val
1               5                   10                  15

Phe Cys Ile

<210> SEQ ID NO 293
<211> LENGTH: 29
<212> TYPE: PRT
<213> ORGANISM: Homo sapiens
<220> FEATURE:
<221> NAME/KEY: SITE
<222> LOCATION: (6)
<223> OTHER INFORMATION: Xaa equals any of the naturally occurring L-
      amino acids

<400> SEQUENCE: 293

Cys Gly Ala Cys Thr Xaa Leu Ser Leu Ser Asp Ser Arg Arg Cys Gly
1               5                   10                  15

Cys Cys Lys Gly Ser Ser Leu Arg His Thr Ala Val Ala
            20                  25

<210> SEQ ID NO 294
<211> LENGTH: 7
<212> TYPE: PRT
<213> ORGANISM: Homo sapiens

<400> SEQUENCE: 294

Gly Arg Pro Thr Arg Pro Ile
1               5

<210> SEQ ID NO 295
<211> LENGTH: 64
<212> TYPE: PRT
<213> ORGANISM: Homo sapiens

<400> SEQUENCE: 295

Asp Pro Arg Val Arg Asp Leu Gln Gln Lys Asp Ile Gly Val Lys Pro
1               5                   10                  15

Glu Phe Ser Phe Asn Ile Pro Arg Ala Lys Arg Glu Leu Ala Gln Leu
            20                  25                  30

Asn Lys Cys Thr Ser Pro Gln Gln Lys Leu Val Cys Leu Arg Lys Val
        35                  40                  45

Val Gln Leu Ile Thr Gln Ser Pro Ser Gln Arg Val Asn Leu Glu Thr
    50                  55                  60

<210> SEQ ID NO 296
<211> LENGTH: 21
<212> TYPE: PRT
<213> ORGANISM: Homo sapiens

<400> SEQUENCE: 296

Gln Gln Lys Asp Ile Gly Val Lys Pro Glu Phe Ser Phe Asn Ile Pro
1               5                   10                  15

Arg Ala Lys Arg Glu
            20

<210> SEQ ID NO 297
<211> LENGTH: 25
<212> TYPE: PRT
<213> ORGANISM: Homo sapiens

<400> SEQUENCE: 297

```
Lys Cys Thr Ser Pro Gln Gln Lys Leu Val Cys Leu Arg Lys Val Val
 1               5                  10                  15

Gln Leu Ile Thr Gln Ser Pro Ser Gln
            20                  25
```

<210> SEQ ID NO 298
<211> LENGTH: 142
<212> TYPE: PRT
<213> ORGANISM: Homo sapiens
<220> FEATURE:
<221> NAME/KEY: SITE
<222> LOCATION: (66)
<223> OTHER INFORMATION: Xaa equals any of the naturally occurring L-
      amino acids

<400> SEQUENCE: 298

```
Gln Lys Glu Trp Lys Leu Phe Leu Arg Gly Arg Gln Asn Glu Lys Ser
 1               5                  10                  15

Gly Tyr Gln Lys Leu Leu Glu Leu Ile Leu Leu Asp Gln Thr Val Arg
            20                  25                  30

Val Val Thr Ala Gly Ser Ala Ile Leu Gln Lys Cys His Phe Tyr Glu
        35                  40                  45

Val Leu Ser Glu Ile Lys Arg Leu Gly Asp His Leu Ala Glu Lys Thr
    50                  55                  60

Ser Xaa Leu Pro Asn His Ser Glu Pro Asp His Asp Thr Asp Ala Gly
65                  70                  75                  80

Leu Glu Arg Thr Asn Pro Glu Tyr Glu Asn Glu Val Glu Ala Ser Met
                85                  90                  95

Asp Met Asp Leu Leu Glu Ser Ser Asn Ile Ser Glu Gly Glu Ile Glu
            100                 105                 110

Arg Leu Ile Asn Leu Leu Glu Glu Val Phe His Leu Met Glu Thr Ala
        115                 120                 125

Pro His Thr Met Ile Gln Gln Pro Val Lys Ser Phe Pro Thr
    130                 135                 140
```

<210> SEQ ID NO 299
<211> LENGTH: 27
<212> TYPE: PRT
<213> ORGANISM: Homo sapiens

<400> SEQUENCE: 299

```
Leu Arg Gly Arg Gln Asn Glu Lys Ser Gly Tyr Gln Lys Leu Leu Glu
 1               5                  10                  15

Leu Ile Leu Leu Asp Gln Thr Val Arg Val Val
            20                  25
```

<210> SEQ ID NO 300
<211> LENGTH: 26
<212> TYPE: PRT
<213> ORGANISM: Homo sapiens

<400> SEQUENCE: 300

```
Ile Leu Gln Lys Cys His Phe Tyr Glu Val Leu Ser Glu Ile Lys Arg
 1               5                  10                  15

Leu Gly Asp His Leu Ala Glu Lys Thr Ser
            20                  25
```

<210> SEQ ID NO 301
<211> LENGTH: 22
<212> TYPE: PRT

-continued

<213> ORGANISM: Homo sapiens

<400> SEQUENCE: 301

Asp Ala Gly Leu Glu Arg Thr Asn Pro Glu Tyr Glu Asn Glu Val Glu
1               5                   10                  15

Ala Ser Met Asp Met Asp
            20

<210> SEQ ID NO 302
<211> LENGTH: 26
<212> TYPE: PRT
<213> ORGANISM: Homo sapiens

<400> SEQUENCE: 302

Asn Ile Ser Glu Gly Glu Ile Glu Arg Leu Ile Asn Leu Leu Glu Glu
1               5                   10                  15

Val Phe His Leu Met Glu Thr Ala Pro His
            20                  25

<210> SEQ ID NO 303
<211> LENGTH: 19
<212> TYPE: PRT
<213> ORGANISM: Homo sapiens
<220> FEATURE:
<221> NAME/KEY: SITE
<222> LOCATION: (8)
<223> OTHER INFORMATION: Xaa equals any of the naturally occurring L-
      amino acids

<400> SEQUENCE: 303

Arg Arg Thr Ser Gly Ser Pro Xaa Ala Ala Gly Ile Arg His Glu Gly
1               5                   10                  15

Gly Phe Ile

<210> SEQ ID NO 304
<211> LENGTH: 149
<212> TYPE: PRT
<213> ORGANISM: Homo sapiens

<400> SEQUENCE: 304

Met Asn Arg His Asn Phe Pro Cys Ser Val His Gln Tyr Glu Ser Ser
1               5                   10                  15

Gly Thr Val Asn Asn Asp Asp Ser Asp Leu Leu Asp Ser Gln Val Gln
            20                  25                  30
Tyr Ser Ala Glu Pro Gln Leu Tyr Gly Asn Ala Thr Ser Asp His Pro
        35                  40                  45

Asn Asn Gln Asp Gln Ser Ser Ser Leu Pro Glu Glu Cys Val Pro Ser
    50                  55                  60
Asp Glu Ser Thr Pro Pro Ser Ile Lys Lys Ile Ile His Val Leu Glu
65                  70                  75                  80

Lys Val Gln Tyr Leu Glu Gln Glu Val Glu Glu Phe Val Gly Lys Lys
                85                  90                  95

Thr Asp Lys Ala Tyr Trp Leu Leu Glu Glu Met Leu Thr Lys Glu Leu
            100                 105                 110

Leu Glu Leu Asp Ser Val Glu Thr Gly Gly Gln Asp Ser Val Arg Gln
        115                 120                 125

Ala Arg Lys Glu Ala Val Cys Lys Ile Gln Ala Ile Leu Glu Lys Lys
    130                 135                 140

Lys Lys Lys Asn Ser
145

-continued

```
<210> SEQ ID NO 305
<211> LENGTH: 87
<212> TYPE: PRT
<213> ORGANISM: Homo sapiens

<400> SEQUENCE: 305

Gly Ala Arg Ala Thr Ala Pro Val Thr Val Arg Pro Thr Ala Ala Thr
 1               5                  10                  15

Thr Gly Leu Gly Val Glu Met Cys Arg Tyr Thr His Leu His Pro Tyr
            20                  25                  30

Ile Leu Phe Ala Leu Asn Leu Pro Ser Leu Pro Phe Pro Gly Gly Cys
        35                  40                  45

Ala Gly Ala Ala Arg Arg Pro Pro Gly Trp Glu Lys Ala Glu Glu
    50                  55                  60

Ala Met Ala Thr Ile Pro Arg Glu Ala Pro Gly Gln Ser Leu Val Glu
 65                  70                  75                  80

Pro Glu Glu Ala Thr Arg Val
                85

<210> SEQ ID NO 306
<211> LENGTH: 25
<212> TYPE: PRT
<213> ORGANISM: Homo sapiens

<400> SEQUENCE: 306

Pro Val Thr Val Arg Pro Thr Ala Ala Thr Thr Gly Leu Gly Val Glu
 1               5                  10                  15

Met Cys Arg Tyr Thr His Leu His Pro
            20                  25

<210> SEQ ID NO 307
<211> LENGTH: 25
<212> TYPE: PRT
<213> ORGANISM: Homo sapiens

<400> SEQUENCE: 307

Pro Tyr Ile Leu Phe Ala Leu Asn Leu Pro Ser Leu Pro Phe Pro Gly
 1               5                  10                  15

Gly Cys Ala Gly Ala Ala Arg Arg Arg
            20                  25

<210> SEQ ID NO 308
<211> LENGTH: 20
<212> TYPE: PRT
<213> ORGANISM: Homo sapiens

<400> SEQUENCE: 308

Lys Ala Glu Glu Ala Met Ala Thr Ile Pro Arg Glu Ala Pro Gly Gln
 1               5                  10                  15

Ser Leu Val Glu
            20

<210> SEQ ID NO 309
<211> LENGTH: 26
<212> TYPE: PRT
<213> ORGANISM: Homo sapiens

<400> SEQUENCE: 309

Met Asn Arg His Asn Phe Pro Cys Ser Val His Gln Tyr Glu Ser Ser
 1               5                  10                  15

Gly Thr Val Asn Asn Asp Asp Ser Asp Leu
```

-continued

```
                    20                  25

<210> SEQ ID NO 310
<211> LENGTH: 24
<212> TYPE: PRT
<213> ORGANISM: Homo sapiens

<400> SEQUENCE: 310

Asp Ser Gln Val Gln Tyr Ser Ala Glu Pro Gln Leu Tyr Gly Asn Ala
 1               5                  10                  15

Thr Ser Asp His Pro Asn Asn Gln
            20

<210> SEQ ID NO 311
<211> LENGTH: 25
<212> TYPE: PRT
<213> ORGANISM: Homo sapiens

<400> SEQUENCE: 311

His Pro Asn Asn Gln Asp Gln Ser Ser Leu Pro Glu Glu Cys Val
 1               5                  10                  15

Pro Ser Asp Glu Ser Thr Pro Pro Ser
            20                  25

<210> SEQ ID NO 312
<211> LENGTH: 24
<212> TYPE: PRT
<213> ORGANISM: Homo sapiens

<400> SEQUENCE: 312

Glu Val Glu Glu Phe Val Gly Lys Lys Thr Asp Lys Ala Tyr Trp Leu
 1               5                  10                  15

Leu Glu Glu Met Leu Thr Lys Glu
            20

<210> SEQ ID NO 313
<211> LENGTH: 24
<212> TYPE: PRT
<213> ORGANISM: Homo sapiens

<400> SEQUENCE: 313

Leu Glu Leu Asp Ser Val Glu Thr Gly Gly Gln Asp Ser Val Arg Gln
 1               5                  10                  15

Ala Arg Lys Glu Ala Val Cys Lys
            20

<210> SEQ ID NO 314
<211> LENGTH: 25
<212> TYPE: PRT
<213> ORGANISM: Homo sapiens

<400> SEQUENCE: 314

Ile Arg His Glu Tyr Pro Val Leu Ile Gln Phe Ser Val Ser Tyr Arg
 1               5                  10                  15

Lys Ser Phe Ile Phe Cys Leu Pro Glu
            20                  25

<210> SEQ ID NO 315
<211> LENGTH: 43
<212> TYPE: PRT
<213> ORGANISM: Homo sapiens
<220> FEATURE:
<221> NAME/KEY: SITE
```

```
<222> LOCATION: (9)
<223> OTHER INFORMATION: Xaa equals any of the naturally occurring L-
      amino acids

<400> SEQUENCE: 315

Ala Asp Val Glu Leu Val Asp Pro Xaa Gly Cys Arg Asn Ser Ala Arg
 1               5                  10                  15

Ala Pro Ala Arg Lys Lys Glu Trp His Ser Trp Ala Trp Pro Arg Ile
             20                  25                  30

Arg Val Ile Arg Ala Arg Glu Ser Leu Gly Ser
         35                  40

<210> SEQ ID NO 316
<211> LENGTH: 31
<212> TYPE: PRT
<213> ORGANISM: Homo sapiens

<400> SEQUENCE: 316

Glu Phe Gly Thr Ser Arg Gly Pro Val Pro Leu Ser Ser Thr Ser Pro
 1               5                  10                  15

Met Pro Ser Arg Leu Val Ile Arg Ala His Ser Leu Leu Phe Ala
             20                  25                  30

<210> SEQ ID NO 317
<211> LENGTH: 30
<212> TYPE: PRT
<213> ORGANISM: Homo sapiens

<400> SEQUENCE: 317

Phe Arg Ala Trp Arg Asn His Gly His Ser Cys Phe Leu Cys Glu Ile
 1               5                  10                  15

Val Ile Arg Ser Gln Phe His Thr Thr Tyr Glu Pro Glu Ala
             20                  25                  30

<210> SEQ ID NO 318
<211> LENGTH: 102
<212> TYPE: PRT
<213> ORGANISM: Homo sapiens

<400> SEQUENCE: 318

Ala Asp Asn Asn Phe Thr Gln Glu Thr Ala Met Thr Met Ile Thr Pro
 1               5                  10                  15

Ser Ser Lys Leu Thr Leu Thr Lys Gly Asn Lys Ser Trp Ser Ser Thr
             20                  25                  30
Ala Val Ala Ala Ala Leu Glu Leu Val Asp Pro Pro Gly Cys Arg Asn
         35                  40                  45

Ser Ala Arg Ala Val Leu Leu Ile Trp Gly His Gly Ser Ser Gly Lys
     50                  55                  60
Met Ala Leu Cys Gly Val Glu Val Ser Pro Arg Val Gly Gly Ser Val
 65                  70                  75                  80

Pro Val His Arg Tyr Leu Leu Ala Ala His Ile His Ser Glu Ala Leu
                 85                  90                  95

Leu Ser Gln Leu Arg Met
            100

<210> SEQ ID NO 319
<211> LENGTH: 24
<212> TYPE: PRT
<213> ORGANISM: Homo sapiens

<400> SEQUENCE: 319

Thr Ala Met Thr Met Ile Thr Pro Ser Ser Lys Leu Thr Leu Thr Lys
```

-continued

```
                1               5                  10                 15
Gly Asn Lys Ser Trp Ser Ser Thr
            20

<210> SEQ ID NO 320
<211> LENGTH: 26
<212> TYPE: PRT
<213> ORGANISM: Homo sapiens

<400> SEQUENCE: 320

Ser Ser Gly Lys Met Ala Leu Cys Gly Val Glu Val Ser Pro Arg Val
  1               5                  10                 15
Gly Gly Ser Val Pro Val His Arg Tyr Leu
            20                  25

<210> SEQ ID NO 321
<211> LENGTH: 7
<212> TYPE: PRT
<213> ORGANISM: Homo sapiens

<400> SEQUENCE: 321

Val Asp Pro Val Lys Gly Gly
  1               5

<210> SEQ ID NO 322
<211> LENGTH: 16
<212> TYPE: PRT
<213> ORGANISM: Homo sapiens

<400> SEQUENCE: 322

Ile Arg His Glu Arg His Glu Leu Val Pro Asn Ser Ala Arg Asp Phe
  1               5                  10                 15

<210> SEQ ID NO 323
<211> LENGTH: 6
<212> TYPE: PRT
<213> ORGANISM: Homo sapiens

<400> SEQUENCE: 323

Ala Thr Ser His Cys Gly
  1               5

<210> SEQ ID NO 324
<211> LENGTH: 48
<212> TYPE: PRT
<213> ORGANISM: Homo sapiens

<400> SEQUENCE: 324

Ala His Gly Gln Ile Glu Gly Lys Ala Leu Thr His Asp His Thr Ala
  1               5                  10                 15
Glu Lys Trp Gln Arg Gln Asp Leu Asn Leu Glu Pro Leu Ala Pro His
            20                  25                 30
Thr Ser Asn Leu Asn His Ser Pro Tyr Asn Thr Thr Tyr Val Val Lys
            35                  40                 45

<210> SEQ ID NO 325
<211> LENGTH: 9
<212> TYPE: PRT
<213> ORGANISM: Homo sapiens

<400> SEQUENCE: 325

Leu Asn Ser Ser Asp Cys Gln Leu Ala
  1               5
```

<210> SEQ ID NO 326
<211> LENGTH: 33
<212> TYPE: PRT
<213> ORGANISM: Homo sapiens

<400> SEQUENCE: 326

Thr Pro His Asn Leu Ser Ala Arg Arg Leu Ser Gly Thr Met Tyr Gly
 1               5                  10                  15

Phe Phe Ala Leu Gln Leu Thr Val Leu Leu Val His Tyr Phe Phe Leu
            20                  25                  30

Ile

<210> SEQ ID NO 327
<211> LENGTH: 40
<212> TYPE: PRT
<213> ORGANISM: Homo sapiens

<400> SEQUENCE: 327

Asn Ser Ala Arg Ala Lys Met Arg Leu Ser Thr Asn Leu Cys Ile Ile
 1               5                  10                  15

Leu Ile Asn Ile Leu Ile Gln Asn Val Leu Asn Phe Asn Arg Lys Ile
            20                  25                  30

Ile Phe Lys Phe Leu Pro Cys Ala
            35                  40

<210> SEQ ID NO 328
<211> LENGTH: 21
<212> TYPE: PRT
<213> ORGANISM: Homo sapiens
<220> FEATURE:
<221> NAME/KEY: SITE
<222> LOCATION: (2)
<223> OTHER INFORMATION: Xaa equals any of the naturally occurring L-
      amino acids
<221> NAME/KEY: SITE
<222> LOCATION: (13)
<223> OTHER INFORMATION: Xaa equals any of the naturally occurring L-
      amino acids

<400> SEQUENCE: 328

Asn Xaa Trp Ile Pro Arg Ala Ala Gly Ile Arg His Xaa Ala Ala Leu
 1               5                  10                  15

Gly Gln Ala Gly Thr
            20

<210> SEQ ID NO 329
<211> LENGTH: 85
<212> TYPE: PRT
<213> ORGANISM: Homo sapiens

<400> SEQUENCE: 329

Leu Leu Phe His Met Lys Leu Arg Lys Glu Val Arg Thr Gly Leu
 1               5                  10                  15

Val Leu Trp Ala Leu Leu Ala Gly Ala Pro Pro Thr Ala Gly Leu
            20                  25                  30

Gln Leu Gln Gly Ser Glu Ala Ile Ser Glu Lys Val Gly Ser Gly Ala
            35                  40                  45

Glu Gly Ser Arg Gly Gln Val Pro Gly Gln Leu Leu Gln Gln Ala Gln
50                  55                  60

Gln Ala Phe His Leu Cys Pro Gln Val Ile His Gly Leu Leu Tyr His
65                  70                  75                  80

Leu Leu His Asp Ile
              85

<210> SEQ ID NO 330
<211> LENGTH: 25
<212> TYPE: PRT
<213> ORGANISM: Homo sapiens

<400> SEQUENCE: 330

Arg Lys Glu Val Glu Arg Thr Gly Leu Val Leu Trp Ala Leu Leu Ala
 1               5                  10                  15

Gly Ala Pro Pro Pro Thr Ala Gly Leu
            20                  25

<210> SEQ ID NO 331
<211> LENGTH: 23
<212> TYPE: PRT
<213> ORGANISM: Homo sapiens

<400> SEQUENCE: 331

Gly Ser Arg Gly Gln Val Pro Gly Gln Leu Leu Gln Gln Ala Gln Gln
 1               5                  10                  15

Ala Phe His Leu Cys Pro Gln
            20

<210> SEQ ID NO 332
<211> LENGTH: 50
<212> TYPE: PRT
<213> ORGANISM: Homo sapiens
<220> FEATURE:
<221> NAME/KEY: SITE
<222> LOCATION: (22)
<223> OTHER INFORMATION: Xaa equals any of the naturally occurring L-
      amino acids

<400> SEQUENCE: 332

Gly Ser Arg Arg His Val Val Gly Lys Pro Gly Thr Pro Cys Arg Tyr
 1               5                  10                  15

Arg Ala Gly Ile Pro Xaa Val Asp Pro Arg Val Arg Ser Ile Thr Val
            20                  25                  30

Ile Val Lys Met Trp Phe Leu Arg Val Val Ala Thr Tyr Gly Gly Val
        35                  40                  45

Glu Arg
    50

<210> SEQ ID NO 333
<211> LENGTH: 18
<212> TYPE: PRT
<213> ORGANISM: Homo sapiens

<400> SEQUENCE: 333

Ile Phe Ser Cys Asp Ser Ile Ala Ile Ile Gln Ile Lys His Leu Ala
 1               5                  10                  15

Phe Pro

<210> SEQ ID NO 334
<211> LENGTH: 34
<212> TYPE: PRT
<213> ORGANISM: Homo sapiens

<400> SEQUENCE: 334

Gly Leu Trp Leu Ser Leu Gly Gly Phe His Glu Arg Gly Gln Asp Trp

-continued

```
                1               5                  10                  15
Glu Gln Thr Gln Lys Ile Tyr Asn Cys His Val Leu Leu Asn Arg Lys
                    20                  25                  30
Gly Gln

<210> SEQ ID NO 335
<211> LENGTH: 68
<212> TYPE: PRT
<213> ORGANISM: Homo sapiens

<400> SEQUENCE: 335

Ala Trp Pro Arg Leu Gly Ala Asp Ser Glu Asn Leu Gln Leu Ser Arg
 1               5                  10                  15

Ala Ala Glu Gln Lys Gly Ala Val Val Ala Thr Tyr Arg Lys Thr His
            20                  25                  30

Leu Cys Asp Val Glu Ile Pro Gly Gln Gly Leu Cys Val Lys Ala Thr
         35                  40                  45

Leu Pro Cys Leu Gly Pro Val Leu Ser His Leu Ser Ala His Gln Gln
     50                  55                  60

Ala Arg Leu Val
 65

<210> SEQ ID NO 336
<211> LENGTH: 27
<212> TYPE: PRT
<213> ORGANISM: Homo sapiens

<400> SEQUENCE: 336

Arg Ala Ala Glu Gln Lys Gly Ala Val Val Ala Thr Tyr Arg Lys Thr
 1               5                  10                  15

His Leu Cys Asp Val Glu Ile Pro Gly Gln Gly
            20                  25

<210> SEQ ID NO 337
<211> LENGTH: 8
<212> TYPE: PRT
<213> ORGANISM: Homo sapiens

<400> SEQUENCE: 337

Arg Arg Asp Ser Arg Ala Gly Ala
 1               5

<210> SEQ ID NO 338
<211> LENGTH: 8
<212> TYPE: PRT
<213> ORGANISM: Homo sapiens

<400> SEQUENCE: 338

Leu Ser Ala Gly Asn His Asp Thr
 1               5

<210> SEQ ID NO 339
<211> LENGTH: 41
<212> TYPE: PRT
<213> ORGANISM: Homo sapiens

<400> SEQUENCE: 339

Lys Gln Val Lys Cys Ala Lys Val Ser Tyr Leu Leu Phe Leu Phe Gln
 1               5                  10                  15

Tyr Cys Ala Ile Asp Ser Cys Ile Lys Phe Trp Asn Ala Gly Ser Ser
            20                  25                  30
```

Trp Leu Ser Ser Val Thr Leu Trp Ser
         35                  40

<210> SEQ ID NO 340
<211> LENGTH: 13
<212> TYPE: PRT
<213> ORGANISM: Homo sapiens

<400> SEQUENCE: 340

Ile Tyr Val Met Asp Thr Ser Arg Ser Thr Asn Pro Val
 1               5                  10

<210> SEQ ID NO 341
<211> LENGTH: 14
<212> TYPE: PRT
<213> ORGANISM: Homo sapiens

<400> SEQUENCE: 341

Asn Met Leu Tyr Ala Cys Ser Ile Leu Tyr Lys Thr Lys Leu
 1               5                  10

<210> SEQ ID NO 342
<211> LENGTH: 19
<212> TYPE: PRT
<213> ORGANISM: Homo sapiens

<400> SEQUENCE: 342

Met Asn Lys Thr Asp Ile Ile Asp His Ser Phe Ala Val Glu Trp Met
 1               5                  10                  15

Gln Asp Phe

<210> SEQ ID NO 343
<211> LENGTH: 13
<212> TYPE: PRT
<213> ORGANISM: Homo sapiens

<400> SEQUENCE: 343

Ala Phe Gln Asp Ala Leu Asn Gln Glu Thr Thr Tyr Val
 1               5                  10

<210> SEQ ID NO 344
<211> LENGTH: 41
<212> TYPE: PRT
<213> ORGANISM: Homo sapiens

<400> SEQUENCE: 344

Asn Leu Thr Arg Ser Met Ser Leu Val Leu Asp Glu Phe Tyr Ser Ser
 1               5                  10                  15

Leu Arg Val Val Gly Val Ser Ala Val Leu Gly Thr Gly Leu Asp Glu
            20                  25                  30

Leu Phe Val Gln Val Thr Ser Ala Ala
         35                  40

<210> SEQ ID NO 345
<211> LENGTH: 10
<212> TYPE: PRT
<213> ORGANISM: Homo sapiens

<400> SEQUENCE: 345

Leu Lys Lys Ser Leu Ala Asn Ala Glu Ser
 1               5                  10

<210> SEQ ID NO 346
<211> LENGTH: 29
<212> TYPE: PRT
<213> ORGANISM: Homo sapiens

<400> SEQUENCE: 346

Lys Asp Met Gly Ser Val Ala Leu Asp Ala Gly Thr Ala Lys Asp Ser
1               5                   10                  15

Leu Ser Pro Val Leu His Pro Ser Asp Leu Ile Leu Thr
            20                  25

<210> SEQ ID NO 347
<211> LENGTH: 28
<212> TYPE: PRT
<213> ORGANISM: Homo sapiens

<400> SEQUENCE: 347

Ala Gly Ser Gly Lys Thr Thr Phe Val Gln Arg Leu Thr Gly His Leu
1               5                   10                  15

His Ala Gln Gly Thr Pro Pro Tyr Val Ile Asn Leu
            20                  25

<210> SEQ ID NO 348
<211> LENGTH: 134
<212> TYPE: PRT
<213> ORGANISM: Homo sapiens
<220> FEATURE:
<221> NAME/KEY: SITE
<222> LOCATION: (63)
<223> OTHER INFORMATION: Xaa equals any of the naturally occurring L-
      amino acids
<221> NAME/KEY: SITE
<222> LOCATION: (98)
<223> OTHER INFORMATION: Xaa equals any of the naturally occurring L-
      amino acids
<221> NAME/KEY: SITE
<222> LOCATION: (119)
<223> OTHER INFORMATION: Xaa equals any of the naturally occurring L-
      amino acids

<400> SEQUENCE: 348

Ser Thr Trp Ile Gln Gln Tyr Met Lys Phe Pro Phe Leu Pro Ile Leu
1               5                   10                  15

Val Met Lys Phe Ile Glu Lys Ala Gln Asn Met Ser Lys Tyr Val Leu
            20                  25                  30

Ile Asp Thr Pro Gly Gln Ile Glu Val Phe Thr Trp Ser Ala Ser Gly
        35                  40                  45

Thr Ile Ile Thr Glu Ala Leu Ala Ser Ser Phe Pro Thr Val Xaa Ile
    50                  55                  60

Tyr Val Met Asp Thr Ser Arg Ser Thr Asn Pro Val Thr Phe Met Cys
65                  70                  75                  80

Asn Met Leu Tyr Ala Cys Ser Ile Leu Tyr Lys Thr Lys Leu Ala Phe
                85                  90                  95

Ile Xaa Gly Met Asn Lys Thr Asp Ile Ile Asp His Ser Phe Ala Val
            100                 105                 110

Glu Trp Met Gln Asp Phe Xaa Ala Phe Gln Asp Ala Leu Asn Gln Glu
        115                 120                 125

Thr Thr Tyr Val Ile Thr
    130

<210> SEQ ID NO 349
<211> LENGTH: 197
<212> TYPE: PRT

-continued

```
<213> ORGANISM: Homo sapiens

<400> SEQUENCE: 349

Gly Phe Pro Arg Cys Leu Glu Ser Arg Asp Tyr Ile Arg His Asn Leu
 1               5                  10                  15

Thr Arg Ser Met Ser Leu Val Leu Asp Glu Phe Tyr Ser Ser Leu Arg
             20                  25                  30

Val Val Gly Val Ser Ala Val Leu Gly Thr Gly Leu Asp Glu Leu Phe
         35                  40                  45

Val Gln Val Thr Ser Ala Ala Glu Glu Tyr Glu Arg Glu Tyr Arg Pro
     50                  55                  60

Glu Tyr Glu Arg Leu Lys Lys Ser Leu Ala Asn Ala Glu Ser Gln Gln
 65                  70                  75                  80

Gln Arg Glu Gln Leu Glu Arg Leu Arg Lys Asp Met Gly Ser Val Ala
             85                  90                  95

Leu Asp Ala Gly Thr Ala Lys Asp Ser Leu Ser Pro Val Leu His Pro
        100                 105                 110

Ser Asp Leu Ile Leu Thr Arg Gly Thr Leu Asp Glu Glu Asp Glu Glu
    115                 120                 125

Ala Asp Ser Asp Thr Asp Asp Ile Asp His Arg Val Thr Glu Glu Ser
130                 135                 140

His Glu Glu Pro Ala Phe Gln Asn Phe Met Gln Glu Ser Met Ala Gln
145                 150                 155                 160

Tyr Trp Lys Arg Asn Asn Lys His Arg Val Thr Glu Glu Ser His Glu
                165                 170                 175

Glu Pro Ala Phe Gln Asn Phe Met Gln Glu Ser Met Ala Gln Tyr Trp
            180                 185                 190

Lys Arg Asn Asn Lys
        195

<210> SEQ ID NO 350
<211> LENGTH: 10
<212> TYPE: PRT
<213> ORGANISM: Homo sapiens

<400> SEQUENCE: 350

Leu Ala Pro Ser Ser Val Gly Ser Ala Ser
 1               5                  10

<210> SEQ ID NO 351
<211> LENGTH: 39
<212> TYPE: PRT
<213> ORGANISM: Homo sapiens

<400> SEQUENCE: 351

Arg Glu Ala Thr Lys Asn Pro Thr His His Arg Ser Thr Pro His Ala
 1               5                  10                  15

Ala Gly Ser Gln Leu Asn Val Pro Gln Pro Cys Phe Pro Leu His
             20                  25                  30

His Gln Ile Lys Thr Ser Pro
        35

<210> SEQ ID NO 352
<211> LENGTH: 38
<212> TYPE: PRT
<213> ORGANISM: Homo sapiens

<400> SEQUENCE: 352
```

-continued

```
Ser Gln Thr Ile Phe Lys Gln Ser Arg His Arg Cys Asp Ser Arg Gln
  1               5                  10                  15

Glu Ser Thr Trp Leu Cys Ser His Glu Lys Asp Ala Thr Lys Met Met
             20                  25                  30

His Leu Asn Asp Asn Ser
             35

<210> SEQ ID NO 353
<211> LENGTH: 48
<212> TYPE: PRT
<213> ORGANISM: Homo sapiens

<400> SEQUENCE: 353

Val Thr Gly Ser Pro Ile Leu Gln Leu Ala Leu Leu Gln Leu Pro Ala
  1               5                  10                  15

Trp Pro Leu Arg Gly Arg Leu Arg Gly Lys Arg His Cys Thr Gly Leu
             20                  25                  30

Asn Leu Ala Ile Ser Gly Asn Gly Gly Glu Trp Gly Gly Arg Gly Glu
             35                  40                  45

<210> SEQ ID NO 354
<211> LENGTH: 19
<212> TYPE: PRT
<213> ORGANISM: Homo sapiens

<400> SEQUENCE: 354

Glu Phe Gly Thr Arg Ser Leu Asp Pro Ser Gly Arg His Arg Val Gly
  1               5                  10                  15

Ala Ala Gly

<210> SEQ ID NO 355
<211> LENGTH: 44
<212> TYPE: PRT
<213> ORGANISM: Homo sapiens

<400> SEQUENCE: 355

Ala Gln Gly Arg Cys Ser Arg Asp Gly Ala Ser Ala His Gly Gly Leu
  1               5                  10                  15

Ser Val Pro Arg Trp Thr Cys Pro Ser Ser Gly Ser His Asn Pro Leu
             20                  25                  30

Pro Leu His Tyr Phe Thr Gln Val Gly Thr Phe Pro
             35                  40

<210> SEQ ID NO 356
<211> LENGTH: 44
<212> TYPE: PRT
<213> ORGANISM: Homo sapiens

<400> SEQUENCE: 356

Cys Arg Val Ser Ala Leu Arg Glu Leu Lys Asp Ser Gln Arg His Gln
  1               5                  10                  15

Gly Ser Leu Ala Gln Arg Ser Asn Ser Gln Ala Pro Arg Arg Thr Ala
             20                  25                  30

Met Glu Arg Thr Glu Thr His Leu Gln Trp Gly Leu
             35                  40

<210> SEQ ID NO 357
<211> LENGTH: 45
<212> TYPE: PRT
<213> ORGANISM: Homo sapiens
```

```
<400> SEQUENCE: 357

Gly Thr Leu Pro Val Pro Gly Val Gln Ser Leu Pro Thr Pro Ser Leu
 1               5                  10                  15

Cys Leu Pro Pro Ser Lys Gly Gly Val Thr Thr Ser Val Ala Lys His
            20                  25                  30

Leu Leu Pro Gly Ser Leu His Pro Gly His Leu Ser Leu
        35                  40                  45

<210> SEQ ID NO 358
<211> LENGTH: 51
<212> TYPE: PRT
<213> ORGANISM: Homo sapiens
<220> FEATURE:
<221> NAME/KEY: SITE
<222> LOCATION: (27)
<223> OTHER INFORMATION: Xaa equals any of the naturally occurring L-
      amino acids

<400> SEQUENCE: 358

Trp Ser Val Cys Leu Ser Val Pro Pro Ser Leu Asn Leu Leu Pro Pro
 1               5                  10                  15

Cys Pro Leu Leu Leu Ala Pro Gly Ser Pro Xaa Pro Leu Leu Ala Ala
            20                  25                  30

Pro Ser His Leu Thr Gln Gly Ser Leu Arg Thr Leu Lys Trp Trp Ile
        35                  40                  45

His Pro Glu
        50

<210> SEQ ID NO 359
<211> LENGTH: 50
<212> TYPE: PRT
<213> ORGANISM: Homo sapiens
<220> FEATURE:
<221> NAME/KEY: SITE
<222> LOCATION: (5)
<223> OTHER INFORMATION: Xaa equals any of the naturally occurring L-
      amino acids

<400> SEQUENCE: 359

Ser Pro Gly Leu Xaa Gly Ile Arg His Glu Gln Pro Ser Lys Leu Met
 1               5                  10                  15

Arg Leu Leu Ser Ser Asn Glu Asp Ala Asn Ile Leu Ser Ser Pro
            20                  25                  30

Thr Asp Arg Ser Met Ser Ser Ser Leu Ser Ala Ser Gln Leu His Thr
        35                  40                  45

Val Asn
        50

<210> SEQ ID NO 360
<211> LENGTH: 25
<212> TYPE: PRT
<213> ORGANISM: Homo sapiens

<400> SEQUENCE: 360

Gln Pro Ser Lys Leu Met Arg Leu Leu Ser Ser Asn Glu Asp Asp Ala
 1               5                  10                  15

Asn Ile Leu Ser Ser Pro Thr Asp Arg
            20                  25

<210> SEQ ID NO 361
<211> LENGTH: 26
<212> TYPE: PRT
```

-continued

<213> ORGANISM: Homo sapiens

<400> SEQUENCE: 361

Gln Leu His Thr Val Asn Met Arg Asp Pro Leu Asn Arg Val Leu Ala
1               5                   10                  15

Asn Leu Phe Leu Leu Ile Ser Ser Ile Leu
            20                  25

<210> SEQ ID NO 362
<211> LENGTH: 17
<212> TYPE: PRT
<213> ORGANISM: Homo sapiens

<400> SEQUENCE: 362

Gly Ser Arg Thr Ala Gly Pro His Thr Gln Phe Val Gln Trp Phe Met
1               5                   10                  15

Glu

<210> SEQ ID NO 363
<211> LENGTH: 16
<212> TYPE: PRT
<213> ORGANISM: Homo sapiens

<400> SEQUENCE: 363

Lys Val Ser Ala Met Ser Ser Pro Lys Val Val Leu Ala Ile Thr Asp
1               5                   10                  15

<210> SEQ ID NO 364
<211> LENGTH: 9
<212> TYPE: PRT
<213> ORGANISM: Homo sapiens

<400> SEQUENCE: 364

Asp Asn Tyr Cys Leu Gln Ile Asn Pro
1               5

<210> SEQ ID NO 365
<211> LENGTH: 13
<212> TYPE: PRT
<213> ORGANISM: Homo sapiens

<400> SEQUENCE: 365

Lys Arg Ile Leu Asn Lys Pro Val Gly Leu Lys Asp Leu
1               5                   10

<210> SEQ ID NO 366
<211> LENGTH: 20
<212> TYPE: PRT
<213> ORGANISM: Homo sapiens

<400> SEQUENCE: 366

Gly Pro Gln Ile Ala Tyr Val Arg Asp Phe Lys Ala Lys Val Gln Tyr
1               5                   10                  15

Phe Arg Phe Trp
            20

<210> SEQ ID NO 367
<211> LENGTH: 21
<212> TYPE: PRT
<213> ORGANISM: Homo sapiens

<400> SEQUENCE: 367

Tyr Phe Val Asn His Asn Thr Arg Ile Thr Gln Trp Glu Asp Pro Arg

```
                1               5              10              15

Ser Gln Gly Gln Leu
                20

<210> SEQ ID NO 368
<211> LENGTH: 23
<212> TYPE: PRT
<213> ORGANISM: Homo sapiens

<400> SEQUENCE: 368

Ile Gly Arg Phe Ile Ala Met Ala Leu Phe His Gly Lys Phe Ile Asp
 1               5                  10                  15

Thr Gly Phe Ser Leu Pro Phe
                20

<210> SEQ ID NO 369
<211> LENGTH: 18
<212> TYPE: PRT
<213> ORGANISM: Homo sapiens

<400> SEQUENCE: 369

Lys Gln Ile Met Trp Phe Trp Gln Phe Val Lys Glu Ile Asp Asn Glu
 1               5                  10                  15

Lys Arg

<210> SEQ ID NO 370
<211> LENGTH: 17
<212> TYPE: PRT
<213> ORGANISM: Homo sapiens

<400> SEQUENCE: 370

Phe Asn Arg Leu Asp Leu Pro Pro Tyr Lys Ser Tyr Glu Gln Leu Lys
 1               5                  10                  15

Glu

<210> SEQ ID NO 371
<211> LENGTH: 474
<212> TYPE: PRT
<213> ORGANISM: Homo sapiens
<220> FEATURE:
<221> NAME/KEY: SITE
<222> LOCATION: (131)
<223> OTHER INFORMATION: Xaa equals any of the naturally occurring L-
      amino acids
<221> NAME/KEY: SITE
<222> LOCATION: (136)
<223> OTHER INFORMATION: Xaa equals any of the naturally occurring L-
      amino acids
<221> NAME/KEY: SITE
<222> LOCATION: (137)
<223> OTHER INFORMATION: Xaa equals any of the naturally occurring L-
      amino acids
<221> NAME/KEY: SITE
<222> LOCATION: (146)
<223> OTHER INFORMATION: Xaa equals any of the naturally occurring L-
      amino acids
<221> NAME/KEY: SITE
<222> LOCATION: (198)
<223> OTHER INFORMATION: Xaa equals any of the naturally occurring L-
      amino acids
<221> NAME/KEY: SITE
<222> LOCATION: (235)
<223> OTHER INFORMATION: Xaa equals any of the naturally occurring L-
      amino acids
<221> NAME/KEY: SITE
<222> LOCATION: (428)
<223> OTHER INFORMATION: Xaa equals any of the naturally occurring L-
      amino acids
```

```
<400> SEQUENCE: 371

Thr His Ala Ser Ala Thr Arg Pro Gly Pro Leu Pro Pro Gly Trp Glu
  1               5                  10                  15

Lys Arg Thr Asp Ser Asn Gly Arg Val Tyr Phe Val Asn His Asn Thr
             20                  25                  30

Arg Ile Thr Gln Trp Glu Asp Pro Arg Ser Gln Gly Gln Leu Asn Glu
         35                  40                  45

Lys Pro Leu Pro Glu Gly Trp Glu Met Arg Phe Thr Val Asp Gly Ile
 50                  55                  60

Pro Tyr Phe Val Asp His Asn Arg Arg Thr Thr Thr Tyr Ile Asp Pro
 65                  70                  75                  80

Arg Thr Gly Lys Ser Ala Leu Asp Asn Gly Pro Gln Ile Ala Tyr Val
             85                  90                  95

Arg Asp Phe Lys Ala Lys Val Gln Tyr Phe Arg Phe Trp Cys Gln Gln
            100                 105                 110

Leu Ala Met Pro Gln His Ile Lys Ile Thr Val Thr Arg Lys Thr Leu
        115                 120                 125

Phe Glu Xaa Ser Phe Gln Gln Xaa Xaa Ser Phe Ser Pro Gln Asp Leu
    130                 135                 140

Arg Xaa Arg Leu Trp Val Ile Phe Pro Gly Glu Gly Leu Asp Tyr
145                 150                 155                 160

Gly Gly Val Ala Arg Glu Trp Phe Phe Leu Leu Ser His Glu Val Leu
                165                 170                 175

Asn Pro Met Tyr Cys Leu Phe Glu Tyr Ala Gly Lys Asp Asn Tyr Cys
            180                 185                 190

Leu Gln Ile Asn Pro Xaa Ser Tyr Ile Asn Pro Asp His Leu Lys Tyr
        195                 200                 205

Phe Arg Phe Ile Gly Arg Phe Ile Ala Met Ala Leu Phe His Gly Lys
    210                 215                 220

Phe Ile Asp Thr Gly Phe Ser Leu Pro Phe Xaa Lys Arg Ile Leu Asn
225                 230                 235                 240

Lys Pro Val Gly Leu Lys Asp Leu Glu Ser Ile Asp Pro Glu Phe Tyr
                245                 250                 255

Asn Ser Leu Ile Trp Val Lys Glu Asn Asn Ile Glu Glu Cys Asp Leu
            260                 265                 270

Glu Met Tyr Phe Ser Val Asp Lys Glu Ile Leu Gly Glu Ile Lys Ser
        275                 280                 285

His Asp Leu Lys Pro Asn Gly Gly Asn Ile Leu Val Thr Glu Glu Asn
    290                 295                 300

Lys Glu Glu Tyr Ile Arg Met Val Ala Glu Trp Arg Leu Ser Arg Gly
305                 310                 315                 320

Val Glu Glu Gln Thr Gln Ala Phe Phe Glu Gly Phe Asn Glu Ile Leu
                325                 330                 335

Pro Gln Gln Tyr Leu Gln Tyr Phe Asp Ala Lys Glu Leu Glu Val Leu
            340                 345                 350

Leu Cys Gly Met Gln Glu Ile Asp Leu Asn Asp Trp Gln Arg His Ala
        355                 360                 365

Ile Tyr Arg His Tyr Ala Arg Thr Ser Lys Gln Ile Met Trp Phe Trp
    370                 375                 380

Gln Phe Val Lys Glu Ile Asp Asn Glu Lys Arg Met Arg Leu Leu Gln
385                 390                 395                 400

Phe Val Thr Gly Thr Cys Arg Leu Pro Val Gly Gly Phe Ala Asp Leu
```

```
                     405                 410                 415
Met Gly Ser Asn Gly Pro Gln Lys Phe Cys Ile Xaa Lys Val Gly Lys
            420                 425                 430

Glu Asn Trp Leu Pro Arg Ser His Thr Cys Phe Asn Arg Leu Asp Leu
        435                 440                 445

Pro Pro Tyr Lys Ser Tyr Glu Gln Leu Lys Glu Lys Leu Leu Phe Ala
    450                 455                 460

Ile Glu Glu Thr Glu Gly Phe Gly Gln Glu
465                 470
```